United States Patent [19]

Hay et al.

[11] Patent Number: 4,732,604

[45] Date of Patent: Mar. 22, 1988

[54] HERBICIDAL SULFONAMIDES

[75] Inventors: James V. Hay, Newark; Barry A. Wexler, Wilmington, both of Del.; Donna F. Zimmerman, Landenberg, Pa.

[73] Assignee: E. I. Du Pont de Nemours and Company, Wilmington, Del.

[21] Appl. No.: 18,271

[22] Filed: Feb. 24, 1987

Related U.S. Application Data

[60] Division of Ser. No. 769,691, Aug. 29, 1985, Pat. No. 4,666,501, which is a continuation-in-part of Ser. No. 680,549, Dec. 11, 1984, abandoned.

[51] Int. Cl.$^4$ .................. C07D 239/69; C07D 401/12; C07D 409/12; A01N 43/54
[52] U.S. Cl. .................................. 71/92; 71/90; 544/321; 544/320; 544/323; 544/324; 544/331; 544/332; 544/122; 544/123
[58] Field of Search .............. 71/92, 90; 544/321, 544/320, 323, 324, 331, 332, 122, 123

[56] References Cited

U.S. PATENT DOCUMENTS

| 4,435,206 | 3/1984 | Levitt | 71/92 |
| 4,522,645 | 6/1985 | Levitt | 71/93 |
| 4,544,401 | 10/1985 | Levitt | 71/92 |
| 4,620,868 | 11/1986 | Kimuna et al. | 71/90 |

FOREIGN PATENT DOCUMENTS

| 30142 | 5/1984 | European Pat. Off. |
| 35893 | 11/1985 | European Pat. Off. |
| 59-152684 | 2/1986 | Japan |
| 83/4305 | 8/1983 | South Africa |

Primary Examiner—John M. Ford

[57] ABSTRACT

This invention relates to certain sulfonylurea compounds having substituents ortho to the sulfonylurea linkage that includes a 3- or 4- membered carbocyclic ring, a saturated 5- or 6- membered carbocyclic ring or a heterocyclic ring which contains 1 heteroatom selected from O, S and $NR_3$, agriculturally suitable compositions thereof and a method of their use as herbicides or plant growth regulants.

27 Claims, No Drawings

HERBICIDAL SULFONAMIDES

RELATED APPLICATIONS

This is a division of application U.S. Ser. No. 769,691 filed Aug. 29, 1985, now U.S. Pat. No 4,666,501, which is a continuation-in-part of application U.S. Ser. No. 680,549 filed Dec. 11, 1984, now abandoned.

BACKGROUND OF THE INVENTION

This invention relates to herbicidally active sulfonylurea compounds, agriculturally suitable compositions containing them and their method of use as herbicides or plant growth regulants.

In the most common situation, the control of undesired vegetation is desired to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

European Patent Application (EP-A) No. 83,975, published July 20, 1983, discloses herbicidal benzenesulfonamides of formula

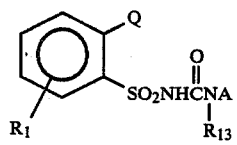

wherein Q is selected from various five or six-membered aromatic or partially unsaturated heterocyclic rings containing 2 or 3 heteroatoms selected from O, S or NR.

U.S. Pat. No. 4,368,069 discloses herbicidal benzenesulfonamides of formula

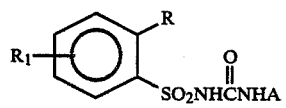

wherein
R is $-(CR_5R_6)_n-R_2$;
n is 0 or 1; and
$R_2$ may be $C_2-C_5$ alkenyl, $C_5-C_6$ cycloalkenyl or $C_2-C_3$ alkenyl substituted with 1-3 chlorine atoms.

European Patent Application (EP-A) No. 85,476, published Aug. 10, 1983, discloses herbicidal benzenesulfonamides of formulae

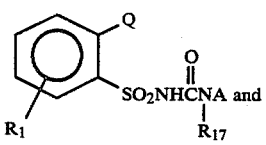

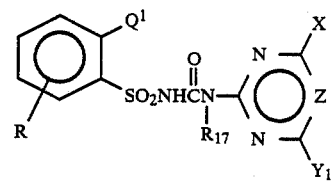

wherein
Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and
$Q^1$ is a 6-membered aromatic heterocycle containing one to three N atoms.

South African Patent Application No. 83/8416, published May, 1984, discloses herbicidal benzenesulfonamides of formula

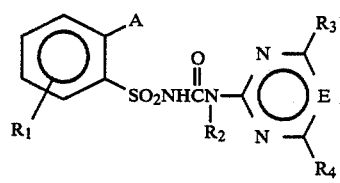

wherein A is an unsaturated or only partially saturated 5- or 6-membered heterocyclic ring system which is bonded through a carbon atom and contains 1, 2 or 3 heteroatoms.

Herbicidal thiophene sulfonamides are disclosed in European Patent Application (EP-A) Nos. 30,142, published June 10, 1981, and 97,122, published Dec. 28, 1983, and in U.S. Pat. Nos. 4,127,405, 4,169,719, 4,398,939 and 4,441,910.

EP-A-95,925, published Dec. 7, 1983, discloses herbicidal pyrazolesulfonamides in which the group adjacent to the sulfonamide moiety may be selected from H, $C_1-C_3$ alkyl, F, Cl, Br, $NO_2$, $OR_{16}$, $CO_2R_{23}$, $S(O)_nR_{24}$ or $SO_2NR_{19}R_{20}$.

EP-A-87,780, published Sept. 7, 1983 discloses pyrazole sulfonamides of general formula

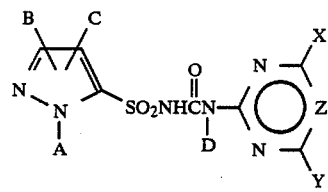

wherein
A is H, $C_1-C_8$ alkyl or optionally substituted phenyl;
B and C are independently H, halogen, $NO_2$, $C_1-C_8$ alkyl, $CO_2R$, etc.; and
D is H or $C_1-C_8$ alkyl.

EP-A-96,003, published Nov. 28, 1983, discloses herbicidal compounds of general formula

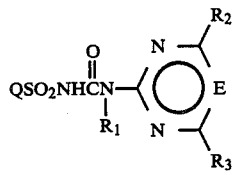

wherein
$R_1$ is H or $C_1$-$C_3$ alkyl; and
Q is an unsubstituted or substituted five-membered heterocyclic radical which is bound by way of a carbon atom and which contains 2 or 3 identical or different heteroatoms.

Herbicidal pyridinesulfonamides are disclosed in European Patent Application Nos. 13,480 published July 23, 1980, 35,893 published Sept. 16, 1981, 97,122 published Dec. 28, 1983 and 103,543 published Mar. 21, 1984 and in U.S. Pat. No. 4,435,206.

U.S. Pat. No. 4,420,325 discloses herbicidal sulfonamides of the following formula

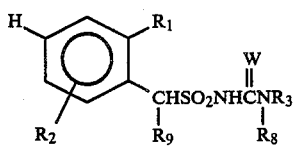

wherein
$R_1$ is F, Cl, Br, $CF_3$, $C_1$-$C_3$ alkoxy, $C_1$-$C_3$ alkyl, $NO_2$, $CO_2R_4$, $SO_2R_5$, $SO_2NR_6R_7$, $SO_2N(OCH_3)CH_3$, $SO_2OCH_2CF_3$, $OSO_2R_5$ or $CH_2L$;
$R_2$ is H, Cl, Br, F, $CF_3$ or $OCH_3$;
$R_9$ is H or $C_1$-$C_3$ alkyl; etc.

SUMMARY OF THE INVENTION

This invention is the discovery of new compounds with herbicidal activity, agriculturally suitable compositions thereof and a method of using said compounds as general or selective preemergent and/or post emergent herbicides. Accordingly the new compounds of the invention are compounds of the formula $$LSO_2NHCNA \overset{W}{\underset{R}{\|}}$$   I wherein
W is O or s;
R is H or $CH_3$;
L is

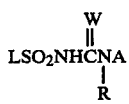   L-1

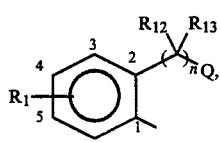   L-2

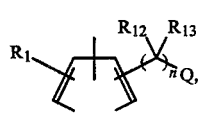   L-3

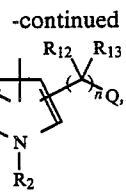   L-4

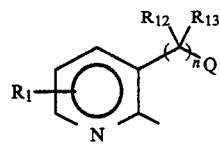   L-5

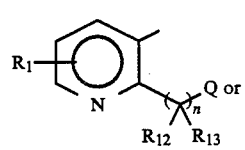   L-6 n is 0 or 1;
$R_1$ is H, $C_1$-$C_3$ alkyl, $C_1$-$C_3$ haloalkyl, halogen, nitro, CN, $C_1$-$C_3$ alkoxy, $SO_2NR^{I}R^{II}$, $C_1$-$C_3$ alkylthio, $C_1$-$C_3$ alkylsulfinyl, $C_1$-$C_3$ alkylsulfonyl, $CO_2R^{III}$, $CH_2CN$, $CH_2OCH_3$ or $CH_2SCH_3$;
$R^{I}$ is H, $C_1$-$C_4$ alkyl, $C_2$-$C_3$ cyanoalkyl, methoxy or ethoxy;
$R^{II}$ is H, $C_1$-$C_4$ alkyl or $C_3$-$C_4$ alkenyl; or
$R^{I}$ and $R^{II}$ may be taken together as —$(CH_2)_3$—, —$(CH_2)_4$—, —$(CH_2)_5$— or —$CH_2CH_2OCH_2CH_2$—;
$R^{III}$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;
$R_2$ is $C_1$-$C_3$ alkyl;
Q is a 3- or 4-membered heterocyclic ring which contains one heteroatom selected from O, S and $NR_3$, or a 3- or 4-membered carbocyclic ring in which one carbon atom may optionally be in the form of a carbonyl group, or a fully-saturated 5- or 6-membered carbocyclic ring, and Q may be optionally substituted with 1-4 substituents selected from halogen, CN, OH, $C_1$-$C_3$ alkyl, $C_1$-$C_3$ alkoxy, $C_1$-$C_3$ alkylthio, $C_2$-$C_4$ alkoxycarbonyl, $C_1$-$C_4$ alkylsulfonyl, ($C_1$-$C_4$ alkyl)-aminosulfamoyl and di($C_1$-$C_4$ alkyl)aminosulfamoyl;
$R_3$ is $C_1$-$C_4$ alkyl;
$R_{12}$ is H or $OR_{14}$;
$R_{13}$ is H or $C_1$-$C_4$ alkyl;
$R_{14}$ is H, $C_1$-$C_4$ alkyl, $C_3$-$C_4$ alkenyl, $C_3$-$C_4$ haloalkenyl, $C_3$-$C_4$ alkynyl, $C_3$-$C_4$ haloalkynyl, $C_2$-$C_4$ alkylcarbonyl, $C(O)NR_{15}R_{16}$, $C_1$-$C_4$ alkylsulfonyl, $C_2$-$C_4$ alkoxyalkyl or $C_2$-$C_4$ alkylthioalkyl;
$R_{15}$ and $R_{16}$ are independently H or $C_1$-$C_2$ alkyl;
A is

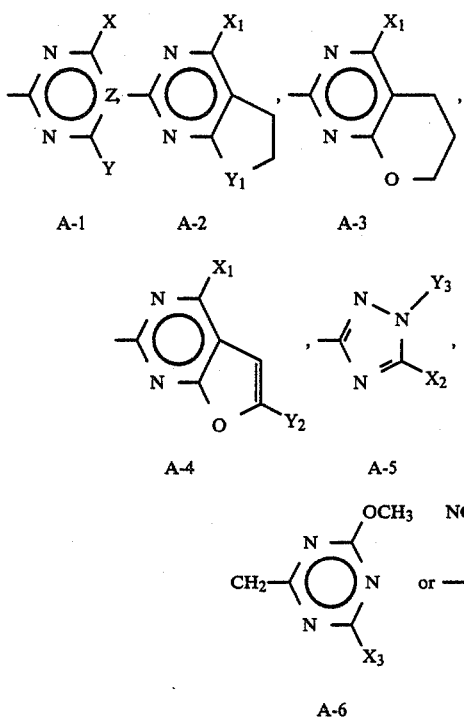

A-1   A-2   A-3

A-4   A-5

A-6   A-7

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl,

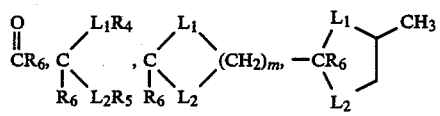

or N(OCH$_3$)CH$_3$;
m is 2 or 3;
$L_1$ and $L_2$ are independently O or S;
$R_4$ and $R_5$ are independently $C_1$–$C_2$ alkyl;
$R_6$ is H or CH$_3$;
Z is CH or N;
$Y_1$ is O or CH$_2$;
$X_1$ is CH$_3$, OCH$_3$, OC$_2$H$_5$ or OCF$_2$H;
$Y_2$ is H or CH$_3$;
$X_2$ is CH$_3$, OCH$_3$ or SCH$_3$;
$Y_3$ is CH$_3$, CH$_2$CH$_3$ or CH$_2$CF$_3$;
$X_3$ is CH$_3$ or OCH$_3$;
$Y_4$ is CH$_3$, OCH$_3$, OC$_2$H$_5$ or Cl; and
$X_4$ is CH$_3$, OCH$_3$, OC$_2$H or CH$_2$OCH$_3$;
and their agriculturally suitable salts; provided that
(a) when X is Cl, F, Br or I, then Z is CH and Y is OCH$_3$, OC$_2$H$_5$, N(OCH$_3$)CH$_3$, NHCH$_3$, N(CH$_3$)$_2$ or OCF$_2$H;
(b) when X or Y is OCF$_2$H, then Z is CH;
(c) when L is L-2 or L-3, then the Q substituent and the sulfonylurea bridge are on adjacent carbon atoms;
(d) when W is S, then R is H, A is A-1, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$ or CH(OCH$_3$)$_2$;
(e) the total number of carbon atoms of $R_{12}$ and $R_{13}$ must be less than or equal to four; and
(f) when the total number of carbon atoms of X and Y is greater than four, then the number of carbons of $R_1$ must be less than or equal to two and the number of carbons of Q must be less than or equal to six.

In the above definitions, the term "alkyl," used either alone or in compound words such as "alkylthio" or "haloalkyl," denotes straight chain or branched alkyl, e.g. methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g. vinyl, 1-propenyl, 2-propenyl, 3-propenyl and the different butenyl isomers.

Alkynyl denotes straight chain or branched alkynes, e.g. ethynyl, 1-propynyl, 2-propynyl and the different butynyl isomers.

Cycloalkyl denotes cyclopropyl, cyclobutyl, cyclopentyl and cyclohexyl.

The term "halogen," either alone or in compound words such as "haloalkyl," denotes fluorine, chlorine, bromine and iodine.

In terms such as $C_2$–$C_3$ alkylthioalkyl, the specified number of carbon atoms is meant to define the *total* number of carbon atoms in that substituent group. For example, $C_2$–$C_3$ alkylthioalkyl would designate CH$_2$SCH$_3$, CH$_2$SC$_2$H$_5$, CH$_2$CH$_2$SCH$_3$ or CH(CH$_3$)SCH$_3$, and $C_2$–$C_5$ alkoxyalkoxy would represent OCH$_2$OCH$_3$ through O(CH$_2$)$_4$OCH$_3$ or OCH$_2$O(CH$_2$)$_3$CH$_3$ and the various structural isomers embraced therein.

Alkoxycarbonyl denotes methoxycarbonyl, ethoxycarbonyl, propoxycarbonyl and isopropoxycarbonyl.

Alkylcarbonyl denotes e.g. acetyl, propionyl, and the different butyryl isomers.

Alkylsulfonyl denotes methylsulfonyl, ethylsulfonyl and the different propylsulfonyl and butylsulfonyl isomers.

Alkylthio, alkylsulfinyl, alkylamino, alkylsulfamoyl etc. are defined in an analogous manner.

The compounds of the invention which are preferred for reasons of increased ease of synthesis and/or greater herbicidal efficacy are:

(1) Compounds of Formula I where Q is

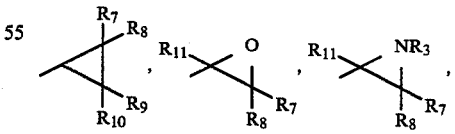

Q-1   Q-2   Q-3

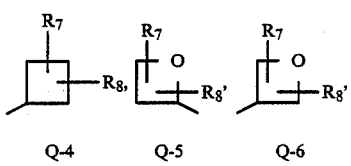

Q-4   Q-5   Q-6

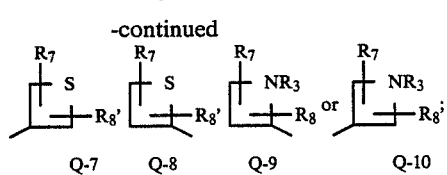

wherein $R_3$ is $C_1$-$C_3$ alkyl;

$R_7$ is H, F, Cl, Br, CN, $CH_3$ or $OCH_3$;

$R_8$ is H, F, Cl, Br, I, CN, OH, $C_1$-$C_3$ alkyl, $C_1$-$C_3$ alkoxy, $C_2$-$C_3$ alkoxycarbonyl, di($C_1$-$C_3$ alkyl)aminosulfamoyl, $C_1$-$C_3$ alkylthio or $C_1$-$C_3$ alkylsulfonyl;

$R_9$ and $R_{10}$ are independently H, $CH_3$, F, Cl or may be taken together to form C=O; and $R_{11}$ is H or $C_1$-$C_3$ alkyl;

provided that (a) when $R_7$ and $R_8$ are attached to the same carbon atom as in Q-1, Q-2 or Q-3, or in Q-4 through Q-10, and $R_7$ is $OCH_3$, then $R_8$ is other than F, Cl, Br, I or OH; and (b) when $R_7$ and $R_8$ are attached to the same carbon atom as in Q-1, Q-2 or Q-3, or in Q-4 through Q-10, and $R_8$ is F, Cl, Br, I or OH, then $R_7$ is other than $OCH_3$.

(2) Compounds of Preferred 1 where
A is A-1,
W is O; and
R is H.

(3) Compounds of Preferred 2 where
$R_1$ is selected from H, F, Cl, $NO_2$, $C_1$-$C_2$ alkyl, $C_1$-$C_2$ haloalkyl, $C_1$-$C_2$ alkoxy, $C_1$-$C_2$ alkylthio, $CH_2OCH_3$ or $CH_2SCH_3$;
$R_{13}$ is H or $CH_3$;
$R_{14}$ is H, $C_1$-$C_2$ alkyl, $CH_2CH=CH_2$ or $CH_2C\equiv CH$;
X is $CH_3$, $OCH_3$, $OC_2H_5$, Cl, F, Br, $OCF_2H$, $CH_2F$, $OCH_2CH_2F$, $OCH_2CHF_2$, $OCH_2CF_3$, $CF_3$, $CH_2Cl$ or $CH_2Br$; and
Y is H, $C_1$-$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $OCF_2H$, $SCF_2H$, cyclopropyl, $C\equiv CH$ or $C\equiv CCH_3$.

(4) Compounds of Preferred 3 where
L is L-1; and
Q is Q-1, Q-2 or Q-4.

(5) Compounds of Preferred 4 where Q is Q-1;

(6) Compounds of Preferred 5 where
$R_1$ is H, Cl, $CH_3$, $OCH_3$ or $SCH_3$ and is not in the 4-position;
$R_7$ is H, F, Cl, $CH_3$ or $OCH_3$;
$R_8$ is H, F, Cl, $CH_3$ or $OCH_3$; and
$R_9$ and $R_{10}$ are independently H, $CH_3$, F or Cl.

(7) Compounds of Preferred 3 where
L is L-2 or L-3; and
Q is Q-1, Q-2 or Q-4.

(8) Compounds of Preferred 7 where
$R_1$ is H;
$R_7$ is H, F, Cl, $CH_3$ or $OCH_3$;
$R_8$ is H, F, Cl, $CH_3$ or $OCH_3$;
$R_9$ and $R_{10}$ are independently H, $CH_3$, F or Cl; and
$R_{11}$ is H or $CH_3$.

(9) Compounds of Preferred 3 where
L is L-4 or L-5; and
Q is Q-1, Q-2 or Q-4.

(10) Compounds of Preffered 9 where
$R_1$ is H;
$R_7$ is H, F, Cl, $CH_3$ or $OCH_3$;
$R_8$ is H, F, Cl, $CH_3$ or $OCH_3$;
$R_9$ and $R_{10}$ are independently H, $CH_3$, F, or Cl; and
$R_{11}$ is H or $CH_3$.

(11) Compounds of Preferred 3 where
L is L-6; and
Q is Q-1, Q-2 or Q-4.

(12) Compounds of Preferred 11 where
$R_1$ is H;
$R_7$ is H, F, Cl, $CH_3$ or $OCH_3$;
$R_8$ is H, F, Cl, $CH_3$ or $OCH_3$;
$R_9$ and $R_{10}$ are independently H, $CH_3$, F or Cl; and
$R_{11}$ is H or $CH_3$.

The compounds of the invention which are specifically preferred for reasons of their expected greatest ease of synthesis and/or greatest herbicidal efficacy are:

2-(2,2-dichlorocyclopropyl)-N-[(4,6-dimethoxypyrimidin-2-yl)aminocarbonyl]benzenesulfonamide, m.p. 193°–195° C.;

2-(2,2-dichlorocyclopropyl)-N-[(4-methoxy-6-methyl-triazin-2-yl)-aminocarbonyl]benzenesulfonamide, m.p. 168°–170° C.; and N-[(4,6-dimethoxypyrimidin-2-yl)aminocarbonyl]-2-(2-oxiranylmethyl)benzenesulfonamide, m.p. 157°–159° C.(d).

DETAILED DESCRIPTION OF THE INVENTION

Synthesis

The compounds of Formula I can be prepared by reacting an appropriate sulfonyl isocyanate or sulfonyl isothiocyanate, II, with an appropriately substituted aminoheterocycle, III, as shown in Equation 1, where R, W, A and L are as previously defined.

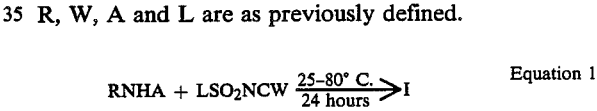

The reaction is best performed in an inert solvent such as methylene chloride or toluene at 25° to 100° C., for 1 to 24 hours. Isolation of the product can be achieved by concentrating the solution and trituration with an appropriate solvent such as butyl chloride.

Alternatively, compounds of Formula I, where W is O, can be prepared by reacting the sulfonamides of Formula IV with the carbamates of Formula V (R'=$CH_3$) in the presence of an excess of trimethylaluminum, as shown in Equation 2, where L, R and A are as previously defined, provided $R_1$ is other than $CO_2R^{III}$.

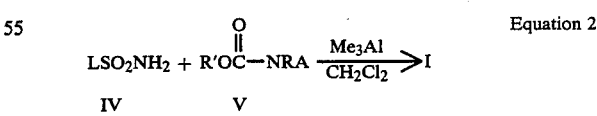

The reactions are best performed in an inert solvent such as methylene chloride at the reflux point of the solution (40° C.) for 10 to 24 hours. Isolation of the product is best achieved by exposing the reaction mixture to acetic acid, separation of the layers and concentrating the organic layer to a solid.

Alternatively, compounds of Formula I can be prepared by exposing a phenyl carbamate V (R'=Ph) to the sulfonamide IV in an appropriate solvent such as dioxane at 25° to 100° C. in the presence of a strong base such as 1,8-diazabicyclo[5.4.0]undec-7-ene; acid workup affords the desired product, as disclosed in European Patent Application (EP-A) No. 44,807. Compounds of Formula I can also be prepared from a phenyl carbamate V and the tert-butyldimethylsilyl-protected sulfonamide IV (LSO$_2$NHSi(CH$_3$)$_2$-t-Bu). Addition of tetrabutylammonium fluoride to a mixture of the carbamate and sulfonamide affords after workup the desired product. The required carbamates can be prepared from the corresponding amines, III, and dimethyl or diphenylcarbonate or methyl or phenylchloroformate and a base such as sodium hydride.

The sulfonyl isocyanates, II, used in the preparation of I are known in the art and can be prepared by known methods. For example, isocyanates can be prepared by exposing an appropriate benzene or heterocyclic sulfonamide to phosgene in the presence of an alkyl isocyanate and an amine catalyst such as 1,4-diazabicyclo[2.2.2]octane at the reflux point of the solvent; see H. Ulrich and A. A. Y. Sayigh, *Newer Methods of Preparative Organic Chemistry*, Vol. VI, p. 223-241. Academic Press, New York and London, W. Forest Ed.

The sulfonyl isothiocyanates, II, used in the preparation of I, where W is S, can be prepared according to the procedure of K. Hartke, *Arch. Pharm.*, 299, 174 (1966).

Sulfonamides of Formula L-1 (compound 3) where Q is Q-1, n=0, R$_1$, and R$_7$ through R$_{10}$ are as previously defined can be prepared in one or more of the ways outlined in Equations 3 through 7.

Equation 3

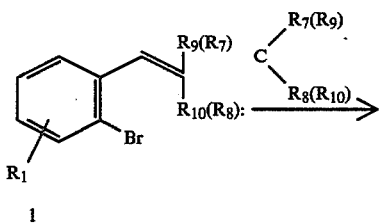

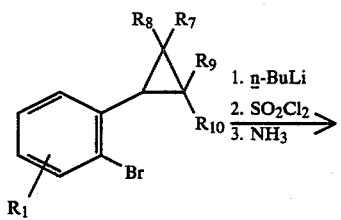

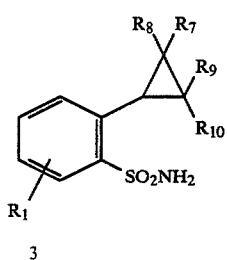

The addition of carbenes to styrene is well known in the art. For further details of such transformations see Keller, W. E., "*Compendium of Phase-Transfer Reactions and Related Synthetic Methods*", Fluka A.G., Switzerland, p 39-64, 1979.

Equation 4

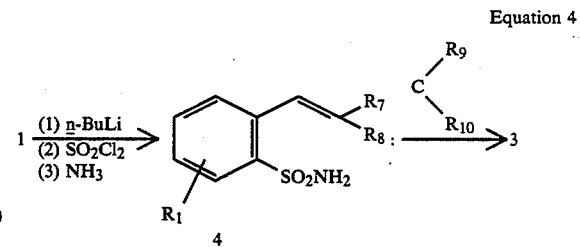

An alternate sequence, outlined below in Equation 5, can be employed in selected cases where lithiation of 2 may be a problem due to functional group incompatibility with n-BuLi, (i.e., R$_7$=CO$_2$CH$_3$).

Equation 5

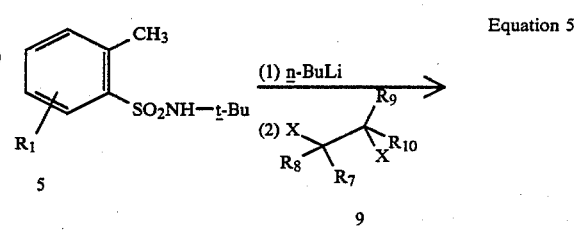

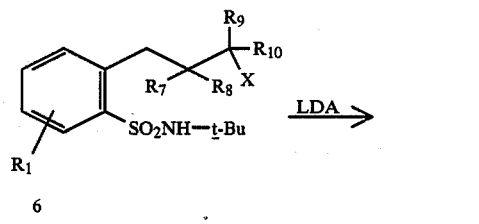

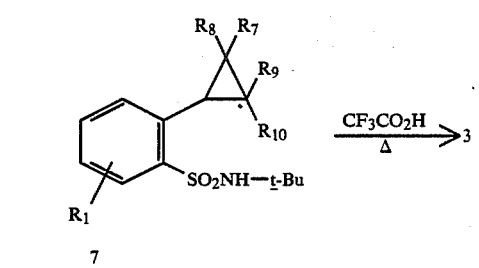

The sulfonamide 3 can also be prepared by direct alkylation with the preformed cyclopropyl methyl halide 8 as outlined in Equation 6.

Equation 6

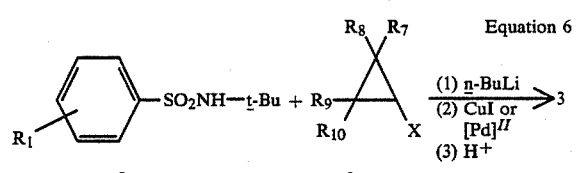

For further details pertaining to this modification of the Ullmann reaction see, S. Gronowitz, and S. Lilgefors, *Chemica Scripta*, 13, 157-161 (1978-79) and A. Minato, K. Tamo, T. Hayasi, K. Suzuki and M. Kumada; *Tetrahedron Letters*, 22, 5319 (1981).

In Equation 5 the dihaloethane 9 may be replaced with other electrophiles such as propylene oxide and its derivatives, as shown in Equation 7.

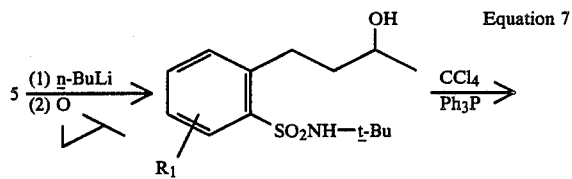

Equation 7

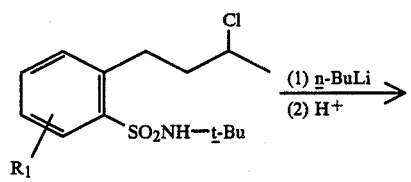

11

3 ($R_7 = CH_3$, $R_8 = R_9 = R_{10} = H$)

The ortho-lithiation of compounds such as 1, 2, 5 and 5a is well known to those skilled in the art. For further details pertaining to this type of transformation see Meyers, A. I., Michlich, B. D., and Nolan, R. L., *J. Org. Chem.*, 39, 2783, 1974.

Sulfonamides of Formula L-1 (Compound 12) where n is 1, Q is Q-1 through Q-3 and $R_1$, $R_3$ and $R_7$ through $R_{13}$ are as previously defined can be prepared in a similar manner to that already described in Equations 3, 4 and 6, with slight modifications of the starting material. For example cyclopropanation of the styrene homolog 13, followed by ortho-lithiation chemistry would afford the target Compound 12 as outlined in Equation 8.

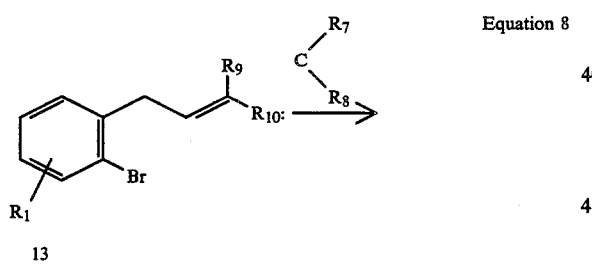

Equation 8

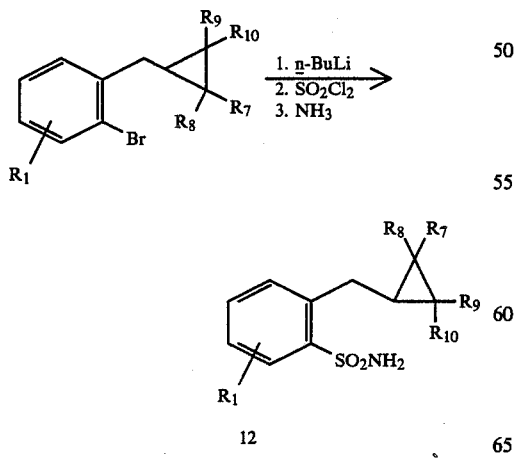

12

In an analogous manner to Equation 6, cyclopropane 12 can be prepared as outlined in Equation 9.

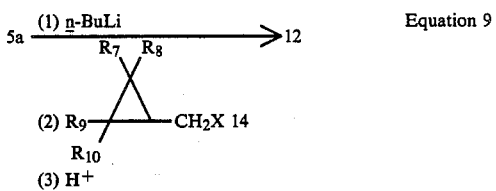

Equation 9

Alternatively, sulfonamide 12 can be prepared by a modified Ullmann reaction utilizing sulfonamide 5 as the starting material as outlined in Equation 10.

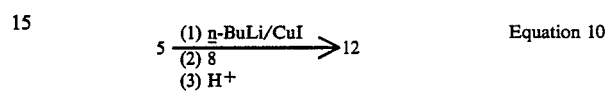

Equation 10

The epoxy sulfonamides of Formula L-1 (Compound 15) where Q is Q-2 and n, $R_1$, $R_7$, $R_8$ and $R_{11}$ are as previously defined can be prepared directly from olefins 1, 4 and 13 via epoxidation using m-chloroperbenzoic acid as described in Equation 11.

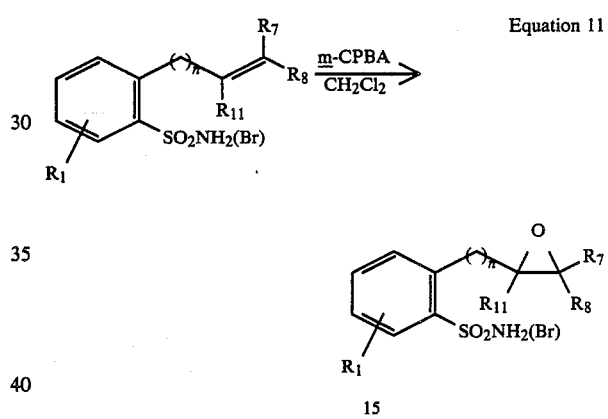

Equation 11

15

Further details pertaining to olefin epoxidations may be found i *Org. Syn.*, Coll. Vol. 1, 494 (1944).

The aziridine sulfonamides where Q is Q-3 and n, $R_1$, $R_3$, $R_7$, $R_8$ and $R_{11}$ are as previously defined such as compound 16 can also be prepared from the corresponding olefins using the procedure outlined in Equation 12.

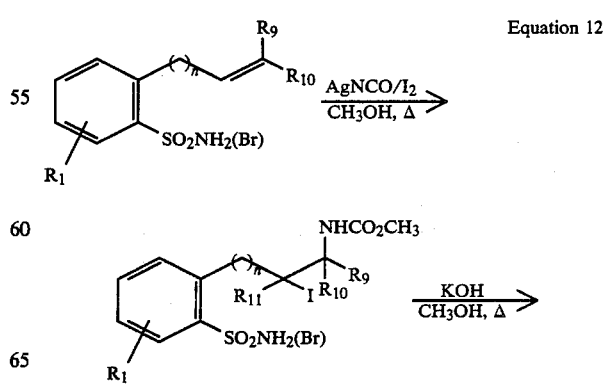

Equation 12

17

-continued

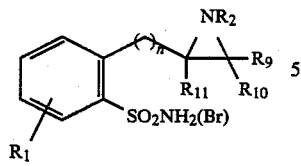

16

For further details see Gebelein, C. O., Swift, G., Swern, D., *J. Org. Chem.*, 32, 3314 (1967).

Sulfonamides of Formula L-2, L-3, L-4, L-5 and L-6, where Q is Q-1 through Q-3 and n, $R_1$, $R_2$, $R_3$ and $R_7$ through $R_{11}$ are as previously defined can be prepared using one or more of the routes previously outlined in Equations 3 through 12.

For example, in the case of L-3, sulfonamide 18 can be prepared using the same route described in Equation 3 or 4. This is outlined in Equation 13.

Equation 13

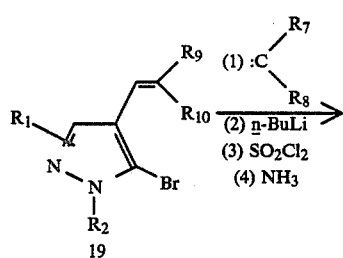

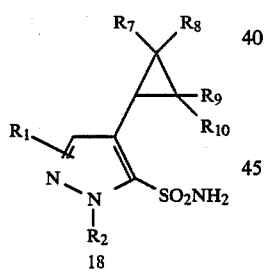

18

Sulfonamides (such as 20) containing a four-membered ring where $R_1$, $R_7$ and $R_8$ are as previously defined may be prepared in one or more of the ways outlined in Equations 14 through 17b.

Equation 14

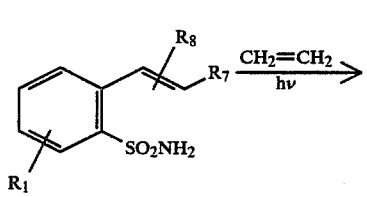

21

-continued

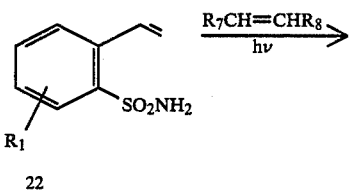

20a

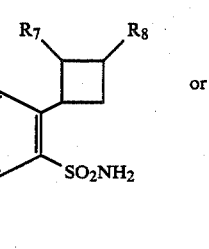

20b

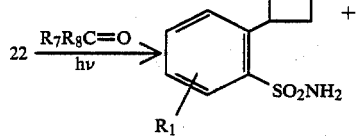

22

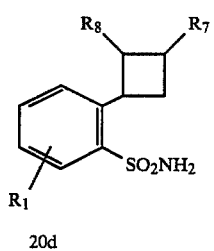

20c

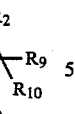

20d

Equation 15

23

15

-continued

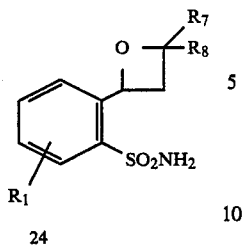

24

For a discussion of photochemical 2+2 cycloadditions of styrene with olefins, aldehydes and ketones (the Paterno-Buchi reaction) see Silversmith, Kitahara, Caserio and Roberts, *J. Am. Chem. Soc.*, 80, 5840 (1958).

An alternate synthesis of compounds such as 20 is via the anionic ring closure of chloride 25 as outlined in Equation 16.

Equation 16

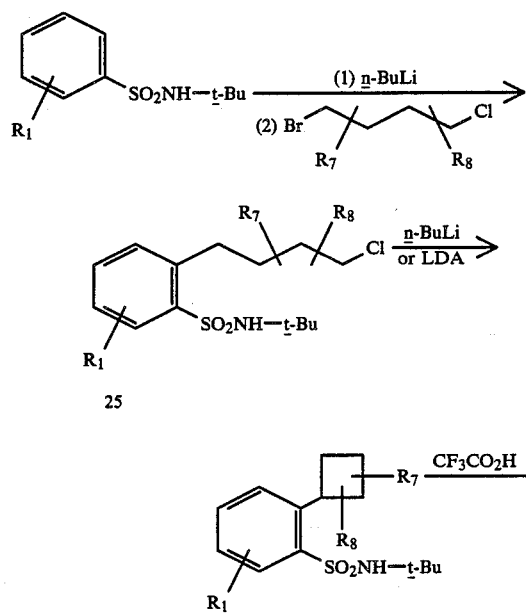

In the similar manner the oxetane ring systems can be formed as shown in Equation 17a and 17b.

Equation 17a

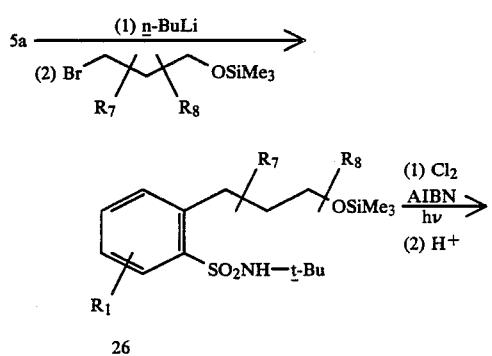

16

-continued

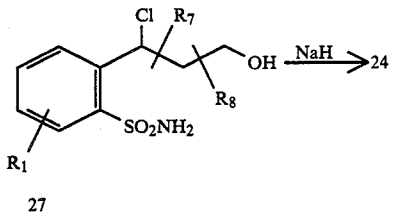

27

Equation 17b

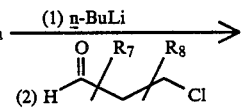

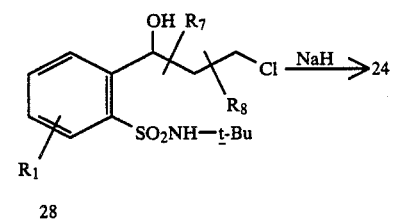

28

The methodology described in Equations 15, 17a and 17b can also be used to prepare the thio and amine analogs, that is sulfonamides of Formula L-1 where Q is Q-7 through Q-10 and $R_1$, $R_3$, $R_7$ and $R_8$ are as previously defined, and n=0 (i.e., 29 and 30).

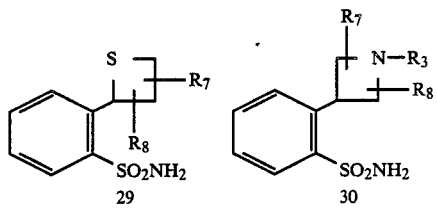

29   30

Examples of anionic four membered ring closures may be found in Corey, E. J. and Seebach, D., *Org. Synth.*, 50, 72 (1970).

Sulfonamides of Formula L-2, L-3, L-4, L-5 and L-6 where Q is Q-4 through Q-10 and R, $R_1$, $R_2$, $R_3$, $R_7$ and $R_8$ are as previously defined can be prepared in a similar manner to that already taught for L-1 in Equations 14 through 17b utilizing the appropriate starting sulfonamides (e.g. 19) as described previously.

In the case where n is 1 the corresponding sulfonamides such as 31 and 32 can be prepared by the procedures outlined in Equation 18a and 18b.

Equation 18a

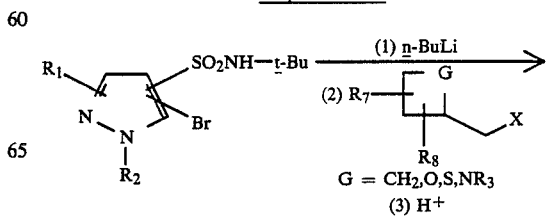

G = $CH_2$, O, S, $NR_3$
(3) $H^+$

-continued

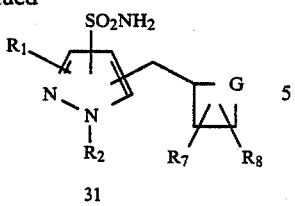
31

Equation 18b

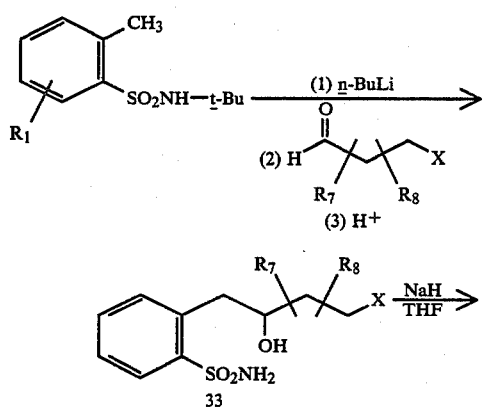
33

32

Sulfonamide 34 where $R_{12}$ is OH, $R_{13}$ is H (n=1) can be prepared as outlined in Equation 19.

Equation 19

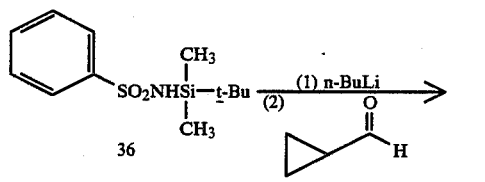
36

35

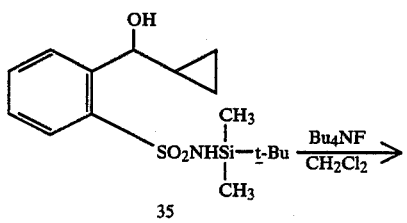
34

The use of the tert-butyldimethylsilyl group allows for low temperature generation of the anion and mild removal of the protecting group. In the same manner alkylation of 36 with ketones such as cyclobutanone allows for the preparation of sulfonamide 37 as outlined in Equation 20.

Equation 20

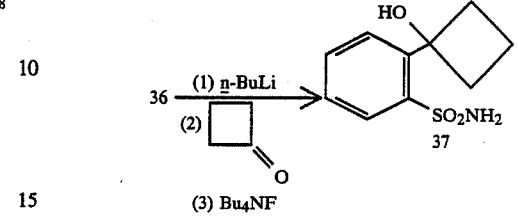
37

Preparation of a heterocyclic sulfonamide wherein $R_{12}$ is H and $R_{13}$ is OH (n=1) is accomplished in the same way as already taught for an aromatic system in Equations 19 and 20. For example, sulfonamide 38 can be prepared from protected pyrazole sulfonamide 39 as outlined in Equation 21.

Equation 21

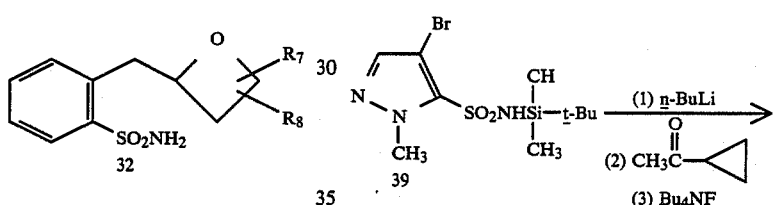

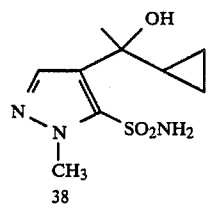
38

Sulfonamides such as 34 or 38 can be used to prepare sulfonamides such as 40. Generation of the alkoxide with sodium hydride followed by the addition of the appropriate alkylating group affords protected alcohols such as 40.

Equation 22

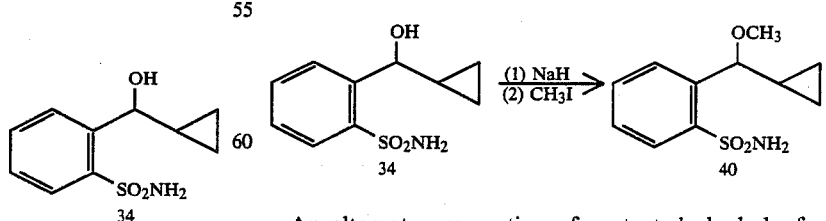
34      40

An alternate preparation of protected alcohols, for example 41, is to trap directly the incipient lithium alkoxide (42) resulting from the condensation of the anion of 36 with aldehydes and ketones. This is depicted in Equation 23.

Equation 23

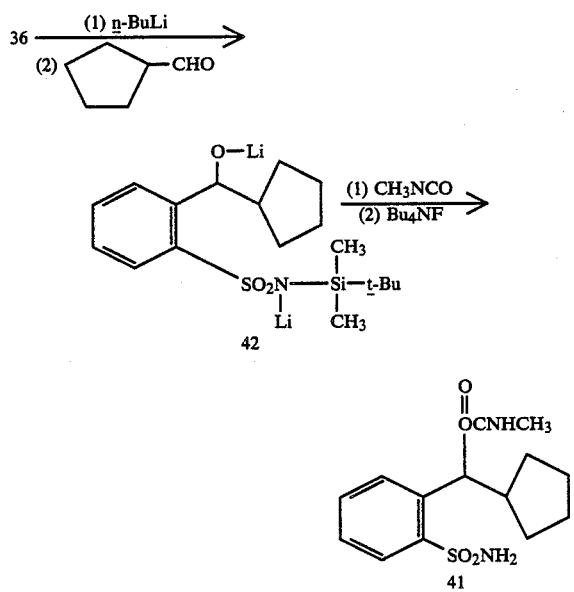

For further information pertaining to the synthesis of pyrazole sulfonamides see: EP-A-95,925; for thiophene sulfonamides, EP-A-30,142; for pyridine sulfonamides, EP-A-13,480, and benzyl sulfonamides, EP-A-51,466 and U.S. Pat. No. 4,420,325.

The heterocyclic amines of Formula III can be prepared by methods known in the literature or simple modifications thereof, by those skilled in the art. For instance, EP-A-84,224 (published July 27, 1983) and W. Braker et al, *J. Am. Chem. Soc.* 1947, 69, 3072 describe methods for preparing aminopyrimidines and triazines substituted by acetal groups. Also, South African Patent Application Nos. 825,045 and 825,671 describe methods for preparing aminopyrimidines and triazines substituted by haloalkyl or haloalkylthio groups such as $OCH_2CH_2F$, $OCH_2CF_3$, $SCF_2H$, and $OCF_2H$ among other groups. South African Patent Application No. 837,434 (published Oct. 5, 1983) describes methods for the synthesis of cyclopropylpyrimidines and triazines substituted by such groups as alkyl, haloalkyl, alkoxy, haloalkoxy, alkylamino, dialkylamino, and alkoxyalkyl.

The 5,6-dihydrofuro[2.3-d]pyrimidin-2-amines, and the cyclopenta[d]pyrimidin-2-amines, of Formula III, where A is A-2, and the 6,7-dihydro-5H-pyrano[2.3-d]pyrimidin-2-amines, the Formula III, where A is A-3, can be prepared as described in EP-A No. 15,863. The furo[2.3-d]pyrimidin-2-amines, of Formula III, where A is A-4, are described in EP-A No. 46,677. Heterocycles of Formula III, where A is A-5, can be prepared as described in EP-A No. 73,562. Heterocycles of Formula III, where A is A-6, can be prepared by methods taught in EP-A-94,260. Heterocycles of Formula III, where A is A-7, can be prepared by methods taught in EP-A-125,864.

In addition, general methods for preparing aminopyrimidines and triazines have been reviewed in the following publications.

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rapaport; and F. C. Schaefer, U.S. Pat. No. 3,154,547 and K. R. Huffman and F. C. Schaefer, *J. Org. Chem.*, 28, 1812 (1963), which describe the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contacting of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compount of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is paticularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is illustrated by the following examples.

EXAMPLE 1

Preparation of 2-Ethenylbenzenesulfonamide

2-Bromostyrene (10.0 g, 54.9 mmol) was added dropwise to n-BuLi in 250 ml of tetrahydrofuran at −78° C. After stirring for 15 minutes the solution was added via a cannula to a solution of sulfurylchloride fluoride (9.7 g, 82.4 mmol) in 50 ml of tetrahydrofuran cooled to −78° C. The reaction mixture was quenched with brine and separated. The organic layer was dried and concentrated to approximately half-volume. This solution was added to anhydrous ammonia (100 ml) cooled to −78° C. The reaction was warmed to room temperature, excess ammonia was removed and the solids were filtered off. The filtrate was concentrated and the resulting oil was triturated with butyl chloride and ethyl acetate to yield the desired sulfonamide, m.p. 103°–105° C.

EXAMPLE 2

Preparation of 2-(2-Oxiranyl)benzenesulfonamide

A solution consisting of 2-ethenylbenzenesulfonamide (1.5 g, 8.1 mmol) m-chloroperbenzoic acid (1.4 g, 8.1 mmol) and potassium carbonate (1.1 g, 8.1 mmol) in 150 ml of chloroform was stirred for 4 days at room temperature. The reaction was filtered and the filtrate was washed with saturated sodium bicarbonate. The organic layer was separated, dried and concentrated.

The resulting oil was flash chromatographed (methylene chloride) to yield the subject compound as a white solid, m.p. 136°–139° C.

EXAMPLE 3

Preparation of
1-Bromo-2-(2,2-Dichlorocyclopropyl)-benzene

A 20 ml solution of 50% sodium hyroxide was added dropwise to 2-bromostyrene (10.0 g, 54.9 mmol) in 100 ml of chloroform. The reaction mixture was warmed to 45° C. for 1 hour. After cooling the solution was separated and the organic layer was dried over magnesium sulfate and concentrated. The resulting liquid was flash chromatographed, affording 11.6 g of the desired compound.

EXAMPLE 4

Preparation of
N-[(4,6-Dimethoxypyrimidin-2-yl)aminocarbonyl]-2-(2-oxiranyl)benzenesulfonamide To a stirring solution of the 2-(2-oxiramyl)benzenesulfonamide (75 mg, 0.376 mmol) and 4,6-dimethoxy-2-aminophenoxycarbonyl pyrimidine (103 mg, 0.37 mmol) in 5 ml of acetonitrile was added 1,8-diazabicyclo[5.4.0]undec-7-ene (57 mg, 0.37 mmol). The reaction was stirred for 3 hours followed by quenching with 3 ml of 5% hydrochloric acid. The solution was diluted with ethyl acetate, separated and dried. The organics were concentrated to yield 140 mg of the desired product, m.p. 177°–179° C.; NMR (200 MHz, CDCl$_3$)δ: 2.3 (dd, 1H); 3.1 (dd, 1H); 3.95 (s, 6H); 4.7 (dd, 1H); 5.88 (s, 1H); 7.0 (br s, 1H); 7.55 (m, 3H) and 8.2 (dd, 1H).

EXAMPLE 5

Preparation of
2-(2,2-Dichlorocyclopropyl)-N-[(4-methoxy-6-methyl-pyrimidin-2-yl)aminocarbonyl]benzenesulfonamide To a stirring solution of 2-(2,2-dichlorocyclopropyl)-benzenesulfonamide (200 mg, 0.75 mmol) and 4-methyl-6-methoxy-2-aminophenoxycarbonyl pyrimidine (195 mg, 0.75 mmol) was added 1,8-diazabicyclo[5.4.0]undec-7-ene (115 mg, 0.75 mmol). Work-up as described in example 4 afforded 180 mg of the desired compound, m.p. 187°–191° C.; NMR (200 MHz, CDCl$_3$)δ: 2.05 (dd, 2H); 2.41 (s, 3H); 3.79 (dd, 1H); 3.94 (s, 3H); 6.27 (s, 1H); 7.2 (d, 1H); 7.57 (m, 3H) and 8.4 (dd, 1H).

EXAMPLE 6

2-[(Cyclopropyl)(hydroxy)methyl]-N-[(dimethyl((1,1-dimethylethyl)silyl]benzenesulfonamide To a stirring solution of n-BuLi (5.2 g, 80.8 mmol) in 300 ml of THF cooled to −10° C. was added dropwise tert-butyldimethylsilylbenzenesulfonamide (10.0 g, 36.7 mmol) in 25 ml of THF. The solution was stirred for one hour. After cooling to −78° C., cyclopropyl aldehyde (2.8 g, 40.0 mmol) was added. The reaction mixture was stirred for 30 minutes, then quenched with brine. The organic layer was separated, dried over magnesium sulfate and concentrated in vacuo. Flash chromatography (20% EtOAc:hexane, v/v) afforded 2.7 g of the desired product as a viscous oil; NMR (200 MHz, CDCl$_3$): δ 0.24 (d, 6H), 0.4 (m, 1H), 0.45–0.8 (m, 3H), 0.88 (s, 9H)), 1.6 (m, 1H), 2.85 (d, 1H), 4.9 (dd, 1H), 5.30 (s, 1H), 5.67 (brs, 1H), 7.41 (t, 1H), 7.54 (t, 1H), 7.76 (d, 1H), 7.98 (d, 1H).

EXAMPLE 7

N-[(4,6-Dimethylpyrimidin-2-yl)aminocarbonyl]-2-(1-hydroxycyclobutyl)benzenesulfonamide To a mixture of the phenylcarbamate of 4,6-dimethyl-2-aminopyrimidine (178 mg, 0.73 mmol) and tert-butyl-dimethylsilane-protected 2-(1-hydroxycylcobutane)-benzenesulfonamide in 5 ml of acetonitrile was added tetrabutylammonium fluoride (231 mg, 0.73 mmol). The reaction mixture was stirred for 5 minutes followed by the addition of 5% HCl. The resulting solids were collected and dried to give 250 mg of the desired product; m.p. 148°–150° C.; NMR (200 MHz, CDCl$_3$); δ 2.45 (s, 7H), 2.58 (m, 5H), 6.76 (s, 1H), 7.47–7.75 (m, 4H), 8.32 (d, 1H).

TABLE OF STRUCTURES

General Structure I

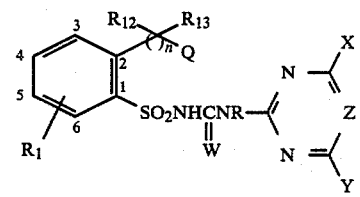

where W is O unless otherwise indicated by *, where W is S.

For ring systems Q-4 through Q-10, the substituents R$_7$ and R$_8$ are attached as follows

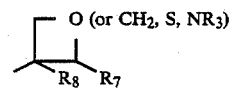

General Structure II

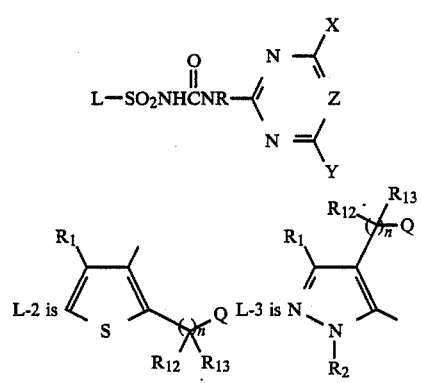

For ring systems Q-4 through Q-10, the substituents R$_7$ and R$_8$ are attached as follows

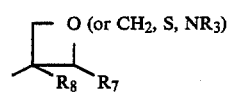

General Structure IIa

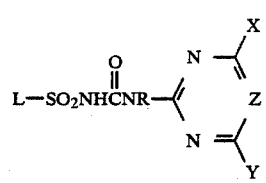

TABLE OF STRUCTURES-continued

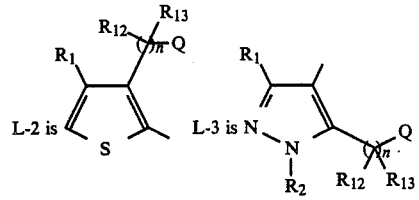

L-2 is (thiophene structure)  L-3 is N (pyrazole structure)

General Structure IIb

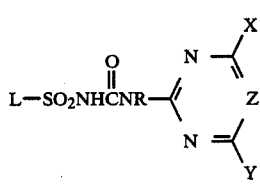

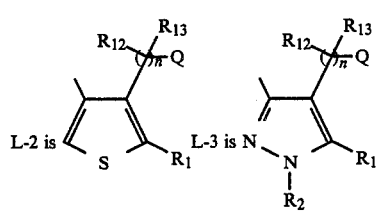

L-2 is (thiophene structure)  L-3 is N (pyrazole structure)

TABLE OF STRUCTURES-continued

General Structure III

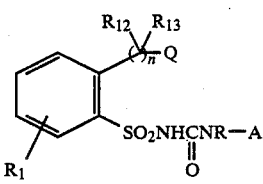

General Structure IV

L-2 and L-3 are as in General Structure II. n = 0

General Structure V

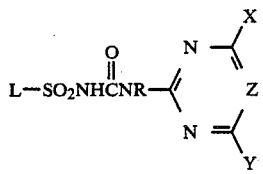

L-2 and L-3 are as in General Structure II,
$R_9$ and $R_{10}$ are C = O   n = 0

TABLE I

General Structure I (wherein $R_{12}$ and $R_{13}$ are H)

| Q | n | R | $R_1$ | $R_7$ | $R_8$ | $R_9$ | $R_{10}$ | $R_{11}$ | X | Y | Z | m.p.(°C.) |
|---|---|---|---|---|---|---|---|---|---|---|---|---|
| Q-1 | 0 | H | H | H | H | H | H | — | $CH_3$ | $CH_3$ | CH | 197–198.5 |
| Q-1 | 0 | H | H | H | H | H | H | — | $CH_3$ | $OCH_3$ | CH | 209–210 |
| Q-1 | 0 | H | H | H | H | H | H | — | $OCH_3$ | $OCH_3$ | CH | 202–204 |
| Q-1 | 0 | $CH_3$ | H | H | H | H | H | — | $CH_3$ | $OCH_3$ | N | 144–146 |
| Q-1 | 0 | H | H | H | H | H | H | — | $CH_3$ | $OCH_3$ | N | 190–191 |
| Q-1 | 0 | H | H | H | H | H | H | — | $OCH_3$ | $OCH_3$ | N | 174–176 |
| Q-1 | 0 | H | H | H | H | H | H | — | Cl | $OCH_3$ | CH | 192–194 |
| Q-1 | 0 | H | H | H | F | H | H | — | $CH_3$ | $CH_3$ | CH | |
| Q-1 | 0 | H | H | H | F | H | H | — | $CH_3$ | $CH_3$ | N | |
| Q-1 | 0 | H | H | H | F | H | H | — | $CH_3$ | $OCH_3$ | CH | |
| Q-1 | 0 | H | H | H | Cl | H | H | — | $OCH_3$ | $OCH_3$ | CH | 174–177 |
| Q-1 | 0 | H | H | H | Cl | H | H | — | $CH_3$ | $CH_3$ | N | 172–175 |
| Q-1 | 0 | H | H | Cl | H | H | H | — | $CH_3$ | $OCH_3$ | CH | 186–188 |
| Q-1 | 0 | H | H | Cl | H | H | H | — | $CH_3$ | $OCH_3$ | N | 156–160 |
| Q-1 | 0 | H | H | H | Br | H | H | — | $CH_3$ | $CH_3$ | CH | |
| Q-1 | 0 | H | H | Br | H | H | H | — | $CH_3$ | $OCH_3$ | CH | |
| Q-1 | 0 | H | H | Br | H | H | H | — | $OCH_3$ | $OCH_3$ | CH | |
| Q-1 | 0 | H | H | H | I | H | H | — | $CH_3$ | $CH_3$ | N | |
| Q-1 | 0 | H | H | H | H | H | H | — | $NHCH_3$ | $OCH_2CH_3$ | N | 203–206 |
| Q-1 | 0 | H | H | H | CN | H | H | — | $OCH_3$ | $OCH_3$ | N | |
| Q-1 | 0 | H | H | CN | H | H | H | — | $OCH_3$ | $OCH_3$ | CH | |
| Q-1 | 0 | H | H | H | $CH_3$ | H | H | — | $CH_3$ | $CH_3$ | CH | 155–159 |
| Q-1 | 0 | H | H | H | $CH_3$ | H | H | — | $CH_3$ | $OCH_3$ | CH | 180–182 |
| Q-1 | 0 | H | H | H | $CH_3$ | H | H | — | $OCH_3$ | $OCH_3$ | CH | 215–216 |
| Q-1 | 0 | H | H | $CH_3$ | H | H | H | — | Cl | $OCH_3$ | N | 175–176 |
| Q-1 | 0 | H | H | $CH_3$ | H | H | H | — | $CH_3$ | $OCH_3$ | N | 154–157 |
| Q-1 | 0 | H | H | H | $CH_2CH_3$ | H | H | — | $OCH_3$ | $OCH_3$ | N | |
| Q-1 | 0 | H | H | $CH_2CH_3$ | H | H | H | — | $CH_3$ | $OCH_3$ | CH | |
| Q-1 | 0 | H | H | H | $CH_2CH_3$ | H | H | — | $OCH_3$ | $OCH_3$ | CH | |
| Q-1 | 0 | H | H | H | $CH_2CH_2CH_3$ | H | H | — | $CH_3$ | $OCH_3$ | N | |
| Q-1 | 0 | H | H | H | Cl | H | H | — | $CH_3$ | $CH_3$ | CH | 182–185 |
| Q-1 | 0 | H | H | H | Cl | H | H | — | $OCH_3$ | $OCH_3$ | N | 139–142 |
| Q-1 | 0 | H | H | H | Cl | H | H | — | Cl | $OCH_3$ | CH | 185–187 |
| Q-1 | 0 | H | H | H | Cl | H | H | — | $OCH_2CH_3$ | $NHCH_3$ | CH | 154–158 |
| Q-1 | 0 | H | H | H | Br | | $CH_3$ | — | $OCH_3$ | $CH_3$ | CH | |
| Q-1 | 0 | H | H | H | Br | H | Cl | — | $OCH_3$ | $CH_3$ | CH | |
| Q-1 | 0 | H | H | H | Br | H | F | — | $CH_3$ | $CH_3$ | N | |
| Q-1 | 0 | H | H | H | Br | H | F | — | $CH_3$ | $OCH_3$ | N | |
| Q-1 | 0 | H | H | H | Br | H | F | — | $OCH_3$ | $OCH_3$ | N | |
| Q-1 | 0 | H | H | H | Br | H | Br | — | $CH_3$ | $OCH_3$ | CH | |
| Q-1 | 0 | H | H | H | I | H | $CH_3$ | — | $OCH_3$ | $OCH_3$ | CH | |
| Q-1 | 0 | H | H | H | CN | H | $CH_3$ | — | $CH_3$ | $OCH_3$ | N | |
| Q-1 | 0 | H | H | H | CN | H | $CH_3$ | — | $OCH_3$ | $OCH_3$ | N | |

TABLE I-continued

| | | | | | | | | | | | |
|---|---|---|---|---|---|---|---|---|---|---|---|
| Q-1 | 0 | H | H | H | CN | H | Cl | — | CH$_3$ | CH$_3$ | CH | |
| Q-1 | 0 | H | H | H | CN | H | F | — | CH$_3$ | OCH$_3$ | CH | |
| Q-1 | 0 | H | H | H | CN | H | Br | — | OCH$_3$ | OCH$_3$ | CH | |
| Q-1 | 0 | H | H | H | CN | CH$_3$ | H | — | CH$_3$ | CH$_3$ | N | |
| Q-1 | 0 | H | H | H | OCH$_3$ | H | CH$_3$ | — | CH$_3$ | OCH$_3$ | N | |
| Q-1 | 0 | H | H | H | OCH$_3$ | H | CH$_3$ | — | OCH$_3$ | OCH$_3$ | N | |
| Q-1 | 0 | H | H | H | OCH$_3$ | H | Cl | — | Cl | OCH$_3$ | CH | |
| Q-1 | 0 | H | H | H | OCH$_3$ | Cl | H | — | CH$_3$ | OCH$_3$ | CH | |
| Q-1 | 0 | H | H | H | OCH$_3$ | F | H | — | OCH$_3$ | OCH$_3$ | CH | |
| Q-1 | 0 | H | H | H | OCH$_3$ | H | Br | — | CH$_3$ | OCH$_3$ | N | |
| Q-1 | 0 | H | H | H | CO$_2$CH$_3$ | H | CH$_3$ | — | OCH$_3$ | OCH$_3$ | N | |
| Q-1 | 0 | H | H | H | CO$_2$CH$_3$ | H | CH$_3$ | — | CH$_3$ | CH$_3$ | CH | |
| Q-1 | 0 | H | H | H | CO$_2$CH$_3$ | H | CH$_3$ | — | CH$_3$ | CH$_3$ | CH | |
| Q-1 | 0 | H | H | H | CO$_2$CH$_3$ | H | F | — | CH$_3$ | OCH$_3$ | CH | |
| Q-1 | 0 | H | H | H | CO$_2$CH$_3$ | H | Cl | — | OCH$_3$ | OCH$_3$ | CH | |
| Q-1 | 0 | H | H | H | CO$_2$CH$_3$ | H | Cl | — | CH$_3$ | OCH$_3$ | N | |
| Q-1 | 0 | H | H | H | CO$_2$CH$_3$ | H | Br | — | OCH$_3$ | OCH$_3$ | N | |
| Q-1 | 0 | H | H | H | SO$_2$N(CH$_3$)$_2$ | H | CH$_3$ | — | CH$_3$ | OCH$_3$ | CH | |
| Q-1 | 0 | H | H | H | SO$_2$N(CH$_3$)$_2$ | H | CH$_3$ | — | OCH$_3$ | OCH$_3$ | CH | |
| Q-1 | 0 | H | H | H | SO$_2$N(CH$_3$)$_2$ | H | F | — | CH$_3$ | OCH$_3$ | CH | |
| Q-1 | 0 | H | H | H | SO$_2$N(CH$_3$)$_2$ | H | Cl | — | CH$_3$ | OCH$_3$ | N | |
| Q-1 | 0 | H | H | H | SO$_2$N(CH$_3$)$_2$ | H | Br | — | OCH$_3$ | OCH$_3$ | CH | |
| Q-1 | 0 | H | H | H | SCH$_3$ | H | CH$_3$ | — | Cl | OCH$_3$ | CH | |
| Q-1 | 0 | H | H | H | SCH$_3$ | H | F | — | OCH$_3$ | OCH$_3$ | N | |
| Q-1 | 0 | H | H | H | SCH$_3$ | H | Cl | — | CH$_3$ | OCH$_3$ | CH | |
| Q-1 | 0 | H | H | H | OCH$_3$ | H | Cl | — | CH$_3$ | OCH$_3$ | CH | |
| Q-1 | 0 | H | H | H | OCH$_3$ | H | H | — | CH$_3$ | CH$_3$ | CH | |
| Q-1 | 0 | H | H | H | OCH$_3$ | H | H | — | OCH$_3$ | CH$_3$ | CH | |
| Q-1 | 0 | H | H | CH$_3$O | H | H | H | — | OCH$_3$ | OCH$_3$ | CH | |
| Q-1 | 0 | H | H | H | OCH$_2$CH$_3$ | H | H | — | CH$_3$ | OCH$_3$ | N | |
| Q-1 | 0 | H | H | H | CO$_2$CH$_3$ | H | H | — | CH$_3$ | OCH$_3$ | N | |
| Q-1 | 0 | H | H | H | CO$_2$CH$_3$ | H | H | — | OCH$_3$ | OCH$_3$ | N | |
| Q-1 | 0 | H | H | H | CO$_2$CH$_3$ | H | H | — | OCH$_3$ | OCH$_3$ | CH | |
| Q-1 | 0 | H | H | H | CO$_2$CH$_3$ | H | H | — | OCH$_3$ | OCH$_3$ | CH | |
| Q-1 | 0 | H | H | H | CO$_2$CH$_2$CH$_3$ | H | H | — | CH$_3$ | OCH$_3$ | N | |
| Q-1 | 0 | H | H | H | SO$_2$N(CH$_3$)$_2$ | H | H | — | OCH$_3$ | OCH$_3$ | N | |
| Q-1 | 0 | H | H | H | SO$_2$N(CH$_3$)$_2$ | H | H | — | CH$_3$ | OCH$_3$ | CH | |
| Q-1 | 0 | H | H | H | SCH$_3$ | H | H | — | OCH$_3$ | OCH$_3$ | CH | |
| Q-1 | 0 | H | H | H | SCH$_3$ | H | H | — | CH$_3$ | CH$_3$ | N | |
| Q-1 | 0 | H | H | H | SO$_2$CH$_3$ | H | H | — | CH$_3$ | OCH$_3$ | N | |
| Q-1 | 0 | H | H | H | SO$_2$CH$_3$ | H | H | — | Cl | OCH$_3$ | CH | |
| Q-1 | 0 | H | H | H | SO$_2$CH$_3$ | H | H | — | CH$_3$ | OCH$_3$ | CH | |
| Q-1 | 0 | H | H | H | SO$_2$CH$_2$CH$_3$ | H | H | — | OCH$_3$ | OCH$_3$ | CH | |
| Q-1 | 0 | H | H | H | CH$_3$ | H | CH$_3$ | — | CH$_3$ | OCH$_3$ | N | |
| Q-1 | 0 | H | H | H | CH$_3$ | H | CH$_3$ | — | CH$_3$ | OCH$_3$ | N | |
| Q-1 | 0 | H | H | H | CH$_3$ | CH$_3$ | H | — | CH$_3$ | CH$_3$ | CH | |
| Q-1 | 0 | H | H | H | CH$_3$ | H | F | — | CH$_3$ | OCH$_3$ | CH | |
| Q-1 | 0 | H | H | H | CH$_3$ | H | F | — | OCH$_3$ | OCH$_3$ | CH | |
| Q-1 | 0 | H | H | H | CH$_3$ | H | F | — | CH$_3$ | OCH$_3$ | N | |
| Q-1 | 0 | H | H | H | CH$_3$ | H | Cl | — | OCH$_3$ | OCH$_3$ | N | |
| Q-1 | 0 | H | H | H | CH$_3$ | Br | H | — | CH$_3$ | OCH$_3$ | CH | |
| Q-1 | 0 | H | H | H | F | H | H | — | CH$_3$ | OCH$_3$ | CH | |
| Q-1 | 0 | H | H | H | F | H | CH$_3$ | — | CH$_3$ | OCH$_3$ | CH | |
| Q-1 | 0 | H | H | H | Cl | H | CH$_3$ | — | CH$_3$ | OCH$_3$ | N | |
| Q-1 | 0 | H | H | H | Cl | H | F | — | OCH$_3$ | OCH$_3$ | CH | |
| Q-1 | 0 | H | H | H | Cl | H | Cl | — | Cl | OCH$_3$ | CH | |
| Q-1 | 0 | H | H | H | Cl | H | Cl | — | OCH$_3$ | OCH$_3$ | N | |
| Q-1 | 0 | H | H | H | Cl | H | Br | — | CH$_3$ | OCH$_3$ | CH | |
| Q-1 | 0 | H | H | H | SO$_2$CH$_3$ | H | CH$_3$ | — | CH$_3$ | CH$_3$ | CH | |
| Q-1 | 0 | H | H | H | SO$_2$CH$_3$ | H | CH$_3$ | — | OCH$_3$ | OCH$_3$ | CH | |
| Q-1 | 0 | H | H | H | SO$_2$CH$_3$ | H | CH$_3$ | — | CH$_3$ | CH$_3$ | N | |
| Q-1 | 0 | H | H | H | SO$_2$CH$_3$ | H | CH$_3$ | — | CH$_3$ | OCH$_3$ | N | |
| Q-1 | 0 | H | H | H | SO$_2$CH$_3$ | H | CH$_3$ | — | OCH$_3$ | OCH$_3$ | N | |
| Q-1 | 0 | H | H | H | SO$_2$CH$_3$ | H | CH$_3$ | — | Cl | OCH$_3$ | CH | |
| Q-1 | 0 | H | H | H | SO$_2$CH$_3$ | H | Cl | — | OCH$_3$ | OCH$_3$ | CH | |
| Q-1 | 0 | H | H | H | SO$_2$CH$_3$ | H | Cl | — | CH$_3$ | OCH$_3$ | N | |
| Q-1 | 0 | H | H | H | SO$_2$CH$_3$ | H | F | — | OCH$_3$ | OCH$_3$ | N | |
| Q-1 | 0 | H | H | H | SO$_2$CH$_3$ | H | Br | — | CH$_3$ | CH$_3$ | CH | |
| Q-1 | 0 | H | H | F | F | H | H | — | CH$_3$ | OCH$_3$ | CH | |
| Q-1 | 0 | H | H | F | F | H | H | — | OCH$_3$ | OCH$_3$ | CH | |
| Q-1 | 0 | H | H | F | F | H | H | — | CH$_3$ | CH$_3$ | N | |
| Q-1 | 0 | H | H | F | F | H | H | — | OCH$_3$ | OCH$_3$ | N | |
| Q-1 | 0 | H | H | F | F | H | H | — | Cl | OCH$_3$ | CH | |
| Q-1 | 0 | H | H | Cl | Cl | H | H | — | CH$_3$ | OCH$_3$ | CH | 187–191 |
| Q-1 | 0 | H | H | Cl | Cl | H | H | — | OCH$_3$ | OCH$_3$ | CH | 193–195 |
| Q-1 | 0 | H | H | Cl | Cl | H | H | — | CH$_3$ | OCH$_3$ | N | 168–170 |
| Q-1 | 0 | H | H | Cl | Cl | H | H | — | OCH$_3$ | OCH$_3$ | N | 190–193 |
| Q-1 | 0 | H | H | Cl | Cl | H | H | — | CH$_3$ | CH$_3$ | CH | 233–235 |
| Q-1 | 0 | H | H | Cl | Cl | H | H | — | CH$_3$ | CH$_3$ | N | 195–199 |
| Q-1 | 0 | H | H | Cl | Cl | H | H | — | Cl | OCH$_3$ | CH | 199–202 |

TABLE I-continued

| | | | | | | | | | | | | |
|---|---|---|---|---|---|---|---|---|---|---|---|---|
| Q-1 | 0 | H | H | Br | Br | H | H | — | CH₃ | OCH₃ | N | |
| Q-1 | 0 | H | H | Br | Br | H | H | — | OCH₃ | OCH₃ | N | |
| Q-1 | 0 | H | H | Br | Br | H | H | — | CH₃ | OCH₃ | CH | |
| Q-1 | 0 | H | H | Br | Br | H | H | — | OCH₃ | OCH₃ | CH | |
| Q-1 | 0 | H | H | Br | Br | H | H | — | CH₃ | CH₃ | CH | |
| Q-1 | 0 | H | H | Br | Br | H | H | — | CH₃ | CH₃ | N | |
| Q-1 | 0 | H | H | I | I | H | H | — | OCH₃ | OCH₃ | CH | |
| Q-1 | 0 | H | H | CN | CN | H | H | — | Cl | OCH₃ | CH | |
| Q-1 | 0 | H | H | CN | CN | H | H | — | OCH₃ | OCH₃ | N | |
| Q-1 | 0 | H | H | CN | CN | H | H | — | OCH₃ | OCH₃ | CH | |
| Q-1 | 0 | H | H | CN | CN | H | H | — | CH₃ | OCH₃ | CH | |
| Q-1 | 0 | H | H | CN | CN | H | H | — | CH₃ | CH₃ | CH | |
| Q-1 | 0 | H | H | CN | CN | H | H | — | OCH₃ | CH₃ | N | |
| Q-1 | 0 | H | H | CH₃ | CH₃ | H | H | — | CH₃ | CH₃ | CH | |
| Q-1 | 0 | H | H | CH₃ | CH₃ | H | H | — | CH₃ | CH₃ | N | |
| Q-1 | 0 | H | H | CH₃ | CH₃ | H | H | — | CH₃ | OCH₃ | N | |
| Q-1 | 0 | H | H | CH₃ | CH₃ | H | H | — | OCH₃ | OCH₃ | N | |
| Q-1 | 0 | H | H | CH₃ | CH₃ | H | H | — | CH₃ | OCH₃ | CH | |
| Q-1 | 0 | H | H | CH₃ | CH₃ | H | H | — | OCH₃ | OCH₃ | CH | |
| Q-1 | 0 | H | H | OCH₃ | OCH₃ | H | H | — | Cl | OCH₃ | CH | 154–156 |
| Q-1 | 0 | H | H | CH₃ | CH₂CH₃ | H | H | — | OCH₃ | OCH₃ | N | |
| Q-1 | 0 | H | H | CH₃ | CH₂CH₃ | H | H | — | CH₃ | CH₃ | CH | |
| Q-1 | 0 | H | H | OCH₃ | OCH₃ | H | H | — | CH₃ | OCH₃ | N | 152–155 |
| Q-1 | 0 | H | H | OCH₃ | OCH₃ | H | H | — | OCH₃ | OCH₃ | CH | 179–180 |
| Q-1 | 0 | H | H | OCH₃ | OCH₃ | H | H | — | CH₃ | CH₃ | N | |
| Q-1 | 0 | H | H | F | F | H | CH₃ | — | CH₃ | CH₃ | CH | |
| Q-1 | 0 | H | H | F | F | H | F | — | OCH₃ | OCH₃ | CH | |
| Q-1 | 0 | H | H | F | F | H | Cl | — | CH₃ | CH₃ | N | |
| Q-1 | 0 | H | H | F | F | H | Br | — | CH₃ | OCH₃ | N | |
| Q-1 | 0 | H | H | Cl | Cl | H | CH₃ | — | OCH₃ | OCH₃ | N | |
| Q-1 | 0 | H | H | Cl | Cl | H | Cl | — | CH₃ | OCH₃ | CH | |
| Q-1 | 0 | H | H | Cl | Cl | H | Cl | — | OCH₃ | OCH₃ | CH | |
| Q-1 | 0 | H | H | Cl | Cl | H | F | — | CH₃ | OCH₃ | N | |
| Q-1 | 0 | H | H | Cl | Cl | H | Br | — | OCH₃ | OCH₃ | N | |
| Q-1 | 0 | H | H | Br | Br | H | CH₃ | — | CH₃ | CH₃ | CH | |
| Q-1 | 0 | H | H | Br | Br | H | CH₃ | — | CH₃ | OCH₃ | CH | |
| Q-1 | 0 | H | H | Br | Br | H | Cl | — | OCH₃ | OCH₃ | CH | |
| Q-1 | 0 | H | H | Br | Br | H | Cl | — | CH₃ | CH₃ | N | |
| Q-1 | 0 | H | H | Br | Br | Cl | H | — | CH₃ | OCH₃ | N | |
| Q-1 | 0 | H | H | Br | Br | H | F | — | OCH₃ | OCH₃ | N | |
| Q-1 | 0 | H | H | Br | Br | H | Br | — | Cl | OCH₃ | CH | |
| Q-1 | 0 | H | H | CN | CN | H | CH₃ | — | CH₃ | OCH₃ | CH | |
| Q-1 | 0 | H | H | CN | CN | H | CH₃ | — | OCH₃ | OCH₃ | CH | |
| Q-1 | 0 | H | H | CN | CN | H | F | — | CH₃ | OCH₃ | N | |
| Q-1 | 0 | H | H | CH₃ | CH₃ | H | CH₃ | — | OCH₃ | OCH₃ | CH | |
| Q-1 | 0 | H | H | CH₃ | CH₃ | H | CH₃ | — | CH₃ | CH₃ | CH | |
| Q-1 | 0 | H | H | CH₃ | CH₃ | CH₃ | H | — | OCH₃ | OCH₃ | CH | |
| Q-1 | 0 | H | H | CH₃ | CH₃ | H | F | — | CH₃ | OCH₃ | N | |
| Q-1 | 0 | H | H | CH₃ | CH₃ | H | F | — | OCH₃ | OCH₃ | N | |
| Q-1 | 0 | H | H | CH₃ | CH₃ | H | Cl | — | CH₃ | OCH₃ | CH | |
| Q-1 | 0 | H | H | CH₃ | CH₃ | H | Cl | — | OCH₃ | OCH₃ | CH | |
| Q-1 | 0 | H | H | CH₃ | CH₃ | H | Br | — | CH₃ | OCH₃ | CH | |
| Q-1 | 0 | H | H | OCH₃ | OCH₃ | H | CH₃ | — | OCH₃ | OCH₃ | CH | |
| Q-1 | 0 | H | H | OCH₃ | OCH₃ | H | CH₃ | — | Cl | OCH₃ | CH | |
| Q-1 | 0 | H | H | OCH₃ | OCH₃ | H | F | — | OCH₃ | OCH₃ | CH | |
| Q-1 | 0 | H | H | CO₂CH₃ | CO₂CH₃ | H | CH₃ | — | CH₃ | OCH₃ | CH | |
| Q-1 | 0 | H | H | F | F | CH₃ | CH₃ | — | CH₃ | OCH₃ | CH | |
| Q-1 | 0 | H | H | F | F | CH₃ | CH₃ | — | OCH₃ | OCH₃ | CH | |
| Q-1 | 0 | H | H | F | F | F | F | — | CH₃ | CH₃ | N | |
| Q-1 | 0 | H | H | F | F | F | F | — | CH₃ | OCH₃ | N | |
| Q-1 | 0 | H | H | F | F | F | F | — | OCH₃ | OCH₃ | N | |
| Q-1 | 0 | H | H | F | F | Cl | Cl | — | Cl | OCH₃ | CH | |
| Q-1 | 0 | H | H | F | F | Cl | Cl | — | CH₃ | OCH₃ | CH | |
| Q-1 | 0 | H | H | F | F | Br | Br | — | OCH₃ | OCH₃ | CH | |
| Q-1 | 0 | H | H | F | F | Br | Br | — | CH₃ | OCH₃ | N | |
| Q-1 | 0 | H | H | Cl | Cl | CH₃ | CH₃ | — | OCH₃ | OCH₃ | N | |
| Q-1 | 0 | H | H | Cl | Cl | CH₃ | CH₃ | — | CH₃ | CH₃ | CH | |
| Q-1 | 0 | H | H | Cl | Cl | CH₃ | CH₃ | — | CH₃ | OCH₃ | CH | |
| Q-1 | 0 | H | H | Cl | Cl | F | F | — | OCH₃ | OCH₃ | CH | |
| Q-1 | 0 | H | H | Cl | Cl | F | F | — | CH₃ | OCH₃ | N | |
| Q-1 | 0 | H | H | Cl | Cl | Cl | Cl | — | OCH₃ | OCH₃ | N | |
| Q-1 | 0 | H | H | Cl | Cl | Cl | Cl | — | CH₃ | OCH₃ | CH | |
| Q-1 | 0 | H | H | Cl | Cl | Br | Br | — | OCH₃ | OCH₃ | CH | |
| Q-1 | 0 | H | H | Cl | Cl | Br | Br | — | CH₃ | OCH₃ | CH | |
| Q-1 | 0 | H | H | I | I | CH₃ | CH₃ | — | CH₃ | OCH₃ | N | |
| Q-1 | 0 | H | H | CN | CN | CH₃ | CH₃ | — | OCH₃ | OCH₃ | CH | |
| Q-1 | 0 | H | H | CN | CN | CH₃ | CH₃ | — | Cl | OCH₃ | CH | |
| Q-1 | 0 | H | H | CN | CN | F | F | — | CH₃ | OCH₃ | CH | |
| Q-1 | 0 | H | H | CN | CN | CH₃ | CH₃ | — | CH₃ | CH₃ | CH | |
| Q-1 | 0 | H | H | CN | CN | F | F | — | OCH₃ | CH₃ | CH | |
| Q-1 | 0 | H | H | CN | CN | F | F | — | OCH₃ | OCH₃ | CH | |

TABLE I-continued

| | | | | | | | | | | |
|---|---|---|---|---|---|---|---|---|---|---|
| Q-1 | 0 | H | H | CN | CN | Cl | Cl | — | CH$_3$ | CH$_3$ | N |
| Q-1 | 0 | H | H | CN | CN | Br | Br | — | CH$_3$ | OCH$_3$ | N |
| Q-1 | 0 | H | H | CN | CN | Br | Br | — | OCH$_3$ | OCH$_3$ | N |
| Q-1 | 0 | H | H | CH$_3$ | CH$_3$ | CH$_3$ | CH$_3$ | — | CH$_3$ | OCH$_3$ | CH |
| Q-1 | 0 | H | H | CH$_3$ | CH$_3$ | CH$_3$ | CH$_3$ | — | OCH$_3$ | OCH$_3$ | CH |
| Q-1 | 0 | H | H | CH$_3$ | CH$_3$ | CH$_3$ | CH$_3$ | — | CH$_3$ | OCH$_3$ | N |
| Q-1 | 0 | H | H | CH$_3$ | CH$_3$ | F | F | — | OCH$_3$ | OCH$_3$ | N |
| Q-1 | 0 | H | H | CH$_3$ | CH$_3$ | Cl | Cl | — | CH$_3$ | CH$_3$ | CH |
| Q-1 | 0 | H | H | CH$_3$ | CH$_3$ | Cl | Cl | — | CH$_3$ | OCH$_3$ | CH |
| Q-1 | 0 | H | H | CH$_3$ | CH$_3$ | Cl | Cl | — | OCH$_3$ | OCH$_3$ | CH |
| Q-1 | 0 | H | H | CH$_3$ | CH$_3$ | Br | Br | — | CH$_3$ | CH$_3$ | N |
| Q-1 | 0 | H | H | CH$_3$ | CH$_3$ | Br | Br | — | CH$_3$ | OCH$_3$ | N |
| Q-1 | 0 | H | H | OCH$_3$ | OCH$_3$ | CH$_3$ | CH$_3$ | — | Cl | OCH$_3$ | CH |
| Q-1 | 0 | H | H | OCH$_3$ | OCH$_3$ | CH$_3$ | CH$_3$ | — | CH$_3$ | OCH$_3$ | CH |
| Q-1 | 0 | H | H | OCH$_3$ | OCH$_3$ | Cl | Cl | — | CH$_3$ | OCH$_3$ | CH |
| Q-1 | 0 | H | H | OCH$_3$ | OCH$_3$ | F | F | — | CH$_3$ | OCH$_3$ | N |
| Q-1 | 0 | H | H | OCH$_3$ | OCH$_3$ | F | F | — | OCH$_3$ | OCH$_3$ | N |
| Q-1 | 0 | H | H | OCH$_3$ | OCH$_3$ | F | F | — | CH$_3$ | CH$_3$ | CH |
| Q-1 | 0 | H | H | OCH$_3$ | OCH$_3$ | Br | Br | — | CH$_3$ | OCH$_3$ | CH |
| Q-1 | 0 | H | H | OCH$_3$ | OCH$_3$ | Br | Br | — | OCH$_3$ | OCH$_3$ | CH |
| Q-1 | 0 | H | H | F | Cl | H | H | — | Cl | OCH$_3$ | CH |
| Q-1 | 0 | H | H | F | Br | H | H | — | CH$_3$ | OCH$_3$ | CH |
| Q-1 | 0 | H | H | F | CH$_3$ | H | H | — | OCH$_3$ | OCH$_3$ | CH |
| Q-1 | 0 | H | H | F | CN | H | H | — | CH$_3$ | CH$_3$ | N |
| Q-1 | 0 | H | H | F | CH$_2$CH$_3$ | H | H | — | OCH$_3$ | OCH$_3$ | N |
| Q-1 | 0 | H | H | F | OCH$_3$ | H | H | — | CH$_3$ | CH$_3$ | CH |
| Q-1 | 0 | H | H | F | CO$_2$CH$_3$ | H | H | — | CH$_3$ | OCH$_3$ | CH |
| Q-1 | 0 | H | H | F | SO$_2$N(CH$_3$)$_2$ | H | H | — | OCH$_3$ | OCH$_3$ | CH |
| Q-1 | 0 | H | H | F | SCH$_3$ | H | H | — | CH$_3$ | OCH$_3$ | N |
| Q-1 | 0 | H | H | F | SO$_2$CH$_3$ | H | H | — | OCH$_3$ | OCH$_3$ | N |
| Q-1 | 0 | H | H | Cl | F | H | H | — | CH$_3$ | CH$_3$ | CH |
| Q-1 | 0 | H | H | Cl | F | H | H | — | OCH$_3$ | OCH$_3$ | CH |
| Q-1 | 0 | H | H | Cl | Br | H | H | — | CH$_3$ | OCH$_3$ | CH |
| Q-1 | 0 | H | H | Cl | F | H | H | — | CH$_3$ | OCH$_3$ | N |
| Q-1 | 0 | H | H | Cl | CN | H | H | — | OCH$_3$ | OCH$_3$ | CH |
| Q-1 | 0 | H | H | Cl | CH$_3$ | H | H | — | Cl | OCH$_3$ | CH |
| Q-1 | 0 | H | H | Cl | CH$_3$ | H | H | — | CH$_3$ | OCH$_3$ | CH |
| Q-1 | 0 | H | H | Cl | OCH$_3$ | H | H | — | CH$_3$ | OCH$_3$ | CH |
| Q-1 | 0 | H | H | Cl | OCH$_3$ | H | H | — | CH$_3$ | CH$_3$ | CH |
| Q-1 | 0 | H | H | Cl | CO$_2$CH$_3$ | H | H | — | OCH$_3$ | OCH$_3$ | CH |
| Q-1 | 0 | H | H | Cl | SO$_2$N(CH$_3$)$_2$ | H | H | — | CH$_3$ | CH$_3$ | N |
| Q-1 | 0 | H | H | Cl | SCH$_3$ | H | H | — | CH$_3$ | OCH$_3$ | N |
| Q-1 | 0 | H | H | Cl | SO$_2$CH$_3$ | H | H | — | OCH$_3$ | OCH$_3$ | N |
| Q-1 | 0 | H | H | Br | F | H | H | — | OCH$_3$ | OCH$_3$ | N |
| Q-1 | 0 | H | H | Br | F | H | H | — | OCH$_3$ | OCH$_3$ | CH |
| Q-1 | 0 | H | H | Br | F | H | H | — | CH$_3$ | OCH$_3$ | N |
| Q-1 | 0 | H | H | Br | Cl | H | H | — | OCH$_3$ | OCH$_3$ | N |
| Q-1 | 0 | H | H | Br | Cl | H | H | — | CH$_3$ | CH$_3$ | CH |
| Q-1 | 0 | H | H | Br | Cl | H | H | — | OCH$_3$ | OCH$_3$ | CH |
| Q-1 | 0 | H | H | Br | Br | H | H | — | CH$_3$ | CH$_3$ | N |
| Q-1 | 0 | H | H | Br | CN | H | H | — | CH$_3$ | OCH$_3$ | N |
| Q-1 | 0 | H | H | Br | CH$_3$ | H | H | — | OCH$_3$ | OCH$_3$ | N |
| Q-1 | 0 | H | H | Br | CH$_3$ | H | H | — | Cl | OCH$_3$ | CH |
| Q-1 | 0 | H | H | Br | CH$_2$CH$_3$ | H | H | — | CH$_3$ | OCH$_3$ | CH |
| Q-1 | 0 | H | H | Br | OCH$_3$ | H | H | — | OCH$_3$ | OCH$_3$ | CH |
| Q-1 | 0 | H | H | Br | OCH$_3$ | H | H | — | CH$_3$ | CH$_3$ | N |
| Q-1 | 0 | H | H | Br | CO$_2$CH$_3$ | H | H | — | CH$_3$ | CH$_3$ | CH |
| Q-1 | 0 | H | H | Br | SO$_2$N(CH$_3$)$_2$ | H | H | — | CH$_3$ | OCH$_3$ | CH |
| Q-1 | 0 | H | H | Br | SCH$_3$ | H | H | — | OCH$_3$ | OCH$_3$ | CH |
| Q-1 | 0 | H | H | Br | SO$_2$CH$_3$ | H | H | — | CH$_3$ | OCH$_3$ | N |
| Q-1 | 0 | H | H | I | F | H | H | — | OCH$_3$ | OCH$_3$ | N |
| Q-1 | 0 | H | H | I | Cl | H | H | — | CH$_3$ | OCH$_3$ | CH |
| Q-1 | 0 | H | H | I | Br | H | H | — | OCH$_3$ | OCH$_3$ | CH |
| Q-1 | 0 | H | H | I | CH$_3$ | H | H | — | OCH$_3$ | OCH$_3$ | CH |
| Q-1 | 0 | H | H | CN | F | H | H | — | CH$_3$ | CH$_3$ | N |
| Q-1 | 0 | H | H | CN | Cl | H | H | — | OCH$_3$ | OCH$_3$ | N |
| Q-1 | 0 | H | H | CN | Br | H | H | — | Cl | OCH$_3$ | CH |
| Q-1 | 0 | H | H | CN | CH$_3$ | H | H | — | OCH$_3$ | OCH$_3$ | N |
| Q-1 | 0 | H | H | CN | CH$_2$CH$_3$ | H | H | — | CH$_3$ | OCH$_3$ | CH |
| Q-1 | 0 | H | H | CN | OCH$_3$ | H | H | — | CH$_3$ | CH$_3$ | CH |
| Q-1 | 0 | H | H | CN | CO$_2$CH$_3$ | H | H | — | OCH$_3$ | CH$_3$ | CH |
| Q-1 | 0 | H | H | CN | SCH$_3$ | H | H | — | CH$_3$ | OCH$_3$ | CH |
| Q-1 | 0 | H | H | CN | SO$_2$CH$_3$ | H | H | — | CH$_3$ | CH$_3$ | N |
| Q-1 | 0 | H | H | H | F | F | Cl | — | CH$_3$ | OCH$_3$ | N |
| Q-1 | 0 | H | H | H | F | F | Cl | — | OCH$_3$ | OCH$_3$ | N |
| Q-1 | 0 | H | H | H | F | Cl | Br | — | OCH$_3$ | OCH$_3$ | CH |
| Q-1 | 0 | H | H | H | F | Br | F | — | OCH$_3$ | OCH$_3$ | CH |
| Q-1 | 0 | H | H | H | CH$_3$ | F | Cl | — | CH$_3$ | OCH$_3$ | N |
| Q-1 | 0 | H | H | H | CH$_3$ | F | Br | — | CH$_3$ | OCH$_3$ | N |
| Q-1 | 0 | H | H | H | CH$_3$ | F | CH$_3$ | — | CH$_3$ | CH$_3$ | CH |
| Q-1 | 0 | H | H | H | CH$_3$ | Br | CH$_3$ | — | CH$_3$ | OCH$_3$ | CH |

TABLE I-continued

| | | | | | | | | | | | |
|---|---|---|---|---|---|---|---|---|---|---|---|
| Q-1 | 0 | H | H | H | CH$_3$ | Cl | CH$_3$ | — | OCH$_3$ | OCH$_3$ | CH |
| Q-1 | 0 | H | H | H | Cl | F | Cl | — | CH$_3$ | CH$_3$ | N |
| Q-1 | 0 | H | H | H | Cl | F | Br | — | CH$_3$ | OCH$_3$ | N |
| Q-1 | 0 | H | H | H | Cl | Br | Cl | — | OCH$_3$ | OCH$_3$ | N |
| Q-1 | 0 | H | H | H | Cl | F | CH$_3$ | — | Cl | OCH$_3$ | CH |
| Q-1 | 0 | H | H | H | CN | F | Cl | — | CH$_3$ | OCH$_3$ | CH |
| Q-1 | 0 | H | H | H | CN | F | Br | — | OCH$_3$ | OCH$_3$ | CH |
| Q-1 | 0 | H | H | H | CN | F | CH$_3$ | — | CH$_3$ | OCH$_3$ | N |
| Q-1 | 0 | H | H | H | CN | Cl | CH$_3$ | — | OCH$_3$ | OCH$_3$ | N |
| Q-1 | 0 | H | H | H | CN | Cl | Br | — | CH$_3$ | CH$_3$ | CH |
| Q-1 | 0 | H | H | H | CH$_3$ | F | Cl | — | CH$_3$ | OCH$_3$ | CH |
| Q-1 | 0 | H | H | H | CH$_3$ | F | Br | — | OCH$_3$ | OCH$_3$ | CH |
| Q-1 | 0 | H | H | H | CH$_3$ | F | CH$_3$ | — | CH$_3$ | OCH$_3$ | N |
| Q-1 | 0 | H | H | H | CH$_3$ | Cl | Br | — | OCH$_3$ | OCH$_3$ | N |
| Q-1 | 0 | H | H | H | CH$_3$ | Cl | Br | — | CH$_3$ | CH$_3$ | CH |
| Q-1 | 0 | H | H | H | CH$_3$ | Br | CH$_3$ | — | OCH$_3$ | OCH$_3$ | CH |
| Q-1 | 0 | H | H | H | CH$_2$CH$_3$ | F | Cl$_3$ | — | CH$_3$ | OCH$_3$ | CH |
| Q-1 | 0 | H | H | H | CH$_2$CH$_2$CH$_3$ | F | Br | — | CH$_3$ | OCH$_3$ | N |
| Q-1 | 0 | H | H | H | OCH$_3$ | F | Cl | — | OCH$_3$ | OCH$_3$ | CH |
| Q-1 | 0 | H | H | H | OCH$_3$ | F | Br | — | Cl | OCH$_3$ | CH |
| Q-1 | 0 | H | H | H | OCH$_3$ | F | CH$_3$ | — | OCH$_3$ | OCH$_3$ | N |
| Q-1 | 0 | H | H | H | OCH$_3$ | Cl | Br | — | CH$_3$ | OCH$_3$ | CH |
| Q-1 | 0 | H | H | F | Cl | F | Cl | — | OCH$_3$ | OCH$_3$ | CH |
| Q-1 | 0 | H | H | F | Cl | F | CH$_3$ | — | CH$_3$ | OCH$_3$ | N |
| Q-1 | 0 | H | H | F | Br | Cl | CH$_3$ | — | OCH$_3$ | OCH$_3$ | N |
| Q-1 | 0 | H | H | Cl | CH$_3$ | CH$_3$ | F | — | CH$_3$ | CH$_3$ | CH |
| Q-1 | 0 | H | H | Br | OCH$_3$ | CH$_3$ | F | — | CH$_3$ | OCH$_3$ | CH |
| Q-1 | 0 | H | H | SCH$_3$ | CO$_2$CH$_3$ | F | Cl | — | OCH$_3$ | OCH$_3$ | CH |
| Q-1 | 0 | H | H | Br | Cl | F | Cl | — | CH$_3$ | OCH$_3$ | N |
| Q-1 | 0 | H | H | Br | I | F | Cl | — | OCH$_3$ | OCH$_3$ | N |
| Q-1 | 0 | H | H | CH$_3$ | CO$_2$CH$_3$ | CH$_3$ | Br | — | CH$_3$ | OCH$_3$ | CH |
| Q-1 | 0 | H | H | Cl | Br | Cl | Br | — | OCH$_3$ | OCH$_3$ | CH |
| Q-1 | 0 | H | H | Cl | Br | Cl | CH$_3$ | — | CH$_3$ | OCH$_3$ | CH |
| Q-1 | 0 | H | H | I | F | F | Br | — | OCH$_3$ | OCH$_3$ | CH |
| Q-1 | 0 | H | H | CN | F | F | Cl | — | Cl | OCH$_3$ | CH |
| Q-1 | 0 | H | H | CN | Br | Cl | CH$_3$ | — | OCH$_3$ | OCH$_3$ | N |
| Q-1 | 1 | H | H | H | H | H | H | — | CH$_3$ | CH$_3$ | CH |
| Q-1 | 1 | H | H | H | H | H | H | — | CH$_3$ | OCH$_3$ | CH |
| Q-1 | 1 | H | H | H | H | H | H | — | OCH$_3$ | OCH$_3$ | CH |
| Q-1 | 1 | H | H | H | H | H | H | — | CH$_3$ | CH$_3$ | N |
| Q-1 | 1 | H | H | H | H | H | H | — | CH$_3$ | OCH$_3$ | N |
| Q-1 | 1 | H | H | H | H | H | H | — | OCH$_3$ | OCH$_3$ | N |
| Q-1 | 1 | H | H | H | H | H | H | — | Cl | OCH$_3$ | CH |
| Q-1 | 1 | H | H | H | F | H | H | — | CH$_3$ | CH$_3$ | CH |
| Q-1 | 1 | H | H | H | F | H | H | — | CH$_3$ | CH$_3$ | N |
| Q-1 | 1 | H | H | H | F | H | H | — | CH$_3$ | OCH$_3$ | CH |
| Q-1 | 1 | H | H | H | Cl | H | H | — | OCH$_3$ | OCH$_3$ | CH |
| Q-1 | 1 | H | H | H | Cl | H | H | — | CH$_3$ | CH$_3$ | N |
| Q-1 | 1 | H | H | Cl | H | H | H | — | CH$_3$ | OCH$_3$ | CH |
| Q-1 | 1 | H | H | Cl | H | H | H | — | CH$_3$ | OCH$_3$ | N |
| Q-1 | 1 | H | H | H | Br | H | H | — | CH$_3$ | CH$_3$ | CH |
| Q-1 | 1 | H | H | Br | H | H | H | — | CH$_3$ | OCH$_3$ | CH |
| Q-1 | 1 | H | H | Br | H | H | H | — | OCH$_3$ | OCH$_3$ | CH |
| Q-1 | 1 | H | H | H | I | H | H | — | CH$_3$ | OCH$_3$ | N |
| Q-1 | 1 | H | H | I | H | H | H | — | CH$_3$ | OCH$_3$ | N |
| Q-1 | 1 | H | H | H | CN | H | H | — | OCH$_3$ | OCH$_3$ | N |
| Q-1 | 1 | H | H | CN | H | H | H | — | OCH$_3$ | OCH$_3$ | CH |
| Q-1 | 1 | H | H | H | CH$_3$ | H | H | — | CH$_3$ | CH$_3$ | CH |
| Q-1 | 1 | H | H | H | CH$_3$ | H | H | — | CH$_3$ | OCH$_3$ | CH |
| Q-1 | 1 | H | H | H | CH$_3$ | H | H | — | CH$_3$ | CH$_3$ | N |
| Q-1 | 1 | H | H | CH$_3$ | H | H | H | — | CH$_3$ | OCH$_3$ | N |
| Q-1 | 1 | H | H | H | CH$_2$CH$_3$ | H | H | — | OCH$_3$ | OCH$_3$ | N |
| Q-1 | 1 | H | H | H | CH$_2$CH$_3$ | H | H | — | OCH$_3$ | OCH$_3$ | CH |
| Q-1 | 1 | H | H | H | CH$_2$CH$_2$CH$_3$ | H | H | — | CH$_3$ | OCH$_3$ | N |
| Q-1 | 1 | H | H | H | OCH$_3$ | H | H | — | CH$_3$ | CH$_3$ | CH |
| Q-1 | 1 | H | H | CH$_3$O | H | H | H | — | OCH$_3$ | OCH$_3$ | CH |
| Q-1 | 1 | H | H | H | OCH$_2$CH$_3$ | H | H | — | CH$_3$ | CH$_3$ | N |
| Q-1 | 1 | H | H | H | CO$_2$CH$_3$ | H | H | — | CH$_3$ | OCH$_3$ | N |
| Q-1 | 1 | H | H | H | CO$_2$CH$_3$ | H | H | — | OCH$_3$ | OCH$_3$ | N |
| Q-1 | 1 | H | H | H | CO$_2$CH$_3$ | H | H | — | CH$_3$ | OCH$_3$ | CH |
| Q-1 | 1 | H | H | H | CO$_2$CH$_3$ | H | H | — | OCH$_3$ | OCH$_3$ | CH |
| Q-1 | 1 | H | H | H | CO$_2$CH$_2$CH$_3$ | H | H | — | CH$_3$ | OCH$_3$ | N |
| Q-1 | 1 | H | H | H | SO$_2$N(CH$_3$)$_2$ | H | H | — | OCH$_3$ | OCH$_3$ | N |
| Q-1 | 1 | H | H | H | SO$_2$N(CH$_3$)$_2$ | H | H | — | CH$_3$ | CH$_3$ | CH |
| Q-1 | 1 | H | H | H | SCH$_3$ | H | H | — | OCH$_3$ | OCH$_3$ | CH |
| Q-1 | 1 | H | H | H | SCH$_3$ | H | H | — | CH$_3$ | OCH$_3$ | N |
| Q-1 | 1 | H | H | H | SO$_2$CH$_3$ | H | H | — | CH$_3$ | OCH$_3$ | N |
| Q-1 | 1 | H | H | SO$_2$CH$_3$ | H | H | H | — | OCH$_3$ | OCH$_3$ | N |
| Q-1 | 1 | H | H | H | SO$_2$CH$_3$ | H | H | — | Cl | OCH$_3$ | CH |
| Q-1 | 1 | H | H | H | SO$_2$CH$_3$ | H | H | — | CH$_3$ | OCH$_3$ | CH |

TABLE I-continued

| | | | | | | | | | | | |
|---|---|---|---|---|---|---|---|---|---|---|---|
| Q-1 | 1 | H | H | H | SO₂CH₂CH₃ | H | H | — | OCH₃ | OCH₃ | CH |
| Q-1 | 1 | H | H | H | CH₃ | H | CH₃ | — | CH₃ | OCH₃ | N |
| Q-1 | 1 | H | H | H | CH₃ | H | CH₃ | — | OCH₃ | OCH₃ | N |
| Q-1 | 1 | H | H | H | CH₃ | CH₃ | H | — | CH₃ | CH₃ | CH |
| Q-1 | 1 | H | H | H | CH₃ | H | F | — | CH₃ | OCH₃ | CH |
| Q-1 | 1 | H | H | H | CH₃ | H | F | — | OCH₃ | OCH₃ | CH |
| Q-1 | 1 | H | H | H | CH₃ | H | F | — | CH₃ | OCH₃ | N |
| Q-1 | 1 | H | H | H | CH₃ | H | Cl | — | OCH₃ | OCH₃ | N |
| Q-1 | 1 | H | H | H | CH₃ | Br | H | — | CH₃ | OCH₃ | CH |
| Q-1 | 1 | H | H | H | F | H | CH₃ | — | OCH₃ | OCH₃ | CH |
| Q-1 | 1 | H | H | H | F | H | CH₃ | — | CH₃ | OCH₃ | CH |
| Q-1 | 1 | H | H | H | Cl | H | CH₃ | — | CH₃ | OCH₃ | N |
| Q-1 | 1 | H | H | H | Cl | H | F | — | OCH₃ | OCH₃ | CH |
| Q-1 | 1 | H | H | H | Cl | H | Cl | — | Cl | OCH₃ | CH |
| Q-1 | 1 | H | H | H | Cl | H | Cl | — | OCH₃ | OCH₃ | N |
| Q-1 | 1 | H | H | H | Cl | H | Br | — | CH₃ | OCH₃ | CH |
| Q-1 | 1 | H | H | H | SO₂CH₃ | H | CH₃ | — | CH₃ | CH₃ | CH |
| Q-1 | 1 | H | H | H | SO₂CH₃ | H | CH₃ | — | OCH₃ | CH₃ | CH |
| Q-1 | 1 | H | H | H | SO₂CH₃ | H | CH₃ | — | OCH₃ | OCH₃ | CH |
| Q-1 | 1 | H | H | H | SO₂CH₃ | H | CH₃ | — | CH₃ | CH₃ | N |
| Q-1 | 1 | H | H | H | SO₂CH₃ | H | CH₃ | — | OCH₃ | OCH₃ | N |
| Q-1 | 1 | H | H | H | SO₂CH₃ | H | CH₃ | — | Cl | OCH₃ | CH |
| Q-1 | 1 | H | H | H | SO₂CH₃ | H | Cl | — | OCH₃ | OCH₃ | CH |
| Q-1 | 1 | H | H | H | SO₂CH₃ | H | Cl | — | CH₃ | OCH₃ | N |
| Q-1 | 1 | H | H | H | SO₂CH₃ | H | F | — | OCH₃ | OCH₃ | N |
| Q-1 | 1 | H | H | H | SO₂CH₃ | H | Br | — | CH₃ | CH₃ | CH |
| Q-1 | 1 | H | H | F | F | H | H | — | CH₃ | OCH₃ | CH |
| Q-1 | 1 | H | H | F | F | H | H | — | OCH₃ | OCH₃ | CH |
| Q-1 | 1 | H | H | F | F | H | H | — | CH₃ | CH₃ | N |
| Q-1 | 1 | H | H | F | F | H | H | — | CH₃ | OCH₃ | N |
| Q-1 | 1 | H | H | F | F | H | H | — | OCH₃ | OCH₃ | N |
| Q-1 | 1 | H | H | F | F | H | H | — | Cl | OCH₃ | CH |
| Q-1 | 1 | H | H | Cl | Cl | H | H | — | CH₃ | OCH₃ | CH |
| Q-1 | 1 | H | H | Cl | Cl | H | H | — | OCH₃ | OCH₃ | CH |
| Q-1 | 1 | H | H | Cl | Cl | H | H | — | CH₃ | OCH₃ | N |
| Q-1 | 1 | H | H | Cl | Cl | H | H | — | OCH₃ | OCH₃ | N |
| Q-1 | 1 | H | H | Cl | Cl | H | H | — | CH₃ | CH₃ | CH |
| Q-1 | 1 | H | H | Cl | Cl | H | H | — | CH₃ | CH₃ | N |
| Q-1 | 1 | H | H | Cl | Cl | H | H | — | Cl | OCH₃ | CH |
| Q-1 | 1 | H | H | Br | Br | H | H | — | CH₃ | OCH₃ | N |
| Q-1 | 1 | H | H | Br | Br | H | H | — | OCH₃ | OCH₃ | N |
| Q-1 | 1 | H | H | Br | Br | H | H | — | CH₃ | OCH₃ | CH |
| Q-1 | 1 | H | H | Br | Br | H | H | — | OCH₃ | OCH₃ | CH |
| Q-1 | 1 | H | H | Br | Br | H | H | — | CH₃ | CH₃ | N |
| Q-1 | 1 | H | H | I | I | H | H | — | OCH₃ | OCH₃ | CH |
| Q-1 | 1 | H | H | CN | CN | H | H | — | Cl | OCH₃ | CH |
| Q-1 | 1 | H | H | CN | CN | H | H | — | OCH₃ | OCH₃ | N |
| Q-1 | 1 | H | H | CN | CN | H | H | — | CH₃ | CH₃ | CH |
| Q-1 | 1 | H | H | F | F | H | CH₃ | — | CH₃ | CH₃ | CH |
| Q-1 | 1 | H | H | F | F | H | CH₃ | — | OCH₃ | CH₃ | CH |
| Q-1 | 1 | H | H | F | F | H | F | — | OCH₃ | OCH₃ | CH |
| Q-1 | 1 | H | H | F | F | H | Cl | — | CH₃ | CH₃ | N |
| Q-1 | 1 | H | H | F | F | H | Br | — | CH₃ | OCH₃ | N |
| Q-1 | 1 | H | H | Cl | Cl | H | CH₃ | — | OCH₃ | CH₃ | N |
| Q-1 | 1 | H | H | Cl | Cl | H | CH₃ | — | CH₃ | OCH₃ | CH |
| Q-1 | 1 | H | H | Cl | Cl | H | Cl | — | OCH₃ | OCH₃ | CH |
| Q-1 | 1 | H | H | Cl | Cl | H | F | — | CH₃ | OCH₃ | N |
| Q-1 | 1 | H | H | Cl | Cl | H | Br | — | OCH₃ | OCH₃ | N |
| Q-1 | 1 | H | H | Br | Br | H | CH₃ | — | CH₃ | CH₃ | CH |
| Q-1 | 1 | H | H | Br | Br | H | CH₃ | — | OCH₃ | CH₃ | CH |
| Q-1 | 1 | H | H | Br | Br | H | Cl | — | OCH₃ | OCH₃ | CH |
| Q-1 | 1 | H | H | Br | Br | H | Cl | — | CH₃ | CH₃ | N |
| Q-1 | 1 | H | H | Br | Br | Cl | H | — | CH₃ | OCH₃ | N |
| Q-1 | 1 | H | H | Br | Br | H | F | — | OCH₃ | OCH₃ | N |
| Q-1 | 1 | H | H | Br | Br | H | Br | — | Cl | OCH₃ | CH |
| Q-1 | 1 | H | H | CN | CN | H | CH₃ | — | CH₃ | OCH₃ | CH |
| Q-1 | 1 | H | H | CN | CN | H | CH₃ | — | OCH₃ | OCH₃ | CH |
| Q-1 | 1 | H | H | CN | CN | H | F | — | CH₃ | OCH₃ | N |
| Q-1 | 1 | H | H | CH₃ | CH₃ | H | CH₃ | — | OCH₃ | OCH₃ | N |
| Q-1 | 1 | H | H | CH₃ | CH₃ | H | CH₃ | — | CH₃ | CH₃ | CH |
| Q-1 | 1 | H | H | CH₃ | CH₃ | H | CH₃ | — | CH₃ | OCH₃ | CH |
| Q-1 | 1 | H | H | CH₃ | CH₃ | CH₃ | H | — | OCH₃ | OCH₃ | CH |
| Q-1 | 1 | H | H | CH₃ | CH₃ | H | F | — | CH₃ | OCH₃ | N |
| Q-1 | 1 | H | H | CH₃ | CH₃ | H | F | — | OCH₃ | OCH₃ | N |
| Q-1 | 1 | H | H | CH₃ | CH₃ | H | Cl | — | CH₃ | OCH₃ | CH |
| Q-1 | 1 | H | H | CH₃ | CH₃ | H | Cl | — | OCH₃ | OCH₃ | CH |
| Q-1 | 1 | H | H | CH₃ | CH₃ | H | Br | — | CH₃ | OCH₃ | CH |
| Q-1 | 1 | H | H | OCH₃ | OCH₃ | H | CH₃ | — | OCH₃ | OCH₃ | CH |
| Q-1 | 1 | H | H | OCH₃ | OCH₃ | H | CH₃ | — | Cl | OCH₃ | CH |
| Q-1 | 1 | H | H | OCH₃ | OCH₃ | H | F | — | OCH₃ | OCH₃ | N |
| Q-1 | 1 | H | H | CN | CN | CH₃ | CH₃ | — | CH₃ | CH₃ | CH |

TABLE I-continued

| Q | n | R | R₁ | R₇ | R₈ | R₁₁ | | X | Y | Z | m.p.(°C.) |
|---|---|---|----|----|----|-----|---|---|---|---|-----------|
| Q-1 | 1 | H | H | CN | CN | F | F | — | OCH₃ | CH₃ | CH |
| Q-1 | 1 | H | H | CN | CN | F | F | — | OCH₃ | OCH₃ | CH |
| Q-1 | 1 | H | H | CN | CN | Cl | Cl | — | CH₃ | CH₃ | N |
| Q-1 | 1 | H | H | CN | CN | Br | Br | — | CH₃ | OCH₃ | N |
| Q-1 | 1 | H | H | CN | CN | Br | Br | — | OCH₃ | OCH₃ | N |
| Q-1 | 1 | H | H | CH₃ | CH₃ | CH₃ | CH₃ | — | CH₃ | OCH₃ | CH |
| Q-1 | 1 | H | H | CH₃ | CH₃ | CH₃ | CH₃ | — | OCH₃ | OCH₃ | CH |
| Q-1 | 1 | H | H | CH₃ | CH₃ | CH₃ | CH₃ | — | CH₃ | OCH₃ | N |
| Q-1 | 1 | H | H | CH₃ | CH₃ | F | F | — | OCH₃ | OCH₃ | N |
| Q-1 | 1 | H | H | CH₃ | CH₃ | Cl | Cl | — | CH₃ | CH₃ | CH |
| Q-1 | 1 | H | H | CH₃ | CH₃ | Cl | Cl | — | OCH₃ | OCH₃ | CH |
| Q-1 | 1 | H | H | CH₃ | CH₃ | Br | Br | — | CH₃ | CH₃ | N |
| Q-1 | 1 | H | H | CH₃ | CH₃ | Br | Br | — | CH₃ | OCH₃ | N |
| Q-1 | 1 | H | H | OCH₃ | OCH₃ | CH₃ | CH₃ | — | Cl | OCH₃ | CH |
| Q-1 | 1 | H | H | OCH₃ | OCH₃ | CH₃ | CH₃ | — | CH₃ | OCH₃ | CH |
| Q-1 | 1 | H | H | OCH₃ | OCH₃ | Cl | Cl | — | OCH₃ | OCH₃ | CH |
| Q-1 | 1 | H | H | OCH₃ | OCH₃ | F | F | — | CH₃ | OCH₃ | N |
| Q-1 | 1 | H | H | OCH₃ | OCH₃ | F | F | — | OCH₃ | OCH₃ | N |
| Q-1 | 1 | H | H | OCH₃ | OCH₃ | F | F | — | CH₃ | CH₃ | CH |
| Q-1 | 1 | H | H | OCH₃ | OCH₃ | Br | Br | — | CH₃ | OCH₃ | CH |
| Q-1 | 1 | H | H | Cl | OCH₃ | H | H | — | CH₃ | CH₃ | CH |
| Q-1 | 1 | H | H | Cl | OCH₃ | H | H | — | OCH₃ | CH₃ | CH |
| Q-1 | 1 | H | H | Cl | CO₂CH₃ | H | H | — | OCH₃ | OCH₃ | CH |
| Q-1 | 1 | H | H | Cl | SO₂N(CH₃)₂ | H | H | — | CH₃ | CH₃ | N |
| Q-1 | 1 | H | H | Cl | SCH₃ | H | H | — | CH₃ | OCH₃ | N |
| Q-1 | 1 | H | H | Cl | SO₂CH₃ | H | H | — | OCH₃ | OCH₃ | N |
| Q-1 | 1 | H | H | Br | F | H | H | — | CH₃ | OCH₃ | CH |
| Q-1 | 1 | H | H | Br | F | H | H | — | OCH₃ | OCH₃ | CH |
| Q-1 | 1 | H | H | Br | F | H | H | — | CH₃ | OCH₃ | N |
| Q-1 | 1 | H | H | Br | Cl | H | H | — | OCH₃ | OCH₃ | N |
| Q-1 | 1 | H | H | Br | Cl | H | H | — | CH₃ | OCH₃ | CH |
| Q-1 | 1 | H | H | Br | Cl | H | H | — | CH₃ | OCH₃ | CH |
| Q-1 | 1 | H | H | Br | Br | H | H | — | Cl | OCH₃ | CH |
| Q-1 | 1 | H | H | Br | CN | H | H | — | CH₃ | CH₃ | N |
| Q-1 | 1 | H | H | Br | CH₃ | H | H | — | CH₃ | OCH₃ | N |
| Q-1 | 1 | H | H | Br | CH₃ | H | H | — | OCH₃ | OCH₃ | N |
| Q-1 | 1 | H | H | Br | CH₃ | H | H | — | Cl | OCH₃ | CH |
| Q-1 | 1 | H | H | Br | CH₂CH₃ | H | H | — | CH₃ | OCH₃ | CH |
| Q-1 | 1 | H | H | Br | OCH₃ | H | H | — | OCH₃ | OCH₃ | CH |
| Q-1 | 1 | H | H | Br | OCH₃ | H | H | — | CH₃ | OCH₃ | N |
| Q-1 | 1 | H | H | Br | OCH₂CH₃ | H | H | — | OCH₃ | OCH₃ | N |
| Q-1 | 1 | H | H | Br | CO₂CH₃ | H | H | — | CH₃ | CH₃ | CH |
| Q-1 | 1 | H | H | Br | SO₂N(CH₃)₂ | H | H | — | CH₃ | OCH₃ | CH |
| Q-1 | 1 | H | H | Br | SCH₃ | H | H | — | OCH₃ | OCH₃ | CH |
| Q-1 | 1 | H | H | Br | SO₂CH₃ | H | H | — | CH₃ | OCH₃ | N |
| Q-1 | 1 | H | H | I | F | H | H | — | OCH₃ | OCH₃ | N |
| Q-1 | 1 | H | H | I | Cl | H | H | — | CH₃ | OCH₃ | CH |
| Q-1 | 1 | H | H | I | Br | H | H | — | OCH₃ | OCH₃ | CH |
| Q-1 | 1 | H | H | I | CH₃ | H | H | — | CH₃ | OCH₃ | CH |
| Q-1 | 1 | H | H | CN | F | H | H | — | CH₃ | OCH₃ | N |
| Q-1 | 1 | H | H | CN | Cl | H | H | — | OCH₃ | OCH₃ | CH |
| Q-1 | 1 | H | H | CN | Br | H | H | — | Cl | OCH₃ | CH |
| Q-1 | 1 | H | H | CN | CH₃ | H | H | — | OCH₃ | OCH₃ | N |
| Q-1 | 1 | H | H | CN | CH₂CH₃ | H | H | — | CH₃ | OCH₃ | CH |
| Q-1 | 1 | H | H | F | Cl | F | Cl | — | OCH₃ | OCH₃ | CH |
| Q-1 | 1 | H | H | F | Cl | F | CH₃ | — | CH₃ | OCH₃ | N |
| Q-1 | 1 | H | H | F | Br | Cl | CH₃ | — | OCH₃ | OCH₃ | N |
| Q-1 | 1 | H | H | Cl | CH₃ | CH₃ | F | — | CH₃ | CH₃ | CH |
| Q-1 | 1 | H | H | Br | OCH₃ | CH₃ | F | — | CH₃ | CH₃ | CH |
| Q-1 | 1 | H | H | Br | Cl | F | Cl | — | CH₃ | OCH₃ | N |
| Q-1 | 1 | H | H | Br | I | F | Cl | — | OCH₃ | OCH₃ | N |
| Q-1 | 1 | H | H | CH₃ | CH₂CH₃ | CH₃ | Br | — | CH₃ | CH₃ | CH |
| Q-1 | 1 | H | H | Cl | Br | Cl | Br | — | OCH₃ | OCH₃ | CH |
| Q-1 | 1 | H | H | Cl | Br | Cl | CH₃ | — | CH₃ | OCH₃ | CH |
| Q-1 | 1 | H | H | CO₂CH₃ | SCH₃ | F | Cl | — | CH₃ | OCH₃ | N |
| Q-1 | 1 | H | H | I | F | F | Br | — | OCH₃ | OCH₃ | CH |
| Q-1 | 1 | H | H | CN | F | F | Cl | — | Cl | OCH₃ | CH |
| Q-1 | 1 | H | H | CN | Br | Cl | CH₃ | — | OCH₃ | OCH₃ | N |

| Q | n | R | R₁ | R₇ | R₈ | R₁₁ | X | Y | Z | m.p.(°C.) |
|---|---|---|----|----|----|-----|---|---|---|-----------|
| Q-2 | 0 | H | H | H | H | H | CH₃ | CH₃ | CH | 158–160 |
| Q-2 | 0 | H | H | H | H | H | CH₃ | OCH₃ | CH | |
| Q-2 | 0 | H | H | H | H | H | OCH₃ | OCH₃ | CH | 177–179 |
| Q-2 | 0 | H | H | H | H | H | CH₃ | CH₃ | N | |
| Q-2 | 0 | H | H | H | H | H | CH₃ | OCH₃ | N | |
| Q-2 | 0 | H | H | H | H | H | OCH₃ | OCH₃ | N | |
| Q-2 | 0 | H | H | H | H | H | Cl | OCH₃ | CH | |
| Q-2 | 0 | H | H | H | CH₃ | H | CH₃ | OCH₃ | CH | |
| Q-2 | 0 | H | H | H | CH₃ | H | OCH₃ | OCH₃ | CH | |
| Q-2 | 0 | H | H | H | CH₃ | H | OCH₃ | OCH₃ | N | |
| Q-2 | 0 | H | H | H | CH₃ | H | CH₃ | OCH₃ | CH | |

TABLE I-continued

| | | | | | | | | | |
|---|---|---|---|---|---|---|---|---|---|
| Q-2 | 0 | H | H | H | Cl | H | CH$_3$ | OCH$_3$ | CH |
| Q-2 | 0 | H | H | H | Cl | H | OCH$_3$ | CH$_3$ | N |
| Q-2 | 0 | H | H | H | Cl | H | OCH$_3$ | OCH$_3$ | CH |
| Q-2 | 0 | H | H | H | Cl | H | Cl | OCH$_3$ | CH |
| Q-2 | 0 | H | H | H | F | H | CH$_3$ | CH$_3$ | N |
| Q-2 | 0 | H | H | H | F | H | CH$_3$ | CH$_3$ | CH |
| Q-2 | 0 | H | H | H | F | H | OCH$_3$ | CH$_3$ | CH |
| Q-2 | 0 | H | H | H | F | H | OCH$_3$ | OCH$_3$ | CH |
| Q-2 | 0 | H | H | H | F | H | CH$_3$ | OCH$_3$ | N |
| Q-2 | 0 | H | H | H | F | H | Cl | OCH$_3$ | CH |
| Q-2 | 0 | H | H | H | CN | H | CH$_3$ | OCH$_3$ | N |
| Q-2 | 0 | H | H | H | CN | H | OCH$_3$ | OCH$_3$ | CH |
| Q-2 | 0 | H | H | H | OCH$_3$ | H | CH$_3$ | OCH$_3$ | N |
| Q-2 | 0 | H | H | H | OCH$_3$ | H | OCH$_3$ | OCH$_3$ | CH |
| Q-2 | 0 | H | H | H | OCH$_3$ | H | OCH$_3$ | OCH$_3$ | N |
| Q-2 | 0 | H | H | H | CO$_2$CH$_3$ | H | CH$_3$ | CH$_3$ | N |
| Q-2 | 0 | H | H | H | CO$_2$CH$_3$ | H | OCH$_3$ | CH$_3$ | CH |
| Q-2 | 0 | H | H | H | CO$_2$CH$_3$ | H | OCH$_3$ | OCH$_3$ | CH |
| Q-2 | 0 | H | H | H | CO$_2$CH$_3$ | H | CH$_3$ | OCH$_3$ | N |
| Q-2 | 0 | H | H | H | CO$_2$CH$_3$ | H | CH$_3$ | CH$_3$ | CH |
| Q-2 | 0 | H | H | H | CO$_2$CH$_3$ | H | OCH$_3$ | OCH$_3$ | N |
| Q-2 | 0 | H | H | H | CO$_2$CH$_3$ | H | Cl | OCH$_3$ | CH |
| Q-2 | 0 | H | H | H | SO$_2$N(CH$_3$)$_2$ | H | CH$_3$ | CH$_3$ | N |
| Q-2 | 0 | H | H | H | SO$_2$N(CH$_3$)$_2$ | H | OCH$_3$ | OCH$_3$ | CH |
| Q-2 | 0 | H | H | H | SO$_2$N(CH$_3$)$_2$ | H | OCH$_3$ | OCH$_3$ | N |
| Q-2 | 0 | H | H | H | SO$_2$N(CH$_3$)$_2$ | H | CH$_3$ | OCH$_3$ | CH |
| Q-2 | 0 | H | H | H | SCH$_3$ | H | OCH$_3$ | OCH$_3$ | CH |
| Q-2 | 0 | H | H | H | SCH$_3$ | H | CH$_3$ | CH$_3$ | CH |
| Q-2 | 0 | H | H | H | SCH$_3$ | H | OCH$_3$ | CH$_3$ | CH |
| Q-2 | 0 | H | H | H | SCH$_3$ | H | Cl | OCH$_3$ | CH |
| Q-2 | 0 | H | H | H | SO$_2$CH$_3$ | H | CH$_3$ | CH$_3$ | CH |
| Q-2 | 0 | H | H | H | SO$_2$CH$_3$ | H | CH$_3$ | OCH$_3$ | CH |
| Q-2 | 0 | H | H | H | SO$_2$CH$_3$ | H | CH$_3$ | OCH$_3$ | N |
| Q-2 | 0 | H | H | F | F | H | CH$_3$ | CH$_3$ | CH |
| Q-2 | 0 | H | H | F | F | H | OCH$_3$ | CH$_3$ | CH |
| Q-2 | 0 | H | H | Cl | Cl | H | OCH$_3$ | OCH$_3$ | CH |
| Q-2 | 0 | H | H | Cl | Cl | H | CH$_3$ | CH$_3$ | N |
| Q-2 | 0 | H | H | F | Cl | H | OCH$_3$ | CH$_3$ | N |
| Q-2 | 0 | H | H | F | CH$_3$ | H | CH$_3$ | CH$_3$ | CH |
| Q-2 | 0 | H | H | CH$_3$ | CH$_3$ | H | OCH$_3$ | OCH$_3$ | CH |
| Q-2 | 0 | H | H | CH$_3$ | CH$_2$CH$_3$ | H | OCH$_3$ | OCH$_3$ | N |
| Q-2 | 0 | H | H | F | Br | H | Cl | OCH$_3$ | CH |
| Q-2 | 0 | H | H | Br | Br | H | Cl | OCH$_3$ | CH |
| Q-2 | 0 | H | H | Br | Br | H | OCH$_3$ | OCH$_3$ | CH |
| Q-2 | 0 | H | H | CO$_2$CH$_3$ | CO$_2$CH$_3$ | H | CH$_3$ | CH$_3$ | N |
| Q-2 | 0 | H | H | CO$_2$CH$_3$ | CO$_2$CH$_3$ | H | CH$_3$ | CH$_3$ | CH |
| Q-2 | 0 | H | H | CO$_2$CH$_3$ | CO$_2$CH$_3$ | H | OCH$_3$ | OCH$_3$ | CH |
| Q-2 | 0 | H | H | CN | CN | H | CH$_3$ | OCH$_3$ | CH |
| Q-2 | 0 | H | H | CN | CN | H | OCH$_3$ | OCH$_3$ | CH |
| Q-2 | 0 | H | H | CN | CN | H | OCH$_3$ | OCH$_3$ | N |
| Q-2 | 0 | H | H | OCH$_3$ | OCH$_3$ | H | CH$_3$ | OCH$_3$ | CH |
| Q-2 | 0 | H | H | OCH$_2$CH$_3$ | OCH$_2$CH$_3$ | H | OCH$_3$ | CH$_3$ | CH |
| Q-2 | 0 | H | H | SCH$_3$ | SCH$_3$ | H | OCH$_3$ | OCH$_3$ | CH |
| Q-2 | 0 | H | H | SCH$_3$ | SCH$_3$ | H | CH$_3$ | CH$_3$ | N |
| Q-2 | 0 | H | H | SO$_2$CH$_3$ | SO$_2$CH$_3$ | H | OCH$_3$ | OCH$_3$ | CH |
| Q-2 | 0 | H | H | SO$_2$CH$_3$ | SO$_2$CH$_3$ | H | OCH$_3$ | OCH$_3$ | N |
| Q-2 | 0 | H | H | H | H | CH$_3$ | CH$_3$ | CH$_3$ | CH |
| Q-2 | 0 | H | H | H | H | CH$_3$ | CH$_3$ | OCH$_3$ | CH |
| Q-2 | 0 | H | H | H | H | CH$_3$ | OCH$_3$ | OCH$_3$ | CH |
| Q-2 | 0 | H | H | H | H | CH$_2$CH$_3$ | CH$_3$ | CH$_3$ | N |
| Q-2 | 0 | H | H | F | H | CH$_3$ | CH$_3$ | OCH$_3$ | N |
| Q-2 | 0 | H | H | Cl | H | CH$_3$ | OCH$_3$ | OCH$_3$ | N |
| Q-2 | 0 | H | H | F | F | CH$_3$ | CH$_3$ | OCH$_3$ | CH |
| Q-2 | 0 | H | H | Br | H | CH$_3$ | OCH$_3$ | OCH$_3$ | CH |
| Q-2 | 0 | H | H | Cl | Cl | CH$_3$ | CH$_3$ | OCH$_3$ | N |
| Q-2 | 0 | H | 5-CH$_3$ | H | H | — | OCH$_3$ | OCH$_3$ | N |
| Q-2 | 0 | H | 5-OCH$_3$ | H | H | — | CH$_3$ | CH$_3$ | CH |
| Q-2 | 0 | H | 5-SCH$_3$ | H | H | — | CH$_3$ | CH$_3$ | CH |
| Q-2 | 0 | H | 5-Cl | Cl | H | — | OCH$_3$ | OCH$_3$ | CH |
| Q-2 | 0 | H | 6-Cl | F | F | CH$_3$ | CH$_3$ | CH$_3$ | N |
| Q-2 | 0 | CH$_3$ | H | H | H | H | OCH$_3$ | OCH$_3$ | N |
| Q-2 | 1 | H | H | H | H | H | OCH$_3$ | OCH$_3$ | CH |
| Q-2 | 1 | H | H | F | F | H | CH$_3$ | CH$_3$ | CH |
| Q-2 | 1 | H | H | F | Cl | H | CH$_3$ | CH$_3$ | N |
| Q-2 | 1 | H | H | CH$_3$ | Cl | H | OCH$_3$ | CH$_3$ | CH |
| Q-2 | 1 | H | H | F | H | H | CH$_3$ | CH$_3$ | CH |
| Q-2 | 1 | H | H | Cl | H | H | OCH$_3$ | OCH$_3$ | CH |
| Q-2 | 1 | H | H | Br | H | H | CH$_3$ | CH$_3$ | N |
| Q-2 | 1 | H | H | Cl | Cl | H | CH$_3$ | OCH$_3$ | CH |
| Q-2 | 1 | H | H | CH$_3$ | H | H | CH$_3$ | OCH$_3$ | CH |
| Q-2 | 1 | H | H | CH | H | H | OCH$_3$ | OCH$_3$ | CH |
| Q-2 | 1 | H | H | CH | CH | H | CH$_3$ | OCH$_3$ | N |

TABLE I-continued

| Q | n | R | R₁ | R₃ | R₇ | R₈ | R₁₁ | X | Y | Z | m.p.(°C.) |
|---|---|---|---|---|---|---|---|---|---|---|---|
| Q-2 | 1 | H | H | CH₃ | Br | H | CH₃ | CH₃ | CH₃ | CH | |
| Q-2 | 1 | H | H | F | Br | H | Cl | OCH₃ | CH | | |
| Q-2 | 1 | H | 5-CH₃ | F | H | H | OCH₃ | OCH₃ | CH | | |
| Q-2 | 1 | H | 5-OCH₃ | Cl | H | CH₃ | CH₃ | CH₃ | N | | |
| Q-2 | 1 | H | 5-Cl | Cl | Cl | CH₂CH₃ | CH₃ | OCH₃ | N | | |

| Q | n | R | R₁ | R₃ | R₇ | R₈ | R₁₁ | X | Y | Z | m.p.(°C.) |
|---|---|---|---|---|---|---|---|---|---|---|---|
| Q-3 | 0 | H | H | CH₃ | H | H | H | CH₃ | CH₃ | CH | |
| Q-3 | 0 | H | H | CH₃ | H | H | H | CH₃ | OCH₃ | CH | |
| Q-3 | 0 | H | H | CH₃ | H | H | H | OCH₃ | OCH₃ | CH | |
| Q-3 | 0 | H | H | CH₃ | H | H | H | CH₃ | CH₃ | N | |
| Q-3 | 0 | H | H | CH₃ | H | H | H | CH₃ | OCH₃ | N | |
| Q-3 | 0 | H | H | CH₃ | H | H | H | Cl | OCH₃ | CH | |
| Q-3 | 0 | H | H | CH₃ | H | CH₃ | H | CH₃ | OCH₃ | CH | |
| Q-3 | 0 | H | H | CH₃ | H | CH₃ | H | OCH₃ | OCH₃ | CH | |
| Q-3 | 0 | H | H | CH₃ | H | CH₃ | H | OCH₃ | OCH₃ | N | |
| Q-3 | 0 | H | H | CH₃ | H | CH₃ | H | CH₃ | OCH₃ | CH | |
| Q-3 | 0 | H | H | CH₃ | H | Cl | H | CH₃ | OCH₃ | CH | |
| Q-3 | 0 | H | H | CH₃ | H | Cl | H | OCH₃ | OCH₃ | N | |
| Q-3 | 0 | H | H | CH₃ | H | Cl | H | OCH₃ | OCH₃ | CH | |
| Q-3 | 0 | H | H | CH₃ | H | Cl | H | Cl | OCH₃ | CH | |
| Q-3 | 0 | H | H | CH₃ | H | F | H | CH₃ | CH₃ | N | |
| Q-3 | 0 | H | H | CH₃ | H | F | H | CH₃ | CH₃ | CH | |
| Q-3 | 0 | H | H | CH₃ | H | F | H | OCH₃ | CH₃ | CH | |
| Q-3 | 0 | H | H | CH₃ | H | F | H | CH₃ | OCH₃ | N | |
| Q-3 | 0 | H | H | CH₃ | H | F | H | Cl | OCH₃ | CH | |
| Q-3 | 0 | H | H | CH₃ | H | CN | H | CH₃ | OCH₃ | N | |
| Q-3 | 0 | H | H | CH₃ | H | CN | H | OCH₃ | OCH₃ | CH | |
| Q-3 | 0 | H | H | CH₃ | H | OCH₃ | H | CH₃ | OCH₃ | N | |
| Q-3 | 0 | H | H | CH₃ | H | OCH₃ | H | OCH₃ | OCH₃ | CH | |
| Q-3 | 0 | H | H | CH₃ | H | OCH₃ | H | OCH₃ | OCH₃ | N | |
| Q-3 | 0 | H | H | CH₃ | H | CO₂CH₃ | H | CH₃ | CH₃ | N | |
| Q-3 | 0 | H | H | CH₃ | H | CO₂CH₃ | H | OCH₃ | CH₃ | CH | |
| Q-3 | 0 | H | H | CH₃ | H | CO₂CH₃ | H | OCH₃ | OCH₃ | CH | |
| Q-3 | 0 | H | H | CH₃ | H | CO₂CH₃ | H | CH₃ | OCH₃ | CH | |
| Q-3 | 0 | H | H | CH₃ | H | CO₂CH₃ | H | CH₃ | CH₃ | CH | |
| Q-3 | 0 | H | H | CH₃ | H | CO₂CH₃ | H | OCH₃ | OCH₃ | N | |
| Q-3 | 0 | H | H | CH₃ | H | CO₂CH₃ | H | Cl | OCH₃ | CH | |
| Q-3 | 0 | H | H | CH₃ | H | SO₂N(CH₃)₂ | H | CH₃ | CH₃ | N | |
| Q-3 | 0 | H | H | CH₃ | H | SO₂N(CH₃)₂ | H | OCH₃ | OCH₃ | CH | |
| Q-3 | 0 | H | H | CH₃ | H | SO₂N(CH₃)₂ | H | OCH₃ | OCH₃ | N | |
| Q-3 | 0 | H | H | CH₃ | H | SO₂N(CH₃)₂ | H | CH₃ | OCH₃ | CH | |
| Q-3 | 0 | H | H | CH₃ | H | SCH₃ | H | OCH₃ | OCH₃ | CH | |
| Q-3 | 0 | H | H | CH₃ | H | SCH₃ | H | CH₃ | CH₃ | Cl | |
| Q-3 | 0 | H | H | CH₃ | H | SCH₃ | H | OCH₃ | CH₃ | CH | |
| Q-3 | 0 | H | H | CH₃ | H | SCH₃ | H | Cl | OCH₃ | CH | |
| Q-3 | 0 | H | H | CH₃ | H | SO₂CH₃ | H | CH₃ | CH₃ | CH | |
| Q-3 | 0 | H | H | CH₃ | H | SO₂CH₃ | H | CH₃ | OCH₃ | CH | |
| Q-3 | 0 | H | H | CH₃ | H | SO₂CH₃ | H | CH₃ | OCH₃ | N | |
| Q-3 | 0 | H | H | CH₃ | F | F | H | CH₃ | CH₃ | CH | |
| Q-3 | 0 | H | H | CH₃ | F | F | H | OCH₃ | CH₃ | Cl | |
| Q-3 | 0 | H | H | CH₃ | Cl | Cl | H | OCH₃ | OCH₃ | CH | |
| Q-3 | 0 | H | H | CH₃ | Cl | Cl | H | CH₃ | CH₃ | N | |
| Q-3 | 0 | H | H | CH₃ | F | Cl | H | OCH₃ | CH₃ | N | |
| Q-3 | 0 | H | H | CH₃ | F | CH₃ | H | CH₃ | CH₃ | CH | |
| Q-3 | 0 | H | H | CH₃ | CH₃ | CH₃ | H | OCH₃ | OCH₃ | CH | |
| Q-3 | 0 | H | H | CH₃ | CH₃ | CH₂CH₃ | H | OCH₃ | OCH₃ | N | |
| Q-3 | 0 | H | H | CH₃ | F | Br | H | Cl | OCH₃ | CH | |
| Q-3 | 0 | H | H | CH₃ | Br | Br | H | OCH₃ | OCH₃ | CH | |
| Q-3 | 0 | H | H | CH₃ | CN | CN | H | CH₃ | OCH₃ | CH | |
| Q-3 | 0 | H | H | CH₃ | CN | CN | H | OCH₃ | OCH₃ | N | |
| Q-3 | 0 | H | H | CH₃ | OCH₃ | OCH₃ | H | CH₃ | OCH₃ | CH | |
| Q-3 | 0 | H | H | CH₃ | H | H | CH₃ | CH₃ | CH₃ | CH | |
| Q-3 | 0 | H | H | CH₃ | H | H | CH₃ | CH₃ | OCH₃ | CH | |
| Q-3 | 0 | H | H | CH₃ | H | H | OCH₃ | OCH₃ | CH₃ | CH | |
| Q-3 | 0 | H | H | CH₃ | H | H | CH₂CH₃ | OCH₃ | CH₃ | N | |
| Q-3 | 0 | H | H | CH₃ | F | H | CH₃ | CH₃ | OCH₃ | N | |
| Q-3 | 0 | H | H | CH₃ | Cl | H | CH₃ | OCH₃ | OCH₃ | CH | |
| Q-3 | 0 | H | H | CH₃ | F | F | CH₃ | CH₃ | CH₃ | CH | |
| Q-3 | 0 | H | H | CH₃ | Br | H | CH₃ | OCH₃ | OCH₃ | CH | |
| Q-3 | 0 | H | H | CH₃ | Cl | Cl | CH₃ | CH₃ | OCH₃ | N | |
| Q-3 | 0 | H | 5-CH₃ | CH₃ | H | H | — | OCH₃ | OCH₃ | N | |
| Q-3 | 0 | H | 6-OCH₃ | CH₃ | H | H | — | CH₃ | CH₃ | CH | |
| Q-3 | 0 | H | 3-SCH₃ | CH₃ | Cl | H | — | CH₃ | OCH₃ | CH | |
| Q-3 | 0 | H | 5-Cl | CH₃ | Cl | H | — | OCH₃ | OCH₃ | N | |
| Q-3 | 0 | H | 6-Cl | CH₂CH₃ | F | F | CH₃ | CH₃ | CH₃ | N | |
| Q-3 | 0 | H | 5-OCH₂F | CH₂CH₃ | Cl | H | H | OCH₃ | OCH₃ | N | |
| Q-3 | 0 | CH₃ | H | CH₂CH₃ | H | H | H | OCH₃ | OCH₃ | N | |
| Q-3 | 1 | H | H | CH₂CH₃ | H | H | H | OCH₃ | OCH₃ | CH | |
| Q-3 | 1 | H | H | CH₃ | F | F | H | CH₃ | OCH₃ | CH | |

TABLE I-continued

| Q | n | R | R₁ | R₇ | R₈ | X | Y | Z | m.p.(°C.) |
|---|---|---|---|---|---|---|---|---|---|
| Q-3 | 1 | H | H | CH₃ | F | Cl | H | CH₃ | OCH₃ | N |
| Q-3 | 1 | H | H | CH₂CH₃CH₃ | CH₃ | Cl | H | OCH₃ | CH₃ | CH |
| Q-3 | 1 | H | H | CH₃ | F | H | H | CH₃ | OCH₃ | CH |
| Q-3 | 1 | H | H | CH₃ | Cl | H | H | OCH₃ | OCH₃ | CH |
| Q-3 | 1 | H | H | CH₃ | Br | H | H | CH₃ | OCH₃ | N |
| Q-3 | 1 | H | H | CH₂CH₃ | Cl | Cl | H | CH₃ | OCH₃ | CH |
| Q-3 | 1 | H | H | CH₃ | CH₃ | H | H | CH₃ | OCH₃ | CH |
| Q-3 | 1 | H | H | CH₃ | CN | H | H | OCH₃ | OCH₃ | CH |
| Q-3 | 1 | H | H | CH₃ | CN | CN | H | CH₃ | OCH₃ | N |
| Q-3 | 1 | H | H | CH₃ | CH₃ | Br | H | CH₃ | CH₃ | CH |
| Q-3 | 1 | H | H | CH₃ | F | Br | H | Cl | OCH₃ | CH |
| Q-3 | 1 | H | 3-CH₃ | CH₃ | F | H | H | OCH₃ | OCH₃ | CH |
| Q-3 | 1 | H | 5-OCH₃ | CH₃ | Cl | H | CH₃ | CH₃ | CH₃ | N |
| Q-3 | 1 | H | 5-Cl | CH₃ | Cl | Cl | CH₂CH₃ | CH₃ | OCH₃ | N |

| Q | n | R | R₁ | R₇ | R₈ | X | Y | Z | m.p.(°C.) |
|---|---|---|---|---|---|---|---|---|---|
| Q-4 | 0 | H | H | H | H | CH₃ | CH₃ | CH | 197–199 |
| Q-4 | 0 | H | H | H | H | CH₃ | OCH₃ | CH | 192–194 |
| Q-4 | 0 | H | H | H | H | OCH₃ | OCH₃ | CH | 194–196 |
| Q-4 | 0 | H | H | H | H | CH₃ | CH₃ | N | |
| Q-4 | 0 | H | H | H | H | CH₃ | OCH₃ | N | 155–158 |
| Q-4 | 0 | H | H | H | H | OCH₃ | OCH₃ | N | 150–152 |
| Q-4 | 0 | H | H | H | H | Cl | OCH₃ | CH | 182–184 |
| Q-4 | 0 | H | H | H | CH₃ | CH₃ | OCH₃ | CH | |
| Q-4 | 0 | H | H | H | CH₃ | OCH₃ | OCH₃ | CH | |
| Q-4 | 0 | H | H | H | CH₃ | OCH₃ | OCH₃ | N | |
| Q-4 | 0 | H | H | H | CH₃ | CH₃ | OCH₃ | CH | |
| Q-4 | 0 | H | H | H | Cl | CH₃ | OCH₃ | CH | |
| Q-4 | 0 | H | H | H | Cl | OCH₃ | CH₃ | N | |
| Q-4 | 0 | H | H | H | Cl | OCH₃ | OCH₃ | CH | |
| Q-4 | 0 | H | H | H | Cl | Cl | OCH₃ | CH | |
| Q-4 | 0 | H | H | H | F | CH₃ | CH₃ | N | |
| Q-4 | 0 | H | H | H | F | CH₃ | CH₃ | CH | |
| Q-4 | 0 | H | H | H | F | OCH₃ | CH₃ | CH | |
| Q-4 | 0 | H | H | H | F | OCH₃ | OCH₃ | CH | |
| Q-4 | 0 | H | H | H | F | CH₃ | OCH₃ | N | |
| Q-4 | 0 | H | H | H | F | Cl | OCH₃ | CH | |
| Q-4 | 0 | H | H | H | CN | CH₃ | OCH₃ | N | |
| Q-4 | 0 | H | H | H | CN | OCH₃ | OCH₃ | CH | |
| Q-4 | 0 | H | H | H | OCH₃ | CH₃ | OCH₃ | N | |
| Q-4 | 0 | H | H | H | OCH₃ | OCH₃ | OCH₃ | CH | |
| Q-4 | 0 | H | H | H | OCH₃ | OCH₃ | OCH₃ | N | |
| Q-4 | 0 | H | H | H | CO₂CH₃ | CH₃ | CH₃ | N | |
| Q-4 | 0 | H | H | H | CO₂CH₃ | OCH₃ | CH₃ | CH | |
| Q-4 | 0 | H | H | H | CO₂CH₃ | OCH₃ | OCH₃ | CH | |
| Q-4 | 0 | H | H | H | CO₂CH₃ | CH₃ | CH₃ | N | |
| Q-4 | 0 | H | H | H | CO₂CH₃ | CH₃ | OCH₃ | N | |
| Q-4 | 0 | H | H | H | CO₂CH₃ | Cl | OCH₃ | CH | |
| Q-4 | 0 | H | H | H | OH | CH₃ | CH₃ | CH | 148–150 |
| Q-4 | 0 | H | H | H | OH | CH₃ | OCH₃ | CH | 163–164 |
| Q-4 | 0 | H | H | H | OH | OCH₃ | OCH₃ | CH | 133–136 |
| Q-4 | 0 | H | H | H | OH | CH₃ | OCH₃ | N | 165–167 |
| Q-4 | 0 | H | H | H | OH | OCH₃ | OCH₃ | N | 160–162 |
| Q-4 | 0 | H | H | H | OH | Cl | OCH₃ | CH | 138–140 |
| Q-4 | 0 | H | H | H | SO₂N(CH₃)₂ | CH₃ | OCH₃ | N | |
| Q-4 | 0 | H | H | H | SO₂N(CH₃)₂ | OCH₃ | OCH₃ | CH | |
| Q-4 | 0 | H | H | H | SO₂N(CH₃)₂ | OCH₃ | OCH₃ | N | |
| Q-4 | 0 | H | H | H | SO₂N(CH₃)₂ | CH₃ | OCH₃ | CH | |
| Q-4 | 0 | H | H | H | SCH₃ | OCH₃ | OCH₃ | CH | |
| Q-4 | 0 | H | H | H | SCH₃ | CH₃ | CH₃ | CH | |
| Q-4 | 0 | H | H | H | SCH₃ | OCH₃ | OCH₃ | CH | |
| Q-4 | 0 | H | H | H | SCH₃ | Cl | OCH₃ | CH | |
| Q-4 | 0 | H | H | H | SO₂CH₃ | CH₃ | CH₃ | CH | |
| Q-4 | 0 | H | H | H | SO₂CH₃ | CH₃ | OCH₃ | CH | |
| Q-4 | 0 | H | H | H | SO₂CH₃ | OCH₃ | OCH₃ | N | |
| Q-4 | 0 | H | H | F | F | CH₃ | CH₃ | CH | |
| Q-4 | 0 | H | H | F | F | OCH₃ | CH₃ | CH | |
| Q-4 | 0 | H | H | Cl | Cl | OCH₃ | OCH₃ | CH | |
| Q-4 | 0 | H | H | Cl | Cl | CH₃ | CH₃ | N | |
| Q-4 | 0 | H | H | F | Cl | OCH₃ | CH₃ | N | |
| Q-4 | 0 | H | H | F | CH₃ | CH₃ | CH₃ | CH | |
| Q-4 | 0 | H | H | H | CH₃ | CH₃ | CH₃ | CH | |
| Q-4 | 0 | H | H | H | CH₃ | CH₂CH₃ | OCH₃ | N | |
| Q-4 | 0 | H | H | F | Br | Cl | OCH₃ | CH | |
| Q-4 | 0 | H | H | Br | Br | OCH₃ | OCH₃ | CH | |
| Q-4 | 0 | H | H | H | CN | CH₃ | OCH₃ | CH | |
| Q-4 | 0 | H | H | H | CN | OCH₃ | OCH₃ | CH | |
| Q-4 | 0 | H | H | H | CN | OCH₃ | OCH₃ | N | |
| Q-4 | 0 | H | H | OCH₃ | OCH₃ | CH₃ | OCH₃ | CH | |
| Q-4 | 0 | H | 5-CH₃ | F | H | CH₃ | OCH₃ | N | |
| Q-4 | 0 | H | 6-CH₃ | Cl | H | OCH₃ | OCH₃ | N | |

TABLE I-continued

| | | | | | | | | |
|---|---|---|---|---|---|---|---|---|
| Q-4 | 0 | H | H | F | F | CH₃ | OCH₃ | CH |
| Q-4 | 0 | H | 3-CH₃ | Br | H | OCH₃ | OCH₃ | CH |
| Q-4 | 0 | H | H | Cl | Cl | CH₃ | OCH₃ | N |
| Q-4 | 0 | H | 5-CH₃ | H | H | OCH₃ | OCH₃ | N |
| Q-4 | 0 | H | 5-OCH₃ | H | H | CH₃ | CH₃ | CH |
| Q-4 | 0 | H | 6-SCH₃ | H | H | CH₃ | OCH₃ | CH |
| Q-4 | 0 | H | 5-Cl | Cl | H | OCH₃ | OCH₃ | CH |
| Q-4 | 0 | H | 3-Cl | F | F | CH₃ | CH₃ | N |
| Q-4 | 0 | H | 5-OCH₂F | Cl | H | OCH₃ | OCH₃ | N |
| Q-4 | 0 | CH₃ | H | H | H | OCH₃ | OCH₃ | N |
| Q-4 | 1 | H | H | H | H | OCH₃ | OCH₃ | CH |
| Q-4 | 1 | H | H | F | F | CH₃ | OCH₃ | CH |
| Q-4 | 1 | H | H | F | Cl | CH₃ | CH₃ | N |
| Q-4 | 1 | H | H | CH₃ | Cl | OCH₃ | CH₃ | CH |
| Q-4 | 1 | H | H | F | H | CH₃ | OCH₃ | CH |
| Q-4 | 1 | H | H | Cl | H | OCH₃ | OCH₃ | CH |
| Q-4 | 1 | H | H | Br | H | CH₃ | OCH₃ | N |
| Q-4 | 1 | H | H | Cl | Cl | CH₃ | OCH₃ | CH |
| Q-4 | 1 | H | H | CH₃ | H | CH₃ | OCH₃ | CH |
| Q-4 | 1 | H | H | CN | H | OCH₃ | OCH₃ | CH |
| Q-4 | 1 | H | H | CN | CN | CH₃ | OCH₃ | N |
| Q-4 | 1 | H | H | CH₃ | Br | CH₃ | CH₃ | CH |
| Q-4 | 1 | H | H | F | Br | Cl | OCH₃ | CH |
| Q-4 | 1 | H | 5-CH₃ | F | H | OCH₃ | OCH₃ | CH |
| Q-4 | 1 | H | 5-OCH₃ | Cl | H | CH₃ | CH₃ | N |
| Q-4 | 1 | H | 5-Cl | Cl | Cl | CH₃ | OCH₃ | N |
| Q-5 | 0 | H | H | H | H | CH₃ | CH₃ | CH |
| Q-5 | 0 | H | H | H | H | CH₃ | OCH₃ | CH |
| Q-5 | 0 | H | H | H | H | OCH₃ | OCH₃ | CH |
| Q-5 | 0 | H | H | H | H | CH₃ | CH₃ | N |
| Q-5 | 0 | H | H | H | H | CH₃ | OCH₃ | N |
| Q-5 | 0 | H | H | H | H | OCH₃ | OCH₃ | N |
| Q-5 | 0 | H | H | H | H | Cl | OCH₃ | CH |
| Q-5 | 0 | H | H | H | CH₃ | CH₃ | OCH₃ | CH |
| Q-5 | 0 | H | H | H | CH₃ | OCH₃ | OCH₃ | CH |
| Q-5 | 0 | H | H | H | CH₃ | OCH₃ | OCH₃ | N |
| Q-5 | 0 | H | H | H | CH₃ | CH₃ | CH₃ | CH |
| Q-5 | 0 | H | H | H | Cl | CH₃ | OCH₃ | CH |
| Q-5 | 0 | H | H | H | Cl | OCH₃ | CH₃ | N |
| Q-5 | 0 | H | H | H | Cl | OCH₃ | OCH₃ | CH |
| Q-5 | 0 | H | H | H | Cl | Cl | OCH₃ | CH |
| Q-5 | 0 | H | H | H | F | CH₃ | CH₃ | N |
| Q-5 | 0 | H | H | H | F | CH₃ | CH₃ | CH |
| Q-5 | 0 | H | H | H | F | OCH₃ | CH₃ | CH |
| Q-5 | 0 | H | H | H | F | OCH₃ | OCH₃ | CH |
| Q-5 | 0 | H | H | H | F | CH₃ | OCH₃ | N |
| Q-5 | 0 | H | H | H | F | Cl | OCH₃ | CH |
| Q-5 | 0 | H | H | H | CN | CH₃ | OCH₃ | N |
| Q-5 | 0 | H | H | H | CN | OCH₃ | OCH₃ | CH |
| Q-5 | 0 | H | H | H | OCH₃ | CH₃ | OCH₃ | N |
| Q-5 | 0 | H | H | H | OCH₃ | OCH₃ | OCH₃ | CH |
| Q-5 | 0 | H | H | H | OCH₃ | OCH₃ | OCH₃ | N |
| Q-5 | 0 | H | H | H | CO₂CH₃ | CH₃ | CH₃ | N |
| Q-5 | 0 | H | H | H | CO₂CH₃ | OCH₃ | CH₃ | CH |
| Q-5 | 0 | H | H | H | CO₂CH₃ | OCH₃ | OCH₃ | CH |
| Q-5 | 0 | H | H | H | CO₂CH₃ | CH₃ | OCH₃ | N |
| Q-5 | 0 | H | H | H | CO₂CH₃ | CH₃ | CH₃ | CH |
| Q-5 | 0 | H | H | H | CO₂CH₃ | OCH₃ | OCH₃ | N |
| Q-5 | 0 | H | H | H | CO₂CH₃ | Cl | OCH₃ | CH |
| Q-5 | 0 | H | H | H | SO₂N(CH₃)₂ | CH₃ | CH₃ | N |
| Q-5 | 0 | H | H | H | SO₂N(CH₃)₂ | OCH₃ | OCH₃ | CH |
| Q-5 | 0 | H | H | H | SO₂N(CH₃)₂ | OCH₃ | OCH₃ | N |
| Q-5 | 0 | H | H | H | SO₂N(CH₃)₂ | CH₃ | CH₃ | CH |
| Q-5 | 0 | H | H | H | SCH₃ | OCH₃ | OCH₃ | CH |
| Q-5 | 0 | H | H | H | SCH₃ | CH₃ | CH₃ | Cl |
| Q-5 | 0 | H | H | H | SCH₃ | OCH₃ | OCH₃ | CH |
| Q-5 | 0 | H | H | H | SCH₃ | Cl | OCH₃ | CH |
| Q-5 | 0 | H | H | H | SO₃CH₃ | CH₃ | CH₃ | CH |
| Q-5 | 0 | H | H | H | SO₃CH₃ | CH₃ | CH₃ | CH |
| Q-5 | 0 | H | H | H | SO₃CH₃ | CH₃ | OCH₃ | N |
| Q-5 | 0 | H | H | F | F | CH₃ | CH₃ | CH |
| Q-5 | 0 | H | H | F | F | OCH₃ | CH₃ | N |
| Q-5 | 0 | H | H | Cl | Cl | OCH₃ | OCH₃ | CH |
| Q-5 | 0 | H | H | Cl | Cl | CH₃ | CH₃ | N |
| Q-5 | 0 | H | H | F | Cl | OCH₃ | CH₃ | N |
| Q-5 | 0 | H | H | F | CH₃ | CH₃ | CH₃ | CH |
| Q-5 | 0 | H | H | CH₃ | CH₃ | OCH₃ | OCH₃ | CH |
| Q-5 | 0 | H | H | CH₃ | CH₂CH₃ | OCH₃ | OCH₃ | N |
| Q-5 | 0 | H | H | F | Br | Cl | OCH₃ | CH |
| Q-5 | 0 | H | H | Br | Br | OCH₃ | OCH₃ | CH |
| Q-5 | 0 | H | H | CO₂CH₃ | CO₂CH₃ | OCH₃ | OCH₃ | CH |

TABLE I-continued

| | | | | | | | | |
|---|---|---|---|---|---|---|---|---|
| Q-5 | 0 | H | H | CN | CN | CH$_3$ | OCH$_3$ | CH |
| Q-5 | 0 | H | H | CN | CN | OCH$_3$ | OCH$_3$ | CH |
| Q-5 | 0 | H | H | CN | CN | OCH$_3$ | OCH$_3$ | N |
| Q-5 | 0 | H | H | OCH$_3$ | OCH$_3$ | CH$_3$ | OCH$_3$ | CH |
| Q-5 | 0 | H | 6-CH$_3$ | CH$_3$ | CH$_3$ | OCH$_3$ | OCH$_3$ | CH |
| Q-5 | 0 | H | 3-CH$_3$ | CH$_3$ | H | CH$_3$ | CH$_3$ | N |
| Q-5 | 0 | H | 5-CH$_3$ | F | H | CH$_3$ | OCH$_3$ | N |
| Q-5 | 0 | H | 5-CH$_3$ | Cl | H | OCH$_3$ | OCH$_3$ | N |
| Q-5 | 0 | H | H | F | F | CH$_3$ | OCH$_3$ | CH |
| Q-5 | 0 | H | 6-CH$_3$ | Br | H | OCH$_3$ | OCH$_3$ | CH |
| Q-5 | 0 | H | H | Cl | Cl | CH$_3$ | OCH$_3$ | CH |
| Q-5 | 0 | H | 3-CH$_3$ | H | H | OCH$_3$ | OCH$_3$ | N |
| Q-5 | 0 | H | 5-OCH$_3$ | H | H | CH$_3$ | CH$_3$ | CH |
| Q-5 | 0 | H | 5-SCH$_3$ | H | H | CH$_3$ | OCH$_3$ | CH |
| Q-5 | 0 | H | 5-Cl | Cl | H | OCH$_3$ | OCH$_3$ | CH |
| Q-5 | 0 | H | 6-Cl | F | F | CH$_3$ | CH$_3$ | N |
| Q-5 | 0 | H | 5-OCH$_2$F | Cl | F | OCH$_3$ | OCH$_3$ | N |
| Q-5 | 0 | CH$_3$ | H | H | H | OCH$_3$ | OCH$_3$ | N |
| Q-5 | 1 | H | H | H | H | OCH$_3$ | OCH$_3$ | CH |
| Q-5 | 1 | H | H | F | F | CH$_3$ | OCH$_3$ | CH |
| Q-5 | 1 | H | H | F | Cl | CH$_3$ | CH$_3$ | N |
| Q-5 | 1 | H | H | CH$_3$ | Cl | OCH$_3$ | CH$_3$ | CH |
| Q-5 | 1 | H | H | F | H | CH$_3$ | OCH$_3$ | CH |
| Q-5 | 1 | H | H | Cl | H | OCH$_3$ | OCH$_3$ | CH |
| Q-5 | 1 | H | H | Br | H | CH$_3$ | OCH$_3$ | N |
| Q-5 | 1 | H | H | Cl | Cl | CH$_3$ | OCH$_3$ | CH |
| Q-5 | 1 | H | H | CH$_3$ | H | CH$_3$ | CH$_3$ | CH |
| Q-5 | 1 | H | H | CN | H | OCH$_3$ | OCH$_3$ | CH |
| Q-5 | 1 | H | H | CN | CN | CH$_3$ | OCH$_3$ | N |
| Q-5 | 1 | H | H | CH$_3$ | Br | CH$_3$ | CH$_3$ | CH |
| Q-5 | 1 | H | H | F | Br | Cl | OCH$_3$ | CH |
| Q-5 | 1 | H | 3-CH$_3$ | F | H | OCH$_3$ | OCH$_3$ | CH |
| Q-5 | 1 | H | 5-OCH$_3$ | Cl | H | CH$_3$ | CH$_3$ | N |
| Q-5 | 1 | H | 6-Cl | Cl | H | CH$_3$ | OCH$_3$ | N |
| Q-6 | 0 | H | H | H | H | CH$_3$ | CH$_3$ | CH |
| Q-6 | 0 | H | H | H | H | CH$_3$ | OCH$_3$ | CH |
| Q-6 | 0 | H | H | H | H | CH$_3$ | CH$_3$ | N |
| Q-6 | 0 | H | H | H | H | CH$_3$ | OCH$_3$ | N |
| Q-6 | 0 | H | H | H | H | OCH$_3$ | OCH$_3$ | N |
| Q-6 | 0 | H | H | H | H | Cl | OCH$_3$ | CH |
| Q-6 | 0 | H | H | H | CH$_3$ | CH$_3$ | OCH$_3$ | CH |
| Q-6 | 0 | H | H | H | CH$_3$ | OCH$_3$ | OCH$_3$ | CH |
| Q-6 | 0 | H | H | H | CH$_3$ | OCH$_3$ | OCH$_3$ | N |
| Q-6 | 0 | H | H | H | CH$_3$ | CH$_3$ | OCH$_3$ | CH |
| Q-6 | 0 | H | H | H | Cl | CH$_3$ | OCH$_3$ | CH |
| Q-6 | 0 | H | H | H | Cl | OCH$_3$ | CH$_3$ | N |
| Q-6 | 0 | H | H | H | Cl | OCH$_3$ | OCH$_3$ | CH |
| Q-6 | 0 | H | H | H | Cl | Cl | OCH$_3$ | CH |
| Q-6 | 0 | H | H | H | F | CH$_3$ | CH$_3$ | N |
| Q-6 | 0 | H | H | H | F | CH$_3$ | CH$_3$ | CH |
| Q-6 | 0 | H | H | H | F | OCH$_3$ | CH$_3$ | CH |
| Q-6 | 0 | H | H | H | F | OCH$_3$ | OCH$_3$ | CH |
| Q-6 | 0 | H | H | H | F | CH$_3$ | OCH$_3$ | N |
| Q-6 | 0 | H | H | H | F | Cl | OCH$_3$ | CH |
| Q-6 | 0 | H | H | H | CN | CH$_3$ | OCH$_3$ | N |
| Q-6 | 0 | H | H | H | CN | OCH$_3$ | OCH$_3$ | CH |
| Q-6 | 0 | H | H | H | OCH$_3$ | CH$_3$ | OCH$_3$ | N |
| Q-6 | 0 | H | H | H | OCH$_3$ | OCH$_3$ | OCH$_3$ | CH |
| Q-6 | 0 | H | H | H | OCH$_3$ | OCH$_3$ | OCH$_3$ | N |
| Q-6 | 0 | H | H | H | CO$_2$CH$_3$ | CH$_3$ | CH$_3$ | N |
| Q-6 | 0 | H | H | H | CO$_2$CH$_3$ | OCH$_3$ | CH$_3$ | CH |
| Q-6 | 0 | H | H | H | CO$_2$CH$_3$ | OCH$_3$ | OCH$_3$ | CH |
| Q-6 | 0 | H | H | H | CO$_2$CH$_3$ | CH$_3$ | OCH$_3$ | N |
| Q-6 | 0 | H | H | H | CO$_2$CH$_3$ | CH$_3$ | CH$_3$ | CH |
| Q-6 | 0 | H | H | H | CO$_2$CH$_3$ | OCH$_3$ | OCH$_3$ | N |
| Q-6 | 0 | H | H | H | CO$_2$CH$_3$ | Cl | OCH$_3$ | CH |
| Q-6 | 0 | H | H | H | SO$_2$N(CH$_3$)$_2$ | CH$_3$ | CH$_3$ | N |
| Q-6 | 0 | H | H | H | SO$_2$N(CH$_3$)$_2$ | OCH$_3$ | OCH$_3$ | CH |
| Q-6 | 0 | H | H | H | SO$_2$N(CH$_3$)$_2$ | OCH$_3$ | OCH$_3$ | N |
| Q-6 | 0 | H | H | H | SO$_2$N(CH$_3$)$_2$ | CH$_3$ | OCH$_3$ | CH |
| Q-6 | 0 | H | H | H | SCH$_3$ | OCH$_3$ | OCH$_3$ | CH |
| Q-6 | 0 | H | H | H | SCH$_3$ | CH$_3$ | CH$_3$ | CH |
| Q-6 | 0 | H | H | H | SCH$_3$ | Cl | OCH$_3$ | CH |
| Q-6 | 0 | H | H | H | SO$_2$CH$_3$ | CH$_3$ | CH$_3$ | CH |
| Q-6 | 0 | H | H | H | SO$_2$CH$_3$ | OCH$_3$ | OCH$_3$ | N |
| Q-6 | 0 | H | H | F | F | CH$_3$ | CH$_3$ | CH |
| Q-6 | 0 | H | H | F | F | OCH$_3$ | CH$_3$ | Cl |
| Q-6 | 0 | H | H | Cl | Cl | OCH$_3$ | OCH$_3$ | CH |
| Q-6 | 0 | H | H | Cl | Cl | CH$_3$ | CH$_3$ | N |

TABLE I-continued

| | | | | | | | | |
|---|---|---|---|---|---|---|---|---|
| Q-6 | 0 | H | H | F | Cl | OCH$_3$ | CH$_3$ | N |
| Q-6 | 0 | H | H | F | CH$_3$ | CH$_3$ | CH$_3$ | CH |
| Q-6 | 0 | H | H | CH$_3$ | CH$_3$ | OCH$_3$ | OCH$_3$ | CH |
| Q-6 | 0 | H | H | CH$_3$ | CH$_2$CH$_3$ | OCH$_3$ | OCH$_3$ | N |
| Q-6 | 0 | H | H | F | Br | Cl | OCH$_3$ | CH |
| Q-6 | 0 | H | H | Br | Br | OCH$_3$ | OCH$_3$ | CH |
| Q-6 | 0 | H | H | CN | CN | CH$_3$ | OCH$_3$ | CH |
| Q-6 | 0 | H | H | CN | CN | OCH$_3$ | OCH$_3$ | CH |
| Q-6 | 0 | H | H | CN | CN | OCH$_3$ | OCH$_3$ | N |
| Q-6 | 0 | H | H | OCH$_3$ | OCH$_3$ | CH$_3$ | OCH$_3$ | CH |
| Q-6 | 0 | H | 5-CH$_3$ | CH$_3$ | H | CH$_3$ | CH$_3$ | N |
| Q-6 | 0 | H | 6-CH$_3$ | F | H | CH$_3$ | OCH$_3$ | N |
| Q-6 | 0 | H | 3-CH$_3$ | Cl | H | OCH$_3$ | OCH$_3$ | N |
| Q-6 | 0 | H | H | F | F | CH$_3$ | OCH$_3$ | CH |
| Q-6 | 0 | H | 5-CH$_3$ | Br | H | OCH$_3$ | OCH$_3$ | CH |
| Q-6 | 0 | H | H | Cl | Cl | CH$_3$ | OCH$_3$ | N |
| Q-6 | 0 | H | 6-CH$_3$ | H | H | OCH$_3$ | OCH$_3$ | N |
| Q-6 | 0 | H | 5-OCH$_3$ | H | H | CH$_3$ | CH$_3$ | CH |
| Q-6 | 0 | H | 5-SCH$_3$ | H | H | CH$_3$ | OCH$_3$ | CH |
| Q-6 | 0 | H | 5-Cl | Cl | H | OCH$_3$ | OCH$_3$ | CH |
| Q-6 | 0 | H | 3-Cl | F | F | CH$_3$ | CH$_3$ | N |
| Q-6 | 0 | H | 5-OCH$_2$F | Cl | H | OCH$_3$ | OCH$_3$ | N |
| Q-6 | 0 | CH$_3$ | H | H | H | OCH$_3$ | OCH$_3$ | N |
| Q-6 | 1 | H | H | H | H | OCH$_3$ | OCH$_3$ | CH |
| Q-6 | 1 | H | H | F | F | CH$_3$ | OCH$_3$ | CH |
| Q-6 | 1 | H | H | F | Cl | CH$_3$ | CH$_3$ | N |
| Q-6 | 1 | H | H | CH$_3$ | Cl | OCH$_3$ | CH$_3$ | CH |
| Q-6 | 1 | H | H | F | H | CH$_3$ | OCH$_3$ | CH |
| Q-6 | 1 | H | H | Cl | H | OCH$_3$ | OCH$_3$ | CH |
| Q-6 | 1 | H | H | Br | H | CH$_3$ | OCH$_3$ | N |
| Q-6 | 1 | H | H | Cl | Cl | CH$_3$ | OCH$_3$ | CH |
| Q-6 | 1 | H | H | CH$_3$ | H | CH$_3$ | CH$_3$ | CH |
| Q-6 | 1 | H | H | CN | H | OCH$_3$ | OCH$_3$ | CH |
| Q-6 | 1 | H | H | CN | CN | CH$_3$ | OCH$_3$ | N |
| Q-6 | 1 | H | H | CH$_3$ | Br | CH$_3$ | CH$_3$ | CH |
| Q-6 | 1 | H | H | F | Br | Cl | OCH$_3$ | CH |
| Q-6 | 1 | H | 3-CH$_3$ | F | H | OCH$_3$ | OCH$_3$ | CH |
| Q-6 | 1 | H | 3-OCH$_3$ | Cl | H | CH$_3$ | CH$_3$ | N |
| Q-6 | 1 | H | 5-Cl | Cl | Cl | CH$_3$ | OCH$_3$ | N |
| Q-7 | 0 | H | H | H | H | CH$_3$ | CH$_3$ | CH |
| Q-7 | 0 | H | H | H | H | CH$_3$ | OCH$_3$ | CH |
| Q-7 | 0 | H | H | H | H | OCH$_3$ | OCH$_3$ | CH |
| Q-7 | 0 | H | H | H | H | CH$_3$ | CH$_3$ | N |
| Q-7 | 0 | H | H | H | H | CH$_3$ | OCH$_3$ | N |
| Q-7 | 0 | H | H | H | H | OCH$_3$ | OCH$_3$ | N |
| Q-7 | 0 | H | H | H | H | Cl | OCH$_3$ | CH |
| Q-7 | 0 | H | H | H | CH$_3$ | CH$_3$ | CH$_3$ | CH |
| Q-7 | 0 | H | H | H | CH$_3$ | OCH$_3$ | OCH$_3$ | CH |
| Q-7 | 0 | H | H | H | CH$_3$ | OCH$_3$ | OCH$_3$ | N |
| Q-7 | 0 | H | H | H | CH$_3$ | CH$_3$ | OCH$_3$ | CH |
| Q-7 | 0 | H | H | H | Cl | CH$_3$ | OCH$_3$ | CH |
| Q-7 | 0 | H | H | H | Cl | OCH$_3$ | CH$_3$ | N |
| Q-7 | 0 | H | H | H | Cl | OCH$_3$ | OCH$_3$ | CH |
| Q-7 | 0 | H | H | H | Cl | Cl | OCH$_3$ | CH |
| Q-7 | 0 | H | H | H | F | CH$_3$ | CH$_3$ | N |
| Q-7 | 0 | H | H | H | F | CH$_3$ | CH$_3$ | CH |
| Q-7 | 0 | H | H | H | F | OCH$_3$ | CH$_3$ | CH |
| Q-7 | 0 | H | H | H | F | OCH$_3$ | OCH$_3$ | CH |
| Q-7 | 0 | H | H | H | F | CH$_3$ | OCH$_3$ | N |
| Q-7 | 0 | H | H | H | F | Cl | OCH$_3$ | CH |
| Q-7 | 0 | H | H | H | CN | CH$_3$ | OCH$_3$ | N |
| Q-7 | 0 | H | H | H | CN | OCH$_3$ | OCH$_3$ | CH |
| Q-7 | 0 | H | H | H | OCH$_3$ | CH$_3$ | CH$_3$ | N |
| Q-7 | 0 | H | H | H | OCH$_3$ | OCH$_3$ | OCH$_3$ | CH |
| Q-7 | 0 | H | H | H | OCH$_3$ | OCH$_3$ | OCH$_3$ | N |
| Q-7 | 0 | H | H | H | CO$_2$CH$_3$ | CH$_3$ | CH$_3$ | N |
| Q-7 | 0 | H | H | H | CO$_2$CH$_3$ | OCH$_3$ | CH$_3$ | CH |
| Q-7 | 0 | H | H | H | CO$_2$CH$_3$ | OCH$_3$ | OCH$_3$ | CH |
| Q-7 | 0 | H | H | H | CO$_2$CH$_3$ | CH$_3$ | OCH$_3$ | N |
| Q-7 | 0 | H | H | H | CO$_2$CH$_3$ | CH$_3$ | CH$_3$ | CH |
| Q-7 | 0 | H | H | H | CO$_2$CH$_3$ | OCH$_3$ | OCH$_3$ | N |
| Q-7 | 0 | H | H | H | CO$_2$CH$_3$ | Cl | OCH$_3$ | CH |
| Q-7 | 0 | H | H | H | SO$_2$N(CH$_3$)$_2$ | CH$_3$ | CH$_3$ | N |
| Q-7 | 0 | H | H | H | SO$_2$N(CH$_3$)$_2$ | OCH$_3$ | OCH$_3$ | CH |
| Q-7 | 0 | H | H | H | SO$_2$N(CH$_3$)$_2$ | OCH$_3$ | OCH$_3$ | N |
| Q-7 | 0 | H | H | H | SO$_2$N(CH$_3$)$_2$ | CH$_3$ | OCH$_3$ | CH |
| Q-7 | 0 | H | H | H | SCH$_3$ | OCH$_3$ | OCH$_3$ | CH |
| Q-7 | 0 | H | H | H | SCH$_3$ | OCH$_3$ | CH$_3$ | Cl |
| Q-7 | 0 | H | H | H | SCH$_3$ | OCH$_3$ | CH$_3$ | CH |
| Q-7 | 0 | H | H | H | SCH$_3$ | Cl | OCH$_3$ | CH |
| Q-7 | 0 | H | H | H | SO$_2$CH$_3$ | CH$_3$ | CH$_3$ | CH |
| Q-7 | 0 | H | H | H | SO$_2$CH$_3$ | CH$_3$ | OCH$_3$ | CH |

TABLE I-continued

| | | | | | | | | |
|---|---|---|---|---|---|---|---|---|
| Q-7 | 0 | H | H | H | SO₂CH₃ | CH₃ | OCH₃ | N |
| Q-7 | 0 | H | H | F | F | CH₃ | CH₃ | CH |
| Q-7 | 0 | H | H | F | F | OCH₃ | CH₃ | Cl |
| Q-7 | 0 | H | H | Cl | Cl | OCH₃ | OCH₃ | CH |
| Q-7 | 0 | H | H | Cl | Cl | CH₃ | CH₃ | N |
| Q-7 | 0 | H | H | F | Cl | OCH₃ | CH₃ | N |
| Q-7 | 0 | H | H | F | CH₃ | CH₃ | CH₃ | CH |
| Q-7 | 0 | H | H | CH₃ | CH₃ | OCH₃ | OCH₃ | CH |
| Q-7 | 0 | H | H | CH₃ | CH₂CH₃ | OCH₃ | OCH₃ | N |
| Q-7 | 0 | H | H | F | Br | Cl | OCH₃ | CH |
| Q-7 | 0 | H | H | Br | Br | OCH₃ | OCH₃ | CH |
| Q-7 | 0 | H | H | CN | CN | CH₃ | OCH₃ | CH |
| Q-7 | 0 | H | H | CN | CN | OCH₃ | OCH₃ | CH |
| Q-7 | 0 | H | H | CN | CN | OCH₃ | OCH₃ | N |
| Q-7 | 0 | H | H | OCH₃ | OCH₃ | CH₃ | OCH₃ | CH |
| Q-7 | 0 | H | 3-CH₃ | CH₃ | H | CH₃ | OCH₃ | CH |
| Q-7 | 0 | H | 5-CH₃ | CH₃ | H | OCH₃ | OCH₃ | CH |
| Q-7 | 0 | CH₃ | H | CH₃ | H | CH₃ | CH₃ | N |
| Q-7 | 0 | CH₃ | H | F | H | CH₃ | OCH₃ | N |
| Q-7 | 0 | H | 5-CH₃ | Cl | H | OCH₃ | OCH₃ | N |
| Q-7 | 0 | H | H | F | F | CH₃ | OCH₃ | CH |
| Q-7 | 0 | H | H | Br | H | OCH₃ | OCH₃ | CH |
| Q-7 | 0 | H | 5-CH₃ | H | H | OCH₃ | OCH₃ | N |
| Q-7 | 0 | H | 6-OCH₃ | H | H | CH₃ | CH₃ | CH |
| Q-7 | 0 | H | 5-SCH₃ | H | H | CH₃ | OCH₃ | CH |
| Q-7 | 0 | H | 3-Cl | Cl | H | OCH₃ | OCH₃ | CH |
| Q-7 | 0 | H | 5-Cl | F | F | CH₃ | CH₃ | N |
| Q-7 | 0 | H | 3-OCH₂F | Cl | H | OCH₃ | OCH₃ | N |
| Q-7 | 0 | CH₃ | H | H | H | OCH₃ | OCH₃ | N |
| Q-7 | 1 | H | H | H | H | OCH₃ | OCH₃ | CH |
| Q-7 | 1 | H | H | F | F | CH₃ | OCH₃ | CH |
| Q-7 | 1 | H | H | F | Cl | CH₃ | CH₃ | N |
| Q-7 | 1 | H | H | CH₃ | Cl | OCH₃ | CH₃ | CH |
| Q-7 | 1 | H | H | F | H | CH₃ | OCH₃ | CH |
| Q-7 | 1 | H | H | Cl | H | OCH₃ | OCH₃ | CH |
| Q-7 | 1 | H | H | Br | H | CH₃ | OCH₃ | N |
| Q-7 | 1 | H | H | Cl | Cl | CH₃ | OCH₃ | CH |
| Q-7 | 1 | H | H | CH₃ | H | CH₃ | OCH₃ | CH |
| Q-7 | 1 | H | H | CN | H | OCH₃ | OCH₃ | CH |
| Q-7 | 1 | H | H | CN | CN | CH₃ | OCH₃ | N |
| Q-7 | 1 | H | H | CH₃ | Br | CH₃ | CH₃ | CH |
| Q-7 | 1 | H | H | F | Br | Cl | OCH₃ | CH |
| Q-7 | 1 | H | 5-CH₃ | F | H | OCH₃ | OCH₃ | CH |
| Q-7 | 1 | H | 5-OCH₃ | Cl | H | CH₃ | CH₃ | N |
| Q-7 | 1 | H | 5-Cl | Cl | H | CH₃ | OCH₃ | N |
| Q-8 | 0 | H | H | H | H | CH₃ | CH₃ | CH |
| Q-8 | 0 | H | H | H | H | CH₃ | OCH₃ | CH |
| Q-8 | 0 | H | H | H | H | OCH₃ | OCH₃ | CH |
| Q-8 | 0 | H | H | H | H | CH₃ | CH₃ | N |
| Q-8 | 0 | H | H | H | H | CH₃ | OCH₃ | N |
| Q-8 | 0 | H | H | H | H | OCH₃ | OCH₃ | N |
| Q-8 | 0 | H | H | H | H | Cl | OCH₃ | CH |
| Q-8 | 0 | H | H | H | CH₃ | CH₃ | OCH₃ | CH |
| Q-8 | 0 | H | H | H | CH₃ | OCH₃ | OCH₃ | CH |
| Q-8 | 0 | H | H | H | CH₃ | OCH₃ | OCH₃ | N |
| Q-8 | 0 | H | H | H | CH₃ | CH₃ | CH₃ | CH |
| Q-8 | 0 | H | H | H | Cl | CH₃ | OCH₃ | CH |
| Q-8 | 0 | H | H | H | Cl | OCH₃ | CH₃ | CH |
| Q-8 | 0 | H | H | H | Cl | OCH₃ | OCH₃ | CH |
| Q-8 | 0 | H | H | H | Cl | Cl | OCH₃ | CH |
| Q-8 | 0 | H | H | H | F | CH₃ | CH₃ | N |
| Q-8 | 0 | H | H | H | F | CH₃ | CH₃ | CH |
| Q-8 | 0 | H | H | H | F | OCH₃ | CH₃ | CH |
| Q-8 | 0 | H | H | H | Br | OCH₃ | OCH₃ | CH |
| Q-8 | 0 | H | H | H | F | CH₃ | OCH₃ | N |
| Q-8 | 0 | H | H | H | F | Cl | OCH₃ | CH |
| Q-8 | 0 | H | H | H | CN | CH₃ | OCH₃ | N |
| Q-8 | 0 | H | H | H | CN | OCH₃ | OCH₃ | CH |
| Q-8 | 0 | H | H | H | OCH₃ | CH₃ | OCH₃ | N |
| Q-8 | 0 | H | H | H | OCH₃ | OCH₃ | CH₃ | CH |
| Q-8 | 0 | H | H | H | OCH₃ | OCH₃ | OCH₃ | N |
| Q-8 | 0 | H | H | H | CO₂CH₃ | CH₃ | CH₃ | N |
| Q-8 | 0 | H | H | H | CO₂CH₃ | OCH₃ | CH₃ | CH |
| Q-8 | 0 | H | H | H | CO₂CH₃ | OCH₃ | OCH₃ | CH |
| Q-8 | 0 | H | H | H | CO₂CH₃ | CH₃ | OCH₃ | N |
| Q-8 | 0 | H | H | H | CO₂CH₃ | OCH₃ | CH₃ | CH |
| Q-8 | 0 | H | H | H | CO₂CH₃ | OCH₃ | OCH₃ | N |
| Q-8 | 0 | H | H | H | CO₂CH₃ | Cl | OCH₃ | CH |
| Q-8 | 0 | H | H | H | SO₂N(CH₃)₂ | CH₃ | CH₃ | N |
| Q-8 | 0 | H | H | H | SO₂N(CH₃)₂ | OCH₃ | OCH₃ | CH |
| Q-8 | 0 | H | H | H | SO₂N(CH₃)₂ | OCH₃ | OCH₃ | N |

TABLE I-continued

| Q | n | R | R₁ | R₃ | R₇ | R₈ | X | Y | Z | m.p.(°C.) |
|---|---|---|---|---|---|---|---|---|---|---|
| Q-8 | 0 | H | H | | H | SO₂N(CH₃)₂ | CH₃ | OCH₃ | CH | |
| Q-8 | 0 | H | H | | H | SCH₃ | OCH₃ | OCH₃ | CH | |
| Q-8 | 0 | H | H | | H | SCH₃ | CH₃ | CH₃ | CH | |
| Q-8 | 0 | H | H | | H | SCH₃ | OCH₃ | CH₃ | CH | |
| Q-8 | 0 | H | H | | H | SCH₃ | Cl | OCH₃ | CH | |
| Q-8 | 0 | H | H | | H | SO₂CH₃ | CH₃ | CH₃ | CH | |
| Q-8 | 0 | H | H | | H | SO₂CH₃ | CH₃ | OCH₃ | CH | |
| Q-8 | 0 | H | H | | H | SO₂CH₃ | CH₃ | OCH₃ | N | |
| Q-8 | 0 | H | H | | F | F | CH₃ | CH₃ | CH | |
| Q-8 | 0 | H | H | | F | F | OCH₃ | CH₃ | Cl | |
| Q-8 | 0 | H | H | | Cl | Cl | OCH₃ | OCH₃ | CH | |
| Q-8 | 0 | H | H | | Cl | Cl | CH₃ | CH₃ | N | |
| Q-8 | 0 | H | H | | F | Cl | OCH₃ | CH₃ | N | |
| Q-8 | 0 | H | H | | F | CH₃ | CH₃ | CH₃ | CH | |
| Q-8 | 0 | H | H | | CH₃ | CH₃ | OCH₃ | OCH₃ | CH | |
| Q-8 | 0 | H | H | | CH₃ | CH₂CH₃ | OCH₃ | OCH₃ | N | |
| Q-8 | 0 | H | H | | F | Br | Cl | OCH₃ | CH | |
| Q-8 | 0 | H | H | | Br | Br | OCH₃ | OCH₃ | CH | |
| Q-8 | 0 | H | H | | CN | CN | CH₃ | OCH₃ | CH | |
| Q-8 | 0 | H | H | | CN | CN | OCH₃ | OCH₃ | CH | |
| Q-8 | 0 | H | H | | CN | CN | OCH₃ | OCH₃ | N | |
| Q-8 | 0 | H | H | | OCH₃ | OCH₃ | CH₃ | OCH₃ | CH | |
| Q-8 | 0 | H | H | | H | Br | CH₃ | CH₃ | CH | |
| Q-8 | 0 | H | H | | H | Br | OCH₃ | CH₃ | CH | |
| Q-8 | 0 | H | H | | H | Br | OCH₃ | OCH₃ | CH | |
| Q-8 | 0 | H | 3-CH₃ | | CH₃ | H | CH₃ | CH₃ | N | |
| Q-8 | 0 | H | 5-CH₃ | | F | H | CH₃ | OCH₃ | N | |
| Q-8 | 0 | H | H | | Cl | H | OCH₃ | OCH₃ | N | |
| Q-8 | 0 | H | H | | F | F | CH₃ | OCH₃ | CH | |
| Q-8 | 0 | H | H | | Br | H | OCH₃ | OCH₃ | N | |
| Q-8 | 0 | H | H | | Cl | Cl | CH₃ | OCH₃ | N | |
| Q-8 | 0 | H | 5-CH₃ | | H | H | OCH₃ | OCH₃ | N | |
| Q-8 | 0 | H | 5-OCH₃ | | H | H | CH₃ | CH₃ | CH | |
| Q-8 | 0 | H | 5-SCH₃ | | H | H | CH₃ | OCH₃ | CH | |
| Q-8 | 0 | H | 5-Cl | | Cl | H | OCH₃ | OCH₃ | CH | |
| Q-8 | 0 | H | 6-Cl | | F | F | CH₃ | CH₃ | N | |
| Q-8 | 0 | H | 5-OCH₂F | | Cl | H | OCH₃ | OCH₃ | N | |
| Q-8 | 0 | CH₃ | H | | H | H | OCH₃ | OCH₃ | N | |
| Q-8 | 1 | H | H | | H | H | OCH₃ | OCH₃ | CH | |
| Q-8 | 1 | H | H | | F | F | CH₃ | OCH₃ | CH | |
| Q-8 | 1 | H | H | | F | Cl | CH₃ | CH₃ | N | |
| Q-8 | 1 | H | H | | CH₃ | Cl | OCH₃ | CH₃ | CH | |
| Q-8 | 1 | H | H | | F | H | CH₃ | OCH₃ | CH | |
| Q-8 | 1 | H | H | | Cl | H | CH₃ | OCH₃ | CH | |
| Q-8 | 1 | H | H | | Br | H | CH₃ | OCH₃ | N | |
| Q-8 | 1 | H | H | | Cl | Cl | CH₃ | OCH₃ | CH | |
| Q-8 | 1 | H | H | | CH₃ | H | CH₃ | OCH₃ | CH | |
| Q-8 | 1 | H | H | | CN | H | OCH₃ | OCH₃ | N | |
| Q-8 | 1 | H | H | | CN | CN | CH₃ | OCH₃ | N | |
| Q-8 | 1 | H | H | | CH₃ | Br | CH₃ | CH₃ | CH | |
| Q-8 | 1 | H | H | | F | Br | Cl | OCH₃ | CH | |
| Q-8 | 1 | H | 5-CH₃ | | F | H | OCH₃ | OCH₃ | CH | |
| Q-8 | 1 | H | 3-OCH₃ | | Cl | H | CH₃ | CH₃ | N | |
| Q-8 | 1 | H | 5-Cl | | Cl | Cl | CH₃ | OCH₃ | N | |
| Q | n | R | R₁ | R₃ | R₇ | R₈ | X | Y | Z | m.p.(°C.) |
| Q-9 | 0 | H | H | CH₃ | H | H | CH₃ | CH₃ | CH | |
| Q-9 | 0 | H | H | CH₃ | H | H | CH₃ | OCH₃ | CH | |
| Q-9 | 0 | H | H | CH₃ | H | H | OCH₃ | OCH₃ | CH | |
| Q-9 | 0 | H | H | CH₃ | H | H | CH₃ | CH₃ | N | |
| Q-9 | 0 | H | H | CH₃ | H | H | CH₃ | OCH₃ | N | |
| Q-9 | 0 | H | H | CH₃ | H | H | OCH₃ | OCH₃ | N | |
| Q-9 | 0 | H | H | CH₃ | H | H | Cl | OCH₃ | CH | |
| Q-9 | 0 | H | H | CH₃ | H | CH₃ | CH₃ | OCH₃ | CH | |
| Q-9 | 0 | H | H | CH₃ | H | CH₃ | CH₃ | CH₃ | CH | |
| Q-9 | 0 | H | H | CH₃ | H | CH₃ | OCH₃ | OCH₃ | CH | |
| Q-9 | 0 | H | H | CH₃ | H | CH₃ | OCH₃ | OCH₃ | N | |
| Q-9 | 0 | H | H | CH₃ | H | CH₃ | CH₃ | CH₃ | CH | |
| Q-9 | 0 | H | H | CH₃ | H | Cl | CH₃ | OCH₃ | CH | |
| Q-9 | 0 | H | H | CH₃ | H | Cl | OCH₃ | CH₃ | N | |
| Q-9 | 0 | H | H | CH₃ | H | Cl | OCH₃ | OCH₃ | CH | |
| Q-9 | 0 | H | H | CH₃ | H | Cl | Cl | OCH₃ | CH | |
| Q-9 | 0 | H | H | CH₃ | H | F | CH₃ | CH₃ | N | |
| Q-9 | 0 | H | H | CH₃ | H | F | CH₃ | CH₃ | CH | |
| Q-9 | 0 | H | H | CH₃ | H | F | OCH₃ | CH₃ | CH | |
| Q-9 | 0 | H | H | CH₃ | H | F | OCH₃ | OCH₃ | CH | |
| Q-9 | 0 | H | H | CH₃ | H | F | CH₃ | OCH₃ | N | |
| Q-9 | 0 | H | H | CH₃ | H | F | Cl | OCH₃ | CH | |
| Q-9 | 0 | H | H | CH₃ | H | CN | CH₃ | OCH₃ | N | |
| Q-9 | 0 | H | H | CH₃ | H | CN | OCH₃ | OCH₃ | CH | |
| Q-9 | 0 | H | H | CH₃ | H | OCH₃ | CH₃ | OCH₃ | N | |
| Q-9 | 0 | H | H | CH₃ | H | OCH₃ | OCH₃ | OCH₃ | CH | |

TABLE I-continued

| | | | | | | | | | |
|---|---|---|---|---|---|---|---|---|---|
| Q-9 | 0 | H | H | CH₃ | H | OCH₃ | OCH₃ | OCH₃ | N |
| Q-9 | 0 | H | H | CH₃ | H | CO₂CH₃ | CH₃ | CH₃ | N |
| Q-9 | 0 | H | H | CH₃ | H | CO₂CH₃ | OCH₃ | OCH₃ | CH |
| Q-9 | 0 | H | H | CH₃ | H | CO₂CH₃ | CH₃ | OCH₃ | N |
| Q-9 | 0 | H | H | CH₃ | H | CO₂CH₃ | CH₃ | CH₃ | CH |
| Q-9 | 0 | H | H | CH₃ | H | CO₂CH₃ | OCH₃ | OCH₃ | N |
| Q-9 | 0 | H | H | CH₃ | H | CO₂CH₃ | Cl | OCH₃ | CH |
| Q-9 | 0 | H | H | CH₃ | H | SO₂N(CH₃)₂ | CH₃ | CH₃ | N |
| Q-9 | 0 | H | H | CH₃ | H | SO₂N(CH₃)₂ | OCH₃ | OCH₃ | CH |
| Q-9 | 0 | H | H | CH₃ | H | SO₂N(CH₃)₂ | OCH₃ | OCH₃ | N |
| Q-9 | 0 | H | H | CH₃ | H | SO₂N(CH₃)₂ | CH₃ | OCH₃ | CH |
| Q-9 | 0 | H | H | CH₃ | H | SCH₃ | OCH₃ | OCH₃ | CH |
| Q-9 | 0 | H | H | CH₃ | H | SCH₃ | CH₃ | CH₃ | CH |
| Q-9 | 0 | H | H | CH₃ | H | SCH₃ | OCH₃ | CH₃ | CH |
| Q-9 | 0 | H | H | CH₃ | H | SCH₃ | Cl | OCH₃ | CH |
| Q-9 | 0 | H | H | CH₃ | H | SO₂CH₃ | CH₃ | CH₃ | CH |
| Q-9 | 0 | H | H | CH₃ | H | SO₂CH₃ | CH₃ | OCH₃ | CH |
| Q-9 | 0 | H | H | CH₃ | H | SO₂CH₃ | CH₃ | OCH₃ | N |
| Q-9 | 0 | H | H | CH₃ | F | F | CH₃ | CH₃ | CH |
| Q-9 | 0 | H | H | CH₃ | F | F | OCH₃ | CH₃ | Cl |
| Q-9 | 0 | H | H | CH₃ | Cl | Cl | OCH₃ | OCH₃ | CH |
| Q-9 | 0 | H | H | CH₃ | Cl | Cl | CH₃ | CH₃ | N |
| Q-9 | 0 | H | H | CH₃ | F | Cl | OCH₃ | CH₃ | N |
| Q-9 | 0 | H | H | CH₃ | F | CH₃ | CH₃ | CH₃ | CH |
| Q-9 | 0 | H | H | CH₃ | CH₃ | CH₃ | OCH₃ | OCH₃ | CH |
| Q-9 | 0 | H | H | CH₃ | CH₃ | CH₂CH₃ | OCH₃ | OCH₃ | N |
| Q-9 | 0 | H | H | CH₃ | F | Br | Cl | OCH₃ | CH |
| Q-9 | 0 | H | H | CH₃ | Br | Br | OCH₃ | OCH₃ | CH |
| Q-9 | 0 | H | H | CH₃ | CN | CN | CH₃ | OCH₃ | CH |
| Q-9 | 0 | H | H | CH₃ | CN | CN | OCH₃ | OCH₃ | CH |
| Q-9 | 0 | H | H | CH₃ | CN | CN | OCH₃ | OCH₃ | N |
| Q-9 | 0 | H | H | CH₃ | OCH₃ | OCH₃ | CH₃ | OCH₃ | CH |
| Q-9 | 0 | H | H | CH₃ | H | Br | CH₃ | CH₃ | CH |
| Q-9 | 0 | H | H | CH₃ | H | Br | CH₃ | OCH₃ | CH |
| Q-9 | 0 | H | H | CH₃ | H | Br | OCH₃ | OCH₃ | CH |
| Q-9 | 0 | H | H | CH₂CH₃ | H | H | CH₃ | CH₃ | N |
| Q-9 | 0 | H | H | CH₃ | F | H | CH₃ | OCH₃ | N |
| Q-9 | 0 | H | H | CH₃ | Cl | H | OCH₃ | OCH₃ | N |
| Q-9 | 0 | H | H | CH₃ | F | F | CH₃ | OCH₃ | CH |
| Q-9 | 0 | H | H | CH₃ | Br | H | OCH₃ | OCH₃ | N |
| Q-9 | 0 | H | H | CH₃ | Cl | Cl | CH₃ | OCH₃ | N |
| Q-9 | 0 | H | 5-SCH₃ | CH₃ | H | H | CH₃ | OCH₃ | CH |
| Q-9 | 0 | H | 5-Cl | CH₃ | Cl | H | OCH₃ | OCH₃ | CH |
| Q-9 | 0 | H | 5-Cl | CH₃ | F | F | CH₃ | CH₃ | N |
| Q-9 | 0 | H | 5-OCH₂F | CH₃ | Cl | H | OCH₃ | OCH₃ | N |
| Q-9 | 0 | CH₃ | H | CH₃ | H | H | OCH₃ | OCH₃ | N |
| Q-9 | 1 | H | H | CH₃ | H | H | OCH₃ | OCH₃ | CH |
| Q-9 | 1 | H | H | CH₃ | F | F | CH₃ | OCH₃ | CH |
| Q-9 | 1 | H | H | CH₃ | F | Cl | CH₃ | CH₃ | N |
| Q-9 | 1 | H | H | CH₃ | CH₃ | Cl | OCH₃ | CH₃ | CH |
| Q-9 | 1 | H | H | CH₃ | F | H | CH₃ | OCH₃ | CH |
| Q-9 | 1 | H | H | CH₃ | Cl | H | OCH₃ | OCH₃ | CH |
| Q-9 | 1 | H | H | H | Br | H | CH₃ | OCH₃ | N |
| Q-9 | 1 | H | H | H | Cl | Cl | CH₃ | OCH₃ | CH |
| Q-9 | 1 | H | H | H | CH₃ | H | CH₃ | OCH₃ | CH |
| Q-9 | 1 | H | H | H | CN | H | OCH₃ | OCH₃ | CH |
| Q-9 | 1 | H | H | H | CN | CN | OCH₃ | OCH₃ | N |
| Q-9 | 1 | H | H | H | CH₃ | Br | CH₃ | CH₃ | CH |
| Q-9 | 1 | H | H | H | F | Br | Cl | OCH₃ | CH |
| Q-9 | 1 | H | 3-CH₃ | H | F | H | OCH₃ | OCH₃ | CH |
| Q-9 | 1 | H | 6-OCH₃ | CH₃ | Cl | H | CH₃ | CH₃ | N |
| Q-10 | 1 | H | 5-Cl | CH₂CH₃ | Cl | Cl | CH₃ | OCH₃ | N |
| Q-10 | 0 | H | H | CH₃ | H | H | CH₃ | CH₃ | CH |
| Q-10 | 0 | H | H | CH₃ | H | H | CH₃ | OCH₃ | CH |
| Q-10 | 0 | H | H | CH₃ | H | H | OCH₃ | OCH₃ | CH |
| Q-10 | 0 | H | H | CH₃ | H | H | CH₃ | CH₃ | N |
| Q-10 | 0 | H | H | CH₃ | H | H | CH₃ | OCH₃ | N |
| Q-10 | 0 | H | H | CH₃ | H | H | OCH₃ | OCH₃ | N |
| Q-10 | 0 | H | H | CH₃ | H | H | Cl | OCH₃ | CH |
| Q-10 | 0 | H | H | CH₃ | H | CH₃ | CH₃ | OCH₃ | CH |
| Q-10 | 0 | H | H | CH₃ | H | CH₃ | OCH₃ | OCH₃ | CH |
| Q-10 | 0 | H | H | CH₃ | H | CH₃ | OCH₃ | OCH₃ | N |
| Q-10 | 0 | H | H | CH₃ | H | CH₃ | CH₃ | CH₃ | N |
| Q-10 | 0 | H | H | CH₃ | H | Cl | OCH₃ | OCH₃ | CH |
| Q-10 | 0 | H | H | CH₃ | H | Cl | OCH₃ | CH₃ | N |
| Q-10 | 0 | H | H | CH₃ | H | Cl | OCH₃ | OCH₃ | CH |
| Q-10 | 0 | H | H | CH₃ | H | Cl | Cl | OCH₃ | CH |
| Q-10 | 0 | H | H | CH₃ | H | F | CH₃ | CH₃ | N |
| Q-10 | 0 | H | H | CH₃ | H | F | CH₃ | CH₃ | CH |
| Q-10 | 0 | H | H | CH₃ | H | F | OCH₃ | CH₃ | CH |
| Q-10 | 0 | H | H | CH₃ | H | F | OCH₃ | OCH₃ | CH |

TABLE I-continued

| Q | n | R | R₁ | | R₇ | R₈ | R₃ | X | Y | Z | |
|---|---|---|---|---|---|---|---|---|---|---|---|
| Q-10 | 0 | H | H | | CH₃ | H | F | CH₃ | OCH₃ | N | |
| Q-10 | 0 | H | H | | CH₃ | H | F | Cl | OCH₃ | CH | |
| Q-10 | 0 | H | H | | CH₃ | H | CN | CH₃ | OCH₃ | N | |
| Q-10 | 0 | H | H | | CH₃ | H | CN | OCH₃ | OCH₃ | CH | |
| Q-10 | 0 | H | H | | CH₃ | H | OCH₃ | CH₃ | OCH₃ | N | |
| Q-10 | 0 | H | H | | CH₃ | H | OCH₃ | OCH₃ | OCH₃ | CH | |
| Q-10 | 0 | H | H | | CH₃ | H | OCH₃ | OCH₃ | OCH₃ | N | |
| Q-10 | 0 | H | H | | CH₃ | H | CO₂CH₃ | CH₃ | CH₃ | N | |
| Q-10 | 0 | H | H | | CH₃ | H | CO₂CH₃ | OCH₃ | CH₃ | CH | |
| Q-10 | 0 | H | H | | CH₃ | H | CO₂CH₃ | OCH₃ | OCH₃ | CH | |
| Q-10 | 0 | H | H | | CH₃ | H | CO₂CH₃ | CH₃ | OCH₃ | N | |
| Q-10 | 0 | H | H | | CH₃ | H | CO₂CH₃ | CH₃ | CH₃ | CH | |
| Q-10 | 0 | H | H | | CH₃ | H | CO₂CH₃ | OCH₃ | OCH₃ | N | |
| Q-10 | 0 | H | H | | CH₃ | H | CO₂CH₃ | Cl | OCH₃ | CH | |
| Q-10 | 0 | H | H | | CH₃ | H | SO₂N(CH₃)₂ | CH₃ | CH₃ | N | |
| Q-10 | 0 | H | H | | CH₃ | H | SO₂N(CH₃)₂ | OCH₃ | OCH₃ | CH | |
| Q-10 | 0 | H | H | | CH₃ | H | SO₂N(CH₃)₂ | OCH₃ | OCH₃ | N | |
| Q-10 | 0 | H | H | | CH₃ | H | SO₂N(CH₃)₂ | CH₃ | OCH₃ | CH | |
| Q-10 | 0 | H | H | | CH₃ | H | SCH₃ | OCH₃ | OCH₃ | CH | |
| Q-10 | 0 | H | H | | CH₃ | H | SCH₃ | CH₃ | CH₃ | CH | |
| Q-10 | 0 | H | H | | CH₃ | H | SCH₃ | OCH₃ | CH₃ | CH | |
| Q-10 | 0 | H | H | | CH₃ | H | SCH₃ | Cl | OCH₃ | CH | |
| Q-10 | 0 | H | H | | CH₃ | H | SO₂CH₃ | CH₃ | CH₃ | CH | |
| Q-10 | 0 | H | H | | CH₃ | H | SO₂CH₃ | CH₃ | OCH₃ | CH | |
| Q-10 | 0 | H | H | | CH₃ | H | SO₂CH₃ | CH₃ | OCH₃ | N | |
| Q-10 | 0 | H | H | | CH₃ | F | F | CH₃ | CH₃ | CH | |
| Q-10 | 0 | H | H | | CH₃ | F | F | OCH₃ | CH₃ | Cl | |
| Q-10 | 0 | H | H | | CH₃ | Cl | Cl | OCH₃ | OCH₃ | CH | |
| Q-10 | 0 | H | H | | CH₃ | Cl | Cl | CH₃ | CH₃ | N | |
| Q-10 | 0 | H | H | | CH₃ | F | Cl | OCH₃ | CH₃ | N | |
| Q-10 | 0 | H | H | | CH₃ | F | CH₃ | CH₃ | CH₃ | CH | |
| Q-10 | 0 | H | H | | CH₃ | CH₃ | CH₃ | OCH₃ | OCH₃ | CH | |
| Q-10 | 0 | H | H | | CH₃ | CH₃ | CH₂CH₃ | OCH₃ | OCH₃ | H | |
| Q-10 | 0 | H | H | | CH₃ | F | Br | Cl | OCH₃ | CH | |
| Q-10 | 0 | H | H | | CH₃ | Br | Br | OCH₃ | OCH₃ | CH | |
| Q-10 | 0 | H | H | | CH₃ | CN | CN | CH₃ | OCH₃ | CH | |
| Q-10 | 0 | H | H | | CH₃ | CN | CN | OCH₃ | OCH₃ | CH | |
| Q-10 | 0 | H | H | | CH₃ | CN | CN | OCH₃ | OCH₃ | N | |
| Q-10 | 0 | H | H | | CH₃ | OCH₃ | OCH₃ | CH₃ | OCH₃ | CH | |

| Q | n | R | R₁ | R₇ | R₈ | R₃ | X | Y | Z | m.p.(°C.) |
|---|---|---|---|---|---|---|---|---|---|---|
| Q-10 | 0 | H | H | H | Br | CH₃ | CH₃ | CH₃ | CH | |
| Q-10 | 0 | H | H | H | Br | CH₃ | OCH₃ | OCH₃ | CH | |
| Q-10 | 0 | H | H | H | H | CH₂CH₂CH₂CH₃ | OCH₃ | CH₃ | N | |
| Q-10 | 0 | H | 5-CH₃ | F | H | CH₃ | CH₃ | OCH₃ | N | |
| Q-10 | 0 | H | H | Cl | H | CH₃ | OCH₃ | OCH₃ | N | |
| Q-10 | 0 | H | H | F | F | CH₃ | OCH₃ | OCH₃ | CH | |
| Q-10 | 0 | H | H | Br | H | CH₃ | OCH₃ | OCH₃ | N | |
| Q-10 | 0 | H | H | Cl | Cl | CH₃ | CH₃ | OCH₃ | N | |
| Q-10 | 0 | H | 6-CH₃ | H | H | CH₂CH₂CH₃ | OCH₃ | OCH₃ | N | |
| Q-10 | 0 | H | 5-OCH₃ | H | H | CH₂CH₃ | CH₃ | CH₃ | CH | |
| Q-10 | 0 | H | 3-SCH₃ | H | H | CH₂CH₂CH₃ | CH₃ | OCH₃ | CH | |
| Q-10 | 0 | H | 6-Cl | Cl | H | CH₂CH₃ | OCH₃ | OCH₃ | CH | |
| Q-10 | 0 | H | 5-Cl | F | F | CH₃ | CH₃ | CH₃ | N | |
| Q-10 | 0 | H | 5-OCH₂F | Cl | H | CH₃ | OCH₃ | OCH₃ | N | |
| Q-10 | 0 | CH₃ | H | H | H | H | OCH₃ | OCH₃ | N | |
| Q-10 | 1 | H | H | H | H | H | OCH₃ | OCH₃ | CH | |
| Q-10 | 1 | H | H | F | F | H | CH₃ | OCH₃ | CH | |
| Q-10 | 1 | H | H | F | Cl | CH₃ | CH₃ | CH₃ | N | |
| Q-10 | 1 | H | H | CH₃ | Cl | H | OCH₃ | CH₃ | CH | |
| Q-10 | 1 | H | H | F | H | H | CH₃ | OCH₃ | CH | |
| Q-10 | 1 | H | H | Cl | H | CH₃ | OCH₃ | OCH₃ | CH | |
| Q-10 | 1 | H | H | Br | H | H | CH₃ | OCH₃ | N | |
| Q-10 | 1 | H | H | Cl | Cl | CH₃ | CH₃ | CH₃ | CH | |
| Q-10 | 1 | H | H | CH₃ | H | CH₃ | CH₃ | CH₃ | CH | |
| Q-10 | 1 | H | H | CN | H | CH₃ | OCH₃ | OCH₃ | CH | |
| Q-10 | 1 | H | H | CN | CN | H | CH₃ | OCH₃ | N | |
| Q-10 | 1 | H | H | CH₃ | Br | H | CH₃ | CH₃ | CH | |
| Q-10 | 1 | H | H | F | Br | CH₃ | Cl | OCH₃ | CH | |
| Q-10 | 1 | H | 3-CH₃ | F | H | H | OCH₃ | OCH₃ | CH | |
| Q-10 | 1 | H | 5-OCH₃ | Cl | H | CH₃ | CH₃ | CH₃ | N | |
| Q-10 | 1 | H | 6-Cl | Cl | Cl | CH₂CH₃ | CH₃ | OCH₃ | N | |

| Q | n | R | R₁ | R₃ | R₇ | R₈ | R₉ | R₁₀ | R₁₁ | X | Y | Z | m.p.(°C.) |
|---|---|---|---|---|---|---|---|---|---|---|---|---|---|
| Q-1 | 0 | H | H | — | H | H | H | H | — | NHCH₃ | OCH₂CH₃ | N | 203–206 |
| Q-1 | 0 | H | H | — | H | H | H | H | — | CH₃ | SCH₃ | CH | |
| Q-1 | 0 | H | H | — | H | H | Cl | H | — | N(CH₃)H | OCH₂CH₃ | N | 154–158 |
| Q-1 | 0 | H | H | — | Cl | Cl | H | H | — | OCH₃ | CH(OCH₃)₂ | CH | |
| Q-1 | 0 | H | H | — | CH₃ | H | H | H | — | OCH₃ | OCH₂CH=CH₂ | CH | |
| Q-1 | 0 | H | H | — | CH₃ | H | H | Cl | — | OCH₂CH₃ | CH | | |
| Q-1 | 0 | H | H | — | F | F | H | H | — | OCH₂CH₃ | OCH₂F | N | |

TABLE I-continued

| Q | n | R | R$_1$ | | R$_7$ | R$_8$ | R$_9$ | R$_{10}$ | R$_{11}$ | X | Y | Z |
|---|---|---|---|---|---|---|---|---|---|---|---|---|
| Q-1 | 0 | H | H | — | H | CN | H | H | — | OCH$_3$ | SCH$_3$ | CH |
| Q-1 | 0 | H | Cl | — | Br | H | H | CH$_3$ | — | OCH$_3$ | Br | CH |
| Q-1 | 0 | H | H | — | H | Br | H | H | — | OCH$_3$ | NH$_2$ | CH |
| Q-1 | 0 | H | H | — | H | Br | Cl | H | — | OCH$_3$ | NHCH$_3$ | N |
| Q-1 | 0 | H | H | — | F | F | Cl | F | — | CH$_3$ | OCH$_2$C≡CH | CH |
| Q-1 | 0 | H | H | — | F | CN | H | H | — | OCH$_3$ | CH$_2$CF$_3$ | CH |
| Q-1 | 0 | H | H | — | H | H | H | H | — | OCF$_2$CH$_3$ | CH$_3$ | N |
| Q-1 | 0 | H | H | — | H | H | H | H | — | OCH$_3$ | C≡CH | CH |
| Q-1 | 0 | H | H | — | Cl | Cl | H | H | — | OCH$_3$ | O‖CCH$_3$ | CH |
| Q-2 | 0 | H | H | — | H | H | H | H | H | OCH$_3$ | OCH$_2$CH$_3$ | N |
| Q-2 | 0 | H | H | — | Cl | H | H | H | H | CH$_3$OCH$_3$ | CH$_2$CF$_3$ | N |
| Q-2 | 0 | H | H | — | Cl | H | CH$_3$ | H | H | OCH$_3$ | N(CH$_3$)$_2$ | N |
| Q-4 | 0 | H | H | — | H | H | H | H | — | CH$_3$ | CH$_2$CH$_3$ | CH |
| Q-4 | 0 | H | H | — | H | H | H | H | — | OCH$_3$ | OCH$_2$OCH$_3$ | CH |
| Q-5 | 0 | H | H | — | Cl | H | H | H | — | OCH$_3$ | SCH$_2$CH$_3$ | CH |
| Q-5 | 0 | H | H | — | Cl | Cl | H | H | — | OCF$_2$H | CH$_2$CH$_3$ | CH |
| Q-5 | 0 | H | H | — | CH$_3$ | H | H | CH$_3$ | — | OCH$_3$ | F | CH |
| Q-9 | 0 | H | H | CH$_3$ | H | H | H | H | — | SCH$_2$CH$_2$F | HNCH$_3$ | CH |
| Q-9 | 0 | H | H | H | H | H | H | F | — | OCH$_3$ | OCH$_2$CH=CH$_2$ | CH |
| Q-3 | 0 | H | H | CH$_3$ | H | H | H | H | H | OCH$_2$CH$_3$ | SCH$_2$CH$_3$ | N |
| Q-3 | 0 | H | H | CH$_3$ | F | H | H | Br | CH$_3$ | OCH$_3$ | I | CH |
| Q-3 | 0 | H | H | H | H | H | H | H | H | OCH$_2$OCH$_2$CH$_3$ | CH$_3$ | CH |
| Q-7 | 0 | H | H | — | H | H | H | H | — | OCH$_2$OCH$_2$CH$_3$ | OCH$_3$ | N |
| Q-7 | 0 | H | H | — | H | H | H | H | — | OCHF$_2$ | N(CH$_3$)$_2$ | CH |
| Q-7 | 0 | H | H | — | Cl | H | H | H | — | OCH$_3$ | N(OCH$_3$)CH$_3$ | N |

| General Structure I (wherein R$_{12}$ and R$_{13}$ are H) (W = S) | | | | | | | | | | | | | |
|---|---|---|---|---|---|---|---|---|---|---|---|---|---|
| Q | n | R | R$_1$ | R$_7$ | R$_8$ | R$_9$ | R$_{10}$ | R$_{11}$ | X | Y | Z | m.p.(°C.) | |
| Q-1 | 0 | H | H | H | H | H | H | — | CH$_3$ | CH$_3$ | CH | | |
| Q-1 | 0 | H | H | H | H | H | H | — | CH$_3$ | OCH$_3$ | CH | | |
| Q-1 | 0 | H | H | H | H | H | H | — | OCH$_3$ | OCH$_3$ | CH | | |
| Q-1 | 0 | H | 5-CH$_3$ | H | H | H | H | — | CH$_3$ | OCH$_3$ | N | | |
| Q-1 | 0 | H | H | H | H | H | H | — | CH$_3$ | OCH$_3$ | N | | |
| Q-1 | 0 | H | H | H | H | H | H | — | OCH$_3$ | OCH$_3$ | N | | |
| Q-1 | 0 | H | H | H | H | H | H | — | Cl | OCH$_3$ | CH | | |
| Q-1 | 0 | H | H | H | F | H | H | — | CH$_3$ | CH$_3$ | CH | | |
| Q-1 | 0 | H | H | H | F | H | H | — | CH$_3$ | CH$_3$ | N | | |
| Q-1 | 0 | H | H | H | F | H | H | — | CH$_3$ | OCH$_3$ | CH | | |
| Q-1 | 0 | H | H | H | Cl | H | H | — | OCH$_3$ | OCH$_3$ | CH | | |
| Q-1 | 0 | H | H | H | Cl | H | H | — | CH$_3$ | CH$_3$ | N | | |
| Q-1 | 0 | H | H | Cl | H | H | H | — | CH$_3$ | OCH$_3$ | CH | | |
| Q-1 | 0 | H | H | Cl | H | H | H | — | CH$_3$ | OCH$_3$ | N | | |
| Q-1 | 0 | H | H | H | Br | H | H | — | CH$_3$ | CH$_3$ | CH | | |
| Q-1 | 0 | H | H | Br | H | H | H | — | CH$_3$ | OCH$_3$ | CH | | |
| Q-1 | 0 | H | H | Br | H | H | H | — | OCH$_3$ | OCH$_3$ | CH | | |
| Q-1 | 0 | H | H | H | I | H | H | — | CH$_3$ | CH$_3$ | N | | |
| Q-1 | 0 | H | H | I | H | H | H | — | CH$_3$ | OCH$_3$ | N | | |
| Q-1 | 0 | H | H | H | CN | H | H | — | OCH$_3$ | OCH$_3$ | N | | |
| Q-1 | 0 | H | H | CN | H | H | H | — | OCH$_3$ | OCH$_3$ | CH | | |
| Q-1 | 0 | H | H | H | CH$_3$ | H | H | — | CH$_3$ | CH$_3$ | CH | | |
| Q-1 | 0 | H | H | H | CH$_3$ | H | H | — | CH$_3$ | OCH$_3$ | CH | | |
| Q-1 | 0 | H | H | H | CH$_3$ | H | H | — | OCH$_3$ | OCH$_3$ | CH | | |
| Q-1 | 0 | H | H | CH$_3$ | H | H | H | — | Cl | OCH$_3$ | N | | |
| Q-1 | 0 | H | H | CH$_3$ | H | H | H | — | CH$_3$ | OCH$_3$ | N | | |
| Q-1 | 0 | H | H | H | CH$_2$CH$_3$ | H | H | — | OCH$_3$ | OCH$_3$ | N | | |
| Q-1 | 0 | H | H | CH$_2$CH$_3$ | H | H | H | — | CH$_3$ | OCH$_3$ | CH | | |
| Q-1 | 0 | H | H | H | CH$_2$CH$_3$ | H | H | — | OCH$_3$ | OCH$_3$ | CH | | |
| Q-1 | 0 | H | H | H | CH$_2$CH$_2$CH$_3$ | H | H | — | CH$_3$ | OCH$_3$ | N | | |
| Q-1 | 0 | H | H | H | Cl | H | H | — | CH$_3$ | CH$_3$ | CH | | |
| Q-1 | 0 | H | H | H | Cl | H | H | — | OCH$_3$ | OCH$_3$ | N | | |
| Q-1 | 0 | H | H | H | Cl | H | H | — | Cl | OCH$_3$ | CH | | |

TABLE IA

| General Structure I (wherein R$_{12}$ is OH; R$_{13}$ is H) | | | | | | | | | | | | |
|---|---|---|---|---|---|---|---|---|---|---|---|---|
| Q | n | R | R$_1$ | R$_7$ | R$_8$ | R$_9$ | R$_{10}$ | R$_{11}$ | X | Y | Z | m.p. (°C.) |
| Q-1 | 1 | H | H | H | H | H | H | — | CH$_3$ | CH$_3$ | CH | 148–150 |
| Q-1 | 1 | H | H | H | H | H | H | — | CH$_3$ | OCH$_3$ | CH | 140–142 |
| Q-1 | 1 | H | H | H | H | H | H | — | OCH$_3$ | OCH$_3$ | CH | 148–150 |
| Q-1 | 1 | H | H | H | H | H | H | — | CH$_3$ | CH$_3$ | N | |
| Q-1 | 1 | H | H | H | H | H | H | — | CH$_3$ | OCH$_3$ | N | 109–111 |
| Q-1 | 1 | H | H | H | H | H | H | — | OCH$_3$ | OCH$_3$ | N | 147–149 |
| Q-1 | 1 | H | H | H | H | H | H | — | Cl | OCH$_3$ | CH | 124–126 |
| Q-1 | 1 | H | H | H | F | H | H | — | CH$_3$ | CH$_3$ | CH | |
| Q-1 | 1 | H | H | H | F | H | H | — | CH$_3$ | CH$_3$ | N | |
| Q-1 | 1 | H | H | H | F | H | H | — | CH$_3$ | OCH$_3$ | CH | |

TABLE IA-continued

General Structure I (wherein $R_{12}$ is OH; $R_{13}$ is H)

| Q | n | R | $R_1$ | $R_7$ | $R_8$ | $R_9$ | $R_{10}$ | $R_{11}$ | X | Y | Z | m.p. (°C.) |
|---|---|---|---|---|---|---|---|---|---|---|---|---|
| Q-1 | 1 | H | H | H | Cl | H | H | — | $OCH_3$ | $OCH_3$ | CH | |
| Q-1 | 1 | H | H | H | Cl | H | H | — | $CH_3$ | $CH_3$ | N | |
| Q-1 | 1 | H | H | Cl | H | H | H | — | $CH_3$ | $OCH_3$ | CH | |
| Q-1 | 1 | H | H | Cl | H | H | H | — | $CH_3$ | $OCH_3$ | N | |
| Q-1 | 1 | H | H | H | Br | H | H | — | $CH_3$ | $CH_3$ | CH | |
| Q-1 | 1 | H | H | Br | H | H | H | — | $CH_3$ | $OCH_3$ | CH | |
| Q-1 | 1 | H | H | Br | H | H | H | — | $OCH_3$ | $OCH_3$ | CH | |
| Q-1 | 1 | H | H | H | I | H | H | — | $CH_3$ | $CH_3$ | N | |
| Q-1 | 1 | H | H | I | H | H | H | — | $CH_3$ | $OCH_3$ | N | |
| Q-1 | 1 | H | H | H | CN | H | H | — | $OCH_3$ | $OCH_3$ | N | |
| Q-1 | 1 | H | H | CN | H | H | H | — | $OCH_3$ | $OCH_3$ | CH | |
| Q-1 | 1 | H | H | H | $CH_3$ | H | H | — | $CH_3$ | $CH_3$ | CH | |
| Q-1 | 1 | H | H | H | $CH_3$ | H | H | — | $CH_3$ | $OCH_3$ | CH | |
| Q-1 | 1 | H | H | H | $CH_3$ | H | H | — | $OCH_3$ | $OCH_3$ | CH | |
| Q-1 | 1 | H | H | $CH_3$ | H | H | H | — | $CH_3$ | $CH_3$ | N | |
| Q-1 | 1 | H | H | $CH_3$ | H | H | H | — | $CH_3$ | $OCH_3$ | N | |
| Q-1 | 1 | H | H | H | $CH_2CH_3$ | H | H | — | $OCH_3$ | $OCH_3$ | N | |
| Q-1 | 1 | H | H | H | $CH_2CH_3$ | H | H | — | $OCH_3$ | $OCH_3$ | CH | |
| Q-1 | 1 | H | H | H | $CH_2CH_2CH_3$ | H | H | — | $CH_3$ | $OCH_3$ | N | |
| Q-1 | 1 | H | H | H | $OCH_3$ | H | H | — | $CH_3$ | $CH_3$ | CH | |
| Q-1 | 1 | H | H | H | $OCH_3$ | H | H | — | $OCH_3$ | $CH_3$ | CH | |
| Q-1 | 1 | H | H | $CH_3O$ | H | H | H | — | $OCH_3$ | $OCH_3$ | CH | |
| Q-1 | 1 | H | H | H | $OCH_2CH_3$ | H | H | — | $CH_3$ | $CH_3$ | N | |
| Q-1 | 1 | H | H | H | $CO_2CH_3$ | H | H | — | $CH_3$ | $OCH_3$ | N | |
| Q-1 | 1 | H | H | H | $CO_2CH_3$ | H | H | — | $OCH_3$ | $OCH_3$ | N | |
| Q-1 | 1 | H | H | H | $CO_2CH_3$ | H | H | — | $CH_3$ | $OCH_3$ | CH | |
| Q-1 | 1 | H | H | H | $CO_2CH_3$ | H | H | — | $OCH_3$ | $OCH_3$ | CH | |
| Q-1 | 1 | H | H | H | $CO_2CH_2CH_3$ | H | H | — | $CH_3$ | $OCH_3$ | N | |
| Q-1 | 1 | H | H | H | $SO_2N(CH_3)_2$ | H | H | — | $OCH_3$ | $OCH_3$ | N | |
| Q-1 | 1 | H | H | H | $SO_2N(CH_3)_2$ | H | H | — | $CH_3$ | $CH_3$ | CH | |
| Q-1 | 1 | H | H | H | $SCH_3$ | H | H | — | $OCH_3$ | $OCH_3$ | CH | |
| Q-1 | 1 | H | H | H | $SCH_3$ | H | H | — | $CH_3$ | $CH_3$ | N | |
| Q-1 | 1 | H | H | H | $SO_2CH_3$ | H | H | — | $CH_3$ | $OCH_3$ | N | |
| Q-1 | 1 | H | H | H | $SO_2CH_3$ | H | H | — | Cl | $OCH_3$ | CH | |
| Q-1 | 1 | H | H | H | $SO_2CH_3$ | H | H | — | $CH_3$ | $OCH_3$ | CH | |
| Q-1 | 1 | H | H | H | $SO_2CH_2CH_3$ | H | H | — | $OCH_3$ | $OCH_3$ | CH | |
| Q-1 | 1 | H | H | H | $CH_3$ | H | $CH_3$ | — | $CH_3$ | $OCH_3$ | N | |
| Q-1 | 1 | H | H | H | $CH_3$ | H | $CH_3$ | — | $OCH_3$ | $OCH_3$ | N | |
| Q-1 | 1 | H | H | H | $CH_3$ | $CH_3$ | H | — | $CH_3$ | $CH_3$ | CH | |
| Q-1 | 1 | H | H | H | $CH_3$ | H | F | — | $CH_3$ | $OCH_3$ | CH | |
| Q-1 | 1 | H | H | H | $CH_3$ | H | F | — | $OCH_3$ | $OCH_3$ | CH | |
| Q-1 | 1 | H | H | H | $CH_3$ | H | F | — | $CH_3$ | $OCH_3$ | N | |
| Q-1 | 1 | H | H | H | $CH_3$ | H | Cl | — | $OCH_3$ | $OCH_3$ | N | |
| Q-1 | 1 | H | H | H | $CH_3$ | Br | H | — | $CH_3$ | $OCH_3$ | CH | |
| Q-1 | 1 | H | H | H | F | H | $CH_3$ | — | $OCH_3$ | $OCH_3$ | CH | |
| Q-1 | 1 | H | H | H | F | H | $CH_3$ | — | $CH_3$ | $CH_3$ | CH | |
| Q-1 | 1 | H | H | H | Cl | H | $CH_3$ | — | $CH_3$ | $OCH_3$ | N | |
| Q-1 | 1 | H | H | H | Cl | H | F | — | $OCH_3$ | $OCH_3$ | CH | |
| Q-1 | 1 | H | H | H | Cl | H | Cl | — | Cl | $OCH_3$ | CH | |
| Q-1 | 1 | H | H | H | Cl | H | Cl | — | $OCH_3$ | $OCH_3$ | N | |
| Q-1 | 1 | H | H | H | Cl | H | Br | — | $CH_3$ | $OCH_3$ | CH | |
| Q-1 | 1 | H | H | H | $SO_2CH_3$ | H | $CH_3$ | — | $CH_3$ | $CH_3$ | CH | |
| Q-1 | 1 | H | H | H | $SO_2CH_3$ | H | $CH_3$ | — | $OCH_3$ | $CH_3$ | CH | |
| Q-1 | 1 | H | H | H | $SO_2CH_3$ | H | $CH_3$ | — | $OCH_3$ | $OCH_3$ | CH | |
| Q-1 | 1 | H | H | H | $SO_2CH_3$ | H | $CH_3$ | — | $CH_3$ | $CH_3$ | N | |
| Q-1 | 1 | H | H | H | $SO_2CH_3$ | H | $CH_3$ | — | $CH_3$ | $OCH_3$ | N | |
| Q-1 | 1 | H | H | H | $SO_2CH_3$ | H | $CH_3$ | — | $OCH_3$ | $OCH_3$ | N | |
| Q-1 | 1 | H | H | H | $SO_2CH_3$ | H | $CH_3$ | — | Cl | $OCH_3$ | CH | |
| Q-1 | 1 | H | H | H | $SO_2CH_3$ | H | Cl | — | $OCH_3$ | $OCH_3$ | CH | |
| Q-1 | 1 | H | H | H | $SO_2CH_3$ | H | Cl | — | $CH_3$ | $OCH_3$ | N | |
| Q-1 | 1 | H | H | H | $SO_2CH_3$ | H | F | — | $OCH_3$ | $OCH_3$ | N | |
| Q-1 | 1 | H | H | H | $SO_2CH_3$ | H | Br | — | $CH_3$ | $CH_3$ | CH | |
| Q-1 | 1 | H | H | F | F | H | H | — | $CH_3$ | $OCH_3$ | CH | |
| Q-1 | 1 | H | H | F | F | H | H | — | $OCH_3$ | $OCH_3$ | CH | |
| Q-1 | 1 | H | H | F | F | H | H | — | $CH_3$ | $CH_3$ | N | |
| Q-1 | 1 | H | H | F | F | H | H | — | $CH_3$ | $OCH_3$ | N | |
| Q-1 | 1 | H | H | F | F | H | H | — | Cl | $OCH_3$ | CH | |
| Q-1 | 1 | H | H | Cl | Cl | H | H | — | $CH_3$ | $OCH_3$ | CH | |
| Q-1 | 1 | H | H | Cl | Cl | H | H | — | $OCH_3$ | $OCH_3$ | CH | |
| Q-1 | 1 | H | H | Cl | Cl | H | H | — | $CH_3$ | $OCH_3$ | N | |
| Q-1 | 1 | H | H | Cl | Cl | H | H | — | $OCH_3$ | $OCH_3$ | N | |
| Q-1 | 1 | H | H | Cl | Cl | H | H | — | $CH_3$ | $CH_3$ | CH | |
| Q-1 | 1 | H | H | Cl | Cl | H | H | — | $CH_3$ | $CH_3$ | N | |
| Q-1 | 1 | H | H | Cl | Cl | H | H | — | Cl | $OCH_3$ | CH | |
| Q-1 | 1 | H | H | Br | Br | H | H | — | $CH_3$ | $OCH_3$ | N | |
| Q-1 | 1 | H | H | Br | Br | H | H | — | $OCH_3$ | $OCH_3$ | N | |
| Q-1 | 1 | H | H | Br | Br | H | H | — | $CH_3$ | $OCH_3$ | CH | |
| Q-1 | 1 | H | H | Br | Br | H | H | — | $OCH_3$ | $OCH_3$ | CH | |
| Q-1 | 1 | H | H | Br | Br | H | H | — | $CH_3$ | $CH_3$ | N | |

TABLE IA-continued

General Structure I (wherein R$_{12}$ is OH; R$_{13}$ is H)

| Q | n | R | R$_1$ | R$_7$ | R$_8$ | R$_9$ | R$_{10}$ | R$_{11}$ | X | Y | Z | m.p. (°C.) |
|---|---|---|---|---|---|---|---|---|---|---|---|---|
| Q-1 | 1 | H | H | I | I | H | H | — | OCH$_3$ | OCH$_3$ | CH | |
| Q-1 | 1 | H | H | CN | CN | H | H | — | Cl | OCH$_3$ | CH | |
| Q-1 | 1 | H | H | CN | CN | H | H | — | OCH$_3$ | OCH$_3$ | N | |
| Q-1 | 1 | H | H | CN | CN | H | H | — | CH$_3$ | OCH$_3$ | CH | |
| Q-1 | 1 | H | H | F | F | H | CH$_3$ | — | CH$_3$ | CH$_3$ | CH | |
| Q-1 | 1 | H | H | F | F | H | CH$_3$ | — | OCH$_3$ | CH$_3$ | CH | |
| Q-1 | 1 | H | H | F | F | H | F | — | OCH$_3$ | OCH$_3$ | CH | |
| Q-1 | 1 | H | H | F | F | H | Cl | — | CH$_3$ | CH$_3$ | N | |
| Q-1 | 1 | H | H | F | F | H | Br | — | CH$_3$ | OCH$_3$ | N | |
| Q-1 | 1 | H | H | Cl | Cl | H | CH$_3$ | — | OCH$_3$ | OCH$_3$ | N | |
| Q-1 | 1 | H | H | Cl | Cl | H | CH$_3$ | — | CH$_3$ | OCH$_3$ | CH | |
| Q-1 | 1 | H | H | Cl | Cl | H | Cl | — | OCH$_3$ | OCH$_3$ | CH | |
| Q-1 | 1 | H | H | Cl | Cl | H | F | — | CH$_3$ | OCH$_3$ | N | |
| Q-1 | 1 | H | H | Cl | Cl | H | Br | — | OCH$_3$ | OCH$_3$ | N | |
| Q-1 | 1 | H | H | Br | Br | H | CH$_3$ | — | CH$_3$ | CH$_3$ | CH | |
| Q-1 | 1 | H | H | Br | Br | H | CH$_3$ | — | CH$_3$ | OCH$_3$ | CH | |
| Q-1 | 1 | H | H | Br | Br | H | Cl | — | OCH$_3$ | OCH$_3$ | CH | |
| Q-1 | 1 | H | H | Br | Br | H | Cl | — | CH$_3$ | CH$_3$ | N | |
| Q-1 | 1 | H | H | Br | Br | Cl | H | — | CH$_3$ | OCH$_3$ | N | |
| Q-1 | 1 | H | H | Br | Br | H | F | — | OCH$_3$ | OCH$_3$ | N | |
| Q-1 | 1 | H | H | Br | Br | H | Br | — | Cl | OCH$_3$ | CH | |
| Q-1 | 1 | H | H | CN | CN | H | CH$_3$ | — | CH$_3$ | OCH$_3$ | CH | |
| Q-1 | 1 | H | H | CN | CN | H | CH$_3$ | — | OCH$_3$ | OCH$_3$ | CH | |
| Q-1 | 1 | H | H | CN | CN | H | F | — | CH$_3$ | OCH$_3$ | N | |
| Q-1 | 1 | H | H | CH$_3$ | CH$_3$ | H | CH$_3$ | — | OCH$_3$ | OCH$_3$ | N | |
| Q-1 | 1 | H | H | CH$_3$ | CH$_3$ | H | CH$_3$ | — | CH$_3$ | CH$_3$ | CH | |
| Q-1 | 1 | H | H | CH$_3$ | CH$_3$ | H | CH$_3$ | — | CH$_3$ | OCH$_3$ | CH | |
| Q-1 | 1 | H | H | CH$_3$ | CH$_3$ | CH$_3$ | H | — | OCH$_3$ | OCH$_3$ | CH | |

TABLE IB

General Structure I (wherein R$_{12}$ is OH; R$_{13}$ is CH$_3$)

| Q | n | R | R$_1$ | R$_7$ | R$_8$ | R$_9$ | R$_{10}$ | R$_{11}$ | X | Y | Z | m.p. (°C.) |
|---|---|---|---|---|---|---|---|---|---|---|---|---|
| Q-1 | 1 | H | H | H | H | H | H | — | CH$_3$ | CH$_3$ | CH | |
| Q-1 | 1 | H | H | H | H | H | H | — | CH$_3$ | OCH$_3$ | CH | |
| Q-1 | 1 | H | H | H | H | H | H | — | OCH$_3$ | OCH$_3$ | CH | |
| Q-1 | 1 | H | H | H | H | H | H | — | CH$_3$ | CH$_3$ | N | |
| Q-1 | 1 | H | H | H | H | H | H | — | CH$_3$ | OCH$_3$ | N | |
| Q-1 | 1 | H | H | H | H | H | H | — | OCH$_3$ | OCH$_3$ | N | |
| Q-1 | 1 | H | H | H | H | H | H | — | Cl | OCH$_3$ | CH | |
| Q-1 | 1 | H | H | H | F | H | H | — | CH$_3$ | CH$_3$ | CH | |
| Q-1 | 1 | H | H | H | F | H | H | — | CH$_3$ | CH$_3$ | N | |
| Q-1 | 1 | H | H | H | F | H | H | — | CH$_3$ | OCH$_3$ | CH | |
| Q-1 | 1 | H | H | H | Cl | H | H | — | OCH$_3$ | OCH$_3$ | CH | |
| Q-1 | 1 | H | H | H | Cl | H | H | — | CH$_3$ | CH$_3$ | N | |
| Q-1 | 1 | H | H | Cl | H | H | H | — | CH$_3$ | OCH$_3$ | CH | |
| Q-1 | 1 | H | H | Cl | H | H | H | — | CH$_3$ | OCH$_3$ | N | |
| Q-1 | 1 | H | H | H | Br | H | H | — | CH$_3$ | CH$_3$ | CH | |
| Q-1 | 1 | H | H | Br | H | H | H | — | CH$_3$ | OCH$_3$ | CH | |
| Q-1 | 1 | H | H | Br | H | H | H | — | OCH$_3$ | OCH$_3$ | CH | |
| Q-1 | 1 | H | H | H | I | H | H | — | CH$_3$ | CH$_3$ | N | |
| Q-1 | 1 | H | H | I | H | H | H | — | CH$_3$ | OCH$_3$ | N | |
| Q-1 | 1 | H | H | H | CN | H | H | — | OCH$_3$ | OCH$_3$ | N | |
| Q-1 | 1 | H | H | CN | H | H | H | — | OCH$_3$ | OCH$_3$ | CH | |
| Q-1 | 1 | H | H | H | CH$_3$ | H | H | — | CH$_3$ | CH$_3$ | CH | |

TABLE IC

General Structure I (wherein R$_{12}$ is OCH$_3$; R$_{13}$ is H)

| Q | n | R | R$_1$ | R$_7$ | R$_8$ | R$_9$ | R$_{10}$ | R$_{11}$ | X | Y | Z | m.p. (°C.) |
|---|---|---|---|---|---|---|---|---|---|---|---|---|
| Q-1 | 1 | H | H | H | H | H | H | — | CH$_3$ | CH$_3$ | CH | |
| Q-1 | 1 | H | H | H | H | H | H | — | CH$_3$ | OCH$_3$ | CH | |
| Q-1 | 1 | H | H | H | H | H | H | — | OCH$_3$ | OCH$_3$ | CH | |
| Q-1 | 1 | H | H | H | H | H | H | — | CH$_3$ | CH$_3$ | N | |
| Q-1 | 1 | H | H | H | H | H | H | — | CH$_3$ | OCH$_3$ | N | |
| Q-1 | 1 | H | H | H | H | H | H | — | OCH$_3$ | OCH$_3$ | N | |
| Q-1 | 1 | H | H | H | H | H | H | — | Cl | OCH$_3$ | CH | |
| Q-1 | 1 | H | H | H | F | H | H | — | CH$_3$ | CH$_3$ | CH | |
| Q-1 | 1 | H | H | H | F | H | H | — | CH$_3$ | CH$_3$ | N | |
| Q-1 | 1 | H | H | H | F | H | H | — | CH$_3$ | OCH$_3$ | CH | |
| Q-1 | 1 | H | H | H | Cl | H | H | — | OCH$_3$ | OCH$_3$ | CH | |
| Q-1 | 1 | H | H | H | Cl | H | H | — | CH$_3$ | CH$_3$ | N | |
| Q-1 | 1 | H | H | Cl | H | H | H | — | CH$_3$ | OCH$_3$ | CH | |
| Q-1 | 1 | H | H | Cl | H | H | H | — | CH$_3$ | OCH$_3$ | N | |
| Q-1 | 1 | H | H | H | Br | H | H | — | CH$_3$ | CH$_3$ | CH | |
| Q-1 | 1 | H | H | H | Br | H | H | — | CH$_3$ | OCH$_3$ | CH | |

TABLE IC-continued

General Structure I (wherein $R_{12}$ is $OCH_3$; $R_{13}$ is H)

| Q | n | R | $R_1$ | $R_7$ | $R_8$ | $R_9$ | $R_{10}$ | $R_{11}$ | X | Y | Z | m.p. (°C.) |
|---|---|---|---|---|---|---|---|---|---|---|---|---|
| Q-1 | 1 | H | H | Br | H | H | H | — | $OCH_3$ | $OCH_3$ | CH | |
| Q-1 | 1 | H | H | H | I | H | H | — | $CH_3$ | $CH_3$ | N | |
| Q-1 | 1 | H | H | I | H | H | H | — | $CH_3$ | $OCH_3$ | N | |
| Q-1 | 1 | H | H | H | CN | H | H | — | $OCH_3$ | $OCH_3$ | N | |
| Q-1 | 1 | H | H | CN | H | H | H | — | $OCH_3$ | $OCH_3$ | CH | |
| Q-1 | 1 | H | H | H | $CH_3$ | H | H | — | $CH_3$ | $CH_3$ | CH | |

TABLE ID

General Structure I (wherein $R_{12}$ is OH; $R_{13}$ is $CH_3$)

| Q | n | R | $R_1$ | $R_7$ | $R_8$ | X | Y | Z | m.p. (°C.) |
|---|---|---|---|---|---|---|---|---|---|
| Q-4 | 1 | H | H | H | H | $CH_3$ | $CH_3$ | CH | |
| Q-4 | 1 | H | H | H | H | $CH_3$ | $OCH_3$ | CH | |
| Q-4 | 1 | H | H | H | H | $OCH_3$ | $OCH_3$ | CH | |
| Q-4 | 1 | H | H | H | H | $CH_3$ | $CH_3$ | N | |
| Q-4 | 1 | H | H | H | H | $CH_3$ | $OCH_3$ | N | |
| Q-4 | 1 | H | H | H | H | $OCH_3$ | $OCH_3$ | N | |
| Q-4 | 1 | H | H | H | H | Cl | $OCH_3$ | CH | |
| Q-4 | 1 | H | H | H | $CH_3$ | $CH_3$ | $OCH_3$ | CH | |
| Q-4 | 1 | H | H | H | $CH_3$ | $OCH_3$ | $OCH_3$ | CH | |
| Q-4 | 1 | H | H | H | $CH_3$ | $OCH_3$ | $OCH_3$ | N | |
| Q-4 | 1 | H | H | H | $CH_3$ | $CH_3$ | $OCH_3$ | CH | |
| Q-4 | 1 | H | H | H | Cl | $CH_3$ | $OCH_3$ | CH | |
| Q-4 | 1 | H | H | H | Cl | $OCH_3$ | $CH_3$ | N | |
| Q-4 | 1 | H | H | H | Cl | $OCH_3$ | $OCH_3$ | CH | |
| Q-4 | 1 | H | H | H | Cl | Cl | $OCH_3$ | CH | |
| Q-4 | 1 | H | H | H | F | $CH_3$ | $CH_3$ | N | |
| Q-4 | 1 | H | H | H | F | $CH_3$ | $CH_3$ | CH | |
| Q-4 | 1 | H | H | H | F | $OCH_3$ | $CH_3$ | CH | |
| Q-4 | 1 | H | H | H | F | $OCH_3$ | $OCH_3$ | CH | |
| Q-4 | 1 | H | H | H | F | $CH_3$ | $OCH_3$ | N | |
| Q-4 | 1 | H | H | H | F | Cl | $OCH_3$ | CH | |
| Q-4 | 1 | H | H | H | CN | $CH_3$ | $OCH_3$ | N | |
| Q-4 | 1 | H | H | H | CN | $OCH_3$ | $OCH_3$ | CH | |
| Q-4 | 1 | H | H | H | $OCH_3$ | $CH_3$ | $OCH_3$ | N | |
| Q-4 | 1 | H | H | H | $OCH_3$ | $OCH_3$ | $CH_3$ | CH | |
| Q-4 | 1 | H | H | H | $OCH_3$ | $OCH_3$ | $OCH_3$ | N | |
| Q-4 | 1 | H | H | H | $CO_2CH_3$ | $CH_3$ | $CH_3$ | N | |
| Q-4 | 1 | H | H | H | $CO_2CH_3$ | $OCH_3$ | $CH_3$ | CH | |
| Q-4 | 1 | H | H | H | $CO_2CH_3$ | $OCH_3$ | $OCH_3$ | CH | |
| Q-4 | 1 | H | H | H | $CO_2CH_3$ | $CH_3$ | $OCH_3$ | N | |
| Q-4 | 1 | H | H | H | $CO_2CH_3$ | $CH_3$ | $CH_3$ | CH | |
| Q-4 | 1 | H | H | H | $CO_2CH_3$ | $OCH_3$ | $OCH_3$ | N | |
| Q-4 | 1 | H | H | H | $CO_2CH_3$ | Cl | $OCH_3$ | CH | |

TABLE IE

General Structure I (wherein $R_{12}$ is OH; $R_{13}$ is $CH_3$)

| Q | n | R | $R_1$ | $R_7$ | $R_8$ | X | Y | Z | m.p. (°C.) |
|---|---|---|---|---|---|---|---|---|---|
| Q-4 | 1 | H | H | H | H | $CH_3$ | $CH_3$ | CH | |
| Q-4 | 1 | H | H | H | H | $CH_3$ | OCH | CH | |
| Q-4 | 1 | H | H | H | H | $OCH_3$ | $OCH_3$ | CH | |
| Q-4 | 1 | H | H | H | H | $CH_3$ | $CH_3$ | N | |
| Q-4 | 1 | H | H | H | H | $CH_3$ | $OCH_3$ | N | |
| Q-4 | 1 | H | H | H | H | $OCH_3$ | $OCH_3$ | N | |
| Q-4 | 1 | H | H | H | H | Cl | $OCH_3$ | CH | |
| Q-4 | 1 | H | H | H | $CH_3$ | $CH_3$ | $OCH_3$ | CH | |
| Q-4 | 1 | H | H | H | $CH_3$ | $OCH_3$ | $OCH_3$ | CH | |
| Q-4 | 1 | H | H | H | $CH_3$ | $OCH_3$ | $OCH_3$ | N | |
| Q-4 | 1 | H | H | H | $CH_3$ | $CH_3$ | $OCH_3$ | CH | |
| Q-4 | 1 | H | H | H | Cl | $CH_3$ | $OCH_3$ | CH | |
| Q-4 | 1 | H | H | H | Cl | $OCH_3$ | $CH_3$ | N | |
| Q-4 | 1 | H | H | H | Cl | $OCH_3$ | $OCH_3$ | CH | |
| Q-4 | 1 | H | H | H | Cl | Cl | $OCH_3$ | CH | |
| Q-4 | 1 | H | H | H | F | $CH_3$ | $CH_3$ | N | |
| Q-4 | 1 | H | H | H | F | $CH_3$ | $CH_3$ | CH | |
| Q-4 | 1 | H | H | H | F | $OCH_3$ | $CH_3$ | CH | |
| Q-4 | 1 | H | H | H | F | $OCH_3$ | $OCH_3$ | CH | |
| Q-4 | 1 | H | H | H | F | $CH_3$ | $OCH_3$ | N | |
| Q-4 | 1 | H | H | H | F | Cl | $OCH_3$ | CH | |
| Q-4 | 1 | H | H | H | CN | $CH_3$ | $OCH_3$ | N | |
| Q-4 | 1 | H | H | H | CN | $OCH_3$ | $OCH_3$ | CH | |
| Q-4 | 1 | H | H | H | $OCH_3$ | $CH_3$ | $OCH_3$ | N | |
| Q-4 | 1 | H | H | H | $OCH_3$ | $OCH_3$ | $OCH_3$ | CH | |
| Q-4 | 1 | H | H | H | $CO_2CH_3$ | $CH_3$ | $CH_3$ | N | |
| Q-4 | 1 | H | H | H | $COCH_3$ | $OCH_3$ | $CH_3$ | CH | |
| Q-4 | 1 | H | H | H | $CO_2CH_3$ | $OCH_3$ | $OCH_3$ | CH | |
| Q-4 | 1 | H | H | H | $CO_2CH_3$ | $CH_3$ | $OCH_3$ | N | |
| Q-4 | 1 | H | H | H | $CO_2CH_3$ | $CH_3$ | $CH_3$ | CH | |
| Q-4 | 1 | H | H | H | $CO_2CH_3$ | $OCH_3$ | $OCH_3$ | N | |
| Q-4 | 1 | H | H | H | $CO_2CH_3$ | Cl | $OCH_3$ | CH | |

TABLE IF

General Structure I (wherein $R_{12}$ is $OCH_3$; $R_{13}$ is H)

| Q | n | R | $R_1$ | $R_7$ | $R_8$ | X | Y | Z | m.p. (°C.) |
|---|---|---|---|---|---|---|---|---|---|
| Q-4 | 1 | H | H | H | H | $CH_3$ | $CH_3$ | CH | |
| Q-4 | 1 | H | H | H | H | $CH_3$ | $OCH_3$ | CH | |
| Q-4 | 1 | H | H | H | H | $OCH_3$ | OCH | CH | |
| Q-4 | 1 | H | H | H | H | $CH_3$ | $CH_3$ | N | |
| Q-4 | 1 | H | H | H | H | $CH_3$ | $OCH_3$ | N | |
| Q-4 | 1 | H | H | H | H | $OCH_3$ | $OCH_3$ | N | |
| Q-4 | 1 | H | H | H | H | Cl | $OCH_3$ | CH | |
| Q-4 | 1 | H | H | H | $CH_3$ | $CH_3$ | $OCH_3$ | CH | |
| Q-4 | 1 | H | H | H | $CH_3$ | $OCH_3$ | $OCH_3$ | CH | |
| Q-4 | 1 | H | H | H | $CH_3$ | $OCH_3$ | $OCH_3$ | N | |
| Q-4 | 1 | H | H | H | $CH_3$ | $CH_3$ | $OCH_3$ | CH | |
| Q-4 | 1 | H | H | H | Cl | $CH_3$ | $OCH_3$ | CH | |
| Q-4 | 1 | H | H | H | Cl | $OCH_3$ | $CH_3$ | N | |
| Q-4 | 1 | H | H | H | Cl | $OCH_3$ | $OCH_3$ | CH | |
| Q-4 | 1 | H | H | H | Cl | Cl | $OCH_3$ | CH | |
| Q-4 | 1 | H | H | H | F | $CH_3$ | $CH_3$ | N | |
| Q-4 | 1 | H | H | H | F | $CH_3$ | $CH_3$ | CH | |
| Q-4 | 1 | H | H | H | F | $OCH_3$ | $CH_3$ | CH | |
| Q-4 | 1 | H | H | H | F | $OCH_3$ | $OCH_3$ | CH | |
| Q-4 | 1 | H | H | H | F | $CH_3$ | $OCH_3$ | N | |
| Q-4 | 1 | H | H | H | F | Cl | $OCH_3$ | CH | |
| Q-4 | 1 | H | H | H | CN | $CH_3$ | $OCH_3$ | N | |
| Q-4 | 1 | H | H | H | CN | $OCH_3$ | $OCH_3$ | CH | |
| Q-4 | 1 | H | H | H | $OCH_3$ | $CH_3$ | $OCH_3$ | N | |
| Q-4 | 1 | H | H | H | $OCH_3$ | $OCH_3$ | $OCH_3$ | CH | |
| Q-4 | 1 | H | H | H | $OCH_3$ | $OCH_3$ | $OCH_3$ | N | |
| Q-4 | 1 | H | H | H | $CO_2CH_3$ | $CH_3$ | $CH_3$ | N | |
| Q-4 | 1 | H | H | H | $CO_2CH_3$ | $OCH_3$ | $CH_3$ | CH | |
| Q-4 | 1 | H | H | H | $CO_2CH_3$ | $OCH_3$ | $OCH_3$ | CH | |
| Q-4 | 1 | H | H | H | $CO_2CH_3$ | $CH_3$ | $OCH_3$ | N | |
| Q-4 | 1 | H | H | H | $CO_2CH_3$ | $CH_3$ | $CH_3$ | CH | |
| Q-4 | 1 | H | H | H | $CO_2CH_3$ | $OCH_3$ | $OCH_3$ | N | |
| Q-4 | 1 | H | H | H | $CO_2CH_3$ | Cl | $OCH_3$ | CH | |

TABLE IG

General Structure I (wherein $R_{12}$ is $OCH_3$; $R_{13}$ is $CH_3$)

| Q | n | R | $R_1$ | $R_7$ | $R_8$ | X | Y | Z | m.p. (°C.) |
|---|---|---|---|---|---|---|---|---|---|
| Q-4 | 1 | H | H | H | H | $CH_3$ | $CH_3$ | CH | |
| Q-4 | 1 | H | H | H | H | $CH_3$ | $OCH_3$ | CH | |
| Q-4 | 1 | H | H | H | H | $OCH_3$ | $OCH_3$ | CH | |
| Q-4 | 1 | H | H | H | H | $CH_3$ | $CH_3$ | N | |
| Q-4 | 1 | H | H | H | H | $CH_3$ | $OCH_3$ | N | |
| Q-4 | 1 | H | H | H | H | $OCH_3$ | $OCH_3$ | N | |
| Q-4 | 1 | H | H | H | H | Cl | $OCH_3$ | CH | |
| Q-4 | 1 | H | H | H | $CH_3$ | $CH_3$ | $OCH_3$ | CH | |
| Q-4 | 1 | H | H | H | $CH_3$ | $OCH_3$ | $OCH_3$ | CH | |

TABLE IG-continued

General Structure I (wherein $R_{12}$ is $OCH_3$; $R_{13}$ is $CH_3$)

| Q | n | R | $R_1$ | $R_7$ | $R_8$ | X | Y | Z | m.p. (°C.) |
|---|---|---|---|---|---|---|---|---|---|
| Q-4 | 1 | H | H | H | $CH_3$ | $OCH_3$ | $OCH_3$ | N | |
| Q-4 | 1 | H | H | H | $CH_3$ | $CH_3$ | $OCH_3$ | CH | |
| Q-4 | 1 | H | H | H | Cl | $CH_3$ | $OCH_3$ | CH | |
| Q-4 | 1 | H | H | H | Cl | $OCH_3$ | $CH_3$ | N | |
| Q-4 | 1 | H | H | H | Cl | $OCH_3$ | $OCH_3$ | CH | |
| Q-4 | 1 | H | H | H | Cl | Cl | $OCH_3$ | CH | |
| Q-4 | 1 | H | H | H | F | $CH_3$ | $CH_3$ | N | |
| Q-4 | 1 | H | H | H | F | $CH_3$ | $CH_3$ | CH | |
| Q-4 | 1 | H | H | H | F | $OCH_3$ | $CH_3$ | CH | |
| Q-4 | 1 | H | H | H | F | $OCH_3$ | $OCH_3$ | CH | |
| Q-4 | 1 | H | H | H | F | $CH_3$ | $OCH_3$ | N | |
| Q-4 | 1 | H | H | H | F | Cl | $OCH_3$ | CH | |
| Q-4 | 1 | H | H | H | CN | $CH_3$ | $OCH_3$ | N | |
| Q-4 | 1 | H | H | H | CN | $OCH_3$ | $OCH_3$ | CH | |
| Q-4 | 1 | H | H | H | $OCH_3$ | $CH_3$ | $OCH_3$ | N | |
| Q-4 | 1 | H | H | H | $OCH_3$ | $OCH_3$ | $OCH_3$ | CH | |
| Q-4 | 1 | H | H | H | $OCH_3$ | $OCH_3$ | $OCH_3$ | N | |
| Q-4 | 1 | H | H | H | $CO_2CH_3$ | $CH_3$ | $CH_3$ | N | |
| Q-4 | 1 | H | H | H | $CO_2CH_3$ | $OCH_3$ | $OCH_3$ | CH | |
| Q-4 | 1 | H | H | H | $CO_2CH_3$ | $CH_3$ | $OCH_3$ | N | |
| Q-4 | 1 | H | H | H | $CO_2CH_3$ | $CH_3$ | $CH_3$ | CH | |
| Q-4 | 1 | H | H | H | $CO_2CH_3$ | $OCH_3$ | $OCH_3$ | N | |
| Q-4 | 1 | H | H | H | $CO_2CH_3$ | Cl | $OCH_3$ | CH | |

TABLE II

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-2 | Q-1 | 0 | H | H | — | | | H | H | H | H | — | $CH_3$ | $CH_3$ | CH | |
| L-2 | Q-1 | 0 | H | H | — | | | H | Cl | H | H | — | $CH_3$ | $OCH_3$ | CH | |
| L-2 | Q-1 | 0 | H | H | — | | | Cl | Cl | H | H | — | $OCH_3$ | $OCH_3$ | CH | |
| L-2 | Q-1 | 0 | H | H | — | | | F | F | H | H | — | $CH_3$ | $CH_3$ | N | |
| L-2 | Q-1 | 0 | H | H | — | | | H | Br | H | H | — | $CH_3$ | $OCH_3$ | N | |
| L-2 | Q-1 | 0 | H | H | — | | | $CH_3$ | H | H | H | — | $OCH_3$ | $OCH_3$ | N | |
| L-2 | Q-1 | 0 | H | H | — | | | H | $OCH_3$ | H | H | — | Cl | $OCH_3$ | CH | |
| L-2 | Q-1 | 0 | H | H | — | | | H | F | H | H | — | $CH_3$ | $OCH_3$ | CH | |
| L-2 | Q-1 | 0 | H | H | — | | | Cl | Br | H | H | — | $OCH_3$ | $OCH_3$ | CH | |
| L-2 | Q-1 | 0 | H | H | — | | | Cl | $CH_3$ | H | H | — | $CH_3$ | $OCH_3$ | N | |
| L-2 | Q-1 | 0 | H | H | — | | | F | $CH_3$ | H | H | — | $OCH_3$ | $OCH_3$ | CH | |
| L-2 | Q-1 | 0 | H | H | — | | | H | Cl | Cl | H | — | $CH_3$ | $CH_3$ | N | |
| L-2 | Q-1 | 0 | H | H | — | | | H | $CH_3$ | F | F | — | $OCH_3$ | $OCH_3$ | CH | |
| L-2 | Q-1 | 0 | H | $CH_3$ | — | | | H | H | H | H | — | Cl | $OCH_3$ | CH | |
| L-2 | Q-1 | 0 | $CH_3$ | H | — | | | H | H | H | H | — | $CH_3$ | $OCH_3$ | N | |
| L-2 | Q-1 | 1 | H | H | — | | | F | F | H | H | — | $OCH_3$ | $OCH_3$ | CH | |
| L-2 | Q-1 | 1 | H | H | — | | | H | H | H | H | — | $OCH_3$ | $OCH_3$ | CH | |
| L-2 | Q-2 | 0 | H | H | — | | | H | H | — | — | H | $CH_3$ | $CH_3$ | CH | |
| L-2 | Q-2 | 0 | H | H | — | | | H | H | — | — | H | $OCH_3$ | $OCH_3$ | CH | |
| L-2 | Q-2 | 0 | H | H | — | | | Cl | H | — | — | H | $CH_3$ | $OCH_3$ | N | |
| L-2 | Q-2 | 0 | H | H | — | | | F | H | — | — | H | Cl | $OCH_3$ | CH | |
| L-2 | Q-2 | 0 | H | H | — | | | H | Br | — | — | H | $OCH_3$ | $OCH_3$ | CH | |
| L-2 | Q-2 | 0 | H | H | — | | | F | F | — | — | H | $OCH_3$ | $OCH_3$ | N | |
| L-2 | Q-2 | 0 | H | H | — | | | Cl | Cl | — | — | H | $CH_3$ | $CH_3$ | CH | |
| L-2 | Q-2 | 0 | H | H | — | | | H | $CH_3$ | — | — | H | $CH_3$ | $OCH_3$ | CH | |
| L-2 | Q-2 | 0 | H | H | — | | | $CH_3$ | $CH_3$ | — | — | H | $OCH_3$ | $OCH_3$ | CH | |
| L-2 | Q-2 | 0 | H | H | — | | | H | $CO_2CH_3$ | — | — | H | $CH_3$ | $CH_3$ | CH | |
| L-2 | Q-2 | 0 | H | H | — | | | H | F | — | — | $CH_3$ | | $OCH_3$ | $OCH_3$ | CH | |
| L-2 | Q-2 | 0 | H | $OCH_3$ | — | | | H | Cl | — | — | H | $OCH_3$ | $CH_3$ | N | |
| L-2 | Q-2 | 0 | $CH_3$ | Cl | — | | | F | $CH_3$ | — | — | $CH_3$ | $CH_3$ | $OCH_3$ | CH | |
| L-2 | Q-2 | 1 | H | H | — | | | H | Cl | — | — | H | $CH_3$ | $OCH_3$ | CH | |
| L-2 | Q-2 | 1 | H | H | — | | | Cl | Cl | — | — | H | $OCH_3$ | $OCH_3$ | N | |
| L-2 | Q-2 | 1 | H | H | — | | | F | $CH_3$ | — | — | H | Cl | $OCH_3$ | CH | |
| L-2 | Q-3 | 0 | H | H | $CH_3$ | | | H | H | — | — | H | $CH_3$ | $CH_3$ | CH | |
| L-2 | Q-3 | 0 | H | H | $CH_3$ | | | H | Cl | — | — | H | $CH_3$ | $OCH_3$ | CH | |
| L-2 | Q-3 | 0 | H | H | $CH_3$ | | | Cl | Cl | — | — | H | $OCH_3$ | $OCH_3$ | CH | |
| L-2 | Q-3 | 0 | H | H | $CH_3$ | | | F | F | — | — | H | $CH_3$ | $CH_3$ | N | |
| L-2 | Q-3 | 0 | H | H | $CH_3$ | | | H | Br | — | — | H | $CH_3$ | $OCH_3$ | N | |
| L-2 | Q-3 | 0 | H | H | $CH_3$ | | | $CH_3$ | H | — | — | H | $OCH_3$ | $OCH_3$ | N | |
| L-2 | Q-3 | 0 | H | H | $CH_3$ | | | H | $OCH_3$ | — | — | H | Cl | $OCH_3$ | CH | |
| L-2 | Q-3 | 0 | H | H | $CH_3$ | | | H | F | — | — | H | $CH_3$ | $OCH_3$ | CH | |
| L-2 | Q-3 | 0 | H | H | $CH_3$ | | | Cl | Br | — | — | H | $OCH_3$ | $OCH_3$ | CH | |
| L-2 | Q-3 | 0 | H | H | $CH_3$ | | | Cl | $CH_3$ | — | — | H | $CH_3$ | $OCH_3$ | N | |
| L-2 | Q-3 | 0 | H | H | $CH_3$ | | | F | $CH_3$ | — | — | $CH_3$ | $OCH_3$ | $OCH_3$ | CH | |
| L-2 | Q-3 | 0 | H | H | $CH_3$ | | | H | Cl | — | — | H | $CH_3$ | $CH_3$ | N | |
| L-2 | Q-3 | 0 | H | H | $CH_3$ | | | H | $CH_3$ | — | — | H | $OCH_3$ | $OCH_3$ | CH | |
| L-2 | Q-3 | 0 | H | $CH_3$ | $CH_3$ | | | H | H | — | — | H | Cl | $OCH_3$ | CH | |
| L-2 | Q-3 | 0 | $CH_3$ | H | $CH_3$ | | | H | H | — | — | H | $CH_3$ | $OCH_3$ | N | |
| L-2 | Q-3 | 1 | H | H | $CH_3$ | | | F | F | — | — | H | $OCH_3$ | $OCH_3$ | CH | |
| L-2 | Q-3 | 1 | H | H | $CH_3$ | | | H | H | — | — | H | $OCH_3$ | $OCH_3$ | CH | |
| L-2 | Q-4 | 0 | H | H | — | | | H | H | — | — | — | $CH_3$ | $CH_3$ | CH | |
| L-2 | Q-4 | 0 | H | H | — | | | H | H | — | — | — | $OCH_3$ | $CH_3$ | CH | |
| L-2 | Q-4 | 0 | H | H | — | | | H | H | — | — | — | $OCH_3$ | $OCH_3$ | CH | |
| L-2 | Q-4 | 0 | H | H | — | | | Cl | H | — | — | — | $CH_3$ | $OCH_3$ | N | |
| L-2 | Q-4 | 0 | H | H | — | | | F | H | — | — | — | Cl | $OCH_3$ | CH | |
| L-2 | Q-4 | 0 | H | H | — | | | H | Br | — | — | — | $OCH_3$ | $OCH_3$ | CH | |
| L-2 | Q-4 | 0 | H | H | — | | | F | F | — | — | — | $OCH_3$ | $OCH_3$ | N | |
| L-2 | Q-4 | 0 | H | H | — | | | Cl | Cl | — | — | — | $CH_3$ | $OCH_3$ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-2 | Q-4 | 0 | H | H | — | | | H | CH$_3$ | — | — | — | CH$_3$ | OCH$_3$ | CH | |
| L-2 | Q-4 | 0 | H | H | — | | | CH$_3$ | CH$_3$ | — | — | — | OCH$_3$ | OCH$_3$ | CH | |
| L-2 | Q-4 | 0 | H | H | — | | | H | CO$_2$CH$_3$ | — | — | — | CH$_3$ | CH$_3$ | CH | |
| L-2 | Q-4 | 0 | H | H | — | | | H | F | — | — | — | OCH$_3$ | OCH$_3$ | CH | |
| L-2 | Q-4 | 0 | H | OCH$_3$ | — | | | H | Cl | — | — | — | OCH$_3$ | CH$_3$ | N | |
| L-2 | Q-4 | 0 | CH$_3$ | Cl | — | | | F | CH$_3$ | — | — | — | CH$_3$ | OCH$_3$ | CH | |
| L-2 | Q-4 | 1 | H | H | — | | | H | Cl | — | — | — | CH$_3$ | OCH$_3$ | CH | |
| L-2 | Q-4 | 1 | H | H | — | | | Cl | Cl | — | — | — | OCH$_3$ | OCH$_3$ | N | |
| L-2 | Q-4 | 1 | H | H | — | | | F | CH$_3$ | — | — | — | Cl | OCH$_3$ | CH | |
| L-2 | Q-5 | 0 | H | H | — | | | H | H | — | — | — | CH$_3$ | CH$_3$ | CH | |
| L-2 | Q-5 | 0 | H | H | — | | | H | Cl | — | — | — | CH$_3$ | OCH$_3$ | CH | |
| L-2 | Q-5 | 0 | H | H | — | | | Cl | Cl | — | — | — | OCH$_3$ | OCH$_3$ | CH | |
| L-2 | Q-5 | 0 | H | H | — | | | F | F | — | — | — | CH$_3$ | CH$_3$ | N | |
| L-2 | Q-5 | 0 | H | H | — | | | H | Br | — | — | — | CH$_3$ | OCH$_3$ | N | |
| L-2 | Q-5 | 0 | H | H | — | | | CH$_3$ | H | — | — | — | OCH$_3$ | OCH$_3$ | N | |
| L-2 | Q-5 | 0 | H | H | — | | | H | OCH$_3$ | — | — | — | Cl | OCH$_3$ | CH | |
| L-2 | Q-5 | 0 | H | H | — | | | H | F | — | — | — | CH$_3$ | OCH$_3$ | CH | |
| L-2 | Q-5 | 0 | H | H | — | | | Cl | Br | — | — | — | OCH$_3$ | OCH$_3$ | CH | |
| L-2 | Q-5 | 0 | H | H | — | | | Cl | CH$_3$ | — | — | — | CH$_3$ | OCH$_3$ | N | |
| L-2 | Q-5 | 0 | H | H | — | | | F | CH$_3$ | — | — | — | OCH$_3$ | OCH$_3$ | CH | |
| L-2 | Q-5 | 0 | H | H | — | | | H | Cl | — | — | — | CH$_3$ | CH$_3$ | N | |
| L-2 | Q-5 | 0 | H | H | — | | | H | CH$_3$ | — | — | — | OCH$_3$ | OCH$_3$ | CH | |
| L-2 | Q-5 | 0 | H | CH$_3$ | — | | | H | H | — | — | — | Cl | OCH$_3$ | CH | |
| L-2 | Q-5 | 0 | CH$_3$ | H | — | | | H | H | — | — | — | CH$_3$ | OCH$_3$ | N | |
| L-2 | Q-5 | 1 | H | H | — | | | F | F | — | — | — | OCH$_3$ | OCH$_3$ | CH | |
| L-2 | Q-5 | 1 | H | H | — | | | H | H | — | — | — | CH$_3$ | CH$_3$ | CH | |
| L-2 | Q-6 | 0 | H | H | — | | | H | H | — | — | — | CH$_3$ | CH$_3$ | CH | |
| L-2 | Q-6 | 0 | H | H | — | | | H | H | — | — | — | OCH$_3$ | CH$_3$ | CH | |
| L-2 | Q-6 | 0 | H | H | — | | | H | H | — | — | — | OCH$_3$ | OCH$_3$ | CH | |
| L-2 | Q-6 | 0 | H | H | — | | | Cl | H | — | — | — | CH$_3$ | OCH$_3$ | N | |
| L-2 | Q-6 | 0 | H | H | — | | | F | H | — | — | — | Cl | OCH$_3$ | CH | |
| L-2 | Q-6 | 0 | H | H | — | | | H | Br | — | — | — | OCH$_3$ | OCH$_3$ | CH | |
| L-2 | Q-6 | 0 | H | H | — | | | F | F | — | — | — | OCH$_3$ | OCH$_3$ | N | |
| L-2 | Q-6 | 0 | H | H | — | | | Cl | Cl | — | — | — | CH$_3$ | OCH$_3$ | CH | |
| L-2 | Q-6 | 0 | H | H | — | | | H | CH$_3$ | — | — | — | CH$_3$ | OCH$_3$ | CH | |
| L-2 | Q-6 | 0 | H | H | — | | | CH$_3$ | CH$_3$ | — | — | — | OCH$_3$ | OCH$_3$ | CH | |
| L-2 | Q-6 | 0 | H | H | — | | | H | CO$_2$CH$_3$ | — | — | — | CH$_3$ | CH$_3$ | CH | |
| L-2 | Q-6 | 0 | H | H | — | | | H | F | — | — | — | OCH$_3$ | OCH$_3$ | CH | |
| L-2 | Q-6 | 0 | H | OCH$_3$ | — | | | H | Cl | — | — | — | OCH$_3$ | CH$_3$ | N | |
| L-2 | Q-6 | 0 | CH$_3$ | Cl | — | | | F | CH$_3$ | — | — | — | CH$_3$ | OCH$_3$ | CH | |
| L-2 | Q-6 | 1 | H | H | — | | | H | Cl | — | — | — | CH$_3$ | OCH$_3$ | CH | |
| L-2 | Q-6 | 1 | H | H | — | | | Cl | Cl | — | — | — | OCH$_3$ | OCH$_3$ | N | |
| L-2 | Q-6 | 1 | H | H | — | | | F | CH$_3$ | — | — | — | Cl | OCH$_3$ | CH | |
| L-2 | Q-7 | 0 | H | H | — | | | H | H | — | — | — | CH$_3$ | CH$_3$ | CH | |
| L-2 | Q-7 | 0 | H | H | — | | | H | Cl | — | — | — | CH$_3$ | OCH$_3$ | CH | |
| L-2 | Q-7 | 0 | H | H | — | | | Cl | Cl | — | — | — | OCH$_3$ | OCH$_3$ | CH | |
| L-2 | Q-7 | 0 | H | H | — | | | F | F | — | — | — | CH$_3$ | CH$_3$ | N | |
| L-2 | Q-7 | 0 | H | H | — | | | H | Br | — | — | — | CH$_3$ | OCH$_3$ | N | |
| L-2 | Q-7 | 0 | H | H | — | | | CH$_3$ | H | — | — | — | OCH$_3$ | OCH$_3$ | N | |
| L-2 | Q-7 | 0 | H | H | — | | | H | OCH$_3$ | — | — | — | Cl | OCH$_3$ | CH | |
| L-2 | Q-7 | 0 | H | H | — | | | H | F | — | — | — | CH$_3$ | OCH$_3$ | CH | |
| L-2 | Q-7 | 0 | H | H | — | | | Cl | Br | — | — | — | OCH$_3$ | OCH$_3$ | CH | |
| L-2 | Q-7 | 0 | H | H | — | | | Cl | CH$_3$ | — | — | — | CH$_3$ | OCH$_3$ | N | |
| L-2 | Q-7 | 0 | H | H | — | | | F | CH$_3$ | — | — | — | OCH$_3$ | OCH$_3$ | CH | |
| L-2 | Q-7 | 0 | H | H | — | | | H | Cl | — | — | — | CH$_3$ | CH$_3$ | N | |
| L-2 | Q-7 | 0 | H | H | — | | | H | CH$_3$ | — | — | — | OCH$_3$ | OCH$_3$ | CH | |
| L-2 | Q-7 | 0 | H | CH$_3$ | — | | | H | H | — | — | — | Cl | OCH$_3$ | CH | |
| L-2 | Q-7 | 0 | CH$_3$ | H | — | | | H | H | — | — | — | CH$_3$ | OCH$_3$ | N | |
| L-2 | Q-7 | 1 | H | H | — | | | F | F | — | — | — | OCH$_3$ | OCH$_3$ | CH | |
| L-2 | Q-7 | 1 | H | H | — | | | H | H | — | — | — | CH$_3$ | CH$_3$ | CH | |
| L-2 | Q-8 | 0 | H | H | — | | | H | H | — | — | — | OCH$_3$ | CH$_3$ | CH | |
| L-2 | Q-8 | 0 | H | H | — | | | H | H | — | — | — | OCH$_3$ | OCH$_3$ | CH | |
| L-2 | Q-8 | 0 | H | H | — | | | Cl | H | — | — | — | CH$_3$ | OCH$_3$ | N | |
| L-2 | Q-8 | 0 | H | H | — | | | F | H | — | — | — | Cl | OCH$_3$ | CH | |
| L-2 | Q-8 | 0 | H | H | — | | | H | Br | — | — | — | OCH$_3$ | OCH$_3$ | CH | |
| L-2 | Q-8 | 0 | H | H | — | | | F | F | — | — | — | OCH$_3$ | OCH$_3$ | N | |
| L-2 | Q-8 | 0 | H | H | — | | | Cl | Cl | — | — | — | CH$_3$ | OCH$_3$ | CH | |
| L-2 | Q-8 | 0 | H | H | — | | | H | CH$_3$ | — | — | — | CH$_3$ | OCH$_3$ | CH | |
| L-2 | Q-8 | 0 | H | H | — | | | CH$_3$ | CH$_3$ | — | — | — | OCH$_3$ | OCH$_3$ | CH | |
| L-2 | Q-8 | 0 | H | H | — | | | H | CO$_2$CH$_3$ | — | — | — | CH$_3$ | CH$_3$ | CH | |
| L-2 | Q-8 | 0 | H | H | — | | | H | F | — | — | — | OCH$_3$ | OCH$_3$ | CH | |
| L-2 | Q-8 | 0 | H | OCH$_3$ | — | | | H | Cl | — | — | — | OCH$_3$ | CH$_3$ | N | |
| L-2 | Q-8 | 0 | CH$_3$ | Cl | — | | | F | CH$_3$ | — | — | — | CH$_3$ | OCH$_3$ | CH | |
| L-2 | Q-8 | 1 | H | H | — | | | H | Cl | — | — | — | CH$_3$ | OCH$_3$ | CH | |
| L-2 | Q-8 | 1 | H | H | — | | | Cl | Cl | — | — | — | OCH$_3$ | OCH$_3$ | N | |
| L-2 | Q-8 | 1 | H | H | — | | | F | CH$_3$ | — | — | — | Cl | OCH$_3$ | CH | |
| L-2 | Q-9 | 0 | H | H | | CH$_3$ | | H | H | — | — | — | CH$_3$ | CH$_3$ | CH | |
| L-2 | Q-9 | 0 | H | H | | CH$_3$ | | H | Cl | — | — | — | CH$_3$ | OCH$_3$ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-2 | Q-9 | 0 | H | H | | $CH_3$ | | Cl | Cl | — | — | — | $OCH_3$ | $OCH_3$ | CH | |
| L-2 | Q-9 | 0 | H | H | | $CH_3$ | | F | F | — | — | — | $CH_3$ | $CH_3$ | N | |
| L-2 | Q-9 | 0 | H | H | | $CH_3$ | | H | Br | — | — | — | $CH_3$ | $OCH_3$ | N | |
| L-2 | Q-9 | 0 | H | H | | $CH_3$ | | $CH_3$ | H | — | — | — | $OCH_3$ | $OCH_3$ | N | |
| L-2 | Q-9 | 0 | H | H | | $CH_3$ | | H | $OCH_3$ | — | — | — | Cl | $OCH_3$ | CH | |
| L-2 | Q-9 | 0 | H | H | | $CH_3$ | | H | F | — | — | — | $CH_3$ | $OCH_3$ | CH | |
| L-2 | Q-9 | 0 | H | H | | $CH_3$ | | Cl | Br | — | — | — | $OCH_3$ | $OCH_3$ | CH | |
| L-2 | Q-9 | 0 | H | H | | $CH_3$ | | Cl | $CH_3$ | — | — | — | $CH_3$ | $OCH_3$ | N | |
| L-2 | Q-9 | 0 | H | H | | $CH_3$ | | F | $CH_3$ | — | — | — | $OCH_3$ | $OCH_3$ | CH | |
| L-2 | Q-9 | 0 | H | H | | $CH_3$ | | H | Cl | — | — | — | $CH_3$ | $CH_3$ | N | |
| L-2 | Q-9 | 0 | H | H | | $CH_3$ | | H | $CH_3$ | — | — | — | $OCH_3$ | $OCH_3$ | CH | |
| L-2 | Q-9 | 0 | H | $CH_3$ | | $CH_3$ | | H | H | — | — | — | Cl | $OCH_3$ | CH | |
| L-2 | Q-9 | 0 | $CH_3$ | H | | $CH_3$ | | H | H | — | — | — | $CH_3$ | $OCH_3$ | N | |
| L-2 | Q-9 | 1 | H | H | | $CH_3$ | | F | F | — | — | — | $OCH_3$ | $OCH_3$ | CH | |
| L-2 | Q-9 | 1 | H | H | | $CH_3$ | | H | H | — | — | — | $OCH_3$ | $OCH_3$ | CH | |
| L-2 | Q-10 | 0 | H | H | | $CH_3$ | | H | H | — | — | — | $CH_3$ | $CH_3$ | CH | |
| L-2 | Q-10 | 0 | H | H | | $CH_3$ | | H | H | — | — | — | $OCH_3$ | $CH_3$ | CH | |
| L-2 | Q-10 | 0 | H | H | | $CH_3$ | | Cl | H | — | — | — | $CH_3$ | $OCH_3$ | N | |
| L-2 | Q-10 | 0 | H | H | | $CH_3$ | | F | H | — | — | — | Cl | $OCH_3$ | CH | |
| L-2 | Q-10 | 0 | H | H | | $CH_3$ | | H | Br | — | — | — | $OCH_3$ | $OCH_3$ | CH | |
| L-2 | Q-10 | 0 | H | H | | $CH_3$ | | F | F | — | — | — | $OCH_3$ | $OCH_3$ | N | |
| L-2 | Q-10 | 0 | H | H | | $CH_3$ | | Cl | Cl | — | — | — | $CH_3$ | $OCH_3$ | CH | |
| L-2 | Q-10 | 0 | H | H | | | | $CH_3$ | H | $CH_3$ | — | — | — | $CH_3$ | $OCH_3$ | CH | |
| L-2 | Q-10 | 0 | H | H | | | | $CH_3$ | $CH_3$ | $CH_3$ | — | — | — | $OCH_3$ | $OCH_3$ | CH | |
| L-2 | Q-10 | 0 | H | H | | | | $CH_3$ | H | $CO_2CH_3$ | — | — | — | $CH_3$ | $CH_3$ | CH | |
| L-2 | Q-10 | 0 | H | H | | | | $CH_3$ | H | F | — | — | — | $OCH_3$ | $OCH_3$ | CH | |
| L-2 | Q-10 | 0 | H | $OCH_3$ | | | | $CH_3$ | H | Cl | — | — | — | $OCH_3$ | $CH_3$ | N | |
| L-2 | Q-10 | 0 | $CH_3$ | Cl | | | | $CH_3$ | F | $CH_3$ | — | — | — | $CH_3$ | $OCH_3$ | CH | |
| L-2 | Q-10 | 1 | H | H | | | | $CH_3$ | H | Cl | — | — | — | $CH_3$ | $OCH_3$ | CH | |
| L-2 | Q-10 | 1 | H | H | | | | $CH_3$ | Cl | Cl | — | — | — | $OCH_3$ | $OCH_3$ | N | |
| L-2 | Q-10 | 1 | H | H | | | | $CH_3$ | F | $CH_3$ | — | — | — | Cl | $OCH_3$ | CH | |
| L-3 | Q-1 | 0 | H | H | | | | $CH_3$ | H | H | H | H | — | $CH_3$ | $CH_3$ | CH | |
| L-3 | Q-1 | 0 | H | H | | | | $CH_3$ | Cl | Cl | H | H | — | $OCH_3$ | $OCH_3$ | CH | |
| L-3 | Q-1 | 0 | H | H | | | | $CH_3$ | F | F | H | H | — | $CH_3$ | $CH_3$ | N | |
| L-3 | Q-1 | 0 | H | H | | | | $CH_3$ | H | Br | H | H | — | $CH_3$ | $OCH_3$ | CH | |
| L-3 | Q-1 | 0 | H | H | | | | $CH_3$ | $CH_3$ | H | H | H | — | $OCH_3$ | $OCH_3$ | N | |
| L-3 | Q-1 | 0 | H | H | | | | $CH_3$ | H | $OCH_3$ | H | H | — | Cl | $OCH_3$ | CH | |
| L-3 | Q-1 | 0 | H | H | | | | $CH_3$ | H | F | H | H | — | $CH_3$ | $OCH_3$ | CH | |
| L-3 | Q-1 | 0 | H | H | | | | $CH_3$ | Cl | Br | H | H | — | $OCH_3$ | $OCH_3$ | CH | |
| L-3 | Q-1 | 0 | H | H | | | | $CH_3$ | Cl | $CH_3$ | H | H | — | $CH_3$ | $CH_3$ | N | |
| L-3 | Q-1 | 0 | H | H | | | | $CH_3$ | F | $CH_3$ | H | H | — | $OCH_3$ | $OCH_3$ | CH | |
| L-3 | Q-1 | 0 | H | H | | | | $CH_3$ | H | Cl | Cl | H | — | $CH_3$ | $CH_3$ | N | |
| L-3 | Q-1 | 0 | H | H | | | | $CH_3$ | H | $CH_3$ | F | F | — | $OCH_3$ | $OCH_3$ | CH | |
| L-3 | Q-1 | 0 | H | $CH_3$ | | | | $CH_3$ | H | H | H | H | — | Cl | $OCH_3$ | CH | |
| L-3 | Q-1 | 0 | $CH_3$ | H | | | | $CH_3$ | H | H | H | H | — | $CH_3$ | $OCH_3$ | N | |
| L-3 | Q-1 | 1 | H | H | | | | $CH_3$ | F | F | H | H | — | $OCH_3$ | $OCH_3$ | CH | |
| L-3 | Q-1 | 1 | H | H | | | | $CH_3$ | H | H | H | H | — | $OCH_3$ | $OCH_3$ | CH | |
| L-3 | Q-2 | 0 | H | H | | | | $CH_3$ | H | H | — | — | H | $CH_3$ | $CH_3$ | CH | |
| L-3 | Q-2 | 0 | H | H | | | | $CH_3$ | H | H | — | — | H | $OCH_3$ | $CH_3$ | CH | |
| L-3 | Q-2 | 0 | H | H | | | | $CH_3$ | H | H | — | — | H | $OCH_3$ | $OCH_3$ | CH | |
| L-3 | Q-2 | 0 | H | H | | | | $CH_3$ | Cl | H | — | — | H | $CH_3$ | $OCH_3$ | N | |
| L-3 | Q-2 | 0 | H | H | | | | $CH_3$ | F | H | — | — | H | Cl | $OCH_3$ | CH | |
| L-3 | Q-2 | 0 | H | H | | | | $CH_3$ | H | Br | — | — | H | $OCH_3$ | $OCH_3$ | CH | |
| L-3 | Q-2 | 0 | H | H | $CH_3$ | — | | F | F | — | — | H | $OCH_3$ | $OCH_3$ | N | |
| L-3 | Q-2 | 0 | H | H | $CH_3$ | — | | Cl | Cl | — | — | H | $CH_3$ | $OCH_3$ | CH | |
| L-3 | Q-2 | 0 | H | H | $CH_3$ | — | | H | $CH_3$ | — | — | H | $CH_3$ | $OCH_3$ | CH | |
| L-3 | Q-2 | 0 | H | H | $CH_3$ | — | | $CH_3$ | $CH_3$ | — | — | H | $OCH_3$ | $OCH_3$ | CH | |
| L-3 | Q-2 | 0 | H | H | $CH_3$ | — | | H | $CO_2CH_3$ | — | — | H | $CH_3$ | $CH_3$ | CH | |
| L-3 | Q-2 | 0 | H | H | $CH_3$ | — | | H | F | — | — | $CH_3$ | $OCH_3$ | $OCH_3$ | CH | |
| L-3 | Q-2 | 0 | H | $OCH_3$ | $CH_3$ | — | | H | Cl | — | — | H | $OCH_3$ | $OCH_3$ | N | |
| L-3 | Q-2 | 0 | $CH_3$ | Cl | $CH_3$ | — | | F | $CH_3$ | — | — | $CH_3$ | $CH_3$ | $OCH_3$ | CH | |
| L-3 | Q-2 | 1 | H | H | $CH_3$ | — | | H | Cl | — | — | H | $CH_3$ | $OCH_3$ | CH | |
| L-3 | Q-2 | 1 | H | H | $CH_3$ | — | | Cl | Cl | — | — | H | $OCH_3$ | $OCH_3$ | N | |
| L-3 | Q-2 | 1 | H | H | $CH_3$ | — | | F | $CH_3$ | — | — | H | Cl | $OCH_3$ | CH | |
| L-3 | Q-3 | 0 | H | H | $CH_3$ | $CH_3$ | | H | H | — | — | H | $CH_3$ | $CH_3$ | CH | |
| L-3 | Q-3 | 0 | H | H | $CH_3$ | $CH_3$ | | H | Cl | — | — | H | $CH_3$ | $OCH_3$ | CH | |
| L-3 | Q-3 | 0 | H | H | $CH_3$ | $CH_3$ | | Cl | Cl | — | — | H | $OCH_3$ | $OCH_3$ | CH | |
| L-3 | Q-3 | 0 | H | H | $CH_3$ | $CH_3$ | | F | F | — | — | H | $CH_3$ | $CH_3$ | N | |
| L-3 | Q-3 | 0 | H | H | $CH_3$ | $CH_3$ | | H | Br | — | — | H | $CH_3$ | $OCH_3$ | N | |
| L-3 | Q-3 | 0 | H | H | $CH_3$ | $CH_3$ | | $CH_3$ | H | — | — | H | $OCH_3$ | $OCH_3$ | N | |
| L-3 | Q-3 | 0 | H | H | $CH_3$ | $CH_3$ | | H | $OCH_3$ | — | — | H | Cl | $OCH_3$ | CH | |
| L-3 | Q-3 | 0 | H | H | $CH_3$ | $CH_3$ | | H | F | — | — | H | $CH_3$ | $OCH_3$ | CH | |
| L-3 | Q-3 | 0 | H | H | $CH_3$ | $CH_3$ | | Cl | Br | — | — | H | $OCH_3$ | $OCH_3$ | CH | |
| L-3 | Q-3 | 0 | H | H | $CH_3$ | $CH_3$ | | Cl | $CH_3$ | — | — | H | $CH_3$ | $CH_3$ | N | |
| L-3 | Q-3 | 0 | H | H | $CH_3$ | $CH_3$ | | F | $CH_3$ | — | — | $CH_3$ | $OCH_3$ | $OCH_3$ | CH | |
| L-3 | Q-3 | 0 | H | H | $CH_3$ | $CH_2CH_3$ | | H | Cl | — | — | H | $CH_3$ | $CH_3$ | N | |
| L-3 | Q-3 | 0 | H | H | $CH_3$ | $CH_3$ | | H | $CH_3$ | — | — | H | $OCH_3$ | $OCH_3$ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-3 | Q-3 | 0 | H | $CH_3$ | $CH_3$ | $CH_3$ | | H | H | — | | H | Cl | $OCH_3$ | CH | |
| L-3 | Q-3 | 0 | $CH_3$ | H | $CH_3$ | $CH_3$ | | H | H | — | | H | $CH_3$ | $OCH_3$ | N | |
| L-3 | Q-3 | 1 | H | H | $CH_3$ | $CH_3$ | | F | F | — | | H | $OCH_3$ | $OCH_3$ | CH | |
| L-3 | Q-3 | 1 | H | H | $CH_3$ | $CH_3$ | | H | H | — | | H | $OCH_3$ | $OCH_3$ | CH | |
| L-3 | Q-4 | 0 | H | H | $CH_3$ | — | | H | H | — | — | | $CH_3$ | $CH_3$ | CH | |
| L-3 | Q-4 | 0 | H | H | $CH_3$ | — | | H | H | — | — | | $OCH_3$ | $CH_3$ | CH | |
| L-3 | Q-4 | 0 | H | H | $CH_3$ | — | | H | H | — | — | | $OCH_3$ | $OCH_3$ | CH | |
| L-3 | Q-4 | 0 | H | H | $CH_3$ | — | | Cl | H | — | — | | $CH_3$ | $OCH_3$ | N | |
| L-3 | Q-4 | 0 | H | H | $CH_3$ | | | F | H | — | — | | Cl | $OCH_3$ | CH | |
| L-3 | Q-4 | 0 | H | H | $CH_3$ | | | H | Br | — | — | | $OCH_3$ | $OCH_3$ | CH | |
| L-3 | Q-4 | 0 | H | H | $CH_3$ | | | F | F | — | — | | $OCH_3$ | $OCH_3$ | N | |
| L-3 | Q-4 | 0 | H | H | $CH_3$ | | | Cl | Cl | — | — | | $CH_3$ | $OCH_3$ | CH | |
| L-3 | Q-4 | 0 | H | H | $CH_3$ | | | H | $CH_3$ | — | — | | $CH_3$ | $OCH_3$ | CH | |
| L-3 | Q-4 | 0 | H | H | $CH_3$ | | | $CH_3$ | $CH_3$ | — | — | | $OCH_3$ | $OCH_3$ | CH | |
| L-3 | Q-4 | 0 | H | H | $CH_3$ | | | H | $CO_2CH_3$ | — | — | | $CH_3$ | $CH_3$ | CH | |
| L-3 | Q-4 | 0 | H | H | $CH_3$ | | | H | F | — | — | | $OCH_3$ | $OCH_3$ | CH | |
| L-3 | Q-4 | 0 | H | $OCH_3$ | $CH_3$ | | | H | Cl | — | — | | $OCH_3$ | $CH_3$ | N | |
| L-3 | Q-4 | 0 | $CH_3$ | Cl | $CH_3$ | | | F | $CH_3$ | — | — | | $CH_3$ | $OCH_3$ | CH | |
| L-3 | Q-4 | 1 | H | H | $CH_3$ | | | H | Cl | — | — | | $CH_3$ | $OCH_3$ | CH | |
| L-3 | Q-4 | 1 | H | H | $CH_3$ | | | Cl | Cl | — | — | | $OCH_3$ | $OCH_3$ | N | |
| L-3 | Q-4 | 1 | H | H | $CH_3$ | | | F | $CH_3$ | — | — | | Cl | $OCH_3$ | CH | |
| L-3 | Q-5 | 0 | H | H | $CH_3$ | | | H | H | — | — | | $CH_3$ | $CH_3$ | CH | |
| L-3 | Q-5 | 0 | H | H | $CH_3$ | | | H | Cl | — | — | | $CH_3$ | $OCH_3$ | CH | |
| L-3 | Q-5 | 0 | H | H | $CH_3$ | | | Cl | Cl | — | — | | $OCH_3$ | $OCH_3$ | CH | |
| L-3 | Q-5 | 0 | H | H | $CH_3$ | | | F | F | — | — | | $CH_3$ | $CH_3$ | N | |
| L-3 | Q-5 | 0 | H | H | $CH_3$ | | | H | Br | — | — | | $CH_3$ | $OCH_3$ | N | |
| L-3 | Q-5 | 0 | H | H | $CH_3$ | | | $CH_3$ | H | — | — | | $OCH_3$ | $OCH_3$ | N | |
| L-3 | Q-5 | 0 | H | H | $CH_3$ | | | H | $OCH_3$ | — | — | | Cl | $OCH_3$ | CH | |
| L-3 | Q-5 | 0 | H | H | $CH_3$ | | | H | F | — | — | | $CH_3$ | $OCH_3$ | CH | |
| L-3 | Q-5 | 0 | H | H | $CH_3$ | | | Cl | Br | — | — | | $OCH_3$ | $OCH_3$ | CH | |
| L-3 | Q-5 | 0 | H | H | $CH_3$ | | | Cl | $CH_3$ | — | — | | $CH_3$ | $OCH_3$ | N | |
| L-3 | Q-5 | 0 | H | H | $CH_3$ | | | F | $CH_3$ | — | — | | $OCH_3$ | $OCH_3$ | CH | |
| L-3 | Q-5 | 0 | H | H | $CH_3$ | | | H | Cl | — | — | | $CH_3$ | $CH_3$ | N | |
| L-3 | Q-5 | 0 | H | H | $CH_3$ | | | H | $CH_3$ | — | — | | $OCH_3$ | $OCH_3$ | CH | |
| L-3 | Q-5 | 0 | H | $CH_3$ | $CH_3$ | | | H | H | — | — | | Cl | $OCH_3$ | CH | |
| L-3 | Q-5 | 0 | $CH_3$ | H | $CH_3$ | | | H | H | — | — | | $CH_3$ | $OCH_3$ | N | |
| L-3 | Q-5 | 1 | H | H | $CH_3$ | | | F | F | — | — | | $OCH_3$ | $OCH_3$ | CH | |
| L-3 | Q-5 | 1 | H | H | $CH_3$ | | | H | H | — | — | | $OCH_3$ | $OCH_3$ | CH | |
| L-3 | Q-6 | 0 | H | H | $CH_3$ | | | H | H | — | — | | $CH_3$ | $CH_3$ | CH | |
| L-3 | Q-6 | 0 | H | H | $CH_3$ | | | H | H | — | — | | $OCH_3$ | $CH_3$ | CH | |
| L-3 | Q-6 | 0 | H | H | $CH_3$ | | | H | H | — | — | | $OCH_3$ | $OCH_3$ | CH | |
| L-3 | Q-6 | 0 | H | H | $CH_3$ | | | Cl | H | — | — | | $CH_3$ | $OCH_3$ | N | |
| L-3 | Q-6 | 0 | H | H | $CH_3$ | | | F | H | — | — | | Cl | $OCH_3$ | CH | |
| L-3 | Q-6 | 0 | H | H | $CH_3$ | | | H | Br | — | — | | $OCH_3$ | $OCH_3$ | CH | |
| L-3 | Q-6 | 0 | H | H | $CH_3$ | | | F | F | — | — | | $OCH_3$ | $OCH_3$ | N | |
| L-3 | Q-6 | 0 | H | H | $CH_3$ | | | Cl | Cl | — | — | | $CH_3$ | $OCH_3$ | CH | |
| L-3 | Q-6 | 0 | H | H | $CH_3$ | | | H | $CH_3$ | — | — | | $CH_3$ | $OCH_3$ | CH | |
| L-3 | Q-6 | 0 | H | H | $CH_3$ | | | $CH_3$ | $CH_3$ | — | — | | $OCH_3$ | $OCH_3$ | CH | |
| L-3 | Q-6 | 0 | H | H | $CH_3$ | | | H | $CO_2CH_3$ | — | — | | $CH_3$ | $CH_3$ | CH | |
| L-3 | Q-6 | 0 | H | H | $CH_3$ | | | H | F | — | — | | $OCH_3$ | $OCH_3$ | CH | |
| L-3 | Q-6 | 0 | H | $OCH_3$ | $CH_3$ | | | H | Cl | — | — | | $OCH_3$ | $CH_3$ | N | |
| L-3 | Q-6 | 0 | $CH_3$ | Cl | $CH_3$ | | | F | $CH_3$ | — | — | | $CH_3$ | $OCH_3$ | CH | |
| L-3 | Q-6 | 1 | H | H | $CH_3$ | | | H | Cl | — | — | | $CH_3$ | $OCH_3$ | CH | |
| L-3 | Q-6 | 1 | H | H | $CH_3$ | | | Cl | Cl | — | — | | $OCH_3$ | $OCH_3$ | N | |
| L-3 | Q-6 | 1 | H | H | $CH_3$ | | | F | $CH_3$ | — | — | | Cl | $OCH_3$ | CH | |
| L-3 | Q-7 | 0 | H | H | $CH_3$ | | | H | H | — | — | | $CH_3$ | $CH_3$ | CH | |
| L-3 | Q-7 | 0 | H | H | $CH_3$ | | | H | Cl | — | — | | $CH_3$ | $CH_3$ | CH | |
| L-3 | Q-7 | 0 | H | H | $CH_3$ | | | Cl | Cl | — | — | | $OCH_3$ | $OCH_3$ | CH | |
| L-3 | Q-7 | 0 | H | H | $CH_3$ | | | F | F | — | — | | $CH_3$ | $CH_3$ | N | |
| L-3 | Q-7 | 0 | H | H | $CH_3$ | | | H | Br | — | — | | $CH_3$ | $OCH_3$ | N | |
| L-3 | Q-7 | 0 | H | H | $CH_3$ | | | $CH_3$ | H | — | — | | $OCH_3$ | $OCH_3$ | N | |
| L-3 | Q-7 | 0 | H | H | $CH_3$ | | | H | $OCH_3$ | — | — | | Cl | $OCH_3$ | CH | |
| L-3 | Q-7 | 0 | H | H | $CH_3$ | | | H | F | — | — | | $CH_3$ | $OCH_3$ | CH | |
| L-3 | Q-7 | 0 | H | H | $CH_3$ | | | Cl | Br | — | — | | $OCH_3$ | $OCH_3$ | CH | |
| L-3 | Q-7 | 0 | H | H | $CH_3$ | | | Cl | $CH_3$ | — | — | | $CH_3$ | $OCH_3$ | N | |
| L-3 | Q-7 | 0 | H | H | $CH_3$ | | | F | $CH_3$ | — | — | | $OCH_3$ | $OCH_3$ | CH | |
| L-3 | Q-7 | 0 | H | H | $CH_3$ | | | H | Cl | — | — | | $CH_3$ | $CH_3$ | N | |
| L-3 | Q-7 | 0 | H | H | $CH_3$ | | | H | $CH_3$ | — | — | | $OCH_3$ | $OCH_3$ | CH | |
| L-3 | Q-7 | 0 | H | $CH_3$ | $CH_3$ | | | H | H | — | — | | Cl | $OCH_3$ | CH | |
| L-3 | Q-7 | 0 | $CH_3$ | H | $CH_3$ | | | H | H | — | — | | $CH_3$ | $OCH_3$ | N | |
| L-3 | Q-7 | 1 | H | H | $CH_3$ | | | F | F | — | — | | $OCH_3$ | $OCH_3$ | CH | |
| L-3 | Q-7 | 1 | H | H | $CH_3$ | | | H | H | — | — | | $OCH_3$ | $OCH_3$ | CH | |
| L-3 | Q-8 | 0 | H | H | $CH_3$ | — | | H | H | — | | | $CH_3$ | $CH_3$ | CH | |
| L-3 | Q-8 | 0 | H | H | $CH_3$ | — | | H | H | — | | | $OCH_3$ | $CH_3$ | CH | |
| L-3 | Q-8 | 0 | H | H | $CH_3$ | — | | H | H | — | | | $OCH_3$ | $OCH_3$ | CH | |
| L-3 | Q-8 | 0 | H | H | $CH_3$ | — | | Cl | H | — | | | $CH_3$ | $OCH_3$ | N | |
| L-3 | Q-8 | 0 | H | H | $CH_3$ | — | | F | H | — | | | Cl | $OCH_3$ | CH | |
| L-3 | Q-8 | 0 | H | H | $CH_3$ | — | | H | Br | — | | | $OCH_3$ | $OCH_3$ | CH | |
| L-3 | Q-8 | 0 | H | H | $CH_3$ | — | | F | F | — | | | $OCH_3$ | $OCH_3$ | N | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-3 | Q-8 | 0 | H | H | $CH_3$ | — | | Cl | Cl | — | | — | $CH_3$ | $OCH_3$ | CH | |
| L-3 | Q-8 | 0 | H | H | $CH_3$ | — | | H | $CH_3$ | — | | — | $CH_3$ | $OCH_3$ | CH | |
| L-3 | Q-8 | 0 | H | H | $CH_3$ | — | | $CH_3$ | $CH_3$ | — | | — | $OCH_3$ | $OCH_3$ | CH | |
| L-3 | Q-8 | 0 | H | H | $CH_3$ | — | | $CH_3$ | $CO_2CH_3$ | — | | — | $CH_3$ | $CH_3$ | CH | |
| L-3 | Q-8 | 0 | H | H | $CH_3$ | — | | H | F | — | | — | $OCH_3$ | $OCH_3$ | CH | |
| L-3 | Q-8 | 0 | H | $OCH_3$ | $CH_3$ | — | | H | Cl | — | | — | $OCH_3$ | $CH_3$ | N | |
| L-3 | Q-8 | 0 | $CH_3$ | Cl | $CH_3$ | — | | F | $CH_3$ | — | | — | $CH_3$ | $OCH_3$ | CH | |
| L-3 | Q-8 | 1 | H | H | $CH_3$ | — | | H | Cl | — | | — | $CH_3$ | $OCH_3$ | CH | |
| L-3 | Q-8 | 1 | H | H | $CH_3$ | — | | Cl | Cl | — | | — | $OCH_3$ | $OCH_3$ | N | |
| L-3 | Q-8 | 1 | H | H | $CH_3$ | — | | F | $CH_3$ | — | | — | Cl | $OCH_3$ | CH | |
| L-3 | Q-9 | 0 | H | H | $CH_3$ | $CH_3$ | | H | H | — | | — | $CH_3$ | $CH_3$ | CH | |
| L-3 | Q-9 | 0 | H | H | $CH_3$ | $CH_3$ | | H | Cl | — | | —. | $CH_3$ | $OCH_3$ | CH | |
| L-3 | Q-9 | 0 | H | H | $CH_3$ | $CH_3$ | | Cl | Cl | — | | — | $OCH_3$ | $OCH_3$ | N | |
| L-3 | Q-9 | 0 | H | H | $CH_3$ | $CH_3$ | | F | F | — | | — | $CH_3$ | $CH_3$ | N | |
| L-3 | Q-9 | 0 | H | H | $CH_3$ | $CH_3$ | | H | Br | — | | — | $CH_3$ | $OCH_3$ | N | |
| L-3 | Q-9 | 0 | H | H | $CH_3$ | $CH_3$ | | $CH_3$ | H | — | | 148 — | $OCH_3$ | $OCH_3$ | N | |
| L-3 | Q-9 | 0 | H | H | $CH_3$ | $CH_3$ | | H | $OCH_3$ | — | | — | Cl | $OCH_3$ | CH | |
| L-3 | Q-9 | 0 | H | H | $CH_3$ | $CH_3$ | | H | F | — | | — | $CH_3$ | $OCH_3$ | CH | |
| L-3 | Q-9 | 0 | H | H | $CH_3$ | $CH_3$ | | Cl | Br | — | | — | $OCH_3$ | $OCH_3$ | CH | |
| L-3 | Q-9 | 0 | H | H | $CH_3$ | $CH_3$ | | Cl | $CH_3$ | — | | — | $CH_3$ | $OCH_3$ | N | |
| L-3 | Q-9 | 0 | H | H | $CH_3$ | $CH_3$ | | F | $CH_3$ | — | | — | $OCH_3$ | $OCH_3$ | CH | |
| L-3 | Q-9 | 0 | H | H | $CH_3$ | $CH_3$ | | H | Cl | — | | — | $CH_3$ | $CH_3$ | N | |
| L-3 | Q-9 | 0 | H | H | $CH_3$ | $CH_2CH_3$ | | H | $CH_3$ | — | | — | $OCH_3$ | $OCH_3$ | CH | |
| L-3 | Q-9 | 0 | H | $CH_3$ | $CH_3$ | $CH_2CH_3$ | | H | H | — | | — | Cl | $OCH_3$ | CH | |
| L-3 | Q-9 | 0 | $CH_3$ | H | $CH_3$ | $CH_2CH_2CH_3$ | | H | H | — | | — | $CH_3$ | $OCH_3$ | N | |
| L-3 | Q-9 | 1 | H | H | $CH_3$ | $CH_3$ | | F | F | — | — | | $OCH_3$ | $OCH_3$ | CH | |
| L-3 | Q-9 | 1 | H | H | $CH_3$ | $CH_2CH_3$ | | H | H | — | — | | $OCH_3$ | $OCH_3$ | CH | |
| L-3 | Q-10 | 0 | H | H | $CH_3$ | $CH_3$ | | H | H | — | — | | $CH_3$ | $CH_3$ | CH | |
| L-3 | Q-10 | 0 | H | H | $CH_3$ | $CH_3$ | | H | H | — | — | | $OCH_3$ | $OCH_3$ | CH | |
| L-3 | Q-10 | 0 | H | H | $CH_3$ | $CH_3$ | | Cl | H | — | — | | $CH_3$ | $OCH_3$ | N | |
| L-3 | Q-10 | 0 | H | H | $CH_3$ | $CH_3$ | | F | H | — | — | | Cl | $OCH_3$ | CH | |
| L-3 | Q-10 | 0 | H | H | $CH_3$ | $CH_3$ | | H | Br | — | — | | $OCH_3$ | $OCH_3$ | CH | |
| L-3 | Q-10 | 0 | H | H | $CH_3$ | $CH_3$ | | F | F | — | — | | $OCH_3$ | $OCH_3$ | N | |
| L-3 | Q-10 | 0 | H | H | $CH_3$ | $CH_3$ | | Cl | Cl | — | — | | $CH_3$ | $OCH_3$ | CH | |
| L-3 | Q-10 | 0 | H | H | $CH_3$ | $CH_3$ | | H | $CH_3$ | — | — | | $OCH_3$ | $OCH_3$ | CH | |
| L-3 | Q-10 | 0 | H | H | $CH_3$ | $CH_3$ | | $CH_3$ | $CH_3$ | — | — | | $CH_3$ | $CH_3$ | CH | |
| L-3 | Q-10 | 0 | H | H | $CH_3$ | $CH_3$ | | H | $CO_2CH_3$ | — | — | | $CH_3$ | $CH_3$ | CH | |
| L-3 | Q-10 | 0 | H | H | $CH_3$ | $CH_3$ | | H | F | — | — | | $OCH_3$ | $OCH_3$ | CH | |
| L-3 | Q-10 | 0 | H | $OCH_3$ | $CH_3$ | $CH_3$ | | H | Cl | — | — | | $OCH_3$ | $CH_3$ | N | |
| L-3 | Q-10 | 0 | $CH_3$ | Cl | $CH_3$ | $CH_3$ | | F | $CH_3$ | — | — | | $CH_3$ | $OCH_3$ | CH | |
| L-3 | Q-10 | 1 | H | H | $CH_3$ | $CH_2CH_3$ | | H | Cl | — | — | | $CH_3$ | $OCH_3$ | CH | |
| L-3 | Q-10 | 1 | H | H | $CH_3$ | $CH_3$ | | Cl | Cl | — | — | | $OCH_3$ | $OCH_3$ | N | |
| L-3 | Q-10 | 1 | H | H | $CH_3$ | $CH_2CH_3$ | | F | $CH_3$ | — | — | | Cl | $OCH_3$ | CH | |
| L-4 | Q-1 | 0 | H | H | — | — | | H | H | H | H | | $CH_3$ | $CH_3$ | CH | |
| L-4 | Q-1 | 0 | H | H | — | — | | Cl | Cl | H | H | | $OCH_3$ | $OCH_3$ | CH | |
| L-4 | Q-1 | 0 | H | H | — | — | | F | F | H | H | | $CH_3$ | $CH_3$ | N | |
| L-4 | Q-1 | 0 | H | H | — | — | | H | Br | H | H | | $CH_3$ | $OCH_3$ | N | |
| L-4 | Q-1 | 0 | H | H | — | — | | $CH_3$ | Br | H | H | | $OCH_3$ | $OCH_3$ | N | |
| L-4 | Q-1 | 0 | H | H | — | — | | H | $OCH_3$ | H | H | | Cl | $OCH_3$ | CH | |
| L-4 | Q-1 | 0 | H | H | — | — | | H | F | H | H | | $CH_3$ | $CH_3$ | CH | |
| L-4 | Q-1 | 0 | H | H | — | — | | Cl | Br | H | H | | $OCH_3$ | $OCH_3$ | CH | |
| L-4 | Q-1 | 0 | H | H | — | — | | Cl | $CH_3$ | H | H | | $CH_3$ | $OCH_3$ | N | |
| L-4 | Q-1 | 0 | H | H | — | — | | F | $CH_3$ | H | H | | $OCH_3$ | $OCH_3$ | CH | |
| L-4 | Q-1 | 0 | H | H | — | — | | H | Cl | Cl | H | | $CH_3$ | $CH_3$ | N | |
| L-4 | Q-1 | 0 | H | H | — | — | | H | $CH_3$ | F | H | | $OCH_3$ | $OCH_3$ | CH | |
| L-4 | Q-1 | 0 | H | $CH_3$ | — | — | | H | H | H | H | | Cl | $OCH_3$ | CH | |
| L-4 | Q-1 | 0 | $CH_3$ | H | — | — | | H | H | H | H | | $CH_3$ | $OCH_3$ | N | |
| L-4 | Q-1 | 1 | H | H | — | — | | F | F | H | H | — | $OCH_3$ | $OCH_3$ | CH | |
| L-4 | Q-1 | 1 | H | H | — | — | | H | H | H | H | — | $OCH_3$ | $OCH_3$ | CH | |
| L-4 | Q-2 | 0 | H | H | — | | | H | H | — | — | H | $CH_3$ | $CH_3$ | CH | |
| L-4 | Q-2 | 0 | H | H | — | | | H | H | — | — | H | $OCH_3$ | $OCH_3$ | CH | |
| L-4 | Q-2 | 0 | H | H | — | | | Cl | H | — | — | H | $CH_3$ | $OCH_3$ | N | |
| L-4 | Q-2 | 0 | H | H | — | | | F | H | — | — | H | Cl | $OCH_3$ | CH | |
| L-4 | Q-2 | 0 | H | H | — | | | H | Br | — | — | H | $OCH_3$ | $OCH_3$ | CH | |
| L-4 | Q-2 | 0 | H | H | — | | | F | F | — | — | H | $OCH_3$ | $OCH_3$ | N | |
| L-4 | Q-2 | 0 | H | H | — | | | Cl | Cl | — | — | H | $CH_3$ | $OCH_3$ | CH | |
| L-4 | Q-2 | 0 | H | H | — | | | H | $CH_3$ | — | — | H | $OCH_3$ | $OCH_3$ | CH | |
| L-4 | Q-2 | 0 | H | H | — | | | $CH_3$ | $CH_3$ | — | — | H | $OCH_3$ | $OCH_3$ | CH | |
| L-4 | Q-2 | 0 | H | H | — | | | H | $CO_2CH_3$ | — | — | H | $CH_3$ | $CH_3$ | CH | |
| L-4 | Q-2 | 0 | H | H | — | | | H | F | — | — | $CH_3$ | $OCH_3$ | $OCH_3$ | CH | |
| L-4 | Q-2 | 0 | H | $OCH_3$ | — | | | H | Cl | — | — | H | $OCH_3$ | $CH_3$ | N | |
| L-4 | Q-2 | 0 | $CH_3$ | Cl | — | | | F | $CH_3$ | — | — | $CH_3$ | $CH_3$ | $OCH_3$ | CH | |
| L-4 | Q-2 | 1 | H | H | — | | | H | Cl | — | — | H | $CH_3$ | $OCH_3$ | CH | |
| L-4 | Q-2 | 1 | H | H | — | | | Cl | Cl | — | — | H | $OCH_3$ | $OCH_3$ | N | |
| L-4 | Q-2 | 1 | H | H | — | | | F | $CH_3$ | — | — | H | Cl | $OCH_3$ | CH | |
| L-4 | Q-3 | 0 | H | H | | $CH_3$ | | H | H | — | — | H | $CH_3$ | $CH_3$ | CH | |
| L-4 | Q-3 | 0 | H | H | | $CH_3$ | | H | Cl | — | — | H | $CH_3$ | $OCH_3$ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-4 | Q-3 | 0 | H | H | | $CH_3$ | | Cl | Cl | — | — | H | $OCH_3$ | $OCH_3$ | CH | |
| L-4 | Q-3 | 0 | H | H | | $CH_3$ | | F | F | — | — | H | $CH_3$ | $CH_3$ | N | |
| L-4 | Q-3 | 0 | H | H | | $CH_3$ | | H | Br | — | — | H | $CH_3$ | $OCH_3$ | N | |
| L-4 | Q-3 | 0 | H | H | | $CH_3$ | | $CH_3$ | H | — | — | H | $OCH_3$ | $OCH_3$ | N | |
| L-4 | Q-3 | 0 | H | H | | $CH_3$ | | H | $OCH_3$ | — | — | H | Cl | $OCH_3$ | CH | |
| L-4 | Q-3 | 0 | H | H | | $CH_3$ | | H | F | — | — | H | $CH_3$ | $OCH_3$ | CH | |
| L-4 | Q-3 | 0 | H | H | | $CH_3$ | | Cl | Br | — | — | H | $OCH_3$ | $OCH_3$ | CH | |
| L-4 | Q-3 | 0 | H | H | | $CH_3$ | | Cl | $CH_3$ | — | — | H | $CH_3$ | $OCH_3$ | N | |
| L-4 | Q-3 | 0 | H | H | | $CH_3$ | | F | $CH_3$ | — | — | H | $OCH_3$ | $OCH_3$ | CH | |
| L-4 | Q-3 | 0 | H | H | | $CH_3$ | | Cl | Cl | — | — | H | $CH_3$ | $CH_3$ | N | |
| L-4 | Q-3 | 0 | H | H | | $CH_3$ | | H | $CH_3$ | — | — | H | $OCH_3$ | $OCH_3$ | CH | |
| L-4 | Q-3 | 0 | H | $CH_3$ | | $CH_3$ | | H | H | — | — | H | Cl | $OCH_3$ | CH | |
| L-4 | Q-3 | 0 | $CH_3$ | H | | $CH_3$ | | H | H | — | — | H | $CH_3$ | $OCH_3$ | N | |
| L-4 | Q-3 | 1 | H | H | | $CH_3$ | | F | F | — | — | H | $OCH_3$ | $OCH_3$ | CH | |
| L-4 | Q-3 | 1 | H | H | | $CH_3$ | | H | H | — | — | H | $OCH_3$ | $OCH_3$ | CH | |
| L-4 | Q-4 | 0 | H | H | | — | | H | H | — | — | — | $CH_3$ | $CH_3$ | CH | |
| L-4 | Q-4 | 0 | H | H | | — | | H | H | — | — | — | $OCH_3$ | $CH_3$ | CH | |
| L-4 | Q-4 | 0 | H | H | | — | | H | H | — | — | — | $OCH_3$ | $OCH_3$ | CH | |
| L-4 | Q-4 | 0 | H | H | | — | | Cl | H | — | — | — | $CH_3$ | $OCH_3$ | N | |
| L-4 | Q-4 | 0 | H | H | | — | | F | H | — | — | — | Cl | $OCH_3$ | CH | |
| L-4 | Q-4 | 0 | H | H | | — | | H | Br | — | — | — | $OCH_3$ | $OCH_3$ | CH | |
| L-4 | Q-4 | 0 | H | H | | — | | F | F | — | — | — | $OCH_3$ | $OCH_3$ | N | |
| L-4 | Q-4 | 0 | H | H | | — | | Cl | Cl | — | — | — | $CH_3$ | $OCH_3$ | CH | |
| L-4 | Q-4 | 0 | H | H | | — | | H | $CH_3$ | — | — | — | $CH_3$ | $OCH_3$ | CH | |
| L-4 | Q-4 | 0 | H | H | | — | | $CH_3$ | $CH_3$ | — | — | — | $OCH_3$ | $OCH_3$ | CH | |
| L-4 | Q-4 | 0 | H | H | | — | | H | $CO_2CH_3$ | — | — | — | $CH_3$ | $CH_3$ | CH | |
| L-4 | Q-4 | 0 | H | H | | — | | H | F | — | — | — | $OCH_3$ | $OCH_3$ | CH | |
| L-4 | Q-4 | 0 | H | $OCH_3$ | | — | | H | Cl | — | — | — | $OCH_3$ | $CH_3$ | N | |
| L-4 | Q-4 | 0 | $CH_3$ | Cl | | — | | F | $CH_3$ | — | — | — | $CH_3$ | $OCH_3$ | CH | |
| L-4 | Q-4 | 1 | H | H | | — | | H | Cl | — | — | — | $CH_3$ | $OCH_3$ | CH | |
| L-4 | Q-4 | 1 | H | H | | — | | Cl | Cl | — | — | — | $OCH_3$ | $OCH_3$ | N | |
| L-4 | Q-4 | 1 | H | H | | — | | F | $CH_3$ | — | — | — | Cl | $OCH_3$ | CH | |
| L-4 | Q-5 | 0 | H | H | | — | | H | H | — | — | — | $CH_3$ | $CH_3$ | CH | |
| L-4 | Q-5 | 0 | H | H | | — | | H | Cl | — | — | — | $CH_3$ | $OCH_3$ | CH | |
| L-4 | Q-5 | 0 | H | H | | — | | Cl | Cl | — | — | — | $OCH_3$ | $OCH_3$ | CH | |
| L-4 | Q-5 | 0 | H | H | | — | | F | F | — | — | — | $CH_3$ | $CH_3$ | N | |
| L-4 | Q-5 | 0 | H | H | | — | | H | Br | — | — | — | $CH_3$ | $OCH_3$ | N | |
| L-4 | Q-5 | 0 | H | H | | — | | $CH_3$ | H | — | — | — | $OCH_3$ | $OCH_3$ | N | |
| L-4 | Q-5 | 0 | H | H | | — | | H | $OCH_3$ | — | — | — | Cl | $OCH_3$ | CH | |
| L-4 | Q-5 | 0 | H | H | | — | | H | F | — | — | — | $CH_3$ | $OCH_3$ | CH | |
| L-4 | Q-5 | 0 | H | H | | — | | Cl | Br | — | — | — | $OCH_3$ | $OCH_3$ | CH | |
| L-4 | Q-5 | 0 | H | H | | — | | Cl | $CH_3$ | — | — | — | $CH_3$ | $OCH_3$ | N | |
| L-4 | Q-5 | 0 | H | H | | — | | F | $CH_3$ | — | — | — | $OCH_3$ | $OCH_3$ | CH | |
| L-4 | Q-5 | 0 | H | H | | — | | H | Cl | — | — | — | $CH_3$ | $CH_3$ | N | |
| L-4 | Q-5 | 0 | H | H | | — | | H | $CH_3$ | — | — | — | $OCH_3$ | $OCH_3$ | CH | |
| L-4 | Q-5 | 0 | H | $CH_3$ | | — | | H | $CH_3$ | — | — | — | Cl | $OCH_3$ | CH | |
| L-4 | Q-5 | 0 | $CH_3$ | H | | — | | H | H | — | — | — | $CH_3$ | $OCH_3$ | N | |
| L-4 | Q-5 | 1 | H | H | | — | | F | F | — | — | — | $OCH_3$ | $OCH_3$ | CH | |
| L-4 | Q-5 | 1 | H | H | | — | | H | H | — | — | — | $OCH_3$ | $OCH_3$ | CH | |
| L-4 | Q-6 | 0 | H | H | | — | | H | H | — | — | — | $CH_3$ | $CH_3$ | CH | |
| L-4 | Q-6 | 0 | H | H | | — | | H | H | — | — | — | $OCH_3$ | $CH_3$ | CH | |
| L-4 | Q-6 | 0 | H | H | | — | | H | H | — | — | — | $OCH_3$ | $OCH_3$ | CH | |
| L-4 | Q-6 | 0 | H | H | | — | | Cl | H | — | — | — | $CH_3$ | $OCH_3$ | N | |
| L-4 | Q-6 | 0 | H | H | | — | | F | H | — | — | — | Cl | $OCH_3$ | CH | |
| L-4 | Q-6 | 0 | H | H | | — | | H | Br | — | — | — | $OCH_3$ | $OCH_3$ | CH | |
| L-4 | Q-6 | 0 | H | H | | — | | F | F | — | — | — | $OCH_3$ | $OCH_3$ | N | |
| L-4 | Q-6 | 0 | H | H | | — | | Cl | Cl | — | — | — | $CH_3$ | $OCH_3$ | CH | |
| L-4 | Q-6 | 0 | H | H | | — | | H | $CH_3$ | — | — | — | $CH_3$ | $OCH_3$ | CH | |
| L-4 | Q-6 | 0 | H | H | | — | | $CH_3$ | $CH_3$ | — | — | — | $OCH_3$ | $OCH_3$ | CH | |
| L-4 | Q-6 | 0 | H | H | | — | | H | $CH_2CH_3$ | — | — | — | $CH_3$ | $CH_3$ | CH | |
| L-4 | Q-6 | 0 | H | H | | — | | H | F | — | — | — | $OCH_3$ | $OCH_3$ | CH | |
| L-4 | Q-6 | 0 | H | $OCH_3$ | | — | | H | Cl | — | — | — | $OCH_3$ | $CH_3$ | N | |
| L-4 | Q-6 | 0 | $CH_3$ | Cl | | — | | F | $CH_3$ | — | — | — | $CH_3$ | $OCH_3$ | CH | |
| L-4 | Q-6 | 1 | H | H | | — | | H | Cl | — | — | — | $CH_3$ | $OCH_3$ | CH | |
| L-4 | Q-6 | 1 | H | H | | — | | Cl | Cl | — | — | — | $OCH_3$ | $OCH_3$ | N | |
| L-4 | Q-6 | 1 | H | H | | — | | F | $CH_3$ | — | — | — | Cl | $OCH_3$ | CH | |
| L-4 | Q-7 | 0 | H | H | | — | | H | H | — | — | — | $CH_3$ | $CH_3$ | CH | |
| L-4 | Q-7 | 0 | H | H | | — | | H | Cl | — | — | — | $CH_3$ | $OCH_3$ | CH | |
| L-4 | Q-7 | 0 | H | H | | — | | Cl | Cl | — | — | — | $OCH_3$ | $OCH_3$ | CH | |
| L-4 | Q-7 | 0 | H | H | | — | | F | F | — | — | — | $CH_3$ | $CH_3$ | N | |
| L-4 | Q-7 | 0 | H | H | | — | | H | Br | — | — | — | $CH_3$ | $OCH_3$ | N | |
| L-4 | Q-7 | 0 | H | H | | — | | $CH_3$ | H | — | — | — | $OCH_3$ | $OCH_3$ | N | |
| L-4 | Q-7 | 0 | H | H | | — | | H | $OCH_3$ | — | — | — | Cl | $OCH_3$ | CH | |
| L-4 | Q-7 | 0 | H | H | | — | | H | F | — | — | — | $CH_3$ | $OCH_3$ | CH | |
| L-4 | Q-7 | 0 | H | H | | — | | Cl | Br | — | — | — | $OCH_3$ | $OCH_3$ | CH | |
| L-4 | Q-7 | 0 | H | H | | — | | Cl | $CH_3$ | — | — | — | $CH_3$ | $OCH_3$ | N | |
| L-4 | Q-7 | 0 | H | H | | — | | F | $CH_3$ | — | — | — | $OCH_3$ | $OCH_3$ | CH | |
| L-4 | Q-7 | 0 | H | H | | — | | H | Cl | — | — | — | $CH_3$ | $CH_3$ | N | |
| L-4 | Q-7 | 0 | H | H | | — | | H | $CH_3$ | — | — | — | $OCH_3$ | $OCH_3$ | CH | |

TABLE II-continued

General Structure II (wherein $R_{12}$ and $R_{13}$ are H)

| L | $Q_1$ | n | R | $R_1$ | $R_2$ | $R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|
| L-4 | Q-7 | 0 | H | CH₃ | — | | H | H | — | — | — | Cl | OCH₃ | CH | |
| L-4 | Q-7 | 0 | CH₃ | H | — | | H | H | — | — | — | CH₃ | OCH₃ | N | |
| L-4 | Q-7 | 1 | H | H | — | | F | F | — | — | — | OCH₃ | OCH₃ | CH | |
| L-4 | Q-7 | 1 | H | H | — | | H | H | — | — | — | OCH₃ | OCH₃ | CH | |
| L-4 | Q-8 | 0 | H | H | — | | H | H | — | — | — | CH₃ | CH₃ | CH | |
| L-4 | Q-8 | 0 | H | H | — | | H | H | — | — | — | OCH₃ | CH₃ | CH | |
| L-4 | Q-8 | 0 | H | H | — | | H | H | — | — | — | OCH₃ | OCH₃ | CH | |
| L-4 | Q-8 | 0 | H | H | — | | Cl | H | — | — | — | CH₃ | OCH₃ | N | |
| L-4 | Q-8 | 0 | H | H | — | | F | H | — | — | — | Cl | OCH₃ | CH | |
| L-4 | Q-8 | 0 | H | H | — | | H | Br | — | — | — | OCH₃ | OCH₃ | CH | |
| L-4 | Q-8 | 0 | H | H | — | | F | F | — | — | — | OCH₃ | OCH₃ | N | |
| L-4 | Q-8 | 0 | H | H | — | | Cl | Cl | — | — | — | CH₃ | OCH₃ | CH | |
| L-4 | Q-8 | 0 | H | H | — | | H | CH₃ | — | — | — | CH₃ | OCH₃ | CH | |
| L-4 | Q-8 | 0 | H | H | — | | CH₃ | CH₃ | — | — | — | OCH₃ | OCH₃ | CH | |
| L-4 | Q-8 | 0 | H | H | — | | H | CH₂CH₃ | — | — | — | CH₃ | CH₃ | CH | |
| L-4 | Q-8 | 0 | H | H | — | | H | F | — | — | — | OCH₃ | OCH₃ | CH | |
| L-4 | Q-8 | 0 | H | OCH₃ | — | | H | Cl | — | — | — | OCH₃ | CH₃ | N | |
| L-4 | Q-8 | 0 | CH₃ | Cl | — | | F | CH₃ | — | — | — | CH₃ | OCH₃ | CH | |
| L-4 | Q-8 | 1 | H | H | — | | H | Cl | — | — | — | CH₃ | OCH₃ | CH | |
| L-4 | Q-8 | 1 | H | H | — | | Cl | Cl | — | — | — | OCH₃ | OCH₃ | N | |
| L-4 | Q-8 | 1 | H | H | — | | F | CH₃ | — | — | — | Cl | OCH₃ | CH | |
| L-4 | Q-9 | 0 | H | H | — | CH₃ | H | H | — | — | — | CH₃ | CH₃ | CH | |
| L-4 | Q-9 | 0 | H | H | — | CH₃ | H | Cl | — | — | — | CH₃ | OCH₃ | CH | |
| L-4 | Q-9 | 0 | H | H | — | CH₃ | Cl | Cl | — | — | — | OCH₃ | OCH₃ | CH | |
| L-4 | Q-9 | 0 | H | H | — | CH₃ | F | F | — | — | — | CH₃ | CH₃ | N | |
| L-4 | Q-9 | 0 | H | H | — | CH₃ | H | Br | — | — | — | CH₃ | OCH₃ | CH | |
| L-4 | Q-9 | 0 | H | H | — | CH₃ | CH₃ | H | — | — | — | OCH₃ | OCH₃ | N | |
| L-4 | Q-9 | 0 | H | H | — | CH₃ | H | OCH₃ | — | — | — | Cl | OCH₃ | CH | |
| L-4 | Q-9 | 0 | H | H | — | CH₃ | H | F | — | — | — | CH₃ | OCH₃ | CH | |
| L-4 | Q-9 | 0 | H | H | — | CH₃ | Cl | Br | — | — | — | OCH₃ | OCH₃ | CH | |
| L-4 | Q-9 | 0 | H | H | — | CH₃ | Cl | CH₃ | — | — | — | CH₃ | OCH₃ | N | |
| L-4 | Q-9 | 0 | H | H | — | CH₃ | F | CH₃ | — | — | — | OCH₃ | OCH₃ | CH | |
| L-4 | Q-9 | 0 | H | H | — | CH₃ | H | Cl | — | — | — | CH₃ | CH₃ | N | |
| L-4 | Q-9 | 0 | H | H | — | CH₃ | H | CH₃ | — | — | — | OCH₃ | OCH₃ | CH | |
| L-4 | Q-9 | 0 | H | CH₃ | — | CH₃ | H | H | — | — | — | Cl | OCH₃ | CH | |
| L-4 | Q-9 | 0 | CH₃ | H | — | CH₃ | H | H | — | — | — | CH₃ | OCH₃ | N | |
| L-4 | Q-9 | 1 | H | H | — | CH₃ | F | F | — | — | — | OCH₃ | OCH₃ | CH | |
| L-4 | Q-9 | 1 | H | H | — | CH₃ | H | H | — | — | — | OCH₃ | OCH₃ | CH | |
| L-4 | Q-10 | 0 | H | H | — | CH₃ | H | H | — | — | — | CH₃ | CH₃ | CH | |
| L-4 | Q-10 | 0 | H | H | — | CH₃ | H | H | — | — | — | OCH₃ | CH₃ | CH | |
| L-4 | Q-10 | 0 | H | H | — | CH₃ | H | H | — | — | — | OCH₃ | OCH₃ | CH | |
| L-4 | Q-10 | 0 | H | H | — | CH₃ | Cl | H | — | — | — | CH₃ | OCH₃ | N | |
| L-4 | Q-10 | 0 | H | H | — | CH₃ | F | H | — | — | — | Cl | OCH₃ | CH | |
| L-4 | Q-10 | 0 | H | H | — | CH₃ | H | Br | — | — | — | OCH₃ | OCH₃ | CH | |
| L-4 | Q-10 | 0 | H | H | — | CH₃ | F | F | — | — | — | OCH₃ | OCH₃ | N | |
| L-4 | Q-10 | 0 | H | H | — | CH₃ | Cl | Cl | — | — | — | CH₃ | OCH₃ | CH | |
| L-4 | Q-10 | 0 | H | H | — | CH₃ | H | CH₃ | — | — | — | CH₃ | OCH₃ | CH | |
| L-4 | Q-10 | 0 | H | H | — | CH₃ | CH₃ | CH₃ | — | — | — | OCH₃ | OCH₃ | CH | |
| L-4 | Q-10 | 0 | H | H | — | CH₃ | H | CO₂CH₃ | — | — | — | CH₃ | CH₃ | CH | |
| L-4 | Q-10 | 0 | H | H | — | CH₃ | H | F | — | — | — | OCH₃ | OCH₃ | CH | |
| L-4 | Q-10 | 0 | H | OCH₃ | — | CH₃ | H | Cl | — | — | — | OCH₃ | CH₃ | N | |
| L-4 | Q-10 | 0 | CH₃ | Cl | — | CH₃ | F | CH₃ | — | — | — | CH₃ | OCH₃ | CH | |
| L-4 | Q-10 | 1 | H | H | — | CH₃ | H | Cl | — | — | — | CH₃ | OCH₃ | CH | |
| L-4 | Q-10 | 1 | H | H | — | CH₃ | Cl | Cl | — | — | — | OCH₃ | OCH₃ | N | |
| L-4 | Q-10 | 1 | H | H | — | CH₃ | F | CH₃ | — | — | — | Cl | OCH₃ | CH | |
| L-5 | Q-1 | 0 | H | H | — | | H | H | H | H | — | CH₃ | CH₃ | CH | |
| L-5 | Q-1 | 0 | H | H | — | | H | Cl | H | H | — | CH₃ | OCH₃ | CH | |
| L-5 | Q-1 | 0 | H | H | — | | Cl | Cl | H | H | — | OCH₃ | OCH₃ | CH | |
| L-5 | Q-1 | 0 | H | H | — | | F | F | H | H | — | CH₃ | CH₃ | N | |
| L-5 | Q-1 | 0 | H | H | — | | H | Br | H | H | — | CH₃ | OCH₃ | N | |
| L-5 | Q-1 | 0 | H | H | — | | CH₃ | H | H | H | — | OCH₃ | OCH₃ | N | |
| L-5 | Q-1 | 0 | H | H | — | | H | OCH₃ | H | H | — | Cl | OCH₃ | CH | |
| L-5 | Q-1 | 0 | H | H | — | | H | F | H | H | — | CH₃ | OCH₃ | CH | |
| L-5 | Q-1 | 0 | H | H | — | | Cl | Br | H | H | — | OCH₃ | OCH₃ | CH | |
| L-5 | Q-1 | 0 | H | H | — | | Cl | CH₃ | H | H | — | CH₃ | OCH₃ | N | |
| L-5 | Q-1 | 0 | H | H | — | | F | CH₃ | H | H | — | OCH₃ | OCH₃ | CH | |
| L-5 | Q-1 | 0 | H | H | — | | H | Cl | Cl | H | — | CH₃ | CH₃ | N | |
| L-5 | Q-1 | 0 | H | H | — | | H | CH₃ | F | F | — | OCH₃ | OCH₃ | CH | |
| L-5 | Q-1 | 0 | H | CH₃ | — | | H | H | H | H | — | Cl | OCH₃ | CH | |
| L-5 | Q-1 | 0 | CH₃ | H | — | | H | H | H | H | — | CH₃ | OCH₃ | N | |
| L-5 | Q-1 | 1 | H | H | — | | F | F | H | H | — | OCH₃ | OCH₃ | CH | |
| L-5 | Q-1 | 1 | H | H | — | | H | H | H | H | — | OCH₃ | OCH₃ | CH | |
| L-5 | Q-2 | 0 | H | H | — | | H | H | — | — | H | CH₃ | CH₃ | CH | |
| L-5 | Q-2 | 0 | H | H | — | | H | H | — | — | H | OCH₃ | CH₃ | CH | |
| L-5 | Q-2 | 0 | H | H | — | | H | H | — | — | H | OCH₃ | OCH₃ | CH | |
| L-5 | Q-2 | 0 | H | H | — | | Cl | H | — | — | H | CH₃ | OCH₃ | N | |
| L-5 | Q-2 | 0 | H | H | — | | F | H | — | — | H | Cl | OCH₃ | CH | |
| L-5 | Q-2 | 0 | H | H | — | | H | Br | — | — | H | OCH₃ | OCH₃ | CH | |
| L-5 | Q-2 | 0 | H | H | — | | F | F | — | — | H | OCH₃ | OCH₃ | N | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-5 | Q-2 | 0 | H | H | | — | | Cl | Cl | — | — | H | CH$_3$ | OCH$_3$ | CH | |
| L-5 | Q-2 | 0 | H | H | | — | | H | CH$_3$ | — | — | H | CH$_3$ | OCH$_3$ | CH | |
| L-5 | Q-2 | 0 | H | H | | — | | CH$_3$ | CH$_3$ | — | — | H | OCH$_3$ | OCH$_3$ | CH | |
| L-5 | Q-2 | 0 | H | H | | — | | H | CO$_2$CH$_3$ | — | — | H | CH$_3$ | CH$_3$ | CH | |
| L-5 | Q-2 | 0 | H | H | | — | | H | F | — | — | CH$_3$ | OCH$_3$ | OCH$_3$ | CH | |
| L-5 | Q-2 | 0 | H | OCH$_3$ | | — | | H | Cl | — | — | H | OCH$_3$ | CH$_3$ | N | |
| L-5 | Q-2 | 0 | CH$_3$ | Cl | | — | | F | CH$_3$ | — | — | CH$_3$ | CH$_3$ | OCH$_3$ | CH | |
| L-5 | Q-2 | 1 | H | H | | — | | H | Cl | — | — | H | CH$_3$ | OCH$_3$ | CH | |
| L-5 | Q-2 | 1 | H | H | | — | | Cl | Cl | — | — | H | OCH$_3$ | OCH$_3$ | N | |
| L-5 | Q-2 | 1 | H | H | | — | | F | CH$_3$ | — | — | H | Cl | OCH$_3$ | CH | |
| L-5 | Q-3 | 0 | H | H | | CH$_3$ | | H | H | — | — | H | CH$_3$ | CH$_3$ | CH | |
| L-5 | Q-3 | 0 | H | H | | CH$_3$ | | H | Cl | — | — | H | CH$_3$ | OCH$_3$ | CH | |
| L-5 | Q-3 | 0 | H | H | | CH$_3$ | | Cl | Cl | — | — | H | OCH$_3$ | OCH$_3$ | CH | |
| L-5 | Q-3 | 0 | H | H | | CH$_3$ | | F | F | — | — | H | CH$_3$ | CH$_3$ | N | |
| L-5 | Q-3 | 0 | H | H | | CH$_3$ | | H | Br | — | — | H | CH$_3$ | OCH$_3$ | N | |
| L-5 | Q-3 | 0 | H | H | | CH$_3$ | | CH$_3$ | H | — | — | H | OCH$_3$ | OCH$_3$ | N | |
| L-5 | Q-3 | 0 | H | H | | CH$_3$ | | H | OCH$_3$ | — | — | H | Cl | OCH$_3$ | CH | |
| L-5 | Q-3 | 0 | H | H | | CH$_3$ | | H | F | — | — | H | CH$_3$ | CH$_3$ | CH | |
| L-5 | Q-3 | 0 | H | H | | CH$_3$ | | Cl | Br | — | — | H | OCH$_3$ | OCH$_3$ | CH | |
| L-5 | Q-3 | 0 | H | H | | CH$_3$ | | Cl | CH$_3$ | — | — | H | CH$_3$ | OCH$_3$ | N | |
| L-5 | Q-3 | 0 | H | H | | CH$_3$ | | F | CH$_3$ | — | — | H | OCH$_3$ | OCH$_3$ | CH | |
| L-5 | Q-3 | 0 | H | H | | CH$_3$ | | H | Cl | — | — | H | CH$_3$ | CH$_3$ | N | |
| L-5 | Q-3 | 0 | H | H | | CH$_3$ | | H | CH$_3$ | — | — | CH$_3$ | OCH$_3$ | OCH$_3$ | CH | |
| L-5 | Q-3 | 0 | H | CH$_3$ | | CH$_3$ | | H | H | — | — | H | Cl | OCH$_3$ | CH | |
| L-5 | Q-3 | 0 | CH$_3$ | H | | CH$_3$ | | H | H | — | — | H | CH$_3$ | OCH$_3$ | N | |
| L-5 | Q-3 | 1 | H | H | | CH$_3$ | | F | F | — | — | H | OCH$_3$ | OCH$_3$ | CH | |
| L-5 | Q-3 | 1 | H | H | | CH$_3$ | | H | H | — | — | H | OCH$_3$ | OCH$_3$ | CH | |
| L-5 | Q-4 | 0 | H | H | | — | | H | H | — | — | — | CH$_3$ | CH$_3$ | CH | |
| L-5 | Q-4 | 0 | H | H | | — | | H | H | — | — | — | OCH$_3$ | CH$_3$ | CH | |
| L-5 | Q-4 | 0 | H | H | | — | | H | H | — | — | — | OCH$_3$ | OCH$_3$ | CH | |
| L-5 | Q-4 | 0 | H | H | | — | | Cl | H | — | — | — | CH$_3$ | OCH$_3$ | N | |
| L-5 | Q-4 | 0 | H | H | | — | | F | H | — | — | — | Cl | OCH$_3$ | CH | |
| L-5 | Q-4 | 0 | H | H | | — | | H | Br | — | — | — | OCH$_3$ | OCH$_3$ | CH | |
| L-5 | Q-4 | 0 | H | H | | — | | F | F | — | — | — | OCH$_3$ | OCH$_3$ | N | |
| L-5 | Q-4 | 0 | H | H | | — | | Cl | Cl | — | — | — | CH$_3$ | OCH$_3$ | CH | |
| L-5 | Q-4 | 0 | H | H | | — | | H | CH$_3$ | — | — | — | CH$_3$ | CH$_3$ | CH | |
| L-5 | Q-4 | 0 | H | H | | — | | CH$_3$ | CH$_3$ | — | — | — | OCH$_3$ | OCH$_3$ | CH | |
| L-5 | Q-4 | 0 | H | H | | — | | H | CO$_2$CH$_3$ | — | — | — | CH$_3$ | CH$_3$ | CH | |
| L-5 | Q-4 | 0 | H | H | | — | | H | F | — | — | — | OCH$_3$ | OCH$_3$ | CH | |
| L-5 | Q-4 | 0 | H | OCH$_3$ | | — | | H | Cl | — | — | — | OCH$_3$ | CH$_3$ | N | |
| L-5 | Q-4 | 0 | CH$_3$ | Cl | | — | | F | CH$_3$ | — | — | — | CH$_3$ | OCH$_3$ | CH | |
| L-5 | Q-4 | 1 | H | H | | — | | H | Cl | — | — | — | CH$_3$ | OCH$_3$ | CH | |
| L-5 | Q-4 | 1 | H | H | | — | | Cl | Cl | — | — | — | OCH$_3$ | OCH$_3$ | N | |
| L-5 | Q-4 | 1 | H | H | | — | | F | CH$_3$ | — | — | — | Cl | OCH$_3$ | CH | |
| L-5 | Q-5 | 0 | H | H | | — | | H | H | — | — | — | CH$_3$ | CH$_3$ | CH | |
| L-5 | Q-5 | 0 | H | H | | — | | H | Cl | — | — | — | CH$_3$ | OCH$_3$ | CH | |
| L-5 | Q-5 | 0 | H | H | | — | | Cl | Cl | — | — | — | OCH$_3$ | OCH$_3$ | CH | |
| L-5 | Q-5 | 0 | H | H | | — | | F | F | — | — | — | CH$_3$ | CH$_3$ | N | |
| L-5 | Q-5 | 0 | H | H | | — | | H | Br | — | — | — | CH$_3$ | OCH$_3$ | N | |
| L-5 | Q-5 | 0 | H | H | | — | | CH$_3$ | H | — | — | — | OCH$_3$ | OCH$_3$ | N | |
| L-5 | Q-5 | 0 | H | H | | — | | H | OCH$_3$ | — | — | — | Cl | OCH$_3$ | CH | |
| L-5 | Q-5 | 0 | H | H | | — | | Cl | Br | — | — | — | OCH$_3$ | OCH$_3$ | CH | |
| L-5 | Q-5 | 0 | H | H | | — | | Cl | CH$_3$ | — | — | — | CH$_3$ | OCH$_3$ | N | |
| L-5 | Q-5 | 0 | H | H | | — | | F | CH$_3$ | — | — | — | OCH$_3$ | OCH$_3$ | CH | |
| L-5 | Q-5 | 0 | H | H | | — | | H | Cl | — | — | — | CH$_3$ | CH$_3$ | N | |
| L-5 | Q-5 | 0 | H | H | | — | | H | CH$_3$ | — | — | — | OCH$_3$ | OCH$_3$ | CH | |
| L-5 | Q-5 | 0 | H | CH$_3$ | | — | | H | H | — | — | — | Cl | OCH$_3$ | CH | |
| L-5 | Q-5 | 0 | CH$_3$ | H | | — | | H | H | — | — | — | CH$_3$ | OCH$_3$ | N | |
| L-5 | Q-5 | 1 | H | H | | — | | F | F | — | — | — | OCH$_3$ | OCH$_3$ | CH | |
| L-5 | Q-5 | 1 | H | H | | — | | H | H | — | — | — | OCH$_3$ | OCH$_3$ | CH | |
| L-5 | Q-6 | 0 | H | H | | — | | H | H | — | — | — | CH$_3$ | CH$_3$ | CH | |
| L-5 | Q-6 | 0 | H | H | | — | | H | H | — | — | — | OCH$_3$ | OCH$_3$ | CH | |
| L-5 | Q-6 | 0 | H | H | | — | | H | H | — | — | — | OCH$_3$ | OCH$_3$ | CH | |
| L-5 | Q-6 | 0 | H | H | | — | | Cl | H | — | — | — | CH$_3$ | OCH$_3$ | N | |
| L-5 | Q-6 | 0 | H | H | | — | | F | H | — | — | — | Cl | OCH$_3$ | CH | |
| L-5 | Q-6 | 0 | H | H | | — | | H | Br | — | — | — | OCH$_3$ | OCH$_3$ | CH | |
| L-5 | Q-6 | 0 | H | H | | — | | F | F | — | — | — | OCH$_3$ | OCH$_3$ | N | |
| L-5 | Q-6 | 0 | H | H | | — | | Cl | Cl | — | — | — | CH$_3$ | OCH$_3$ | CH | |
| L-5 | Q-6 | 0 | H | H | | — | | H | CH$_3$ | — | — | — | CH$_3$ | CH$_3$ | CH | |
| L-5 | Q-6 | 0 | H | H | | — | | CH$_3$ | CH$_3$ | — | — | — | OCH$_3$ | OCH$_3$ | CH | |
| L-5 | Q-6 | 0 | H | H | | — | | H | CO$_2$CH$_3$ | — | — | — | CH$_3$ | CH$_3$ | CH | |
| L-5 | Q-6 | 0 | H | H | | — | | H | F | — | — | — | OCH$_3$ | OCH$_3$ | CH | |
| L-5 | Q-6 | 0 | H | OCH$_3$ | | — | | H | Cl | — | — | — | OCH$_3$ | CH$_3$ | N | |
| L-5 | Q-6 | 0 | CH$_3$ | Cl | | — | | F | CH$_3$ | — | — | — | CH$_3$ | OCH$_3$ | CH | |
| L-5 | Q-6 | 1 | H | H | | — | | H | Cl | — | — | — | CH$_3$ | OCH$_3$ | CH | |
| L-5 | Q-6 | 1 | H | H | | — | | Cl | Cl | — | — | — | OCH$_3$ | OCH$_3$ | N | |
| L-5 | Q-6 | 1 | H | H | | — | | F | CH$_3$ | — | — | — | Cl | OCH$_3$ | CH | |
| L-5 | Q-7 | 0 | H | H | | — | | H | H | — | — | — | CH$_3$ | CH$_3$ | CH | |
| L-5 | Q-7 | 0 | H | H | | — | | H | Cl | — | — | — | CH$_3$ | OCH$_3$ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-5 | Q-7 | 0 | H | H | | | — | Cl | Cl | — | — | — | $OCH_3$ | $OCH_3$ | CH | |
| L-5 | Q-7 | 0 | H | H | | | — | F | F | — | — | — | $CH_3$ | $CH_3$ | N | |
| L-5 | Q-7 | 0 | H | H | | | — | H | Br | — | — | — | $CH_3$ | $OCH_3$ | N | |
| L-5 | Q-7 | 0 | H | H | | | — | $CH_3$ | H | — | — | — | $OCH_3$ | $OCH_3$ | N | |
| L-5 | Q-7 | 0 | H | H | | | — | H | $OCH_3$ | — | — | — | Cl | $OCH_3$ | CH | |
| L-5 | Q-7 | 0 | H | H | | | — | H | F | — | — | — | $CH_3$ | $OCH_3$ | CH | |
| L-5 | Q-7 | 0 | H | H | | | — | Cl | Br | — | — | — | $OCH_3$ | $OCH_3$ | CH | |
| L-5 | Q-7 | 0 | H | H | | | — | Cl | $CH_3$ | — | — | — | $CH_3$ | $OCH_3$ | N | |
| L-5 | Q-7 | 0 | H | H | | | — | F | $CH_3$ | — | — | — | $OCH_3$ | $OCH_3$ | CH | |
| L-5 | Q-7 | 0 | H | H | | | — | H | Cl | — | — | — | $CH_3$ | $CH_3$ | N | |
| L-5 | Q-7 | 0 | H | H | | | — | H | $CH_3$ | — | — | — | $OCH_3$ | $OCH_3$ | CH | |
| L-5 | Q-7 | 0 | H | $CH_3$ | | | — | H | H | — | — | — | Cl | $OCH_3$ | CH | |
| L-5 | Q-7 | 0 | $CH_3$ | H | | | — | H | H | — | — | — | $CH_3$ | $OCH_3$ | N | |
| L-5 | Q-7 | 1 | H | H | | | — | F | F | — | — | — | $OCH_3$ | $OCH_3$ | CH | |
| L-5 | Q-7 | 1 | H | H | | | — | H | H | — | — | — | $OCH_3$ | $OCH_3$ | CH | |
| L-5 | Q-8 | 0 | H | H | | | — | H | H | — | — | — | $CH_3$ | $CH_3$ | CH | |
| L-5 | Q-8 | 0 | H | H | | | — | H | H | — | — | — | $OCH_3$ | $CH_3$ | CH | |
| L-5 | Q-8 | 0 | H | H | | | — | H | H | — | — | — | $OCH_3$ | $OCH_3$ | CH | |
| L-5 | Q-8 | 0 | H | H | | | — | Cl | H | — | — | — | $CH_3$ | $OCH_3$ | N | |
| L-5 | Q-8 | 0 | H | H | | | — | F | H | — | — | — | Cl | $OCH_3$ | CH | |
| L-5 | Q-8 | 0 | H | H | | | — | H | Br | — | — | — | $OCH_3$ | $OCH_3$ | CH | |
| L-5 | Q-8 | 0 | H | H | | | — | F | F | — | — | — | $OCH_3$ | $OCH_3$ | N | |
| L-5 | Q-8 | 0 | H | H | | | — | Cl | Cl | — | — | — | $CH_3$ | $OCH_3$ | CH | |
| L-5 | Q-8 | 0 | H | H | | | — | H | $CH_3$ | — | — | — | $CH_3$ | $OCH_3$ | CH | |
| L-5 | Q-8 | 0 | H | H | | | — | H | $CH_3$ | — | — | — | $CH_3$ | $OCH_3$ | CH | |
| L-5 | Q-8 | 0 | H | H | | | — | $CH_3$ | $CH_3$ | — | — | — | $OCH_3$ | $OCH_3$ | CH | |
| L-5 | Q-8 | 0 | H | H | | | — | H | $CO_2CH_3$ | — | — | — | $CH_3$ | $CH_3$ | CH | |
| L-5 | Q-8 | 0 | H | H | | | — | H | F | — | — | — | $OCH_3$ | $OCH_3$ | CH | |
| L-5 | Q-8 | 0 | H | $OCH_3$ | | | — | H | Cl | — | — | — | $OCH_3$ | $CH_3$ | N | |
| L-5 | Q-8 | 0 | H | $OCH_3$ | | | — | H | Cl | — | — | — | $OCH_3$ | $CH_3$ | N | |
| L-5 | Q-8 | 0 | $CH_3$ | Cl | | | — | F | $CH_3$ | — | — | — | $CH_3$ | $OCH_3$ | CH | |
| L-5 | Q-8 | 1 | H | H | | | — | H | Cl | — | — | — | $CH_3$ | $OCH_3$ | CH | |
| L-5 | Q-8 | 1 | H | H | | | — | Cl | Cl | — | — | — | $OCH_3$ | $OCH_3$ | N | |
| L-5 | Q-8 | 1 | H | H | | | — | F | $CH_3$ | — | — | — | Cl | $OCH_3$ | CH | |
| L-5 | Q-9 | 0 | H | H | | $CH_3$ | — | H | H | — | — | — | $CH_3$ | $CH_3$ | CH | |
| L-5 | Q-9 | 0 | H | H | | $CH_3$ | — | H | Cl | — | — | — | $CH_3$ | $OCH_3$ | CH | |
| L-5 | Q-9 | 0 | H | H | | $CH_3$ | — | Cl | Cl | — | — | — | $OCH_3$ | $OCH_3$ | CH | |
| L-5 | Q-9 | 0 | H | H | | $CH_3$ | — | F | F | — | — | — | $CH_3$ | $CH_3$ | N | |
| L-5 | Q-9 | 0 | H | H | | $CH_3$ | — | H | Br | — | — | — | $CH_3$ | $OCH_3$ | N | |
| L-5 | Q-9 | 0 | H | H | | $CH_3$ | — | $CH_3$ | H | — | — | — | $OCH_3$ | $OCH_3$ | N | |
| L-5 | Q-9 | 0 | H | H | | $CH_3$ | — | H | $OCH_3$ | — | — | — | Cl | $OCH_3$ | CH | |
| L-5 | Q-9 | 0 | H | H | | $CH_3$ | — | H | H | — | — | — | $CH_3$ | $OCH_3$ | CH | |
| L-5 | Q-9 | 0 | H | H | | $CH_3$ | — | Cl | Br | — | — | — | $OCH_3$ | $OCH_3$ | CH | |
| L-5 | Q-9 | 0 | H | H | | $CH_3$ | — | Cl | $CH_3$ | — | — | — | $CH_3$ | $OCH_3$ | N | |
| L-5 | Q-9 | 0 | H | H | | $CH_3$ | — | F | $CH_3$ | — | — | — | $OCH_3$ | $OCH_3$ | CH | |
| L-5 | Q-9 | 0 | H | H | | $CH_3$ | — | H | Cl | — | — | — | $CH_3$ | $CH_3$ | N | |
| L-5 | Q-9 | 0 | H | H | | $CH_3$ | — | H | $CH_3$ | — | — | — | $OCH_3$ | $OCH_3$ | CH | |
| L-5 | Q-9 | 0 | H | $CH_3$ | | $CH_3$ | — | H | H | — | — | — | Cl | $OCH_3$ | CH | |
| L-5 | Q-9 | 0 | $CH_3$ | H | | $CH_3$ | — | H | H | — | — | — | $CH_3$ | $OCH_3$ | N | |
| L-5 | Q-9 | 1 | H | H | | $CH_3$ | — | F | F | — | — | — | $OCH_3$ | $OCH_3$ | CH | |
| L-5 | Q-9 | 1 | H | H | | $CH_3$ | — | H | H | — | — | — | $OCH_3$ | $OCH_3$ | CH | |
| L-5 | Q-10 | 0 | H | H | | $CH_3$ | — | H | H | — | — | — | $CH_3$ | $CH_3$ | CH | |
| L-5 | Q-10 | 0 | H | H | | $CH_3$ | — | H | H | — | — | — | $OCH_3$ | $CH_3$ | CH | |
| L-5 | Q-10 | 0 | H | H | | $CH_3$ | — | H | H | — | — | — | $OCH_3$ | $OCH_3$ | CH | |
| L-5 | Q-10 | 0 | H | H | | $CH_3$ | — | Cl | H | — | — | — | $CH_3$ | $OCH_3$ | N | |
| L-5 | Q-10 | 0 | H | H | | $CH_3$ | — | F | H | — | — | — | Cl | $OCH_3$ | CH | |
| L-5 | Q-10 | 0 | H | H | | $CH_3$ | — | H | Br | — | — | — | $OCH_3$ | $OCH_3$ | CH | |
| L-5 | Q-10 | 0 | H | H | | $CH_3$ | — | F | F | — | — | — | $OCH_3$ | $OCH_3$ | N | |
| L-5 | Q-10 | 0 | H | H | | $CH_2CH_3$ | — | Cl | Cl | — | — | — | $CH_3$ | $OCH_3$ | CH | |
| L-5 | Q-10 | 0 | H | H | | $CH_3$ | — | H | $CH_3$ | — | — | — | $CH_3$ | $OCH_3$ | CH | |
| L-5 | Q-10 | 0 | H | H | | $CH_3$ | — | $CH_3$ | $CH_3$ | — | — | — | $OCH_3$ | $OCH_3$ | CH | |
| L-5 | Q-10 | 0 | H | H | | $CH_3$ | — | H | $CO_2CH_3$ | — | — | — | $CH_3$ | $CH_3$ | CH | |
| L-5 | Q-10 | 0 | H | H | | $CH_3$ | — | H | F | — | — | — | $OCH_3$ | $OCH_3$ | CH | |
| L-5 | Q-10 | 0 | H | $OCH_3$ | | $CH_3$ | — | H | Cl | — | — | — | $OCH_3$ | $CH_3$ | N | |
| L-5 | Q-10 | 0 | $CH_3$ | Cl | | $CH_3$ | — | F | $CH_3$ | — | — | — | $CH_3$ | $OCH_3$ | CH | |
| L-5 | Q-10 | 1 | H | H | | $CH_3$ | — | H | Cl | — | — | — | $CH_3$ | $OCH_3$ | CH | |
| L-5 | Q-10 | 1 | H | H | | $CH_3$ | — | Cl | Cl | — | — | — | $OCH_3$ | $OCH_3$ | N | |
| L-5 | Q-10 | 1 | H | H | | $CH_3$ | — | F | $CH_3$ | — | — | — | Cl | $OCH_3$ | CH | |
| L-6 | Q-1 | 0 | H | H | | | — | H | H | H | H | — | $CH_3$ | $CH_3$ | CH | |
| L-6 | Q-1 | 0 | H | H | | | — | H | Cl | H | H | — | $CH_3$ | $CH_3$ | CH | |
| L-6 | Q-1 | 0 | H | H | | | — | Cl | Cl | H | H | — | $OCH_3$ | $OCH_3$ | CH | |
| L-6 | Q-1 | 0 | H | H | | | — | F | F | H | H | — | $CH_3$ | $CH_3$ | N | |
| L-6 | Q-1 | 0 | H | H | | | — | H | Br | H | H | — | $CH_3$ | $OCH_3$ | N | |
| L-6 | Q-1 | 0 | H | H | | | — | $CH_3$ | H | H | H | — | $OCH_3$ | $OCH_3$ | N | |
| L-6 | Q-1 | 0 | H | H | | | — | H | $OCH_3$ | H | H | — | Cl | $OCH_3$ | CH | |
| L-6 | Q-1 | 0 | H | H | | | — | H | F | H | H | — | Cl | $OCH_3$ | CH | |
| L-6 | Q-1 | 0 | H | H | | | — | Cl | Br | H | H | — | $OCH_3$ | $OCH_3$ | CH | |
| L-6 | Q-1 | 0 | H | H | | | — | Cl | $CH_3$ | H | H | — | $CH_3$ | $OCH_3$ | N | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C) |
|---|---|---|---|---|---|---|---|---|---|---|---|---|---|---|---|---|
| L-6 | Q-1 | 0 | H | H | | | — | F | CH$_3$ | H | H | — | OCH$_3$ | OCH$_3$ | CH | |
| L-6 | Q-1 | 0 | H | H | | | — | H | Cl | Cl | H | — | CH$_3$ | CH$_3$ | N | |
| L-6 | Q-1 | 0 | H | H | | | — | H | CH$_3$ | F | F | — | OCH$_3$ | OCH$_3$ | CH | |
| L-6 | Q-1 | 0 | H | CH$_3$ | | | — | H | H | H | H | — | Cl | OCH$_3$ | CH | |
| L-6 | Q-1 | 0 | CH$_3$ | H | | | — | H | H | H | H | — | CH$_3$ | OCH$_3$ | N | |
| L-6 | Q-1 | 1 | H | H | | | — | F | F | H | H | — | OCH$_3$ | OCH$_3$ | CH | |
| L-6 | Q-1 | 1 | H | H | | | — | H | H | H | H | — | OCH$_3$ | OCH$_3$ | CH | |
| L-6 | Q-2 | 0 | H | H | | | — | H | H | — | — | H | CH$_3$ | CH$_3$ | CH | |
| L-6 | Q-2 | 0 | H | H | | | — | H | H | — | — | H | OCH$_3$ | CH$_3$ | CH | |
| L-6 | Q-2 | 0 | H | H | | | — | H | H | — | — | H | OCH$_3$ | OCH$_3$ | CH | |
| L-6 | Q-2 | 0 | H | H | | | — | Cl | H | — | — | H | CH$_3$ | OCH$_3$ | N | |
| L-6 | Q-2 | 0 | H | H | | | — | F | H | — | — | H | Cl | OCH$_3$ | CH | |
| L-6 | Q-2 | 0 | H | H | | | — | H | Br | — | — | H | OCH$_3$ | OCH$_3$ | CH | |
| L-6 | Q-2 | 0 | H | H | | | — | F | F | — | — | H | OCH$_3$ | OCH$_3$ | N | |
| L-6 | Q-2 | 0 | H | H | | | — | Cl | Cl | — | — | H | CH$_3$ | OCH$_3$ | CH | |
| L-6 | Q-2 | 0 | H | H | | | — | H | CH$_3$ | — | — | H | CH$_3$ | OCH$_3$ | CH | |
| L-6 | Q-2 | 0 | H | H | | | — | CH$_3$ | CH$_3$ | — | — | H | OCH$_3$ | OCH$_3$ | CH | |
| L-6 | Q-2 | 0 | H | H | | | — | H | CO$_2$CH$_3$ | — | — | H | CH$_3$ | CH$_3$ | CH | |
| L-6 | Q-2 | 0 | H | H | | | — | H | F | — | — | CH$_3$ | OCH$_3$ | OCH$_3$ | CH | |
| L-6 | Q-2 | 0 | H | OCH$_3$ | | | — | H | Cl | — | — | H | OCH$_3$ | CH$_3$ | N | |
| L-6 | Q-2 | 0 | CH$_3$ | Cl | | | — | F | CH$_3$ | — | — | CH$_3$ | CH$_3$ | OCH$_3$ | CH | |
| L-6 | Q-2 | 1 | H | H | | | — | H | Cl | — | — | H | CH$_3$ | OCH$_3$ | CH | |
| L-6 | Q-2 | 1 | H | H | | | — | Cl | Cl | — | — | H | OCH$_3$ | OCH$_3$ | N | |
| L-6 | Q-2 | 1 | H | H | | | — | F | CH$_3$ | — | — | H | Cl | OCH$_3$ | CH | |
| L-6 | Q-3 | 0 | H | H | | | CH$_3$ | H | H | — | — | H | CH$_3$ | CH$_3$ | CH | |
| L-6 | Q-3 | 0 | H | H | | | CH$_3$ | H | Cl | — | — | H | CH$_3$ | OCH$_3$ | CH | |
| L-6 | Q-3 | 0 | H | H | | | CH$_3$ | Cl | Cl | — | — | H | OCH$_3$ | OCH$_3$ | CH | |
| L-6 | Q-3 | 0 | H | H | | | CH$_3$ | F | F | — | — | H | CH$_3$ | CH$_3$ | N | |
| L-6 | Q-3 | 0 | H | H | | | CH$_3$ | H | Br | — | — | H | CH$_3$ | OCH$_3$ | N | |
| L-6 | Q-3 | 0 | H | H | | | CH$_3$ | CH$_3$ | H | — | — | H | OCH$_3$ | OCH$_3$ | N | |
| L-6 | Q-3 | 0 | H | H | | | CH$_3$ | H | OCH$_3$ | — | — | H | Cl | OCH$_3$ | CH | |
| L-6 | Q-3 | 0 | H | H | | | CH$_3$ | H | F | — | — | H | CH$_3$ | OCH$_3$ | CH | |
| L-6 | Q-3 | 0 | H | H | | | CH$_3$ | Cl | Br | — | — | CH$_3$ | OCH$_3$ | OCH$_3$ | CH | |
| L-6 | Q-3 | 0 | H | H | | | CH$_3$ | Cl | CH$_3$ | — | — | CH$_3$ | CH$_3$ | OCH$_3$ | N | |
| L-6 | Q-3 | 0 | H | H | | | CH$_3$ | F | CH$_3$ | — | — | H | OCH$_3$ | OCH$_3$ | CH | |
| L-6 | Q-3 | 0 | H | H | | | CH$_3$ | H | Cl | — | — | H | CH$_3$ | CH$_3$ | N | |
| L-6 | Q-3 | 0 | H | H | | | CH$_3$ | H | CH$_3$ | — | — | H | OCH$_3$ | OCH$_3$ | CH | |
| L-6 | Q-3 | 0 | H | CH$_3$ | | | CH$_3$ | H | H | — | — | H | Cl | OCH$_3$ | CH | |
| L-6 | Q-3 | 0 | CH$_3$ | H | | | CH$_3$ | H | H | — | — | H | CH$_3$ | OCH$_3$ | N | |
| L-6 | Q-3 | 1 | H | H | | | CH$_3$ | F | F | — | — | H | OCH$_3$ | OCH$_3$ | CH | |
| L-6 | Q-3 | 1 | H | H | | | CH$_3$ | H | H | — | — | H | OCH$_3$ | OCH$_3$ | CH | |
| L-6 | Q-4 | 0 | H | H | | | — | H | H | — | — | — | CH$_3$ | CH$_3$ | CH | |
| L-6 | Q-4 | 0 | H | H | | | — | H | H | — | — | — | OCH$_3$ | CH$_3$ | CH | |
| L-6 | Q-4 | 0 | H | H | | | — | H | H | — | — | — | OCH$_3$ | OCH$_3$ | CH | |
| L-6 | Q-4 | 0 | H | H | | | — | Cl | H | — | — | — | CH$_3$ | OCH$_3$ | N | |
| L-6 | Q-4 | 0 | H | H | | | — | F | H | — | — | — | Cl | OCH$_3$ | CH | |
| L-6 | Q-4 | 0 | H | H | | | — | H | Br | — | — | — | OCH$_3$ | OCH$_3$ | CH | |
| L-6 | Q-4 | 0 | H | H | | | — | F | F | — | — | — | OCH$_3$ | OCH$_3$ | N | |
| L-6 | Q-4 | 0 | H | H | | | — | Cl | Cl | — | — | — | CH$_3$ | OCH$_3$ | CH | |
| L-6 | Q-4 | 0 | H | H | | | — | H | CH$_3$ | — | — | — | CH$_3$ | OCH$_3$ | CH | |
| L-6 | Q-4 | 0 | H | H | | | — | CH$_3$ | CH$_3$ | — | — | — | OCH$_3$ | OCH$_3$ | CH | |
| L-6 | Q-4 | 0 | H | H | | | — | H | CO$_2$CH$_3$ | — | — | — | CH$_3$ | CH$_3$ | CH | |
| L-6 | Q-4 | 0 | H | H | | | — | H | F | — | — | — | CH$_3$ | OCH$_3$ | CH | |
| L-6 | Q-4 | 0 | H | OCH$_3$ | | | — | H | Cl | — | — | — | OCH$_3$ | CH$_3$ | N | |
| L-6 | Q-4 | 0 | CH$_3$ | Cl | | | — | F | CH$_3$ | — | — | — | CH$_3$ | OCH$_3$ | CH | |
| L-6 | Q-4 | 1 | H | H | | | — | H | Cl | — | — | — | CH$_3$ | OCH$_3$ | CH | |
| L-6 | Q-4 | 1 | H | H | | | — | Cl | Cl | — | — | — | OCH$_3$ | OCH$_3$ | N | |
| L-6 | Q-4 | 1 | H | H | | | — | F | CH$_3$ | — | — | — | Cl | OCH$_3$ | CH | |
| L-6 | Q-5 | 0 | H | H | | | — | H | H | — | — | — | CH$_3$ | CH$_3$ | CH | |
| L-6 | Q-5 | 0 | H | H | | | — | H | Cl | — | — | — | CH$_3$ | OCH$_3$ | CH | |
| L-6 | Q-5 | 0 | H | H | | | — | Cl | Cl | — | — | — | OCH$_3$ | OCH$_3$ | CH | |
| L-6 | Q-5 | 0 | H | H | | | — | F | F | — | — | — | CH$_3$ | CH$_3$ | N | |
| L-6 | Q-5 | 0 | H | H | | | — | H | Br | — | — | — | CH$_3$ | OCH$_3$ | N | |
| L-6 | Q-5 | 0 | H | H | | | — | CH$_3$ | H | — | — | — | OCH$_3$ | OCH$_3$ | N | |
| L-6 | Q-5 | 0 | H | H | | | — | H | OCH$_3$ | — | — | — | Cl | OCH$_3$ | CH | |
| L-6 | Q-5 | 0 | H | H | | | — | H | F | — | — | — | CH$_3$ | OCH$_3$ | CH | |
| L-6 | Q-5 | 0 | H | H | | | — | Cl | Br | — | — | — | OCH$_3$ | OCH$_3$ | CH | |
| L-6 | Q-5 | 0 | H | H | | | — | Cl | CH$_3$ | — | — | — | CH$_3$ | OCH$_3$ | N | |
| L-6 | Q-5 | 0 | H | H | | | — | F | CH$_3$ | — | — | — | OCH$_3$ | OCH$_3$ | CH | |
| L-6 | Q-5 | 0 | H | H | | | — | H | Cl | — | — | — | CH$_3$ | CH$_3$ | N | |
| L-6 | Q-5 | 0 | H | H | | | — | H | CH$_3$ | — | — | — | OCH$_3$ | OCH$_3$ | CH | |
| L-6 | Q-5 | 0 | H | CH$_3$ | | | — | H | H | — | — | — | Cl | OCH$_3$ | CH | |
| L-6 | Q-5 | 0 | CH$_3$ | H | | | — | H | H | — | — | — | CH$_3$ | OCH$_3$ | N | |
| L-6 | Q-5 | 1 | H | H | | | — | F | F | — | — | — | OCH$_3$ | OCH$_3$ | CH | |
| L-6 | Q-5 | 1 | H | H | | | — | H | H | — | — | — | OCH$_3$ | OCH$_3$ | CH | |
| L-6 | Q-6 | 0 | H | H | | | — | H | H | — | — | — | CH$_3$ | CH$_3$ | CH | |
| L-6 | Q-6 | 0 | H | H | | | — | H | H | — | — | — | OCH$_3$ | CH$_3$ | CH | |
| L-6 | Q-6 | 0 | H | H | | | — | H | H | — | — | — | OCH$_3$ | OCH$_3$ | CH | |
| L-6 | Q-6 | 0 | H | H | | | — | Cl | H | — | — | — | CH$_3$ | OCH$_3$ | N | |

TABLE II-continued

General Structure II (wherein R₁₂ and R₁₃ are H)

| L | Q₁ | n | R | R₁ | R₂ | R₃ | R₂R₃ | R₇ | R₈ | R₉ | R₁₀ | R₁₁ | X | Y | Z | m.p. (°C.) |
|---|---|---|---|---|---|---|---|---|---|---|---|---|---|---|---|---|
| L-6 | Q-6 | 0 | H | H | | | — | F | H | — | — | — | Cl | OCH₃ | CH | |
| L-6 | Q-6 | 0 | H | H | | | — | H | Br | — | — | — | OCH₃ | OCH₃ | CH | |
| L-6 | Q-6 | 0 | H | H | | | — | F | F | — | — | — | OCH₃ | OCH₃ | N | |
| L-6 | Q-6 | 0 | H | H | | | — | Cl | Cl | — | — | — | CH₃ | OCH₃ | CH | |
| L-6 | Q-6 | 0 | H | H | | | — | H | CH₃ | — | — | — | CH₃ | OCH₃ | CH | |
| L-6 | Q-6 | 0 | H | H | | | — | CH₃ | CH₃ | — | — | — | OCH₃ | OCH₃ | CH | |
| L-6 | Q-6 | 0 | H | H | | | — | H | CO₂CH₃ | — | — | — | CH₃ | CH₃ | CH | |
| L-6 | Q-6 | 0 | H | H | | | — | H | F | — | — | — | OCH₃ | OCH₃ | CH | |
| L-6 | Q-6 | 0 | H | OCH₃ | | | — | H | Cl | — | — | — | OCH₃ | CH₃ | N | |
| L-6 | Q-6 | 0 | CH₃ | Cl | | | — | F | CH₃ | — | — | — | CH₃ | OCH₃ | CH | |
| L-6 | Q-6 | 1 | H | H | | | — | H | Cl | — | — | — | CH₃ | OCH₃ | CH | |
| L-6 | Q-6 | 1 | H | H | | | — | Cl | Cl | — | — | — | OCH₃ | OCH₃ | N | |
| L-6 | Q-6 | 1 | H | H | | | — | F | CH₃ | — | — | — | Cl | OCH₃ | CH | |
| L-6 | Q-7 | 0 | H | H | | | — | H | H | — | — | — | CH₃ | CH₃ | CH | |
| L-6 | Q-7 | 0 | H | H | | | — | H | Cl | — | — | — | CH₃ | OCH₃ | CH | |
| L-6 | Q-7 | 0 | H | H | | | — | Cl | Cl | — | — | — | OCH₃ | OCH₃ | CH | |
| L-6 | Q-7 | 0 | H | H | | | — | F | F | — | — | — | CH₃ | CH₃ | N | |
| L-6 | Q-7 | 0 | H | H | | | — | H | Br | — | — | — | CH₃ | OCH₃ | N | |
| L-6 | Q-7 | 0 | H | H | | | — | CH₃ | H | — | — | — | OCH₃ | OCH₃ | N | |
| L-6 | Q-7 | 0 | H | H | | | — | H | OCH₃ | — | — | — | Cl | OCH₃ | CH | |
| L-6 | Q-7 | 0 | H | H | | | — | H | F | — | — | — | CH₃ | OCH₃ | CH | |
| L-6 | Q-7 | 0 | H | H | | | — | Cl | Br | — | — | — | OCH₃ | OCH₃ | CH | |
| L-6 | Q-7 | 0 | H | H | | | — | Cl | CH₃ | — | — | — | CH₃ | OCH₃ | N | |
| L-6 | Q-7 | 0 | H | H | | | — | F | CH₃ | — | — | — | OCH₃ | OCH₃ | N | |
| L-6 | Q-7 | 0 | H | H | | | — | H | Cl | — | — | — | CH₃ | CH₃ | N | |
| L-6 | Q-7 | 0 | H | H | | | — | H | CH₃ | — | — | — | OCH₃ | OCH₃ | CH | |
| L-6 | Q-7 | 0 | H | CH₃ | | | — | H | H | — | — | — | Cl | OCH₃ | CH | |
| L-6 | Q-7 | 0 | CH₃ | H | | | — | H | H | — | — | — | CH₃ | OCH₃ | N | |
| L-6 | Q-7 | 1 | H | H | | | — | F | F | — | — | — | OCH₃ | OCH₃ | CH | |
| L-6 | Q-7 | 1 | H | H | | | — | H | H | — | — | — | OCH₃ | OCH₃ | CH | |
| L-6 | Q-8 | 0 | H | H | | | — | H | H | — | — | — | CH₃ | CH₃ | CH | |
| L-6 | Q-8 | 0 | H | H | | | — | H | H | — | — | — | OCH₃ | CH₃ | CH | |
| L-6 | Q-8 | 0 | H | H | | | — | H | H | — | — | — | OCH₃ | OCH₃ | CH | |
| L-6 | Q-8 | 0 | H | H | | | — | Cl | H | — | — | — | CH₃ | OCH₃ | N | |
| L-6 | Q-8 | 0 | H | H | | | — | F | H | — | — | — | Cl | OCH₃ | CH | |
| L-6 | Q-8 | 0 | H | H | | | — | H | Br | — | — | — | OCH₃ | OCH₃ | CH | |
| L-6 | Q-8 | 0 | H | H | | | — | F | F | — | — | — | OCH₃ | OCH₃ | N | |
| L-6 | Q-8 | 0 | H | H | | | — | Cl | Cl | — | — | — | CH₃ | CH₃ | CH | |
| L-6 | Q-8 | 0 | H | H | | | — | H | CH₃ | — | — | — | CH₃ | OCH₃ | CH | |
| L-6 | Q-8 | 0 | H | H | | | — | CH₃ | CH₃ | — | — | — | OCH₃ | OCH₃ | CH | |
| L-6 | Q-8 | 0 | H | H | | | — | H | CO₂CH₃ | — | — | — | CH₃ | CH₃ | CH | |
| L-6 | Q-8 | 0 | H | H | | | — | H | F | — | — | — | OCH₃ | OCH₃ | CH | |
| L-6 | Q-8 | 0 | H | OCH₃ | | | — | H | Cl | — | — | — | OCH₃ | CH₃ | N | |
| L-6 | Q-8 | 0 | CH₃ | Cl | | | — | F | CH₃ | — | — | — | CH₃ | OCH₃ | CH | |
| L-6 | Q-8 | 1 | H | H | | | — | H | Cl | — | — | — | CH₃ | OCH₃ | CH | |
| L-6 | Q-8 | 1 | H | H | | | — | Cl | Cl | — | — | — | OCH₃ | OCH₃ | N | |
| L-6 | Q-8 | 1 | H | H | | | — | F | CH₃ | — | — | — | Cl | OCH₃ | CH | |
| L-6 | Q-9 | 0 | H | H | | | CH₃ | H | H | — | — | — | CH₃ | CH₃ | CH | |
| L-6 | Q-9 | 0 | H | H | | | CH₃ | H | Cl | — | — | — | CH₃ | OCH₃ | CH | |
| L-6 | Q-9 | 0 | H | H | | | CH₃ | Cl | Cl | — | — | — | OCH₃ | OCH₃ | CH | |
| L-6 | Q-9 | 0 | H | H | | | CH₃ | F | F | — | — | — | CH₃ | CH₃ | N | |
| L-6 | Q-9 | 0 | H | H | | | CH₃ | H | Br | — | — | — | CH₃ | OCH₃ | N | |
| L-6 | Q-9 | 0 | H | H | | | CH₃ | CH₃ | H | — | — | — | OCH₃ | OCH₃ | N | |
| L-6 | Q-9 | 0 | H | H | | | CH₃ | H | OCH₃ | — | — | — | Cl | OCH₃ | CH | |
| L-6 | Q-9 | 0 | H | H | | | CH₃ | H | F | — | — | — | CH₃ | OCH₃ | CH | |
| L-6 | Q-9 | 0 | H | H | | | CH₂CH₃ | Cl | Br | — | — | — | OCH₃ | OCH₃ | CH | |
| L-6 | Q-9 | 0 | H | H | | | CH₂CH₃ | Cl | CH₃ | — | — | — | CH₃ | OCH₃ | N | |
| L-6 | Q-9 | 0 | H | H | | | CH₃ | F | CH₃ | — | — | — | OCH₃ | OCH₃ | CH | |
| L-6 | Q-9 | 0 | H | H | | | CH₃ | H | Cl | — | — | — | CH₃ | CH₃ | N | |
| L-6 | Q-9 | 0 | H | H | | | CH₃ | H | CH₃ | — | — | — | OCH₃ | OCH₃ | CH | |
| L-6 | Q-9 | 0 | H | CH₃ | | | CH₃ | H | H | — | — | — | Cl | OCH₃ | CH | |
| L-6 | Q-9 | 0 | CH₃ | OCH₃ | | | CH₃ | H | H | — | — | — | CH₃ | OCH₃ | N | |
| L-6 | Q-9 | 1 | H | H | | | CH₃ | F | F | — | — | — | OCH₃ | OCH₃ | CH | |
| L-6 | Q-9 | 1 | H | H | | | CH₃ | H | H | — | — | — | OCH₃ | OCH₃ | CH | |
| L-6 | Q-10 | 0 | H | H | | | CH₃ | H | H | — | — | — | CH₃ | CH₃ | CH | |
| L-6 | Q-10 | 0 | H | H | | | CH₃ | H | H | — | — | — | OCH₃ | OCH₃ | CH | |
| L-6 | Q-10 | 0 | H | H | | | CH₃ | Cl | H | — | — | — | CH₃ | OCH₃ | N | |
| L-6 | Q-10 | 0 | H | H | | | CH₃ | F | H | — | — | — | Cl | OCH₃ | CH | |
| L-6 | Q-10 | 0 | H | H | | | CH₃ | F | Br | — | — | — | OCH₃ | OCH₃ | CH | |
| L-6 | Q-10 | 0 | H | H | | | CH₃ | F | F | — | — | — | OCH₃ | OCH₃ | N | |
| L-6 | Q-10 | 0 | H | H | | | CH₃ | Cl | Cl | — | — | — | CH₃ | CH₃ | CH | |
| L-6 | Q-10 | 0 | H | H | | | CH₃ | H | CH₃ | — | — | — | CH₃ | OCH₃ | CH | |
| L-6 | Q-10 | 0 | H | H | | | CH₃ | CH₃ | CH₃ | — | — | — | OCH₃ | OCH₃ | CH | |
| L-6 | Q-10 | 0 | H | H | | | CH₃ | H | CO₂CH₃ | — | — | — | CH₃ | CH₃ | CH | |
| L-6 | Q-10 | 0 | H | H | | | CH₃ | H | F | — | — | — | OCH₃ | OCH₃ | CH | |
| L-6 | Q-10 | 0 | H | OCH₃ | | | CH₃ | H | Cl | — | — | — | OCH₃ | CH₃ | N | |
| L-6 | Q-10 | 0 | CH | Cl | | | CH₃ | F | CH₃ | — | — | — | CH₃ | OCH₃ | CH | |
| L-6 | Q-10 | 0 | CH₃ | Cl | | | CH₃ | F | CH₃ | — | — | — | CH₃ | OCH₃ | CH | |
| L-6 | Q-10 | 1 | H | H | | | CH₃ | H | Cl | — | — | — | CH₃ | OCH₃ | CH | |

TABLE II-continued

General Structure II (wherein $R_{12}$ and $R_{13}$ are H)

| L | $Q_1$ | n | R | $R_1$ | $R_2$ | $R_3$ | $R_2R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|---|---|
| L-6 | Q-10 | 1 | H | H | | $CH_3$ | | Cl | Cl | — | — | — | $OCH_3$ | $OCH_3$ | N | |
| L-6 | Q-10 | 1 | H | H | | $CH_3$ | | F | $CH_3$ | — | — | — | Cl | $OCH_3$ | CH | |

TABLE IIA

General Structure II (wherein $R_{12}$ is OH and $R_{13}$ is H)

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-1 | 1 | H | H | — | H | H | H | H | — | $CH_3$ | $CH_3$ | CH | |
| L-2 | Q-1 | 1 | H | H | — | H | Cl | H | H | — | $CH_3$ | $OCH_3$ | CH | |
| L-2 | Q-1 | 1 | H | H | — | Cl | Cl | H | H | — | $OCH_3$ | $OCH_3$ | CH | |
| L-2 | Q-1 | 1 | H | H | — | F | F | H | H | — | $CH_3$ | $CH_3$ | N | |
| L-2 | Q-1 | 1 | H | H | — | H | Br | H | H | — | $CH_3$ | $OCH_3$ | N | |
| L-2 | Q-1 | 1 | H | H | — | $CH_3$ | H | H | H | — | $OCH_3$ | $OCH_3$ | N | |
| L-2 | Q-1 | 1 | H | H | — | H | $OCH_3$ | H | H | — | Cl | $OCH_3$ | CH | |
| L-2 | Q-1 | 1 | H | H | — | H | F | H | H | — | $CH_3$ | $OCH_3$ | CH | |
| L-2 | Q-1 | 1 | H | H | — | Cl | Br | H | H | — | $OCH_3$ | $OCH_3$ | CH | |
| L-2 | Q-1 | 1 | H | H | — | Cl | $CH_3$ | H | H | — | $CH_3$ | $OCH_3$ | N | |
| L-2 | Q-1 | 1 | H | H | — | F | $CH_3$ | H | H | — | $OCH_3$ | $OCH_3$ | CH | |
| L-2 | Q-1 | 1 | H | H | — | H | Cl | Cl | H | — | $CH_3$ | $CH_3$ | N | |
| L-2 | Q-1 | 1 | H | H | — | H | $CH_3$ | F | F | — | $OCH_3$ | $OCH_3$ | CH | |
| L-2 | Q-1 | 1 | H | $CH_3$ | — | H | H | H | H | — | Cl | $OCH_3$ | CH | |
| L-2 | Q-1 | 1 | $CH_3$ | H | — | H | H | H | H | — | $CH_3$ | $OCH_3$ | N | |
| L-2 | Q-1 | 1 | H | H | — | F | F | H | H | — | $OCH_3$ | $OCH_3$ | N | |
| L-2 | Q-1 | 1 | H | H | — | H | H | H | H | — | $OCH_3$ | $OCH_3$ | CH | |
| L-2 | Q-2 | 1 | H | H | — | H | H | — | — | H | $CH_3$ | $CH_3$ | CH | |
| L-2 | Q-2 | 1 | H | H | — | H | H | — | — | H | $OCH_3$ | $CH_3$ | CH | |
| L-2 | Q-2 | 1 | H | H | — | H | H | — | — | H | $OCH_3$ | $OCH_3$ | CH | |
| L-2 | Q-2 | 1 | H | H | — | Cl | H | — | — | H | $CH_3$ | $OCH_3$ | N | |
| L-2 | Q-2 | 1 | H | H | — | F | H | — | — | H | Cl | $OCH_3$ | CH | |
| L-2 | Q-2 | 1 | H | H | — | H | Br | — | — | H | $OCH_3$ | $OCH_3$ | CH | |
| L-2 | Q-2 | 1 | H | H | — | F | F | — | — | H | $OCH_3$ | $OCH_3$ | N | |
| L-2 | Q-2 | 1 | H | H | — | Cl | Cl | — | — | H | $CH_3$ | $OCH_3$ | CH | |
| L-2 | Q-2 | 1 | H | H | — | H | $CH_3$ | — | — | H | $CH_3$ | $OCH_3$ | CH | |
| L-2 | Q-2 | 1 | H | H | — | $CH_3$ | $CH_3$ | — | — | H | $OCH_3$ | $OCH_3$ | CH | |
| L-2 | Q-2 | 1 | H | H | — | H | $CO_2CH_3$ | — | — | H | $CH_3$ | $CH_3$ | CH | |
| L-2 | Q-2 | 1 | H | H | — | H | F | — | — | $CH_3$ | $OCH_3$ | $OCH_3$ | CH | |
| L-2 | Q-2 | 1 | H | $OCH_3$ | — | H | Cl | — | — | H | $OCH_3$ | $CH_3$ | N | |
| L-2 | Q-2 | 1 | $CH_3$ | Cl | — | F | $CH_3$ | — | — | $CH_3$ | $CH_3$ | $OCH_3$ | CH | |

TABLE IIB

General Structure II (wherein $R_{12}$ is $OCH_3$ and $R_{13}$ is H)

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-1 | 1 | H | H | — | H | H | H | H | — | $CH_3$ | $CH_3$ | CH | |
| L-2 | Q-1 | 1 | H | H | — | H | Cl | H | H | — | $CH_3$ | $OCH_3$ | CH | |
| L-2 | Q-1 | 1 | H | H | — | Cl | Cl | H | H | — | $OCH_3$ | $OCH_3$ | CH | |
| L-2 | Q-1 | 1 | H | H | — | F | F | H | H | — | $CH_3$ | $CH_3$ | N | |
| L-2 | Q-1 | 1 | H | H | — | H | Br | H | H | — | $CH_3$ | $OCH_3$ | N | |
| L-2 | Q-1 | 1 | H | H | — | $CH_3$ | H | H | H | — | $OCH_3$ | $OCH_3$ | N | |
| L-2 | Q-1 | 1 | H | H | — | H | $OCH_3$ | H | H | — | Cl | $OCH_3$ | CH | |
| L-2 | Q-1 | 1 | H | H | — | H | F | H | H | — | $CH_3$ | $OCH_3$ | CH | |
| L-2 | Q-1 | 1 | H | H | — | Cl | Br | H | H | — | $OCH_3$ | $OCH_3$ | CH | |
| L-2 | Q-1 | 1 | H | H | — | Cl | $CH_3$ | H | H | — | $CH_3$ | $OCH_3$ | N | |
| L-2 | Q-1 | 1 | H | H | — | F | $CH_3$ | H | H | — | $OCH_3$ | $OCH_3$ | CH | |
| L-2 | Q-1 | 1 | H | H | — | H | Cl | Cl | H | — | $CH_3$ | $CH_3$ | N | |
| L-2 | Q-1 | 1 | H | H | — | H | $CH_3$ | F | F | — | $OCH_3$ | $OCH_3$ | CH | |
| L-2 | Q-1 | 1 | H | $CH_3$ | — | H | H | H | H | — | Cl | $OCH_3$ | CH | |
| L-2 | Q-1 | 1 | $CH_3$ | H | — | H | H | H | H | — | $CH_3$ | $OCH_3$ | N | |
| L-2 | Q-1 | 1 | H | H | — | F | F | H | H | — | $OCH_3$ | $OCH_3$ | CH | |
| L-2 | Q-1 | 1 | H | H | — | H | H | H | H | — | $OCH_3$ | $OCH_3$ | CH | |
| L-2 | Q-2 | 1 | H | H | — | H | H | — | — | H | $CH_3$ | $CH_3$ | CH | |
| L-2 | Q-2 | 1 | H | H | — | H | H | — | — | H | $OCH_3$ | $CH_3$ | CH | |
| L-2 | Q-2 | 1 | H | H | — | H | H | — | — | H | $OCH_3$ | $OCH_3$ | CH | |
| L-2 | Q-2 | 1 | H | H | — | Cl | H | — | — | H | $CH_3$ | $OCH_3$ | N | |
| L-2 | Q-2 | 1 | H | H | — | F | H | — | — | H | Cl | $OCH_3$ | CH | |
| L-2 | Q-2 | 1 | H | H | — | H | Br | — | — | H | $OCH_3$ | $OCH_3$ | CH | |
| L-2 | Q-2 | 1 | H | H | — | F | F | — | — | H | $OCH_3$ | $OCH_3$ | N | |
| L-2 | Q-2 | 1 | H | H | — | Cl | Cl | — | — | H | $CH_3$ | $OCH_3$ | CH | |
| L-2 | Q-2 | 1 | H | H | — | H | $CH_3$ | — | — | H | $CH_3$ | $OCH_3$ | CH | |
| L-2 | Q-2 | 1 | H | H | — | $CH_3$ | $CH_3$ | — | — | H | $OCH_3$ | $OCH_3$ | CH | |
| L-2 | Q-2 | 1 | H | H | — | H | $CO_2CH_3$ | — | — | H | $CH_3$ | $CH_3$ | CH | |
| L-2 | Q-2 | 1 | H | H | — | H | F | — | — | $CH_3$ | $OCH_3$ | $OCH_3$ | CH | |
| L-2 | Q-2 | 1 | H | $OCH_3$ | — | H | Cl | — | — | H | $OCH_3$ | $CH_3$ | N | |

TABLE IIB-continued

General Structure II (wherein $R_{12}$ is $OCH_3$ and $R_{13}$ is H)

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-2 | 1 | $CH_3$ | Cl | — | F | $CH_3$ | — | — | $CH_3$ | $CH_3$ | $OCH_3$ | CH | |

TABLE IIC

General Structure II (wherein $R_{12}$ is OH and $R_{13}$ is H)

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-4 | 1 | H | H | — | H | H | — | — | — | $CH_3$ | $CH_3$ | CH | |
| L-2 | Q-4 | 1 | H | H | — | H | Cl | — | — | — | $CH_3$ | $OCH_3$ | CH | |
| L-2 | Q-4 | 1 | H | H | — | Cl | Cl | — | — | — | $OCH_3$ | $OCH_3$ | CH | |
| L-2 | Q-4 | 1 | H | H | — | F | F | — | — | — | $CH_3$ | $CH_3$ | N | |
| L-2 | Q-4 | 1 | H | H | — | H | Br | — | — | — | $CH_3$ | $OCH_3$ | N | |
| L-2 | Q-4 | 1 | H | H | — | $CH_3$ | H | — | — | — | $OCH_3$ | $OCH_3$ | N | |
| L-2 | Q-4 | 1 | H | H | — | H | $OCH_3$ | — | — | — | Cl | $OCH_3$ | CH | |
| L-2 | Q-4 | 1 | H | H | — | H | F | — | — | — | $CH_3$ | $OCH_3$ | CH | |
| L-2 | Q-4 | 1 | H | H | — | Cl | Br | — | — | — | $OCH_3$ | $OCH_3$ | CH | |
| L-2 | Q-4 | 1 | H | H | — | Cl | $CH_3$ | — | — | — | $CH_3$ | $OCH_3$ | N | |
| L-2 | Q-4 | 1 | H | H | — | F | $CH_3$ | — | — | — | $OCH_3$ | $OCH_3$ | CH | |
| L-2 | Q-4 | 1 | H | H | — | H | Cl | — | — | — | $CH_3$ | $CH_3$ | N | |
| L-2 | Q-4 | 1 | H | H | — | H | $CH_3$ | — | — | — | $OCH_3$ | $OCH_3$ | CH | |
| L-2 | Q-4 | 1 | H | $CH_3$ | — | H | H | — | — | — | Cl | $OCH_3$ | CH | |
| L-2 | Q-4 | 1 | $CH_3$ | H | — | H | H | — | — | — | $CH_3$ | $OCH_3$ | N | |
| L-2 | Q-4 | 1 | H | H | — | F | F | — | — | — | $OCH_3$ | $OCH_3$ | CH | |
| L-2 | Q-4 | 1 | H | H | — | H | H | — | — | — | $OCH_3$ | $OCH_3$ | CH | |
| L-2 | Q-4 | 1 | H | H | — | H | H | — | — | H | $CH_3$ | $CH_3$ | CH | |
| L-2 | Q-4 | 1 | H | H | — | H | H | — | — | H | $OCH_3$ | $CH_3$ | CH | |
| L-2 | Q-4 | 1 | H | H | — | H | H | — | — | H | $OCH_3$ | $OCH_3$ | CH | |
| L-2 | Q-4 | 1 | H | H | — | Cl | H | — | — | H | $CH_3$ | $OCH_3$ | N | |
| L-2 | Q-4 | 1 | H | H | — | F | H | — | — | H | Cl | $OCH_3$ | CH | |
| L-2 | Q-4 | 1 | H | H | — | H | Br | — | — | H | $OCH_3$ | $OCH_3$ | CH | |
| L-2 | Q-4 | 1 | H | H | — | F | F | — | — | H | $OCH_3$ | $OCH_3$ | N | |
| L-2 | Q-4 | 1 | H | H | — | Cl | Cl | — | — | H | $CH_3$ | $OCH_3$ | CH | |
| L-2 | Q-4 | 1 | H | H | — | H | $CH_3$ | — | — | H | $CH_3$ | $OCH_3$ | CH | |
| L-2 | Q-4 | 1 | H | H | — | $CH_3$ | $CH_3$ | — | — | H | $OCH_3$ | $OCH_3$ | CH | |
| L-2 | Q-4 | 1 | H | H | — | H | $CO_2CH_3$ | — | — | H | $CH_3$ | $CH_3$ | CH | |
| L-2 | Q-4 | 1 | H | H | — | H | F | — | — | $CH_3$ | $OCH_3$ | $OCH_3$ | CH | |
| L-2 | Q-4 | 1 | H | $OCH_3$ | — | H | Cl | — | — | H | $OCH_3$ | $CH_3$ | N | |
| L-2 | Q-4 | 1 | $CH_3$ | Cl | — | F | $CH_3$ | — | — | $CH_3$ | $CH_3$ | $OCH_3$ | CH | |

| L | $Q_1$ | n | R | $R_1$ | $R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-4 | Q-1 | 1 | $CH_3$ | H | — | H | H | H | H | — | $CH_3$ | $OCH_3$ | N | |
| L-4 | Q-1 | 1 | H | H | — | F | F | H | H | — | $OCH_3$ | $OCH_3$ | CH | |
| L-4 | Q-1 | 1 | H | H | — | H | H | H | H | — | $OCH_3$ | $OCH_3$ | CH | |
| L-4 | Q-2 | 1 | H | H | — | H | H | — | — | H | $CH_3$ | $CH_3$ | CH | |
| L-4 | Q-2 | 1 | H | H | — | H | H | — | — | H | $OCH_3$ | $CH_3$ | CH | |
| L-4 | Q-2 | 1 | H | H | — | H | H | — | — | H | $OCH_3$ | $OCH_3$ | CH | |
| L-4 | Q-2 | 1 | H | H | — | Cl | H | — | — | H | $CH_3$ | $OCH_3$ | N | |
| L-4 | Q-2 | 1 | H | H | — | F | H | — | — | H | Cl | $OCH_3$ | CH | |
| L-4 | Q-2 | 1 | H | H | — | H | Br | — | — | H | $OCH_3$ | $OCH_3$ | CH | |
| L-4 | Q-2 | 1 | H | H | — | F | F | — | — | H | $OCH_3$ | $OCH_3$ | N | |
| L-4 | Q-2 | 1 | H | H | — | Cl | Cl | — | — | H | $CH_3$ | $OCH_3$ | CH | |
| L-4 | Q-2 | 1 | H | H | — | H | $CH_3$ | — | — | H | $CH_3$ | $OCH_3$ | CH | |
| L-4 | Q-2 | 1 | H | H | — | $CH_3$ | $CH_3$ | — | — | H | $OCH_3$ | $OCH_3$ | CH | |
| L-4 | Q-2 | 1 | H | H | — | H | $CO_2CH_3$ | — | — | H | $CH_3$ | $CH_3$ | CH | |
| L-4 | Q-2 | 1 | H | H | — | H | F | — | — | $CH_3$ | $OCH_3$ | $OCH_3$ | CH | |
| L-4 | Q-2 | 1 | H | $OCH_3$ | — | H | Cl | — | — | H | $OCH_3$ | $CH_3$ | N | |
| L-4 | Q-2 | 1 | $CH_3$ | Cl | — | F | $CH_3$ | — | — | $CH_3$ | $CH_3$ | $OCH_3$ | CH | |
| L-4 | Q-2 | 1 | H | H | — | H | Cl | — | — | H | $CH_3$ | $OCH_3$ | CH | |
| L-4 | Q-2 | 1 | H | H | — | Cl | Cl | — | — | H | $OCH_3$ | $OCH_3$ | N | |
| L-4 | Q-2 | 1 | H | H | — | F | $CH_3$ | — | — | H | Cl | $OCH_3$ | CH | |
| L-4 | Q-3 | 1 | H | H | $CH_3$ | H | H | — | — | H | $CH_3$ | $CH_3$ | CH | |
| L-4 | Q-3 | 1 | H | H | $CH_3$ | H | Cl | — | — | H | $CH_3$ | $OCH_3$ | CH | |
| L-4 | Q-3 | 1 | H | H | $CH_3$ | Cl | Cl | — | — | H | $OCH_3$ | $OCH_3$ | CH | |
| L-4 | Q-3 | 1 | H | H | $CH_3$ | F | F | — | — | H | $CH_3$ | $CH_3$ | N | |
| L-4 | Q-3 | 1 | H | H | $CH_3$ | H | Br | — | — | H | $CH_3$ | $CH_3$ | N | |
| L-4 | Q-3 | 1 | H | H | $CH_3$ | $CH_3$ | H | — | — | H | $OCH_3$ | $OCH_3$ | N | |
| L-4 | Q-3 | 1 | H | H | $CH_3$ | H | $OCH_3$ | — | — | H | Cl | $OCH_3$ | CH | |
| L-4 | Q-3 | 1 | H | H | $CH_3$ | H | F | — | — | H | $CH_3$ | $OCH_3$ | CH | |
| L-4 | Q-3 | 1 | H | H | $CH_3$ | Cl | Br | — | — | H | $OCH_3$ | $OCH_3$ | CH | |
| L-4 | Q-3 | 1 | H | H | $CH_3$ | Cl | $CH_3$ | — | — | H | $CH_3$ | $OCH_3$ | N | |
| L-4 | Q-3 | 1 | H | H | $CH_3$ | F | $CH_3$ | — | — | H | $OCH_3$ | $OCH_3$ | CH | |
| L-4 | Q-3 | 1 | H | H | $CH_3$ | Cl | Cl | — | — | H | $CH_3$ | $CH_3$ | N | |
| L-5 | Q-10 | 1 | H | H | $CH_3$ | F | H | — | — | — | Cl | $OCH_3$ | CH | |
| L-5 | Q-10 | 1 | H | H | $CH_3$ | H | Br | — | — | — | $OCH_3$ | $OCH_3$ | CH | |
| L-5 | Q-10 | 1 | H | H | $CH_3$ | F | F | — | — | — | $OCH_3$ | $OCH_3$ | N | |
| L-5 | Q-10 | 1 | H | H | $CH_2CH_3$ | Cl | Cl | — | — | — | $CH_3$ | $OCH_3$ | CH | |

TABLE IIC-continued

General Structure II (wherein $R_{12}$ is OH and $R_{13}$ is H)

| L | Q₁ | n | R | R₁ | R₂ | R₇ | R₈ | R₉ | R₁₀ | R₁₁ | X | Y | Z |
|---|---|---|---|---|---|---|---|---|---|---|---|---|---|
| L-5 | Q-10 | 1 | H | H | CH₃ | H | CH₃ | — | — | — | CH₃ | OCH₃ | CH |
| L-5 | Q-10 | 1 | H | H | CH₃ | CH₃ | CH₃ | — | — | — | OCH₃ | OCH₃ | CH |
| L-5 | Q-10 | 1 | H | H | CH₃ | H | CO₂CH₃ | — | — | — | CH₃ | CH₃ | CH |
| L-5 | Q-10 | 1 | H | H | CH₃ | H | F | — | — | — | OCH₃ | OCH₃ | CH |
| L-5 | Q-10 | 1 | H | OCH₃ | CH₃ | H | Cl | — | — | — | OCH₃ | CH₃ | N |
| L-5 | Q-10 | 1 | CH₃ | Cl | CH₃ | F | CH₃ | — | — | — | CH₃ | OCH₃ | CH |
| L-5 | Q-10 | 1 | H | H | CH₃ | H | Cl | — | — | — | CH₃ | OCH₃ | CH |
| L-5 | Q-10 | 1 | H | H | CH₃ | Cl | Cl | — | — | — | OCH₃ | OCH₃ | N |
| L-5 | Q-10 | 1 | H | H | CH₃ | F | CH₃ | — | — | — | Cl | OCH₃ | CH |
| L-6 | Q-1 | 1 | H | H | — | H | H | H | H | — | CH₃ | CH₃ | CH |
| L-6 | Q-1 | 1 | H | H | — | H | Cl | H | H | — | CH₃ | OCH₃ | CH |
| L-6 | Q-1 | 1 | H | H | — | Cl | Cl | H | H | — | OCH₃ | OCH₃ | CH |
| L-6 | Q-1 | 1 | H | H | — | F | F | H | H | — | CH₃ | CH₃ | N |
| L-6 | Q-1 | 1 | H | H | — | H | Br | H | H | — | CH₃ | OCH₃ | N |
| L-6 | Q-1 | 1 | H | H | — | CH₃ | H | H | H | — | OCH₃ | OCH₃ | N |
| L-6 | Q-1 | 1 | H | H | — | H | OCH₃ | H | H | — | Cl | OCH₃ | CH |
| L-6 | Q-1 | 1 | H | H | — | H | F | H | H | — | CH₃ | Cl | CH |
| L-6 | Q-1 | 1 | H | H | — | Cl | Br | H | H | — | OCH₃ | OCH₃ | CH |
| L-6 | Q-1 | 1 | H | H | — | Cl | CH₃ | H | H | — | CH₃ | OCH₃ | N |
| L-6 | Q-1 | 1 | H | H | — | F | CH₃ | H | H | — | OCH₃ | OCH₃ | CH |
| L-6 | Q-1 | 1 | H | H | — | H | Cl | Cl | H | — | CH₃ | CH₃ | N |
| L-6 | Q-1 | 1 | H | H | — | H | CH₃ | F | F | — | OCH₃ | OCH₃ | CH |
| L-6 | Q-1 | 1 | H | CH₃ | — | H | H | H | H | — | Cl | OCH₃ | CH |
| L-6 | Q-1 | 1 | CH₃ | H | — | H | H | H | H | — | CH₃ | OCH₃ | N |
| L-6 | Q-1 | 1 | H | H | — | F | F | H | H | — | OCH₃ | OCH₃ | CH |
| L-6 | Q-1 | 1 | H | H | — | H | H | H | H | — | OCH₃ | OCH₃ | CH |
| L-6 | Q-2 | 1 | H | H | — | H | H | — | — | H | CH₃ | CH₃ | CH |
| L-6 | Q-2 | 1 | H | H | — | H | H | — | — | H | OCH₃ | CH₃ | CH |

TABLE IID

General Structure IIa (where $R_{12}$ and $R_{13}$ are H)

| L | Q₁ | n | R | R₁ | R₂ | R₇ | R₈ | R₉ | R₁₀ | R₁₁ | X | Y | Z | m.p. (°C.) |
|---|---|---|---|---|---|---|---|---|---|---|---|---|---|---|
| L-2 | Q-1 | 0 | H | H | — | H | H | H | H | — | CH₃ | CH₃ | CH | |
| L-2 | Q-1 | 0 | H | H | — | H | Cl | H | H | — | CH₃ | OCH₃ | CH | |
| L-2 | Q-1 | 0 | H | H | — | Cl | Cl | H | H | — | OCH₃ | OCH₃ | CH | |
| L-2 | Q-1 | 0 | H | H | — | F | F | H | H | — | CH₃ | CH₃ | N | |
| L-2 | Q-1 | 0 | H | H | — | H | Br | H | H | — | CH₃ | OCH₃ | N | |
| L-2 | Q-1 | 0 | H | H | — | CH₃ | H | H | H | — | OCH₃ | OCH₃ | N | |
| L-2 | Q-1 | 0 | H | H | — | H | OCH₃ | H | H | — | Cl | OCH₃ | CH | |
| L-2 | Q-1 | 0 | H | H | — | H | F | H | H | — | CH₃ | OCH₃ | CH | |
| L-2 | Q-1 | 0 | H | H | — | Cl | Br | H | H | — | OCH₃ | OCH₃ | CH | |
| L-2 | Q-1 | 0 | H | H | — | Cl | CH₃ | H | H | — | CH₃ | OCH₃ | N | |
| L-2 | Q-1 | 0 | H | H | — | F | CH₃ | H | H | — | OCH₃ | OCH₃ | CH | |
| L-2 | Q-1 | 0 | H | H | — | H | Cl | Cl | H | — | CH₃ | CH₃ | N | |
| L-2 | Q-1 | 0 | H | H | — | H | CH₃ | F | F | — | OCH₃ | OCH₃ | CH | |
| L-2 | Q-1 | 0 | H | CH₃ | — | H | H | H | H | — | Cl | OCH₃ | CH | |
| L-2 | Q-1 | 0 | CH₃ | H | — | H | H | H | H | — | CH₃ | OCH₃ | N | |
| L-2 | Q-1 | 1 | H | H | — | F | F | H | H | — | OCH₃ | OCH₃ | CH | |
| L-2 | Q-1 | 1 | H | H | — | H | H | H | H | — | OCH₃ | OCH₃ | CH | |
| L-2 | Q-2 | 0 | H | H | — | H | H | — | — | H | CH₃ | CH₃ | CH | |
| L-2 | Q-2 | 0 | H | H | — | H | H | — | — | H | OCH₃ | CH₃ | CH | |
| L-2 | Q-2 | 0 | H | H | — | H | H | — | — | H | OCH₃ | OCH₃ | CH | |
| L-2 | Q-2 | 0 | H | H | — | Cl | H | — | — | H | CH₃ | OCH₃ | N | |
| L-2 | Q-2 | 0 | H | H | — | F | H | — | — | H | Cl | OCH₃ | CH | |
| L-2 | Q-2 | 0 | H | H | — | H | Br | — | — | H | OCH₃ | OCH₃ | CH | |
| L-2 | Q-2 | 0 | H | H | — | F | F | — | — | H | OCH₃ | OCH₃ | N | |
| L-2 | Q-2 | 0 | H | H | — | Cl | Cl | — | — | H | CH₃ | OCH₃ | N | |
| L-2 | Q-2 | 0 | H | H | — | H | CH₃ | — | — | H | CH₃ | OCH₃ | CH | |
| L-2 | Q-2 | 0 | H | H | — | CH₃ | CH₃ | — | — | H | OCH₃ | OCH₃ | CH | |
| L-2 | Q-2 | 0 | H | H | — | H | CO₂CH₃ | — | — | H | CH₃ | CH₃ | CH | |
| L-2 | Q-2 | 0 | H | H | — | H | F | — | — | CH₃ | OCH₃ | OCH₃ | CH | |
| L-2 | Q-2 | 0 | H | OCH₃ | — | H | Cl | — | — | H | OCH₃ | CH₃ | N | |
| L-2 | Q-2 | 0 | CH₃ | Cl | — | F | CH₃ | — | — | CH₃ | CH₃ | OCH₃ | CH | |

| L | Q₁ | n | R | R₁ | R₃ | R₇ | R₈ | R₉ | R₁₀ | R₁₁ | X | Y | Z | m.p. (°C.) |
|---|---|---|---|---|---|---|---|---|---|---|---|---|---|---|
| L-2 | Q-2 | 1 | H | H | — | H | Cl | — | — | H | CH₃ | OCH₃ | CH | |
| L-2 | Q-2 | 1 | H | H | — | Cl | Cl | — | — | H | OCH₃ | OCH₃ | N | |
| L-2 | Q-2 | 1 | H | H | — | F | CH₃ | — | — | H | Cl | OCH₃ | CH | |
| L-2 | Q-3 | 0 | H | H | CH₃ | H | H | — | — | H | CH₃ | CH₃ | CH | |
| L-2 | Q-3 | 0 | H | H | CH₃ | H | Cl | — | — | H | CH₃ | OCH₃ | CH | |
| L-2 | Q-3 | 0 | H | H | CH₃ | Cl | Cl | — | — | H | OCH₃ | OCH₃ | CH | |
| L-2 | Q-3 | 0 | H | H | CH₃ | F | F | — | — | H | CH₃ | CH₃ | N | |
| L-2 | Q-3 | 0 | H | H | CH₃ | H | Br | — | — | H | CH₃ | OCH₃ | N | |
| L-2 | Q-3 | 0 | H | H | CH₃ | CH₃ | H | — | — | H | OCH₃ | OCH₃ | N | |
| L-2 | Q-3 | 0 | H | H | CH₃ | H | OCH₃ | — | — | H | Cl | OCH₃ | CH | |
| L-2 | Q-3 | 0 | H | H | CH₃ | H | F | — | — | H | CH₃ | OCH₃ | CH | |

TABLE IID-continued

General Structure IIa (where $R_{12}$ and $R_{13}$ are H)

| L | Q₁ | n | R | R₁ | R₂ | R₇ | R₈ | R₉ | R₁₀ | R₁₁ | X | Y | Z |
|---|---|---|---|---|---|---|---|---|---|---|---|---|---|
| L-2 | Q-3 | 0 | H | H | CH₃ | Cl | Br | — | — | H | OCH₃ | OCH₃ | CH |
| L-2 | Q-3 | 0 | H | H | CH₃ | Cl | CH₃ | — | — | H | CH₃ | OCH₃ | N |
| L-2 | Q-3 | 0 | H | H | CH₃ | F | CH₃ | — | — | CH₃ | OCH₃ | OCH₃ | CH |
| L-2 | Q-3 | 0 | H | H | CH₃ | H | Cl | — | — | H | CH₃ | CH₃ | N |
| L-2 | Q-3 | 0 | H | H | CH₃ | H | CH₃ | — | — | H | OCH₃ | OCH₃ | CH |
| L-2 | Q-3 | 0 | H | CH₃ | CH₃ | H | H | — | — | H | Cl | OCH₃ | CH |
| L-2 | Q-3 | 0 | CH₃ | H | CH₃ | H | H | — | — | H | CH₃ | OCH₃ | N |
| L-2 | Q-3 | 1 | H | H | CH₃ | F | F | — | — | H | OCH₃ | OCH₃ | CH |
| L-2 | Q-3 | 1 | H | H | CH₃ | H | H | — | — | H | OCH₃ | OCH₃ | CH |
| L-2 | Q-4 | 0 | H | H | — | H | H | — | — | — | CH₃ | CH₃ | CH |
| L-2 | Q-4 | 0 | H | H | — | H | H | — | — | — | OCH₃ | CH₃ | CH |
| L-2 | Q-4 | 0 | H | H | — | H | H | — | — | — | OCH₃ | OCH₃ | CH |
| L-2 | Q-4 | 0 | H | H | — | Cl | H | — | — | — | CH₃ | OCH₃ | N |
| L-2 | Q-4 | 0 | H | H | — | F | H | — | — | — | Cl | OCH₃ | CH |
| L-2 | Q-4 | 0 | H | H | — | H | Br | — | — | — | OCH₃ | OCH₃ | CH |
| L-2 | Q-4 | 0 | H | H | — | F | F | — | — | — | OCH₃ | OCH₃ | N |
| L-2 | Q-4 | 0 | H | H | — | Cl | Cl | — | — | — | CH₃ | OCH₃ | CH |
| L-2 | Q-4 | 0 | H | H | — | H | CH₃ | — | — | — | CH₃ | OCH₃ | CH |
| L-2 | Q-4 | 0 | H | H | — | CH₃ | CH₃ | — | — | — | OCH₃ | OCH₃ | CH |
| L-2 | Q-4 | 0 | H | H | — | H | CO₂CH₃ | — | — | — | CH₃ | CH₃ | CH |
| L-2 | Q-4 | 0 | H | H | — | H | F | — | — | — | OCH₃ | OCH₃ | CH |
| L-2 | Q-4 | 0 | H | OCH₃ | — | H | Cl | — | — | — | OCH₃ | CH₃ | N |
| L-2 | Q-8 | 0 | H | H | — | H | CO₂CH₃ | — | — | — | CH₃ | CH₃ | CH |
| L-2 | Q-8 | 0 | H | H | — | H | F | — | — | — | OCH₃ | OCH₃ | CH |
| L-2 | Q-8 | 0 | H | OCH₃ | — | H | Cl | — | — | — | OCH₃ | CH₃ | N |
| L-2 | Q-8 | 0 | CH₃ | Cl | — | F | CH₃ | — | — | — | CH₃ | OCH₃ | CH |
| L-2 | Q-8 | 1 | H | H | — | H | Cl | — | — | — | CH₃ | OCH₃ | CH |
| L-2 | Q-8 | 1 | H | H | — | Cl | Cl | — | — | — | OCH₃ | OCH₃ | N |
| L-2 | Q-8 | 1 | H | H | — | F | CH₃ | — | — | — | Cl | OCH₃ | CH |
| L-2 | Q-9 | 0 | H | H | CH₃ | H | H | — | — | — | CH₃ | CH₃ | CH |
| L-2 | Q-9 | 0 | H | H | CH₃ | H | Cl | — | — | — | CH₃ | OCH₃ | CH |
| L-2 | Q-9 | 0 | H | H | CH₃ | Cl | Cl | — | — | — | OCH₃ | OCH₃ | CH |
| L-2 | Q-9 | 0 | H | H | CH₃ | F | F | — | — | — | CH₃ | CH₃ | CH |
| L-2 | Q-9 | 0 | H | H | CH₃ | H | Br | — | — | — | CH₃ | OCH₃ | N |
| L-2 | Q-9 | 0 | H | H | CH₃ | CH₃ | H | — | — | — | OCH₃ | OCH₃ | N |
| L-2 | Q-9 | 0 | H | H | CH₃ | H | OCH₃ | — | — | — | Cl | OCH₃ | CH |
| L-2 | Q-9 | 0 | H | H | CH₃ | H | F | — | — | — | CH₃ | OCH₃ | CH |
| L-2 | Q-9 | 0 | H | H | CH₃ | Cl | Br | — | — | — | OCH₃ | OCH₃ | CH |
| L-2 | Q-9 | 0 | H | H | CH₃ | Cl | CH₃ | — | — | — | CH₃ | OCH₃ | N |
| L-2 | Q-9 | 0 | H | H | CH₃ | F | CH₃ | — | — | — | OCH₃ | OCH₃ | CH |
| L-2 | Q-9 | 0 | H | H | CH₃ | H | Cl | — | — | — | CH₃ | CH₃ | N |
| L-2 | Q-9 | 0 | H | H | CH₃ | H | CH₃ | — | — | — | OCH₃ | OCH₃ | CH |
| L-2 | Q-9 | 0 | H | CH₃ | CH₃ | H | H | — | — | — | Cl | OCH₃ | CH |
| L-2 | Q-9 | 0 | CH₃ | H | CH₃ | H | H | — | — | — | CH₃ | OCH₃ | N |
| L-2 | Q-9 | 1 | H | H | CH₃ | F | F | — | — | — | OCH₃ | OCH₃ | CH |
| L-2 | Q-9 | 1 | H | H | CH₃ | H | H | — | — | — | OCH₃ | OCH₃ | CH |
| L-2 | Q-10 | 0 | H | H | CH₃ | H | H | — | — | — | CH₃ | CH₃ | CH |
| L-2 | Q-10 | 0 | H | H | CH₃ | H | H | — | — | — | OCH₃ | CH₃ | CH |
| L-2 | Q-10 | 0 | H | H | CH₃ | H | H | — | — | — | OCH₃ | OCH₃ | CH |
| L-2 | Q-10 | 0 | H | H | CH₃ | Cl | H | — | — | — | CH₃ | OCH₃ | N |
| L-2 | Q-10 | 0 | H | H | CH₃ | F | H | — | — | — | Cl | OCH₃ | CH |
| L-2 | Q-10 | 0 | H | H | CH₃ | H | Br | — | — | — | OCH₃ | OCH₃ | CH |
| L-2 | Q-10 | 0 | H | H | CH₃ | F | F | — | — | — | OCH₃ | OCH₃ | N |
| L-2 | Q-10 | 0 | H | H | CH₃ | Cl | Cl | — | — | — | CH₃ | OCH₃ | CH |

| L | Q₁ | n | R | R₁ | R₂ | R₇ | R₈ | R₉ | R₁₀ | R₁₁ | X | Y | Z | m.p. (°C.) |
|---|---|---|---|---|---|---|---|---|---|---|---|---|---|---|
| L-3 | Q-1 | 0 | H | H | CH₃ | H | H | H | H | — | CH₃ | CH₃ | CH | |
| L-3 | Q-1 | 0 | H | H | CH₃ | H | Cl | H | H | — | CH₃ | OCH₃ | CH | |
| L-3 | Q-1 | 0 | H | H | CH₃ | Cl | Cl | H | H | — | OCH₃ | OCH₃ | CH | |
| L-3 | Q-1 | 0 | H | H | CH₃ | F | F | H | H | — | CH₃ | CH₃ | N | |
| L-3 | Q-1 | 0 | H | H | CH₃ | H | Br | H | H | — | CH₃ | OCH₃ | N | |
| L-3 | Q-1 | 0 | H | H | CH₃ | CH₃ | H | H | H | — | OCH₃ | OCH₃ | N | |
| L-3 | Q-1 | 0 | H | H | CH₃ | H | OCH₃ | H | H | — | Cl | OCH₃ | CH | |
| L-3 | Q-1 | 0 | H | H | CH₃ | H | F | H | H | — | CH₃ | OCH₃ | CH | |
| L-3 | Q-1 | 0 | H | H | CH₃ | Cl | Br | H | H | — | OCH₃ | OCH₃ | CH | |
| L-3 | Q-1 | 0 | H | H | CH₃ | Cl | CH₃ | H | H | — | CH₃ | CH₃ | N | |
| L-3 | Q-1 | 0 | H | H | CH₃ | F | CH₃ | H | H | — | OCH₃ | OCH₃ | CH | |
| L-3 | Q-1 | 0 | H | H | CH₃ | H | Cl | Cl | H | — | CH₃ | CH₃ | N | |
| L-3 | Q-1 | 0 | H | H | CH₃ | H | CH₃ | F | F | — | OCH₃ | OCH₃ | CH | |
| L-3 | Q-1 | 0 | H | CH₃ | CH₃ | H | H | H | H | — | Cl | OCH₃ | CH | |
| L-3 | Q-1 | 0 | CH₃ | H | CH₃ | H | H | H | H | — | CH₃ | OCH₃ | N | |
| L-3 | Q-1 | 1 | H | H | CH₃ | F | F | H | H | — | OCH₃ | OCH₃ | CH | |
| L-3 | Q-1 | 1 | H | H | CH₃ | H | H | H | H | — | OCH₃ | OCH₃ | CH | |
| L-3 | Q-2 | 0 | H | H | CH₃ | H | H | — | — | H | CH₃ | CH₃ | CH | |
| L-3 | Q-2 | 0 | H | H | CH₃ | H | H | — | — | H | OCH₃ | CH₃ | CH | |
| L-3 | Q-2 | 0 | H | H | CH₃ | H | H | — | — | H | OCH₃ | OCH₃ | CH | |
| L-3 | Q-2 | 0 | H | H | CH₃ | Cl | H | — | — | H | CH₃ | OCH₃ | N | |
| L-3 | Q-2 | 0 | H | H | CH₃ | F | H | — | — | H | Cl | OCH₃ | CH | |
| L-3 | Q-2 | 0 | H | H | CH₃ | H | Br | — | — | H | OCH₃ | OCH₃ | CH | |

TABLE IID-continued

General Structure IIa (where $R_{12}$ and $R_{13}$ are H)

| L | $Q_1$ | n | R | $R_1$ | $R_2$ | $R_7$ | $R_8$ | $R_3$ | $R_{10}$ | $R_{11}$ | X | Y | Z | m.p. (°C.) |
|---|---|---|---|---|---|---|---|---|---|---|---|---|---|---|
| L-3 | Q-2 | 0 | H | H | $CH_3$ | F | F | — | — | H | $OCH_3$ | $OCH_3$ | N | |
| L-3 | Q-2 | 0 | H | H | $CH_3$ | Cl | Cl | — | — | H | $CH_3$ | $OCH_3$ | CH | |
| L-3 | Q-2 | 0 | H | H | $CH_3$ | H | $CH_3$ | — | — | H | $CH_3$ | $OCH_3$ | CH | |
| L-3 | Q-2 | 0 | H | H | $CH_3$ | $CH_3$ | $CH_3$ | — | — | H | $OCH_3$ | $OCH_3$ | CH | |
| L-3 | Q-2 | 0 | H | H | $CH_3$ | H | $CO_2CH_3$ | — | — | H | $CH_3$ | $CH_3$ | CH | |
| L-3 | Q-2 | 0 | H | H | $CH_3$ | H | F | — | — | $CH_3$ | $OCH_3$ | $OCH_3$ | CH | |
| L-3 | Q-2 | 0 | H | $OCH_3$ | $CH_3$ | H | Cl | — | — | H | $OCH_3$ | $CH_3$ | N | |
| L-3 | Q-2 | 0 | $CH_3$ | Cl | $CH_3$ | F | $CH_3$ | — | — | $CH_3$ | $CH_3$ | $OCH_3$ | CH | |
| L-3 | Q-2 | 1 | H | H | $CH_3$ | H | Cl | — | — | H | $CH_3$ | $OCH_3$ | CH | |
| L-3 | Q-2 | 1 | H | H | $CH_3$ | Cl | Cl | — | — | H | $OCH_3$ | $OCH_3$ | N | |
| L-3 | Q-2 | 1 | H | H | $CH_3$ | F | $CH_3$ | — | — | H | Cl | $OCH_3$ | CH | |
| L-3 | Q-3 | 0 | H | H | $CH_3$ | H | H | $CH_3$ | — | H | $CH_3$ | $CH_3$ | CH | |
| L-3 | Q-3 | 0 | H | H | $CH_3$ | H | Cl | $CH_3$ | — | H | $CH_3$ | $OCH_3$ | CH | |
| L-3 | Q-3 | 0 | H | H | $CH_3$ | Cl | Cl | $CH_3$ | — | H | $OCH_3$ | $OCH_3$ | CH | |
| L-3 | Q-3 | 0 | H | H | $CH_3$ | F | F | $CH_3$ | — | H | $CH_3$ | $CH_3$ | N | |
| L-3 | Q-3 | 0 | H | H | $CH_3$ | H | Br | $CH_3$ | — | H | $CH_3$ | $OCH_3$ | N | |
| L-3 | Q-3 | 0 | H | H | $CH_3$ | $CH_3$ | H | $CH_3$ | — | H | $OCH_3$ | $OCH_3$ | N | |
| L-3 | Q-3 | 0 | H | H | $CH_3$ | H | $OCH_3$ | $CH_3$ | — | H | Cl | $OCH_3$ | CH | |
| L-3 | Q-3 | 0 | H | H | $CH_3$ | H | F | $CH_3$ | — | H | $CH_3$ | $OCH_3$ | CH | |
| L-3 | Q-3 | 0 | H | H | $CH_3$ | Cl | Br | $CH_3$ | — | H | $OCH_3$ | $OCH_3$ | CH | |
| L-3 | Q-3 | 0 | H | H | $CH_3$ | Cl | $CH_3$ | $CH_3$ | — | H | $CH_3$ | $OCH_3$ | N | |
| L-3 | Q-3 | 0 | H | H | $CH_3$ | F | $CH_3$ | $CH_3$ | — | $CH_3$ | $OCH_3$ | $OCH_3$ | CH | |
| L-3 | Q-3 | 0 | H | H | $CH_3$ | H | Cl | $CH_2CH_3$ | — | H | $CH_3$ | $CH_3$ | N | |
| L-3 | Q-3 | 0 | H | H | $CH_3$ | H | $CH_3$ | $CH_3$ | — | H | $OCH_3$ | $OCH_3$ | CH | |
| L-3 | Q-3 | 0 | H | $CH_3$ | $CH_3$ | H | H | $CH_3$ | — | H | Cl | $OCH_3$ | CH | |
| L-3 | Q-3 | 0 | $CH_3$ | H | $CH_3$ | H | H | $CH_3$ | — | H | $CH_3$ | $OCH_3$ | N | |
| L-3 | Q-3 | 1 | H | H | $CH_3$ | F | F | $CH_3$ | — | H | $OCH_3$ | $OCH_3$ | CH | |
| L-3 | Q-3 | 1 | H | H | $CH_3$ | H | H | $CH_3$ | — | H | $OCH_3$ | $OCH_3$ | CH | |
| L-3 | Q-4 | 0 | H | H | $CH_3$ | H | H | — | — | — | $CH_3$ | $CH_3$ | CH | |
| L-3 | Q-4 | 0 | H | H | $CH_3$ | H | H | — | — | — | $OCH_3$ | $CH_3$ | CH | |
| L-3 | Q-4 | 0 | H | H | $CH_3$ | H | H | — | — | — | $OCH_3$ | $OCH_3$ | CH | |
| L-3 | Q-4 | 0 | H | H | $CH_3$ | Cl | H | — | — | — | $CH_3$ | $OCH_3$ | N | |

| L | $Q_1$ | n | R | $R_1$ | $R_2$ | $R_7$ | $R_8$ | $R_9$ | $R_3$ | $R_{11}$ | X | Y | Z | m.p. (°C.) |
|---|---|---|---|---|---|---|---|---|---|---|---|---|---|---|
| L-3 | Q-8 | 0 | H | H | $CH_3$ | H | H | — | — | — | $CH_3$ | $CH_3$ | CH | |
| L-3 | Q-8 | 0 | H | H | $CH_3$ | H | H | — | — | — | $OCH_3$ | $CH_3$ | CH | |
| L-3 | Q-8 | 0 | H | H | $CH_3$ | H | H | — | — | — | $OCH_3$ | $OCH_3$ | CH | |
| L-3 | Q-8 | 0 | H | H | $CH_3$ | Cl | H | — | — | — | $CH_3$ | $OCH_3$ | N | |
| L-3 | Q-8 | 0 | H | H | $CH_3$ | F | H | — | — | — | Cl | $OCH_3$ | CH | |
| L-3 | Q-8 | 0 | H | H | $CH_3$ | H | Br | — | — | — | $OCH_3$ | $OCH_3$ | CH | |
| L-3 | Q-8 | 0 | H | H | $CH_3$ | F | F | — | — | — | $OCH_3$ | $OCH_3$ | N | |
| L-3 | Q-8 | 0 | H | H | $CH_3$ | Cl | Cl | — | — | — | $CH_3$ | $OCH_3$ | CH | |
| L-3 | Q-8 | 0 | H | H | $CH_3$ | H | $CH_3$ | — | — | — | $CH_3$ | $OCH_3$ | CH | |
| L-3 | Q-8 | 0 | H | H | $CH_3$ | $CH_3$ | $CH_3$ | — | — | — | $OCH_3$ | $OCH_3$ | CH | |
| L-3 | Q-8 | 0 | H | H | $CH_3$ | $CH_3$ | $CO_2CH_3$ | — | — | — | $CH_3$ | $CH_3$ | CH | |
| L-3 | Q-8 | 0 | H | H | $CH_3$ | H | F | — | — | — | $OCH_3$ | $OCH_3$ | CH | |
| L-3 | Q-8 | 0 | H | $OCH_3$ | $CH_3$ | H | Cl | — | — | — | $OCH_3$ | $CH_3$ | N | |
| L-3 | Q-8 | 0 | $CH_3$ | Cl | $CH_3$ | F | $CH_3$ | — | — | — | $CH_3$ | $OCH_3$ | CH | |
| L-3 | Q-8 | 1 | H | H | $CH_3$ | H | Cl | — | — | — | $CH_3$ | $OCH_3$ | CH | |
| L-3 | Q-8 | 1 | H | H | $CH_3$ | Cl | Cl | — | — | — | $OCH_3$ | $OCH_3$ | N | |
| L-3 | Q-8 | 1 | H | H | $CH_3$ | F | $CH_3$ | — | — | — | Cl | $OCH_3$ | CH | |
| L-3 | Q-9 | 0 | H | H | $CH_3$ | H | H | — | $CH_3$ | — | $CH_3$ | $CH_3$ | CH | |
| L-3 | Q-9 | 0 | H | H | $CH_3$ | H | Cl | — | $CH_3$ | — | $CH_3$ | $OCH_3$ | CH | |
| L-3 | Q-9 | 0 | H | H | $CH_3$ | Cl | Cl | — | $CH_3$ | — | $OCH_3$ | $OCH_3$ | CH | |
| L-3 | Q-9 | 0 | H | H | $CH_3$ | F | F | — | $CH_3$ | — | $CH_3$ | $CH_3$ | N | |
| L-3 | Q-9 | 0 | H | H | $CH_3$ | H | Br | — | $CH_3$ | — | $CH_3$ | $OCH_3$ | N | |
| L-3 | Q-9 | 0 | H | H | $CH_3$ | $CH_3$ | H | — | $CH_3$ | — | $OCH_3$ | $OCH_3$ | N | |
| L-3 | Q-9 | 0 | H | H | $CH_3$ | H | $OCH_3$ | — | $CH_3$ | — | Cl | $OCH_3$ | CH | |
| L-3 | Q-9 | 0 | H | H | $CH_3$ | H | F | — | $CH_3$ | — | $CH_3$ | $OCH_3$ | CH | |
| L-3 | Q-9 | 0 | H | H | $CH_3$ | Cl | Br | — | $CH_3$ | — | $OCH_3$ | $OCH_3$ | CH | |
| L-3 | Q-9 | 0 | H | H | $CH_3$ | Cl | $CH_3$ | — | $CH_3$ | — | $CH_3$ | $OCH_3$ | N | |
| L-3 | Q-9 | 0 | H | H | $CH_3$ | F | $CH_3$ | — | $CH_3$ | — | $OCH_3$ | $OCH_3$ | CH | |
| L-3 | Q-9 | 0 | H | H | $CH_3$ | H | Cl | — | $CH_3$ | — | $CH_3$ | $CH_3$ | N | |
| L-3 | Q-9 | 0 | H | H | $CH_3$ | H | $CH_3$ | — | $CH_2CH_3$ | — | $OCH_3$ | $OCH_3$ | CH | |
| L-3 | Q-9 | 0 | H | $CH_3$ | $CH_3$ | H | H | — | $CH_2CH_3$ | — | Cl | $OCH_3$ | CH | |
| L-3 | Q-9 | 0 | $CH_3$ | H | $CH_3$ | H | H | — | $CH_2CH_2CH_3$ | — | $CH_3$ | $OCH_3$ | N | |

TABLE IIE

General Structure IIb (wherein $R_{12}$ and $R_{13}$ are H)

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-1 | 0 | H | H | — | H | H | H | H | — | $CH_3$ | $CH_3$ | CH | |
| L-2 | Q-1 | 0 | H | H | — | H | Cl | H | H | — | $CH_3$ | $OCH_3$ | CH | |
| L-2 | Q-1 | 0 | H | H | — | Cl | Cl | H | H | — | $OCH_3$ | $OCH_3$ | CH | |

TABLE IIE-continued

General Structure IIb (wherein $R_{12}$ and $R_{13}$ are H)

| L | $Q_1$ | n | R | $R_1$ | $R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-1 | 0 | H | H | — | F | F | H | H | — | CH$_3$ | CH$_3$ | N | |
| L-2 | Q-1 | 0 | H | H | — | H | Br | H | H | — | CH$_3$ | OCH$_3$ | N | |
| L-2 | Q-1 | 0 | H | H | — | CH$_3$ | H | H | H | — | OCH$_3$ | OCH$_3$ | N | |
| L-2 | Q-1 | 0 | H | H | — | H | OCH$_3$ | H | H | — | Cl | OCH$_3$ | CH | |
| L-2 | Q-1 | 0 | H | H | — | H | F | H | H | — | CH$_3$ | OCH$_3$ | CH | |
| L-2 | Q-1 | 0 | H | H | — | Cl | Br | H | H | — | OCH$_3$ | OCH$_3$ | CH | |
| L-2 | Q-1 | 0 | H | H | — | Cl | CH$_3$ | H | H | — | CH$_3$ | OCH$_3$ | N | |
| L-2 | Q-1 | 0 | H | H | — | F | CH$_3$ | H | H | — | OCH$_3$ | OCH$_3$ | CH | |
| L-2 | Q-1 | 0 | H | H | — | H | Cl | Cl | H | — | CH$_3$ | CH$_3$ | N | |
| L-2 | Q-1 | 0 | H | H | — | H | CH$_3$ | F | F | — | OCH$_3$ | OCH$_3$ | CH | |
| L-2 | Q-1 | 0 | H | CH$_3$ | — | H | H | H | H | — | Cl | OCH$_3$ | CH | |
| L-2 | Q-1 | 0 | CH$_3$ | H | — | H | H | H | H | — | CH$_3$ | OCH$_3$ | N | |
| L-2 | Q-1 | 1 | H | H | — | F | F | H | H | — | OCH$_3$ | OCH$_3$ | CH | |
| L-2 | Q-1 | 1 | H | H | — | H | H | H | H | — | OCH$_3$ | OCH$_3$ | CH | |
| L-2 | Q-2 | 0 | H | H | — | H | H | — | — | H | CH$_3$ | CH$_3$ | CH | |
| L-2 | Q-2 | 0 | H | H | — | H | H | — | — | H | OCH$_3$ | CH$_3$ | CH | |
| L-2 | Q-2 | 0 | H | H | — | H | H | — | — | H | OCH$_3$ | OCH$_3$ | CH | |
| L-2 | Q-2 | 0 | H | H | — | Cl | H | — | — | H | CH$_3$ | OCH$_3$ | N | |
| L-2 | Q-2 | 0 | H | H | — | F | H | — | — | H | Cl | OCH$_3$ | CH | |
| L-2 | Q-2 | 0 | H | H | — | H | Br | — | — | H | OCH$_3$ | OCH$_3$ | CH | |
| L-2 | Q-2 | 0 | H | H | — | F | F | — | — | H | OCH$_3$ | OCH$_3$ | N | |
| L-2 | Q-2 | 0 | H | H | — | Cl | Cl | — | — | H | CH$_3$ | OCH$_3$ | CH | |
| L-2 | Q-2 | 0 | H | H | — | H | CH$_3$ | — | — | H | CH$_3$ | OCH$_3$ | CH | |
| L-2 | Q-2 | 0 | H | H | — | CH$_3$ | CH$_3$ | — | — | H | OCH$_3$ | OCH$_3$ | CH | |
| L-2 | Q-2 | 0 | H | H | — | H | CO$_2$CH$_3$ | — | — | H | CH$_3$ | CH$_3$ | CH | |
| L-2 | Q-2 | 0 | H | H | — | H | F | — | — | CH$_3$ | OCH$_3$ | OCH$_3$ | CH | |
| L-2 | Q-2 | 0 | H | OCH$_3$ | — | H | Cl | — | — | H | OCH$_3$ | CH$_3$ | N | |
| L-2 | Q-2 | 0 | CH$_3$ | Cl | — | F | CH$_3$ | — | — | CH$_3$ | CH$_3$ | OCH$_3$ | CH | |
| L-2 | Q-1 | 0 | H | H | — | H | OH | — | H | — | CH$_3$ | CH$_3$ | CH | |

| L | $Q_1$ | n | R | $R_1$ | $R_3$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-1 | 0 | H | H | — | H | OH | — | H | — | CH$_3$ | OCH$_3$ | CH | |
| L-2 | Q-1 | 0 | H | H | — | H | OH | — | H | — | OCH$_3$ | OCH$_3$ | CH | |
| L-2 | Q-1 | 0 | H | H | — | H | OH | — | H | — | CH$_3$ | OCH$_3$ | N | |
| L-2 | Q-1 | 0 | H | H | — | H | OH | — | H | — | OCH$_3$ | OCH$_3$ | N | |
| L-2 | Q-1 | 0 | H | H | — | H | OH | — | H | — | Cl | OCH$_3$ | N | |
| L-2 | Q-2 | 1 | H | H | — | H | Cl | — | — | H | CH$_3$ | OCH$_3$ | CH | |
| L-2 | Q-2 | 1 | H | H | — | Cl | Cl | — | — | H | OCH$_3$ | OCH$_3$ | N | |
| L-2 | Q-2 | 1 | H | H | — | F | CH$_3$ | — | — | H | Cl | OCH$_3$ | CH | |
| L-2 | Q-3 | 0 | H | H | CH$_3$ | H | H | — | — | H | CH$_3$ | CH$_3$ | CH | |
| L-2 | Q-3 | 0 | H | H | CH$_3$ | H | Cl | — | — | H | CH$_3$ | OCH$_3$ | CH | |
| L-2 | Q-3 | 0 | H | H | CH$_3$ | Cl | Cl | — | — | H | OCH$_3$ | OCH$_3$ | CH | |
| L-2 | Q-3 | 0 | H | H | CH$_3$ | F | F | — | — | H | CH$_3$ | CH$_3$ | N | |
| L-2 | Q-3 | 0 | H | H | CH$_3$ | H | Br | — | — | H | CH$_3$ | OCH$_3$ | N | |
| L-2 | Q-3 | 0 | H | H | CH$_3$ | CH$_3$ | H | — | — | H | OCH$_3$ | OCH$_3$ | N | |
| L-2 | Q-3 | 0 | H | H | CH$_3$ | H | OCH$_3$ | — | — | H | Cl | OCH$_3$ | CH | |
| L-2 | Q-3 | 0 | H | H | CH$_3$ | H | F | — | — | H | CH$_3$ | OCH$_3$ | CH | |
| L-2 | Q-3 | 0 | H | H | CH$_3$ | Cl | Br | — | — | H | OCH$_3$ | OCH$_3$ | CH | |
| L-2 | Q-3 | 0 | H | H | CH$_3$ | Cl | CH$_3$ | — | — | H | CH$_3$ | OCH$_3$ | N | |
| L-2 | Q-3 | 0 | H | H | CH$_3$ | F | CH$_3$ | — | — | CH$_3$ | OCH$_3$ | OCH$_3$ | CH | |
| L-2 | Q-3 | 0 | H | H | CH$_3$ | H | Cl | — | — | H | CH$_3$ | CH$_3$ | N | |
| L-2 | Q-3 | 0 | H | H | CH$_3$ | H | CH$_3$ | — | — | H | OCH$_3$ | OCH$_3$ | CH | |
| L-2 | Q-3 | 0 | H | CH$_3$ | CH$_3$ | H | H | — | — | H | Cl | OCH$_3$ | CH | |
| L-2 | Q-3 | 0 | CH$_3$ | H | CH$_3$ | H | H | — | — | H | CH$_3$ | OCH$_3$ | N | |
| L-2 | Q-3 | 1 | H | H | CH$_3$ | F | F | — | — | H | OCH$_3$ | OCH$_3$ | CH | |
| L-2 | Q-3 | 1 | H | H | CH$_3$ | H | H | — | — | H | OCH$_3$ | OCH$_3$ | CH | |
| L-2 | Q-4 | 0 | H | H | — | H | H | — | — | — | CH$_3$ | CH$_3$ | CH | |
| L-2 | Q-4 | 0 | H | H | — | H | H | — | — | — | OCH$_3$ | CH$_3$ | CH | |
| L-2 | Q-4 | 0 | H | H | — | H | H | — | — | — | OCH$_3$ | OCH$_3$ | CH | |
| L-2 | Q-4 | 0 | H | H | — | Cl | H | — | — | — | CH$_3$ | OCH$_3$ | N | |
| L-2 | Q-4 | 0 | H | H | — | F | H | — | — | — | Cl | OCH$_3$ | CH | |
| L-2 | Q-4 | 0 | H | H | — | H | Br | — | — | — | OCH$_3$ | OCH$_3$ | CH | |
| L-2 | Q-4 | 0 | H | H | — | F | F | — | — | — | OCH$_3$ | OCH$_3$ | N | |
| L-2 | Q-4 | 0 | H | H | — | Cl | Cl | — | — | — | CH$_3$ | OCH$_3$ | CH | |

| L | $Q_1$ | n | R | $R_1$ | $R_2$ | $R_7$ | $R_8$ | $R_9$ | $R_{10}$ | $R_{11}$ | X | Y | Z | m.p. (°C.) |
|---|---|---|---|---|---|---|---|---|---|---|---|---|---|---|
| L-2 | Q-4 | 0 | H | H | — | H | CH$_3$ | — | — | — | CH$_3$ | OCH$_3$ | CH | |
| L-2 | Q-4 | 0 | H | H | — | CH$_3$ | CH$_3$ | — | — | — | OCH$_3$ | OCH$_3$ | CH | |
| L-2 | Q-4 | 0 | H | H | — | H | CO$_2$CH$_3$ | — | — | — | CH$_3$ | CH$_3$ | CH | |
| L-2 | Q-4 | 0 | H | H | — | H | F | — | — | — | OCH$_3$ | OCH$_3$ | CH | |
| L-2 | Q-4 | 0 | H | OCH$_3$ | — | H | Cl | — | — | — | OCH$_3$ | CH$_3$ | N | |
| L-2 | Q-4 | 0 | CH$_3$ | Cl | — | F | CH$_3$ | — | — | — | CH$_3$ | OCH$_3$ | CH | |
| L-2 | Q-4 | 1 | H | H | — | H | Cl | — | — | — | CH$_3$ | OCH$_3$ | CH | |
| L-2 | Q-4 | 1 | H | H | — | Cl | Cl | — | — | — | OCH$_3$ | OCH$_3$ | N | |
| L-2 | Q-4 | 1 | H | H | — | F | CH$_3$ | — | — | — | Cl | OCH$_3$ | CH | |
| L-2 | Q-5 | 0 | H | H | — | H | H | — | — | — | CH$_3$ | CH$_3$ | CH | |
| L-2 | Q-5 | 0 | H | H | — | H | Cl | — | — | — | CH$_3$ | OCH$_3$ | CH | |
| L-2 | Q-5 | 0 | H | H | — | Cl | Cl | — | — | — | OCH$_3$ | OCH$_3$ | CH | |
| L-2 | Q-5 | 0 | H | H | — | F | F | — | — | — | CH$_3$ | CH$_3$ | N | |

TABLE IIE-continued

General Structure IIb (wherein $R_{12}$ and $R_{13}$ are H)

| | | | | | | | | | | | | | |
|---|---|---|---|---|---|---|---|---|---|---|---|---|---|
| L-2 | Q-5 | 0 | H | H | — | H | Br | — | — | — | CH$_3$ | OCH$_3$ | N |
| L-2 | Q-5 | 0 | H | H | — | CH$_3$ | H | — | — | — | OCH$_3$ | OCH$_3$ | N |
| L-2 | Q-5 | 0 | H | H | — | H | OCH$_3$ | — | — | — | Cl | OCH$_3$ | CH |
| L-2 | Q-5 | 0 | H | H | — | H | F | — | — | — | CH$_3$ | OCH$_3$ | CH |
| L-2 | Q-5 | 0 | H | H | — | Cl | Br | — | — | — | OCH$_3$ | OCH$_3$ | CH |
| L-2 | Q-5 | 0 | H | H | — | Cl | CH$_3$ | — | — | — | CH$_3$ | OCH$_3$ | N |
| L-2 | Q-5 | 0 | H | H | — | F | CH$_3$ | — | — | — | OCH$_3$ | OCH$_3$ | CH |
| L-2 | Q-5 | 0 | H | H | — | H | Cl | — | — | — | CH$_3$ | CH$_3$ | N |
| L-2 | Q-5 | 0 | H | H | — | H | CH$_3$ | — | — | — | OCH$_3$ | OCH$_3$ | CH |
| L-2 | Q-5 | 0 | H | CH$_3$ | — | H | H | — | — | — | Cl | OCH$_3$ | CH |
| L-2 | Q-5 | 0 | CH$_3$ | H | — | H | H | — | — | — | CH$_3$ | OCH$_3$ | N |
| L-2 | Q-5 | 1 | H | H | — | F | F | — | — | — | OCH$_3$ | OCH$_3$ | CH |
| L-2 | Q-5 | 1 | H | H | — | H | H | — | — | — | OCH$_3$ | OCH$_3$ | CH |
| L-2 | Q-6 | 0 | H | H | — | H | H | — | — | — | CH$_3$ | CH$_3$ | CH |
| L-2 | Q-6 | 0 | H | H | — | H | H | — | — | — | OCH$_3$ | CH$_3$ | CH |
| L-2 | Q-6 | 0 | H | H | — | H | H | — | — | — | OCH$_3$ | OCH$_3$ | CH |
| L-2 | Q-6 | 0 | H | H | — | Cl | H | — | — | — | CH$_3$ | OCH$_3$ | N |
| L-2 | Q-6 | 0 | H | H | — | F | H | — | — | — | Cl | OCH$_3$ | CH |
| L-2 | Q-6 | 0 | H | H | — | H | Br | — | — | — | OCH$_3$ | OCH$_3$ | CH |
| L-2 | Q-6 | 0 | H | H | — | F | F | — | — | — | OCH$_3$ | OCH$_3$ | N |
| L-2 | Q-6 | 0 | H | H | — | Cl | Cl | — | — | — | CH$_3$ | OCH$_3$ | CH |
| L-2 | Q-6 | 0 | H | H | — | H | CH$_3$ | — | — | — | CH$_3$ | OCH$_3$ | CH |
| L-2 | Q-6 | 0 | H | H | — | CH$_3$ | CH$_3$ | — | — | — | OCH$_3$ | OCH$_3$ | CH |
| L-2 | Q-6 | 0 | H | H | — | H | CO$_2$CH$_3$ | — | — | — | Cl | CH$_3$ | CH |
| L-2 | Q-6 | 0 | H | H | — | H | F | — | — | — | OCH$_3$ | OCH$_3$ | CH |
| L-3 | Q-1 | 0 | H | H | CH$_3$ | H | H | H | H | — | CH$_3$ | CH$_3$ | CH |
| L-3 | Q-1 | 0 | H | H | CH$_3$ | H | Cl | H | H | — | CH$_3$ | OCH$_3$ | CH |
| L-3 | Q-1 | 0 | H | H | CH$_3$ | Cl | Cl | H | H | — | OCH$_3$ | OCH$_3$ | CH |
| L-3 | Q-1 | 0 | H | H | CH$_3$ | F | F | H | H | — | CH$_3$ | CH$_3$ | N |
| L-3 | Q-1 | 0 | H | H | CH$_3$ | H | Br | H | H | — | CH$_3$ | OCH$_3$ | N |
| L-3 | Q-1 | 0 | H | H | CH$_3$ | CH$_3$ | H | H | H | — | OCH$_3$ | OCH$_3$ | N |
| L-3 | Q-1 | 0 | H | H | CH$_3$ | H | OCH$_3$ | H | H | — | Cl | OCH$_3$ | CH |
| L-3 | Q-1 | 0 | H | H | CH$_3$ | H | F | H | H | — | CH$_3$ | OCH$_3$ | CH |
| L-3 | Q-1 | 0 | H | H | CH$_3$ | Cl | Br | H | H | — | OCH$_3$ | OCH$_3$ | CH |
| L-3 | Q-1 | 0 | H | H | CH$_3$ | Cl | CH$_3$ | H | H | — | CH$_3$ | CH$_3$ | N |
| L-3 | Q-1 | 0 | H | H | CH$_3$ | F | CH$_3$ | H | H | — | OCH$_3$ | OCH$_3$ | CH |
| L-3 | Q-1 | 0 | H | H | CH$_3$ | H | Cl | Cl | H | — | CH$_3$ | CH$_3$ | N |
| L-3 | Q-1 | 0 | H | H | CH$_3$ | H | CH$_3$ | F | F | — | OCH$_3$ | OCH$_3$ | CH |
| L-3 | Q-1 | 0 | H | CH$_3$ | CH$_3$ | H | H | H | H | — | Cl | OCH$_3$ | CH |
| L-3 | Q-1 | 0 | CH$_3$ | H | CH$_3$ | H | H | H | H | — | CH$_3$ | OCH$_3$ | N |
| L-3 | Q-1 | 1 | H | H | CH$_3$ | F | F | H | H | — | OCH$_3$ | OCH$_3$ | CH |
| L-3 | Q-1 | 1 | H | H | CH$_3$ | H | H | H | H | — | OCH$_3$ | OCH$_3$ | CH |
| L-3 | Q-2 | 0 | H | H | CH$_3$ | H | H | — | — | H | CH$_3$ | CH$_3$ | CH |
| L-3 | Q-2 | 0 | H | H | CH$_3$ | H | H | — | — | H | OCH$_3$ | CH$_3$ | CH |
| L-3 | Q-2 | 0 | H | H | CH$_3$ | H | H | — | — | H | OCH$_3$ | OCH$_3$ | CH |
| L-3 | Q-2 | 0 | H | H | CH$_3$ | Cl | H | — | — | H | CH$_3$ | OCH$_3$ | N |
| L-3 | Q-2 | 0 | H | H | CH$_3$ | F | H | — | — | H | Cl | OCH$_3$ | CH |
| L-3 | Q-2 | 0 | H | H | CH$_3$ | H | Br | — | — | H | OCH$_3$ | OCH$_3$ | CH |
| L-3 | Q-4 | 0 | H | H | CH$_3$ | F | H | — | — | — | Cl | OCH$_3$ | CH |
| L-3 | Q-4 | 0 | H | H | CH$_3$ | H | Br | — | — | — | OCH$_3$ | OCH$_3$ | CH |
| L-3 | Q-4 | 0 | H | H | CH$_3$ | F | F | — | — | — | OCH$_3$ | OCH$_3$ | N |
| L-3 | Q-4 | 0 | H | H | CH$_3$ | Cl | Cl | — | — | — | CH$_3$ | OCH$_3$ | CH |
| L-3 | Q-4 | 0 | H | H | CH$_3$ | H | CH$_3$ | — | — | — | CH$_3$ | OCH$_3$ | CH |
| L-3 | Q-4 | 0 | H | H | CH$_3$ | CH$_3$ | CH$_3$ | — | — | — | OCH$_3$ | OCH$_3$ | CH |
| L-3 | Q-4 | 0 | H | H | CH$_3$ | H | CO$_2$CH$_3$ | — | — | — | CH$_3$ | CH$_3$ | CH |
| L-3 | Q-4 | 0 | H | H | CH$_3$ | H | F | — | — | — | OCH$_3$ | OCH$_3$ | CH |
| L-3 | Q-4 | 0 | H | OCH$_3$ | CH$_3$ | H | Cl | — | — | — | OCH$_3$ | OCH$_3$ | N |
| L-3 | Q-4 | 0 | CH$_3$ | Cl | CH$_3$ | F | CH$_3$ | — | — | — | CH$_3$ | OCH$_3$ | CH |
| L-3 | Q-4 | 1 | H | H | CH$_3$ | H | Cl | — | — | — | CH$_3$ | OCH$_3$ | CH |
| L-3 | Q-4 | 1 | H | H | CH$_3$ | Cl | Cl | — | — | — | OCH$_3$ | OCH$_3$ | N |
| L-3 | Q-4 | 1 | H | H | CH$_3$ | F | CH$_3$ | — | — | — | Cl | OCH$_3$ | CH |
| L-3 | Q-5 | 0 | H | H | CH$_3$ | H | H | — | — | — | CH$_3$ | CH$_3$ | CH |
| L-3 | Q-5 | 0 | H | H | CH$_3$ | H | Cl | — | — | — | CH$_3$ | OCH$_3$ | CH |
| L-3 | Q-5 | 0 | H | H | CH$_3$ | Cl | Cl | — | — | — | OCH$_3$ | OCH$_3$ | CH |
| L-3 | Q-5 | 0 | H | H | CH$_3$ | F | F | — | — | — | CH$_3$ | CH$_3$ | N |
| L-3 | Q-5 | 0 | H | H | CH$_3$ | H | Br | — | — | — | CH$_3$ | OCH$_3$ | N |
| L-3 | Q-5 | 0 | H | H | CH$_3$ | CH$_3$ | H | — | — | — | OCH$_3$ | OCH$_3$ | N |
| L-3 | Q-5 | 0 | H | H | CH$_3$ | H | OCH$_3$ | — | — | — | Cl | OCH$_3$ | CH |
| L-3 | Q-5 | 0 | H | H | CH$_3$ | H | F | — | — | — | CH$_3$ | OCH$_3$ | CH |
| L-3 | Q-5 | 0 | H | H | CH$_3$ | Cl | Br | — | — | — | OCH$_3$ | OCH$_3$ | CH |
| L-3 | Q-5 | 0 | H | H | CH$_3$ | Cl | CH$_3$ | — | — | — | CH$_3$ | CH$_3$ | N |
| L-3 | Q-5 | 0 | H | H | CH$_3$ | F | CH$_3$ | — | — | — | OCH$_3$ | OCH$_3$ | CH |
| L-3 | Q-5 | 0 | H | H | CH$_3$ | H | Cl | — | — | — | CH$_3$ | CH$_3$ | N |
| L-3 | Q-5 | 0 | H | H | CH$_3$ | H | CH$_3$ | — | — | — | OCH$_3$ | OCH$_3$ | CH |
| L-3 | Q-5 | 0 | H | CH$_3$ | CH$_3$ | H | H | — | — | — | Cl | OCH$_3$ | CH |
| L-3 | Q-5 | 0 | CH$_3$ | H | CH$_3$ | H | H | — | — | — | CH$_3$ | OCH$_3$ | N |
| L-3 | Q-5 | 1 | H | H | CH$_3$ | F | F | — | — | — | OCH$_3$ | OCH$_3$ | CH |
| L-3 | Q-5 | 1 | H | H | CH$_3$ | H | H | — | — | — | OCH$_3$ | OCH$_3$ | CH |
| L-3 | Q-6 | 0 | H | H | CH$_3$ | H | H | — | — | — | CH$_3$ | CH$_3$ | CH |
| L-3 | Q-6 | 0 | H | H | CH$_3$ | H | H | — | — | — | OCH$_3$ | CH$_3$ | CH |

TABLE IIE-continued

General Structure IIb (wherein $R_{12}$ and $R_{13}$ are H)

| L | $Q_1$ | n | R | $R_1$ | $R_2$ | $R_7$ | $R_8$ | $R_9$ | $R_3$ | $R_{10}$ | X | Y | Z | m.p. (°C.) |
|---|---|---|---|---|---|---|---|---|---|---|---|---|---|---|
| L-3 | Q-9 | 1 | H | H | $CH_3$ | F | F | — | $CH_3$ | — | $OCH_3$ | $OCH_3$ | CH | |
| L-3 | Q-9 | 1 | H | H | $CH_3$ | H | H | — | $CH_2CH_3$ | — | $OCH_3$ | $OCH_3$ | CH | |
| L-3 | Q-10 | 0 | H | H | $CH_3$ | H | H | — | $CH_3$ | — | $CH_3$ | $CH_3$ | CH | |
| L-3 | Q-10 | 0 | H | H | $CH_3$ | H | H | — | $CH_3$ | — | $OCH_3$ | $CH_3$ | CH | |
| L-3 | Q-10 | 0 | H | H | $CH_3$ | H | H | — | $CH_3$ | — | $OCH_3$ | $OCH_3$ | CH | |
| L-3 | Q-10 | 0 | H | H | $CH_3$ | Cl | H | — | $CH_3$ | — | $CH_3$ | $OCH_3$ | N | |
| L-3 | Q-10 | 0 | H | H | $CH_3$ | F | H | — | $CH_3$ | — | Cl | $OCH_3$ | CH | |
| L-3 | Q-10 | 0 | H | H | $CH_3$ | H | Br | — | $CH_3$ | — | $OCH_3$ | $OCH_3$ | CH | |
| L-3 | Q-10 | 0 | H | H | $CH_3$ | F | F | — | $CH_3$ | — | $OCH_3$ | $OCH_3$ | N | |
| L-3 | Q-10 | 0 | H | H | $CH_3$ | Cl | Cl | — | $CH_3$ | — | $CH_3$ | $OCH_3$ | CH | |
| L-3 | Q-10 | 0 | H | H | $CH_3$ | H | $CH_3$ | — | $CH_3$ | — | $CH_3$ | $OCH_3$ | CH | |
| L-3 | Q-10 | 0 | H | H | $CH_3$ | $CH_3$ | $CH_3$ | — | $CH_3$ | — | $OCH_3$ | $OCH_3$ | CH | |
| L-3 | Q-10 | 0 | H | H | $CH_3$ | H | $CO_2CH_3$ | — | $CH_3$ | — | $CH_3$ | $CH_3$ | CH | |
| L-3 | Q-10 | 0 | H | H | $CH_3$ | H | F | — | $CH_3$ | — | $OCH_3$ | $OCH_3$ | CH | |
| L-3 | Q-10 | 0 | H | $OCH_3$ | $CH_3$ | H | Cl | — | $CH_3$ | — | $OCH_3$ | $CH_3$ | N | |
| L-3 | Q-10 | 0 | $CH_3$ | Cl | $CH_3$ | F | $CH_3$ | — | $CH_3$ | — | $CH_3$ | $OCH_3$ | CH | |
| L-3 | Q-10 | 1 | H | H | $CH_3$ | H | Cl | — | $CH_2CH_3$ | — | $CH_3$ | $OCH_3$ | CH | |
| L-3 | Q-10 | 1 | H | H | $CH_3$ | Cl | Cl | — | $CH_3$ | — | $OCH_3$ | $OCH_3$ | N | |
| L-3 | Q-10 | 1 | H | H | $CH_3$ | F | $CH_3$ | — | $CH_2CH_3$ | — | Cl | $OCH_3$ | CH | |

TABLE III

General Structure III (wherein $R_{12}$ and $R_{13}$ are H)

| A | Q | n | R | $R_1$ | $R_3$ | $R_7$ | $R_8$ | $R_9$ | $R_{10}$ | $R_{11}$ | $X_1$ | $Y_1$ | $Y_2$ | $X_2$ | $Y_3$ | $X_3$ | m.p. (°C.) |
|---|---|---|---|---|---|---|---|---|---|---|---|---|---|---|---|---|---|
| A-2 | Q-1 | 0 | H | H | — | H | H | H | H | — | $CH_3$ | O | — | — | — | — | |
| A-2 | Q-1 | 0 | H | H | — | H | H | H | H | — | $CH_3$ | $CH_2$ | — | — | — | — | |
| A-2 | Q-1 | 0 | H | H | — | H | H | H | H | — | $OCH_3$ | O | — | — | — | — | |
| A-2 | Q-5 | 0 | H | H | — | H | H | — | — | — | $CH_3$ | $CH_2$ | — | — | — | — | |
| A-2 | Q-2 | 0 | H | H | — | H | Cl | — | — | H | $OCF_2H$ | O | — | — | — | — | |
| A-3 | Q-1 | 0 | H | H | — | H | H | H | H | — | $CH_3$ | — | — | — | — | — | |
| A-3 | Q-1 | 0 | H | H | — | H | H | H | H | — | $OCH_3$ | — | — | — | — | — | |
| A-3 | Q-1 | 0 | H | H | — | H | F | H | Cl | — | $OCF_2H$ | — | — | — | — | — | |
| A-3 | Q-1 | 1 | H | H | — | Cl | Cl | H | H | — | $CH_3$ | — | — | — | — | — | |
| A-3 | Q-1 | 0 | H | H | — | $CH_3$ | H | H | H | — | $OCH_3$ | — | — | — | — | — | |
| A-3 | Q-4 | 0 | H | H | — | H | H | — | — | — | $OCH_3$ | — | — | — | — | — | |
| A-3 | Q-3 | 0 | H | H | $CH_3$ | H | $CH_3$ | — | — | H | $CH_3$ | — | — | — | — | — | |
| A-4 | Q-1 | 0 | H | H | — | H | H | H | H | — | $CH_3$ | — | H | — | — | — | |
| A-4 | Q-1 | 0 | H | H | — | H | Cl | H | H | — | $OCH_3$ | — | H | — | — | — | |
| A-4 | Q-1 | 1 | H | H | — | F | F | Cl | $CH_3$ | — | $CH_3$ | — | $CH_3$ | — | — | — | |
| A-4 | Q-6 | 0 | H | H | — | H | H | — | — | — | $OCH_3$ | — | H | — | — | — | |
| A-4 | Q-7 | 0 | H | H | — | $CH_3$ | F | — | — | — | $CH_3$ | — | $CH_3$ | — | — | — | |
| A-5 | Q-1 | 0 | H | H | — | H | H | H | H | — | — | — | — | $CH_3$ | $CH_3$ | — | |
| A-5 | Q-1 | 0 | H | H | — | Cl | H | H | Cl | — | — | — | — | $OCH_3$ | $CH_3$ | — | |
| A-5 | Q-10 | 0 | H | H | $CH_3$ | H | H | — | — | — | — | — | — | $CH_3$ | $CH_2CF_3$ | — | |
| A-6 | Q-1 | 0 | H | H | — | H | H | H | H | — | — | — | — | — | — | $CH_3$ | |

| A | Q | n | R | $R_1$ | $R_7$ | $R_8$ | $R_9$ | $R_{10}$ | $R_{11}$ | $X_4$ | $Y_4$ | Z | m.p. (°C.) |
|---|---|---|---|---|---|---|---|---|---|---|---|---|---|
| A-7 | Q-1 | 0 | H | H | H | H | H | H | — | $CH_3$ | $CH_3$ | CH | |
| A-7 | Q-1 | 0 | H | H | H | H | H | H | — | $CH_3$ | $OCH_3$ | N | |
| A-7 | Q-2 | 0 | H | H | H | H | — | — | H | $CH_3$ | $OCH_3$ | CH | |
| A-7 | Q-2 | 0 | H | H | H | H | — | — | H | $OCH_3$ | $OCH_3$ | N | |
| A-7 | Q-4 | 0 | H | H | H | H | — | — | — | $OCH_3$ | $OCH_3$ | CH | |
| A-7 | Q-4 | 0 | H | H | H | H | — | — | — | $CH_3$ | $CH_3$ | N | |

TABLE IV

General Structure IV

| L | Q | A | $R_1$ | $R_2$ | $R_3$ | $R_7$ | $R_8$ | $R_9$ | $R_{10}$ | $R_{11}$ | $X_1$ | $Y_1$ | $Y_2$ | $X_2$ | $Y_3$ | $X_3$ | m.p. (°C.) |
|---|---|---|---|---|---|---|---|---|---|---|---|---|---|---|---|---|---|
| L-2 | Q-1 | A-2 | H | — | — | H | H | H | H | — | $CH_3$ | O | — | — | — | — | |
| L-2 | Q-6 | A-4 | H | — | — | H | Cl | — | — | — | $OCH_3$ | — | H | — | — | — | |
| L-2 | Q-10 | A-5 | H | — | $CH_3$ | H | H | — | — | — | — | — | — | $OCH_3$ | $CH_3$ | — | |
| L-3 | Q-1 | A-3 | H | $CH_3$ | — | H | H | H | H | — | $OCH_3$ | — | — | — | — | — | |
| L-3 | Q-1 | A-6 | H | $CH_3$ | — | Cl | H | H | H | — | — | — | — | — | — | $OCH_3$ | |
| L-3 | Q-3 | A-2 | H | $CH_3$ | $CH_3$ | H | H | — | — | H | $OCH_3$ | $CH_2$ | — | — | — | — | |
| L-4 | Q-1 | A-3 | H | — | — | H | H | H | H | — | $OCH_3$ | — | — | — | — | — | |
| L-4 | Q-1 | A-4 | H | — | — | H | F | H | H | — | $OCH_3$ | — | $CH_3$ | — | — | — | |
| L-4 | Q-2 | A-2 | H | — | — | H | $CH_3$ | — | — | H | $OCF_2H$ | O | — | — | — | — | |
| L-4 | Q-3 | A-4 | H | — | $CH_3$ | H | H | — | — | H | $CH_3$ | — | $CH_3$ | — | — | — | |
| L-5 | Q-1 | A-2 | H | — | — | H | H | H | H | — | $OCH_2CH_3$ | $CH_2$ | — | — | — | — | |
| L-5 | Q-1 | A-6 | H | — | — | H | Cl | H | H | — | — | — | — | — | — | $CH_3$ | |
| L-5 | Q-4 | A-2 | H | — | — | H | H | — | — | — | $OCH_3$ | O | — | — | — | — | |
| L-5 | Q-7 | A-5 | H | — | — | H | H | — | — | — | — | — | — | $SCH_3$ | $CH_3$ | — | |

TABLE IV-continued

General Structure IV

| L | Q | A | $R_1$ | $R_2$ | $R_3$ | $R_7$ | $R_8$ | $R_9$ | $R_{10}$ | $R_{11}$ | $X_1$ | $Y_1$ | $Y_2$ | $X_2$ | $Y_3$ | $X_3$ | m.p. (°C.) |
|---|---|---|---|---|---|---|---|---|---|---|---|---|---|---|---|---|---|
| L-6 | Q-1 | A-2 | H | — | — | H | H | H | H | — | $CH_3$ | O | — | — | — | — | |
| L-6 | Q-5 | A-2 | H | — | — | H | $CH_3$ | — | — | — | $CH_3$ | $CH_2$ | — | — | — | — | |
| L-6 | Q-8 | A-6 | H | — | — | H | H | — | — | — | — | — | — | — | — | $OCH_3$ | |
| L-6 | Q-9 | A-2 | H | — | $CH_3$ | H | H | — | — | — | $OCH_3$ | O | — | — | — | — | |
| L-2 | Q-1 | A-2 | H | — | — | H | OH | — | — | — | $OCH_3$ | O | — | — | — | — | |

TABLE V

General Structure V (where $R_9$ and $R_{10}$ are a carbonyl group)

| L | Q | R | $R_1$ | $R_2$ | $R_7$ | $R_8$ | X | Y | Z | m.p.(°C.) |
|---|---|---|---|---|---|---|---|---|---|---|
| L-1 | Q-1 | H | H | — | H | H | $CH_3$ | $CH_3$ | CH | |
| L-1 | Q-1 | H | H | — | H | H | $OCH_3$ | $CH_3$ | CH | |
| L-1 | Q-1 | H | H | — | H | H | $OCH_3$ | $OCH_3$ | CH | |
| L-1 | Q-1 | H | H | — | H | H | $CH_3$ | $CH_3$ | N | |
| L-1 | Q-1 | H | H | — | H | H | $OCH_3$ | $CH_3$ | N | |
| L-1 | Q-1 | H | H | — | H | H | $OCH_3$ | $OCH_3$ | N | |
| L-1 | Q-1 | H | H | — | H | Cl | $CH_3$ | $OCH_3$ | CH | |
| L-1 | Q-1 | H | H | — | H | F | $CH_3$ | $OCH_3$ | N | |
| L-1 | Q-1 | H | H | — | H | Br | $OCH_3$ | $OCH_3$ | CH | |
| L-1 | Q-1 | H | H | — | H | CN | $OCH_3$ | $OCH_3$ | CH | |
| L-1 | Q-1 | H | H | — | H | $CH_3$ | $CH_3$ | $OCH_3$ | N | |
| L-1 | Q-1 | H | H | — | H | $OCH_3$ | $CH_3$ | $CH_3$ | CH | |
| L-1 | Q-1 | H | H | — | H | $CO_2CH_3$ | $OCH_3$ | $OCH_3$ | N | |
| L-1 | Q-1 | H | H | — | H | $SO_2N(CH_3)_2$ | $CH_3$ | $OCH_3$ | CH | |
| L-1 | Q-1 | H | H | — | H | $SCH_3$ | $CH_3$ | $OCH_3$ | CH | |
| L-1 | Q-1 | H | H | — | H | $SO_2CH_3$ | $CH_3$ | $CH_3$ | N | |
| L-1 | Q-1 | $CH_3$ | H | — | H | H | $OCH_3$ | $OCH_3$ | CH | |
| L-2 | Q-1 | H | H | — | H | H | $CH_3$ | $OCH_3$ | CH | |
| L-2 | Q-1 | H | H | — | H | H | $OCH_3$ | $OCH_3$ | N | |
| L-3 | Q-1 | H | H | $CH_3$ | H | H | $OCH_3$ | $CH_3$ | CH | |
| L-3 | Q-1 | H | H | $CH_3$ | H | H | $OCH_3$ | $OCH_3$ | CH | |
| L-4 | Q-1 | H | H | — | H | H | $CH_3$ | $OCH_3$ | N | |
| L-4 | Q-1 | H | H | — | H | $CH_3$ | $CH_3$ | $OCH_3$ | CH | |
| L-5 | Q-1 | H | H | — | H | H | $OCH_3$ | $OCH_3$ | CH | |
| L-5 | Q-1 | H | H | — | H | Cl | $CH_3$ | $CH_3$ | CH | |
| L-6 | Q-1 | H | H | — | H | H | $OCH_3$ | $OCH_3$ | N | |
| L-6 | Q-1 | H | H | — | H | H | $CH_3$ | $CH_3$ | N | |
| L-6 | Q-1 | H | H | — | Cl | Cl | $OCH_3$ | $OCH_3$ | CH | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

Wettable Powder

| | |
|---|---|
| N—[(4,6-dimethoxypyrimidin-2-yl)aminocarbonyl]-2-(2-oxiranylmethyl)benzenesulfonamide, | 50% |
| sodium alkylnaphthalenesulfonate | 2% |
| low viscosity methyl cellulose | 2% |
| diatomaceous earth | 46% |

The ingredients are blended, coarsely hammermilled and then air-milled to produce particles essentially all below 10 microns in diameter. The product is reblended before packaging.

EXAMPLE 9

Granule

| | |
|---|---|
| Wettable Powder of Example 8 | 5% |
| attapulgite granules | 95% |
| (U.S.S. 20–40 mesh; 0.84–0.42 mm) | |

A slurry of wettable powder containing 25% solids is sprayed on the surface of attapulgite granules in a double-cone blender. The granules are dried and packaged.

EXAMPLE 10

Extruded Pellet

| | |
|---|---|
| N—[(4,6-dimethoxypyrimidin-2-yl)aminocarbonyl]-2-(2-oxiranylmethyl)benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

Low Strength Granule

| | |
|---|---|
| 2-(2,2-dichlorocyclopropyl)-N—[(4-methoxy-6-methyl)-aminocarbonyl]benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 12

Aqueous Suspension

| | |
|---|---|
| 2-(2,2-dichlorocyclopropyl)-N—[(4-methoxy-6-methyl)-aminocarbonyl]benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Oil Suspension

| | |
|---|---|
| N—[(4,6-dimethoxypyrimidin-2-yl)aminocarbonyl]-2-(2-oxiranylmethyl)benzenesulfonamide | 35% |
| blend of polyalchol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 14

Granule

| | |
|---|---|
| 2-(2,2-dichlorocyclopropyl)-N—[(4,6-dimethoxypyrimidin-2-yl)aminocarbonyl]benzenesulfonamide | 80% |
| wetting agent | 1% |
| crude ligninsulfonate salt (containing 5–20% of the natural sugars) | 10% |

-continued

| | |
|---|---|
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

EXAMPLE 15

High Strength Concentrate

| | |
|---|---|
| N—[(4,6-dimethoxypyrimidin-2-yl)aminocarbonyl]-2-(2-oxiranylmethyl)benzenesulfonamide | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE 16

Wettable Powder

| | |
|---|---|
| 2-(2,2-dichlorocyclopropyl)-N—[(4-methoxy-6-methyl)-aminocarbonyl]benzenesulfonamide | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 17

Wettable Powder

| | |
|---|---|
| 2-(2,2-dichlorocyclopropyl)-N—[(4,6-dimethoxypyrimidin-2-yl)aminocarbonyl]benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 18

Dust

| | |
|---|---|
| N—[(4,6-dimethoxypyrimidin-2-yl)aminocarbonyl]-2-(2-oxiranylmethyl)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulants. Many of them have utility for broad-spectrum pre- and or postemergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice and wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foilage present, etc. In general terms, the subject compounds should be applied at levels of arount 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), cheatgrass (*Bromus secalinus*), velvetleaf (*Abutilon theophrasti*), sicklepod (*Cassia obtusifolia*), morningglory (*Ipomoea* sp.), cocklebur (*Xanthium* sp.), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, sicklepod with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis or necrosis;
B=burn;
D=defoliation;
E=emergence inhibition;
G=growth retardation;

H=formative effects;
U=unusual pigmentation
X=axillary stimulation;
S=albinism; and
6Y=abscised buds or flowers.

Compounds

[Structure: phenyl-(CH2)n-Q with SO2NHCNH-pyrimidine/triazine ring bearing X, Y, Z]

| Compound | n | Q | X | Y | Z |
|---|---|---|---|---|---|
| 1 | 0 | 2,2-dichlorocyclopropyl | CH3 | CH3 | CH |
| 2 | 0 | 2,2-dichlorocyclopropyl | CH3 | OCH3 | CH |
| 3 | 0 | 2,2-dichlorocyclopropyl | OCH3 | OCH3 | CH |
| 4 | 0 | 2,2-dichlorocyclopropyl | CH3 | CH3 | N |
| 5 | 0 | 2,2-dichlorocyclopropyl | CH3 | OCH3 | N |
| 6 | 0 | 2,2-dichlorocyclopropyl | OCH3 | OCH3 | N |

-continued
Compounds

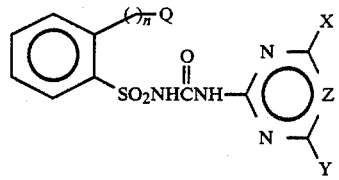

| Compound | n | Q | X | Y | Z |
|---|---|---|---|---|---|
| 7 | 1 | cyclopropyl-O | OCH3 | OCH3 | CH |
| 8 | 0 | cyclopropyl-O | OCH3 | OCH3 | CH |
| 9 | 0 | cyclopropyl-O | CH3 | CH3 | CH |

TABLE A

| Rate (kg/ha) | Compound 1 0.05 | Compound 2 0.05 | Compound 3 0.05 | Compound 4 0.05 | Compound 5 0.05 |
|---|---|---|---|---|---|
| | | POSTEMERGENCE | | | |
| Morningglory | 0 | 2C,5G | 5C,8G | 4C,8G | 10C |
| Cocklebur | 5G | 9C | 9C | 3C,8G | 9C |
| Velvetleaf | 2C,8G | 9C | 10C | 4C,8H | 10C |
| Nutsedge | 0 | 10C | 9C | 0 | 9C |
| Crabgrass | 0 | 2G | 4G | 0 | 2G |
| Barnyardgrass | 0 | 8H | 3H | 0 | 2H |
| Cheatgrass | 0 | 2C,6G | 2C,6G | 0 | 2C |
| Wild Oats | 0 | 2G | 0 | 0 | 0 |
| Wheat | 0 | 0 | 0 | 0 | 3G |
| Corn | 0 | 2C,8H | 1C,4G | 0 | 3C,8H |
| Soybean | 2C,9G | 4C,9G | 5C,9G | 2C,9G | 3C,9G |
| Rice | 5G | 2C,7G | 2C,6G | 3G | 5G |
| Sorghum | 2H | 2G | 2G | 0 | 2C,5H |
| Sugar Beets | 0 | 5G | 4C,8G | 5C,9G | 9C |
| Cotton | 4C,8H | 5C,9G | 5C,9G | 4C,8H | 5C,9G |
| Bushbean | | | | | |
| Cassia | | | | | |
| | | PREEMERGENCE | | | |
| Morningglory | 4G | 8G | 7G | 7H | 9G |
| Cocklebur | — | 8H | 9G | 2C | 9H |
| Velvetleaf | 2G | 9G | 9G | 0 | 9G |
| Nutsedge | 0 | 9G | 10E | 0 | 4G |
| Crabgrass | 0 | 2G | 2C,8G | 0 | 0 |
| Barnyardgrass | 0 | 2C,9H | 2C,7H | 0 | 2C,3H |
| Cheatgrass | 2G | 5C,9H | 5C,9H | 0 | 5G |
| Wild Oats | 0 | 3C,8G | 3G | 0 | 2G |
| Wheat | 0 | 6G | 2G | 0 | 0 |
| Corn | 2G | 2C,9H | 2C,8G | 2G | 4G |
| Soybean | 0 | 4C,8H | 7G | 3C,2H | 4C,8H |
| Rice | 3G | 4C,8G | 2C,8H | 0 | 4G |
| Sorghum | 5G | 4C,8H | 2C,7H | 0 | 2C,5G |
| Sugar Beets | 5G | 8G | 9G | 3C,5G | 10E |
| Cotton | 5G | 9G | 8G | 5G | 9G |
| Bushbean | | | | | |
| Cassia | | | | | |

| Rate (kg/ha) | Compound 6 0.05 | Compound 7 0.05 | Compound 8 0.05 | Compound 9 0.05 |
|---|---|---|---|---|
| | POSTEMERGENCE | | | |
| Morningglory | 10C | 2C,8G | 1C | 0 |
| Cocklebur | 10C | 8H | 2C,7G | 2G |
| Velvetleaf | 10C | — | 9C | 2G |
| Nutsedge | 9C | 10C | 4C,9G | 1C |
| Crabgrass | 0 | 1C,5G | 1C | 0 |
| Barnyardgrass | 0 | 5C,9H | 4C,9H | 2C,4H |
| Cheatgrass | 1C | — | 3G | 0 |
| Wild Oats | 0 | 2G | 0 | 0 |

TABLE A-continued

| | | | | |
|---|---|---|---|---|
| Wheat | 0 | 2G | 0 | 0 |
| Corn | 3C,8H | 2C,8H | 2C,7H | 2C,5G |
| Soybean | 4C,9G | 4C,8H | 3C,9G,7X | 2C,2H |
| Rice | 3G | 4C,9G | 6G | 3G |
| Sorghum | 2C,5H | 2C,9H | 2C,7H | 2C,5G |
| Sugar Beets | 10C | 9C | 9C | 2C,5G |
| Cotton | 9C | 4C,4H | 9C | 1H |
| Bushbean | | 5C,9G | — | — |
| Cassia | | 2C,9G | — | — |
| PREEMERGENCE | | | | |
| Morningglory | 8G | 7G | 5G | 0 |
| Cocklebur | 9C | 9H | 0 | 0 |
| Velvetleaf | 5C,9G | — | 0 | 0 |
| Nutsedge | 7G | 5G | 0 | 0 |
| Crabgrass | 0 | 2C | 0 | 0 |
| Barnyardgrass | 2C | 4C,8H | 0 | 0 |
| Cheatgrass | 0 | — | 0 | 0 |
| Wild Oats | 0 | 3C,6G | 0 | 0 |
| Wheat | 0 | 1C,3G | 0 | 0 |
| Corn | 2C,6G | 2C,8H | 0 | 1H |
| Soybean | 3C,8H | 2C,8H | 2C | 1H |
| Rice | 3G | 3C,8G | 0 | 4G |
| Sorghum | 2G | 3C,9G | 1C | 2G |
| Sugar Beets | 5C,9G | 9G | 6G | 2H |
| Cotton | 9G | — | 2G | 0 |
| Bushbean | | — | — | — |
| Cassia | | 5C,9H | — | — |

What is claimed is:

1. A compound of the formula $$LSO_2NHCNA \overset{W}{\underset{R}{\|}}$$   I wherein
W is O or S;
R is H or $CH_3$;
L is

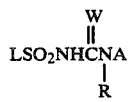  L-1

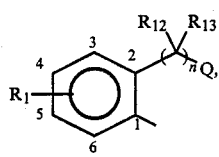  L-2

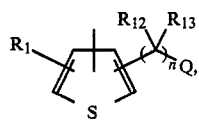  L-3

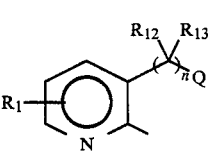  L-4

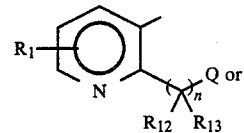  L-5

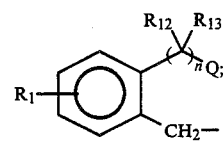  L-6 n is 0 or 1;
$R_1$ is H, $C_1$–$C_3$ alkyl, $C_1$–$C_3$ haloalkyl, halogen, nitro, CN, $C_1$–$C_3$ alkoxy, $SO_2NR^IR^{II}$, $C_1$–$C_3$ alkylthio, $C_1$–$C_3$ alkylsulfinyl, $C_1$–$C_3$ alkylsulfonyl, $CO_2R^{III}$, $CH_2CN$, $CH_2OCH_3$ or $CH_2SCH_3$;
$R^I$ is H, $C_1$–$C_4$ alkyl, $C_2$–$C_3$ cyanoalkyl, methoxy or ethoxy;
$R^{II}$ is H, $C_1$–$C_4$ alkyl or $C_3$–$C_4$ alkenyl; or
$R^I$ and $R^{II}$ may be taken together as —$(CH_2)_3$—, —$(CH_2)_4$—, —$(CH_2)_5$— or —$CH_2CH_2OCH_2CH_2$—;
$R^{III}$ is $C_1$–$C_4$ alkyl, $C_3$–$C_4$ alkenyl, $C_3$–$C_4$ alkynyl, $C_2$–$C_4$ haloalkyl, $C_2$–$C_3$ cyanoalkyl, $C_5$–$C_6$ cycloalkyl, $C_4$–$C_7$ cycloalkylalkyl or $C_2$–$C_4$ alkoxyalkyl;
$R_2$ is $C_1$–$C_3$ alkyl;
Q is a 3- or 4-membered heterocyclic ring which contains one heteroatom selected from O, S and $NR_3$, or a 3- or 4-membered carbocyclic ring in which one carbon atom may optionally be in the form of a carbonyl group, or a fully-saturated 5- or 6-membered carbocyclic ring, and Q may be optionally substituted with 1–4 substituents selected from halogen, CN, OH, $C_1$–$C_3$ alkyl, $C_1$–$C_3$ alkoxy, $C_1$–$C_3$ alkylthio, $C_2$–$C_4$ alkoxycarbonyl, $C_1$–$C_4$ alkylsulfonyl, ($C_1$–$C_4$ alkyl)-aminosulfamoyl and di($C_1$–$C_4$ alkyl)aminosulfamoyl;
$R_3$ is $C_1$–$C_4$ alkyl;
$R_{12}$ is H or $OR_{14}$;
$R_{13}$ is H or $C_1$–$C_4$ alkyl;

$R_{14}$ is H, $C_1$–$C_4$ alkyl, $C_3$–$C_4$ alkenyl, $C_3$–$C_4$ haloalkenyl, $C_3$–$C_4$ alkynyl, $C_3$–$C_4$ haloalkynyl, $C_2$–$C_4$ alkylcarbonyl, $C(O)NR_{15}R_{16}$, $C_1$–$C_4$ alkylsulfonyl, $C_2$–$C_4$ alkoxyalkyl or $C_2$–$C_4$ alkylthioalkyl;

$R_{15}$ and $R_{16}$ are independently H or $C_1$–$C_2$ alkyl;

A is

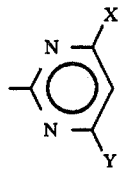    A-1

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ haloalkylthio, $C_1$–$C_4$ alkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_3$–$C_5$ cycloalkyl, $C_2$–$C_4$ alkynyl,

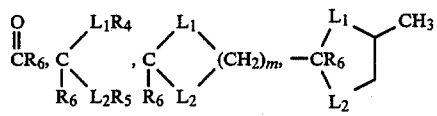

or $N(OCH_3)CH_3$;

m is 2 or 3;

$L_1$ and $L_2$ are independently O or S;

$R_4$ and $R_5$ are independently $C_1$–$C_2$ alkyl;

$R_6$ is H or $CH_3$;

and their agriculturally suitable salts; provided that (a) when X is Cl, F, Br or I, then Y is $OCH_3$, $OC_2H_5$, $N(OCH_3)CH_3$, $NHCH_3$, $N(CH_3)_2$ or $OCF_2H$;

(b) when L is L-2 or L-3, then the Q substituent and the sulfonylurea bridge are on adjacent carbon atoms;

(c) when W is S, then R is H, and Y is $CH_3$, $OCH_3$, $OC_2H$, $CH_2OCH_3$, $C_2H_5$, $CF_3$, $SCH_3$, $OCH_2CH=CH_2$, $OCH_2\equiv CH$, $OCH_2CH_2OCH_3$ or $CH(OCH_3)_2$;

(d) the total number of carbon atoms of $R_{12}$ and $R_{13}$ must be less than or equal to four; and (e) when the total number of carbon atoms of X and Y is greater than four, then the number of carbons of $R_1$ must be less than or equal to two and the number of carbons of Q must be less than or equal to six.

2. The compounds of claim 1 wherein Q is

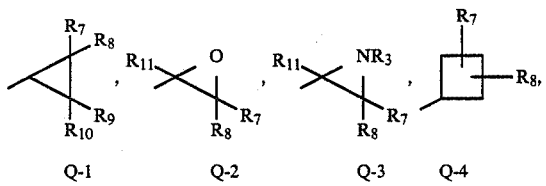

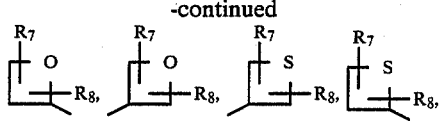

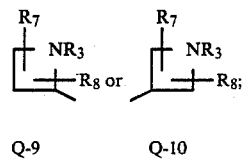

wherein $R_3$ is $C_1$–$C_3$ alkyl;

$R_7$ is H, F, Cl, Br, CN, $CH_3$ or $OCH_3$;

$R_8$ is H, F, Cl, Br, I, CN, OH, $C_1$–$C_3$ alkyl, $C_1$–$C_3$ alkoxy, $C_2$–$C_3$ alkoxycarbonyl, di($C_1$–$C_3$ alkyl)aminosulfamoyl, $C_1$–$C_3$ alkylthio or $C_1$–$C_3$ alkylsulfonyl;

$R_9$ and $R_{10}$ are independently H, $CH_3$, F, Cl or may be taken together to form C=O; and $R_{11}$ is H or $C_1$–$C_3$ alkyl;

provided that (a) when $R_7$ and $R_8$ are attached to the same carbon atom as in Q-1, Q-2 or Q-3, or in Q-4 through Q-10, and $R_7$ is $OCH_3$, then $R_8$ is other than F, Cl, Br, I or OH; and (b) when $R_7$ and $R_8$ are attached to the same carbon atom as in Q-1, Q-2 or Q-3, or in Q-4 through Q-10, and $R_8$ is F, Cl, Br, I or OH, then $R_7$ is other than $OCH_3$.

3. The compounds of claim 2 where
W is O; and
R is H.

4. The compounds of claim 3 where
$R_1$ is selected from H, F, Cl, $NO_2$, $C_1$–$C_2$ alkyl, $C_1$–$C_2$ haloalkyl, $C_1$–$C_2$ alkoxy, $C_1$–$C_2$ alkylthio, $CH_2OCH_3$ or $CH_2SCH_3$;

$R_{13}$ is H or $CH_3$;

$R_{14}$ is H, $C_1$–$C_2$ alkyl, $CH_2CH=CH_2$ or $CH_2C\equiv CH$;

X is $CH_3$, $OCH_3$, $OC_2H_5$, Cl, F, Br, $OCF_2H$, $CH_2F$, $OCH_2CH_2F$, $OCH_2CHF_2$, $OCH_2CF_3$, $CF_3$, $CH_2Cl$ or $CH_2Br$; and Y is H, $C_1$–$C_3$ alkyl, $OCH_3$, $OC_2H_5$, $CH_2OCH_3$, $NHCH_3$, $N(OCH_3)CH_3$, $N(CH_3)_2$, $CF_3$, $SCH_3$, $OCH_2CH=CH_2$, $OCH_2C\equiv CH$, $CH_2OC_2H_5$, $OCH_2CH_2OCH_3$, $CH_2SCH_3$, $OCF_2H$, $SCF_2H$, cyclopropyl, $C\equiv CH$ or $C\equiv CCH_3$.

5. The compounds of claim 4 where
L is L-1; and
Q is Q-1, Q-2 or Q-4.

6. The compounds of claim 5 where Q is Q-1;

7. The compounds of claim 6 where
$R_1$ is H, Cl, $CH_3$, $OCH_3$ or $SCH_3$ and is not in the 4-position;
$R_7$ is H, F, Cl, $CH_3$ or $OCH_3$;
$R_8$ is H, F, Cl, $CH_3$ or $OCH_3$; and
$R_9$ and $R_{10}$ are independently H, $CH_3$, F or Cl.

8. The compound of claim 1 which is 2-(2,2-dichlorocyclopropyl)-N-[(4,6-dimethoxypyrimidin-2-yl)-aminocarbonyl]benzenesulfonamide.

9. The compound of claim 1 which is N-[(4,6-dimethoxypyrimidin-2-yl)aminocarbonyl]-2-(2-oxiranylmethyl)benzenesulfonamide.

10. An agriculturally suitable composition for controlling the growth of undesired vegetation which comprises an effective amount of a compound of claim 1 and at least one of the following: surfactant, solid or liquid diluent.

11. An agriculturally suitable composition for controlling the growth of undesired vegetation which comprises an effective amount of a compound of claim 2 and at least one of the following: surfactant, solid or liquid diluent.

12. An agriculturally suitable composition for controlling the growth of undesired vegetation which comprises an effective amount of a compound of claim 3 and at least one of the following: surfactant, solid or liquid diluent.

13. An agriculturally suitable composition for controlling the growth of undesired vegetation which comprises an effective amount of a compound of claim 4 and at least one of the following: surfactant, solid or liquid diluent.

14. An agriculturally suitable composition for controlling the growth of undesired vegetation which comprises an effective amount of a compound of claim 5 and at least one of the following: surfactant, solid or liquid diluent.

15. An agriculturally suitable composition for controlling the growth of undesired vegetation which comprises an effective amount of a compound of claim 6 and at least one of the following: surfactant, solid or liquid diluent.

16. An agriculturally suitable composition for controlling the growth of undesired vegetation which comprises an effective amount of a compound of claim 7 and at least one of the following: surfactant, solid or liquid diluent.

17. An agriculturally suitable composition for controlling the growth of undesired vegetation which comprises an effective amount of a compound of claim 8 and at least one of the following: surfactant, solid or liquid diluent.

18. An agriculturally suitable composition for controlling the growth of undesired vegetation which comprises an effective amount of a compound of claim 9 and at least one of the following: surfactant, solid or liquid diluent.

19. A method for controlling the growth of undesired vegetation which comprises applying to the locus to be protected an effective amount of a compound of claim 1.

20. A method for controlling the growth of undesired vegetation which comprises applying to the locus to be protected an effective amount of a compound of claim 2.

21. A method for controlling the growth of undesired vegetation which comprises applying to the locus to be protected an effective amount of a compound of claim 3.

22. A method for controlling the growth of undesired vegetation which comprises applying to the locus to be protected an effective amount of a compound of claim 4.

23. A method for controlling the growth of undesired vegetation which comprises applying to the locus to be protected an effective amount of a compound of claim 5.

24. A method for controlling the growth of undesired vegetation which comprises applying to the locus to be protected an effective amount of a compound of claim 6.

25. A method for controlling the growth of undesired vegetation which comprises applying to the locus to be protected an effective amount of a compound of claim 7.

26. A method for controlling the growth of undesired vegetation which comprises applying to the locus to be protected an effective amount of a compound of claim 8.

27. A method for controlling the growth of undesired vegetation which comprises applying to the locus to be protected an effective amount of a compound of claim 9.

* * * * *

UNITED STATES PATENT AND TRADEMARK OFFICE
CERTIFICATE OF CORRECTION

PATENT NO. : 4,732,604
DATED : March 22, 1988
INVENTOR(S) : James V. Hay, Barry A. Wexler and Donna F. Zimmerman It is certified that error appears in the above—identified patent and that said Letters Patent is hereby corrected as shown below:

Claim 1, column 113, at proviso (c) the substituent

"$OCH_2 \equiv CH$" is incorrect and should be

-- $OCH_2C \equiv CH$ --.

Signed and Sealed this

Third Day of January, 1989

Attest:

DONALD J. QUIGG

Attesting Officer

Commissioner of Patents and Trademarks